United States Patent
Sette et al.

(10) Patent No.: US 11,421,006 B2
(45) Date of Patent: Aug. 23, 2022

(54) T CELL EPITOPES FROM COCKROACH AND METHODS OF MAKING AND USING SAME

(71) Applicant: LA JOLLA INSTITUTE FOR ALLERGY AND IMMUNOLOGY, La Jolla, CA (US)

(72) Inventors: Alessandro Sette, La Jolla, CA (US); Bjoern Peters, San Diego, CA (US); Jason Greenbaum, San Diego, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 586 days.

(21) Appl. No.: 14/398,719

(22) PCT Filed: May 3, 2013

(86) PCT No.: PCT/US2013/039566
§ 371 (c)(1),
(2) Date: Nov. 3, 2014

(87) PCT Pub. No.: WO2013/166453
PCT Pub. Date: Nov. 7, 2013

(65) Prior Publication Data
US 2015/0110819 A1    Apr. 23, 2015

Related U.S. Application Data

(60) Provisional application No. 61/642,384, filed on May 3, 2012.

(51) Int. Cl.
| | | |
|---|---|---|
| *C07K 14/435* | (2006.01) | |
| *A61K 39/00* | (2006.01) | |
| *A61K 39/35* | (2006.01) | |
| *G01N 33/569* | (2006.01) | |

(52) U.S. Cl.
CPC .... *C07K 14/43563* (2013.01); *A61K 39/0003* (2013.01); *A61K 39/35* (2013.01); *G01N 33/56977* (2013.01); *A61K 2039/55* (2013.01); *A61K 2039/577* (2013.01); *G01N 2333/43552* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 5,869,288 A | 2/1999 | Chapman et al. | |
| 9,005,627 B2* | 4/2015 | Reymond | A61K 39/36 424/184.1 |
| 2008/0103091 A1* | 5/2008 | Siahaan | C07K 14/4713 424/1.69 |
| 2012/0100163 A1 | 4/2012 | Brimnes et al. | |

FOREIGN PATENT DOCUMENTS

| | | | |
|---|---|---|---|
| WO | 1999/34826 A1 | 7/1999 | |
| WO | 2003/047618 A2 | 6/2003 | |
| WO | WO 2006/100673 | * 9/2006 | ............. G01N 33/53 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Kinnunen et al. 'Potential of an altered peptide ligand of lipocalin allergen Bos d 2 for peptide immunotherapy.' J. Allerg. Clin. Immunol. 119:965-72, 2007.*
Schein et al. 'Bioinformatics approaches to classifying allergens and predicting cross-reactivity.' Immunol. Allergy Clin. North Am. 27(1):1-27, 2007.*
Friedl-Hajek et al. 'Identification of a highly promiscuous and an HLA allele-specific T-cell epitope in the birch major allergen Bet v 1:HLA restriction, epitope mapping and TCR sequence comparisons.' Clin. Exp. Allergy 29:478-487, 1999.*
Santiago et al. Molecular mimicry between cockroach and helminth glutathione S-transferases promotes cross-reactivity and cross-sensitization. (J Allergy Clin Immunol .130:248-56, 2012.*
Campbell et al. 'Monoclonal Antibody Technology.', edited by R. H. Burdon, Elsevier, 1987, pp. 29-30.*

(Continued)

*Primary Examiner* — Nora M Rooney
(74) *Attorney, Agent, or Firm* — Pillsbury Winthrop Shaw Pittmann LLP

(57) ABSTRACT

The invention provides Cockroach proteins, peptides, subsequences, portions, homologues, variants and derivatives thereof, and methods and uses and medicaments of such proteins, peptides, subsequences, portions, homologues, variants and derivatives thereof. Such methods, uses and medicaments include modulating an immune response, protecting a subject against or treating a subject for an allergic response, allergic disorder or allergic disease and inducing immunological tolerance to the allergen (e.g., Cockroach allergen) in a subject.

11 Claims, 3 Drawing Sheets

Specification includes a Sequence Listing.

(56) References Cited

OTHER PUBLICATIONS

Harlow et al. 'Antibodies A Laboratory Manual.' Cold Spring Harbor, New York. Cold Spring Harbor Press: 141-157,1988.*
Arruda et al. 'Cockroach allergens and asthma.' J. Allergy Clin Immunol. 107:419-428, 2001.*
Gao, Review Article: Sensitization to Cockroach Allergen: Immune Reuglation and Genetice Determinants, Clin. Dev. Immunol. 2012, 2012:1-8.

* cited by examiner

Exhaustiveness of T cell predictions

Representative patterns of T cell restriction

T cell responses against Bla g allergens are differentially polarized at the level of individual donors

T CELL EPITOPES FROM COCKROACH AND METHODS OF MAKING AND USING SAME

RELATED APPLICATION INFORMATION

This application is the National Phase of International Application No. PCT/US2013/039566, filed May 3, 2013, which designated the U.S. and that International Application was published under PCT Article 21(2) in English, which claims priority to U.S. Provisional Application No. 61/642,384, filed May 3, 2012, all of which applications are expressly incorporated herein by reference in their entirety.

GOVERNMENT SUPPORT

This invention received government support from the National Institutes Health contract NIH-NIAIDHHSN272200700048C. The government has certain rights in the invention.

SEQUENCE LISTING

The instant application contains a Sequence Listing which has been submitted electronically in ASCII format and is hereby incorporated by reference in its entirety. Said ASCII copy is named LIAI-Jul-29-2019-SubSEQ0434767.txt and is 63,154 bytes in size.

FIELD OF THE INVENTION

The invention relates to Cockroach proteins, peptides, subsequences, portions, homologues, variants and derivatives thereof, and methods and uses and medicaments of such proteins, peptides, including methods of modulating an immune response, protecting a subject against or treating a subject for an allergic response, allergic disorder or allergic disease and inducing immunological tolerance to the allergen in a subject.

INTRODUCTION

Bla g allergens are major targets of IgE responses associated with Cockroach allergies.

However, little is known about corresponding T cell responses, despite potential involvement in immunopathology and clinical efficacy of Specific ImmunoTherapy (SIT).

Allergy to Cockroach, a significant health problem worldwide, is associated with urban development and often inner city environments, as well as clinical consequences. A number of Cockroach proteins are potent environmental aeroallergens. There is evidence that early life exposure (1) to Cockroach allergens leads to allergic sensitization to Cockroaches, which has been shown to have a strong correlation with the incidence of asthma (2), particularly in children (3-5), and asthma exacerbations (3, 6). Childhood sensitization to Cockroach allergens also has been associated with an increased risk for persistent asthma and bronchial hyperresponsiveness and with a greater loss of lung function (7). In general, Cockroach allergens are an important cause of asthma exacerbations in many parts of the world (8, 9).

At the immunological level, Cockroach allergies are mediated by both humoral and cellular responses (10-14). Regarding humoral responses, IgE levels (measured by radioallergosorbent test or skin test) against Cockroach allergens are highly correlated with clinical allergic status, and they are commonly used in the diagnosis of Cockroach allergies. By comparison, much less is known regarding the role of T cells in allergy and asthmatic reactions to Cockroach Ags (15).

Both German (*Blattella germanica*) and American (*Periplaneta americana*) Cockroach species can induce allergic responses, although the German Cockroach is most frequently associated with severe clinical allergy in the United States, and the American Cockroach is associated with allergies in tropical areas (4). Allergen proteins expressed by the two species are highly homologous. Several different allergens have been identified on the basis of their reactivity with IgE from allergic patients, and their sequences have been determined (4, 16). These allergens include the Bla g 1, 2, 4, 5, 6, and 7 allergens. Indeed, the study of the patterns of serological reactivity to these Ags has contributed to definition of their relevance in Cockroach allergy, which can aid in the design of diagnostics and immunotherapeutics (17-23).

In contrast to this wealth of information on antibody responses, no T cell epitopes have been defined for any of the Bla g allergens, and the frequency, phenotype, and specificity of T cell responses are unexplored. Specifically, the pattern of immunodominance of T cell responses is unknown, and it is also unknown whether T cell responses correlate with IgE responses. These knowledge gaps are particularly relevant because of the potential role of T cells in both the development of Cockroach allergies and in the efficacy of Cockroach specific immunotherapy (SIT).

A key issue, is whether both generation of IgE responses and SIT is mediated by linked or unlinked T cell-B cell (T-B) cooperation at the level of individual allergenic proteins. A debate centers on whether induction of T cell responses against one particular allergen can provide help for IgE responses directed against a different allergen, or whether help is restricted to the IgE response to the same allergen. Modulation of T cell responses may be able to act in an unlinked mode if the two allergens are both present in the same allergy-inducing substance. Recent clinical trials have reported some successful results from SIT regimens utilizing one or few recombinant Ags for the treatment of allergic symptoms caused by complex allergens, suggesting that unlinked mechanisms may indeed play a role in SIT clinical efficacy (24). In the context of Cockroach allergies, it is unknown whether the same allergens are recognized by T cell and humoral responses, and whether it is necessary that IgE-producing B cells receive help from T cells specific for the same allergens, or whether unlinked help also contributes to the generation of responses.

Cockroach immunotherapy is not commonly used, and reports on its effectiveness are very limited (25, 26). Little is known regarding the immunological basis for its clinical efficacy. In the case of other allergens, several non-mutually exclusive mechanisms have been proposed, including: 1) induction on IgG antibodies that can prevent the allergenic effects caused by IgE or block IgE facilitated allergen uptake and presentation, and 2) inhibition of Th2 responses by modulation of T cell responses, either by altering the Th1/Th2 balance or by induction of IL-10-producing regulatory T cells (27, 28). Inhibition of Th2 responses would lead to an eventual decrease in IgE titers. Indeed, it has been proposed that induction of IL-10-producing Tregs by the s.c. administration of allergen extract might be responsible for the clinical benefit (29, 30). Furthermore, in the Cockroach Phl p 1 system (31) most allergen-specific T cell clones raised before SIT revealed a Th2-like pattern of cytokine production, whereas those established after SIT revealed Th1 characteristics. Previous work in the Cockroach allergen system delineated frequently recognized epitopes associated with 10 major known Cockroach allergens (32). When individuals that had undergone SIT were compared with individuals that were allergic to Cockroach, but were not SIT treated, a generalized decrease in Th2 responses was detected and no increase in either Th1 or IL-10 responses. In this context the study of Bla g specific T cell responses is of interest to examine whether these potential mechanisms are also associated with successful SIT treatment for Cockroach allergies.

SUMMARY

Disclosed herein are novel Cockroach peptides, as well as methods and uses of and medicaments including such novel Cockroach proteins and peptides. Cockroach proteins and peptides disclosed herein include epitopes and allergens. Also disclosed herein are Cockroach proteins, peptides, subsequences, portions, homologues, variants and derivatives thereof, and methods and uses of and medicaments including such Cockroach proteins and peptides.

In accordance with the invention, there are provided proteins and peptides including, consisting of or consisting essentially of an amino acid sequence of a Cockroach protein or a subsequence, portion, homologue, variant or derivative thereof. In certain embodiments a Cockroach protein comprises, consists of or consists essentially of an amino acid sequence of a protein or peptide set out in any of Tables I to X (SEQ ID NOs 1-201) or a subsequence, portion, homologue, variant or derivative thereof, or a protein or peptide set out in Table I (SEQ ID NOs 1-25) or Table VII (SEQ ID NOs 26-57), or a subsequence, portion, homologue, variant or derivative thereof.

In particular embodiments of the invention there are provided proteins and peptides including, consisting of or consisting essentially of an amino acid sequence set forth as: ALREKVLGLPAIKAWVAKRP (SEQ ID NO: 1), VAISRYLGKQFGLSG (SEQ ID NO: 2), GEPIRFLLSYGEKDFEDYRF (SEQ ID NO: 3), ISDFRAAIANYHYDA (SEQ ID NO: 4), YFVAILDYLNHMAKE (SEQ ID NO: 5), EEFCTLASRFLVEED (SEQ ID NO: 6), PEQIQLLKKAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), SMPFGKTPVLEIDGK (SEQ ID NO: 11), FAVATITHAAELQRV (SEQ ID NO: 12), EQISVLRKAFDAFDREKSGS (SEQ ID NO: 13), EVTLAAKFIIEEDS (SEQ ID NO: 14), PEFQSIVQTLNAMPEYQNLL (SEQ ID NO: 15), PELQNFLNFLEANGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVDSLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELREAFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTLNAMPEYQNLL (SEQ ID NO: 27), PELQNFLNFLEANGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQNFLTVFDSTSCN (SEQ ID NO: 23), ISSQYYIQQNGNLCY (SEQ ID NO: 21), HFFIGDFFVDHYYSE (SEQ ID NO: 18), GEPIRFLLSYGEKDF (SEQ ID NO: 28), FLLSYGEKDFEDYRF (SEQ ID NO: 29), SMPFGKTPVLEIDGK (SEQ ID NO: 11), VAISRYLGKQFGLSG (SEQ ID NO: 2), ISDFRAAIANYHYDA (SEQ ID NO: 4), EVVKANGGYLAAGKL (SEQ ID NO: 30), YFVAILDYLNHMAKE (SEQ ID NO: 5), HMAKEDLVANQPNLK (SEQ ID NO: 31), DLVANQPNLKALREK (SEQ ID NO: 32), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAFDREKSGS (SEQ ID NO: 36), EFVTLAAKFIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38), GYITTNVLREILKEL (SEQ ID NO: 25), DLLGIPHIPVTARKH (SEQ ID NO: 39), LETSPEFKALYDAIR (SEQ ID NO: 40), SPEFQSIVGTLEAMP (SEQ ID NO: 41), LEAMPEYQNLIQKLK (SEQ ID NO: 42), VDHIIELIHQIFNIV (SEQ ID NO: 43), ELIHQIFNIVRDTRG (SEQ ID NO: 44), IFNIVRDTRGLPEDL (SEQ ID NO: 45), LPEDLQDFLALIPTD (SEQ ID NO: 46), QDFLALIPTDQVLAI (SEQ ID NO: 47), LIPTDQVLAIAADYL (SEQ ID NO: 48), QVLAIAADYLANDAE (SEQ ID NO: 49), AADYLANDAEVKAAV (SEQ ID NO: 50), ANDAEVKAAVEYLKS (SEQ ID NO: 51), DSLPEFKNFLNFLQT (SEQ ID NO: 52), FKNFLNFLQTNGLNA (SEQ ID NO: 53), NFLQTNGLNAIEFLN (SEQ ID NO: 54), NGLNAIEFLNNIHDL (SEQ ID NO: 55), IEFLNNIHDLLGIPH (SEQ ID NO: 56), TGLIDDIAILPVDD (SEQ ID NO: 57), DIIAILPVDDLYALF (SEQ ID NO: 58), LPVDDLYALFQEKLE (SEQ ID NO: 59), LYALFQEKLETSPEF (SEQ ID NO: 60), KALYDAIRSPEFQSE (SEQ ID NO: 61), AIRSPEFQSIVETLK (SEQ ID NO: 62), EFQSIVETLKAMPEY (SEQ ID NO: 63), VETLKAMPEYQSLIQ (SEQ ID NO: 64), AMPEYQSLIQKLKDK (SEQ ID NO: 65), QSLIQKLKDKGVDVD (SEQ ID NO: 66), EDLQDFLALIPIDQI (SEQ ID NO: 67), FLALIPIDQILAIAA (SEQ ID NO: 68), PIDQILAIAADYLAN (SEQ ID NO: 69), DYLANDAEVQAAVEY (SEQ ID NO: 70), AAVEYLKSDEFETIV (SEQ ID NO: 71), LKSDEFETIVVTVDS (SEQ ID NO: 72), FETIVVTVDSLPEFK (SEQ ID NO: 20), LNAIEFINNIHDLLG (SEQ ID NO: 73), FINNIHDLLGIPHIP (SEQ ID NO: 74), HDLLGIPHIPATGRK (SEQ ID NO: 75), VGINGLIDDVIAILP (SEQ ID NO: 76), LIDDVIAILPVDELY (SEQ ID NO: 77), IAILPVDELYALFQE (SEQ ID NO: 78), VDELYALFQEKLESS (SEQ ID NO: 79), ALFQEKLESSPEFKA (SEQ ID NO: 80), RSPEFQSIVQTLKAM (SEQ ID NO: 81), QSIVQTLKAMPEYQD (SEQ ID NO: 82), PEYQDLIQRLKDKGV (SEQ ID NO: 83), LIQRLKDKGVDVDHF (SEQ ID NO: 84), DHFIELIKKLFGLSH (SEQ ID NO: 85), VDVDKIIELIRAFLG (SEQ ID NO: 86), IIELIRALFGLTLNA (SEQ ID NO: 87), RALFGLTLNAKASRN (SEQ ID NO: 88), LTLNAKASRNLQDDL (SEQ ID NO: 89), LQDDLQDFLALIPVD (SEQ ID NO: 90), QDFLALIPVDQIIAI (SEQ ID NO: 91), DEFETIVVALDALPE (SEQ ID NO: 92), IVVALDALPELQNFL (SEQ ID NO: 93), IDFLNGIHDLLGIPH (SEQ ID NO: 94), GIHDLLGIPHIPVSG (SEQ ID NO: 95), RKYHIRRGVGITGLI (SEQ ID NO: 96), DDVLAILPIEDLKAL (SEQ ID NO: 97), ILPIEDLKALFNEKL (SEQ ID NO: 98), ETSPDFLALYNAIRS (SEQ ID NO: 99), FLALYNAIRSPEFQS (SEQ ID NO: 100), PEFQSIVQTLNAMPE (SEQ ID NO: 26), IVQTLNAMPEYQNLL (SEQ ID NO: 27), NAMPEYQNLLQKLRE (SEQ ID NO: 101), YQNLLQKLREKGVDV (SEQ ID NO: 102), LIRALFGLTLNGKAS (SEQ ID NO: 103), FGLTLNGKASRNLQD (SEQ ID NO: 104), VDQIIAI-ATDYLAND (SEQ ID NO: 105), AIATDYLANDAEVQA (SEQ ID NO: 106), AEVQAAVAYLQSDEF (SEQ ID NO: 107), AVAYLQSDEFETIVV (SEQ ID NO: 108), QSDEFE-TIVVTLDAL (SEQ ID NO: 109), ETIVVTLDALPELQN (SEQ ID NO: 110), PELQNFLNFLEANGL (SEQ ID NO: 16), FLNFLEANGLNAIDF (SEQ ID NO: 111), LNGIHDLLGIPHIPV (SEQ ID NO: 112), DLLGIPHIPVS-GRKY (SEQ ID NO: 113), VGITGLIDDVLAILP (SEQ ID NO: 114), LIDDVLAILPDDLK (SEQ ID NO: 8), LAIL-PLDDLKALFNE (SEQ ID NO: 115), LDDLKALFNEK-LETS (SEQ ID NO: 116), PDFLALYNAIKSPEF (SEQ ID NO: 117), LYNAIKSPEFQSIVQ (SEQ ID NO: 118), MIGLKLVTVLFAVAT (SEQ ID NO: 119), LVTVLFA-VATITHAA (SEQ ID NO: 120), FAVATITHAAELQRV (SEQ ID NO: 12), ITHAAELQRVPLYKL (SEQ ID NO: 121), ELQRVPLYKLVHVFI (SEQ ID NO: 122), PLYKLVHVFINTQYA (SEQ ID NO: 19), VHVFINTQY-AGITKI (SEQ ID NO: 123), NTQYAGITKIGNQNF (SEQ ID NO: 124), GITKIGNQNFLTVFD (SEQ ID NO: 125), GNQNFLTVFDSTSCN (SEQ ID NO: 23), PNLQKYEKLKPKYIS (SEQ ID NO: 126), YEKLKPKY-ISDGNVQ (SEQ ID NO: 127), PKYISDGNVQVKFFD (SEQ ID NO: 128), DGNVQVKFFDTGSAV (SEQ ID NO: 129), VKFFDTGSAVGRGIE (SEQ ID NO: 130), GRGIED-SLTISNLTT (SEQ ID NO: 131), LSQEVCILSADVVVG (SEQ ID NO: 132), CILSADVVVGIAAPG (SEQ ID NO: 133), KGKTVLENFVEENLI (SEQ ID NO: 134), LENFVEENLIAPVFS (SEQ ID NO: 135), EENLIA-PVFSIHHAR (SEQ ID NO: 136), APVFSIHHARFQDGE (SEQ ID NO: 137), IFGGSDWKYVDGEFT (SEQ ID NO: 138), DWKYVDGEFTYVLPV (SEQ ID NO: 139), DGEFTYVPLVGDDSW (SEQ ID NO: 140), YVPLVGDD-SWKFRLD (SEQ ID NO: 141), GDDSWKFRLDGVKIG (SEQ ID NO: 142), PAGTQAIIDTSKAII (SEQ ID NO: 143), AIIDTSKAIIVGPKA (SEQ ID NO: 144), SKAIIVGPKAYVNPI (SEQ ID NO: 145), VGPKAYVN-PINEAIG (SEQ ID NO: 146), SLPDVTFVINGRNFN (SEQ ID NO: 147), TFVINGRNFNISSQY (SEQ ID NO: 148), GRNFNISSQYYIQQN (SEQ ID NO: 149), ISSQYYIQQNGNLCY (SEQ ID NO: 21), HFFIGDFFVDHYYSE (SEQ ID NO: 18), DFFVDHYY-SEFNWEN (SEQ ID NO: 150), LDYERFRGSWIIAAG (SEQ ID NO: 151), FRGSWIIAAGTSEAL (SEQ ID NO: 152), IIAAGTSEALTQYKC (SEQ ID NO: 153), WIDRFSYDDALVSKY (SEQ ID NO: 154), YNDKGKAFSAPYSVL (SEQ ID NO: 155), KAFSAPY-SVLATDYE (SEQ ID NO: 156), PYSVLATDYENYAIV (SEQ ID NO: 157), ATDYENYAIVEGCPA (SEQ ID NO: 158), AANGHVIYVQIRFSV (SEQ ID NO: 159), VIYVQIRFSVRRFHP (SEQ ID NO: 160), IRFSVRRFHPKLGKD (SEQ ID NO: 161), EMIQHYTLDQVNQHK (SEQ ID NO: 162), KAIEEDLKHFNLKYE (SEQ ID NO: 163), KHFNLKYEDLHSTCH (SEQ ID NO: 164), KLTYCPVKALGEPIR (SEQ ID NO: 165), GEPIRFLLSY-GEKDF (SEQ ID NO: 28), FLLSYGEKDFEDYRF (SEQ ID NO: 29), SMPFGKTPVLEIDGK (SEQ ID NO: 11), QTHQSVAISRYLGKO (SEQ ID NO: 166), VAIS-RYLGKQFGLSG (SEQ ID NO: 2), NLEIDMIVDTISDFR (SEQ ID NO: 167), MIVDTISDFRAAIAN (SEQ ID NO: 168), ISDFRAAIANYHYDA (SEQ ID NO: 4), TKKFDEVVKANGGYL (SEQ ID NO: 169), EVVKANG-GYLAAGKL (SEQ ID NO: 30), NGGYLAAGKLTWADF (SEQ ID NO: 170), TWADFYFVAILDYLN (SEQ ID NO: 171), YFVAILDYLNHMAKE (SEQ ID NO: 5), LDYLNH-MAKEDLVAN (SEQ ID NO: 172), HMAKEDLVA-NQPNLK (SEQ ID NO: 31), DLVANQPNLKALREK (SEQ ID NO: 32), QPNLKALREKVLGLP (SEQ ID NO: 173), ALREKVLGLPAIKAW (SEQ ID NO: 33), VLGLPAI-KAWVAKRP (SEQ ID NO: 34), QDFLALIPTDQVLAI (SEQ ID NO: 47), LRKAFDAFDREKSGS (SEQ ID NO: 36), VEEILRLMGQPFNRR (SEQ ID NO: 174), ADKS-GRLEFDEFVTL (SEQ ID NO: 175), RLEFDEFVT-LAAKFI (SEQ ID NO: 176), EFVTLAAKFIIEEDS (SEQ ID NO: 14), EAMEKELREAFRLYD (SEQ ID NO: 24), CLREILRELDEQLTS (SEQ ID NO: 177), DELDMMIEEI-DADGS (SEQ ID NO: 178), SGTVDFDEFMEMMTG (SEQ ID NO: 22), AEQVVLLKKAFDAFD (SEQ ID NO: 179), MVGTILEMLGTRLDQ (SEQ ID NO: 37), GELE-FEEFCTLASRF (SEQ ID NO: 180), EEFCTLASRFLV-EED (SEQ ID NO: 6), HELREAFRLYDKEGN (SEQ ID NO: 181), DKEGNGYITTAVLRE (SEQ ID NO: 182), GYITTAVLREILKEL (SEQ ID NO: 183), AVL-REILKELDDKIT (SEQ ID NO: 184), PEQIQLLK-KAFDAFD (SEQ ID NO: 7), MVGTILEMLGHRLDD (SEQ ID NO: 17), DMLQEIIAEVDADGS (SEQ ID NO: 185), GELEFEEFVSLASRF (SEQ ID NO: 186), EEFVSLASRFLVEED (SEQ ID NO: 38), GYITTNVL-REILKEL (SEQ ID NO: 25), MDAIKKKMQAMKLEK (SEQ ID NO: 187), KKMQAMKLEKDNAMD (SEQ ID NO: 188), LQKKIQQIENDLDQT (SEQ ID NO: 189), MEQLMQVNALKDEKD (SEQ ID NO: 190), KALQNAE-SEVAALNR (SEQ ID NO: 191), AESEVAALNRRIQLL (SEQ ID NO: 192), AALNRRIQLLEEDLE (SEQ ID NO: 193), RSEERLATATAKLAE (SEQ ID NO: 194), LATAT-AKLAEASQAA (SEQ ID NO: 195), GESKIVELEEELRVV (SEQ ID NO: 196), VELEEELRVVGNNLK (SEQ ID NO: 197), ELRVVGNNLKSLEVS (SEQ ID NO: 198), LREEEYKQQIKTLNT (SEQ ID NO: 199), YKQQIKTLN-TRLKEA (SEQ ID NO: 200) or ICDDLDMTFTELIGN (SEQ ID NO: 201).

In other embodiments of the invention there are provided proteins and peptides including, consisting of or consisting essentially of an amino acid sequence set forth as: ALREKVLGLPAIKAWVAKRP (SEQ ID NO: 1), GEPIRFLLSYGEKDFEDYRF (SEQ ID NO: 3), EEFCT-LASRFLVEED (SEQ ID NO: 6), PEQIQLLKKAFDAFD (SEQ ID NO: 7), LIDDVLAILPDDLK (SEQ ID NO: 8), HMAKEDLVANQPNLKALREK (SEQ ID NO: 9), TKKFDEVVKANGGYLAAGKL (SEQ ID NO: 10), FAVATITHAAELQRV (SEQ ID NO: 12), EQISVLRKAFDAFDREKSGS (SEQ ID NO: 13), EVT-LAAKFIIEEDS (SEQ ID NO: 14), PEFQSIVQTL-NAMPEYQNLL (SEQ ID NO: 15), PELQNFLNFLEA-NGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVD-SLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELRE-AFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTL-NAMPEYQNLL (SEQ ID NO: 27), PELQNFLNFLEA-NGL (SEQ ID NO: 16), LIDDVLAILPDDLK (SEQ ID NO: 8), FAVATITHAAELQRV (SEQ ID NO: 12), PLYHLVHVFINTQYA (SEQ ID NO: 19), GNQN-FLTVFDSTSCN (SEQ ID NO: 23), ISSQYYIQQNGNLCY (SEQ ID NO: 21), HFFIGDFFVDHYYSE (SEQ ID NO: 18), EQISVLRKAFDAFDR (SEQ ID NO: 35), LRKAFDAFDREKSGS (SEQ ID NO: 36), EFVTLAAK-FIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38), GYITTNVLREILKEL (SEQ ID NO: 25), DLLGIPHIPVTARKH (SEQ ID NO: 39), LETSPEFKALYDAIR (SEQ ID NO: 40), SPEFQSIVGTLEAMP (SEQ ID NO: 41), LEAMPEYQNLIQKLK (SEQ ID NO: 42), VDHIIELIHQIFNIV (SEQ ID NO: 43), ELIHQIFNIVRDTRG (SEQ ID NO: 44), IFNIVRDTRGLPEDL (SEQ ID NO: 45), LPEDLQDFLALIPTD (SEQ ID NO: 46), QDFLALIPTDQVLAI (SEQ ID NO: 47), LIPTDQVLAIAADYL (SEQ ID NO: 48), QVLAIAADYLANDAE (SEQ ID NO: 49), AADYLANDAEVKAAV (SEQ ID NO: 50), ANDAEVKAAVEYLKS (SEQ ID NO: 51), DSLPEFKNFLNFLQT (SEQ ID NO: 52), FKNFLNFLQTNGLNA (SEQ ID NO: 53), NFLQTNGLNAIEFLN (SEQ ID NO: 54), NGLNAIEFLNNIHDL (SEQ ID NO: 55), IEFLNNIHDLLGIPH (SEQ ID NO: 56), TGLIDDIIAILPVDD (SEQ ID NO: 57), DIIAILPVDDLYALF (SEQ ID NO: 58), LPVDDLYALFQEKLE (SEQ ID NO: 59), LYALFQEKLETSPEF (SEQ ID NO: 60), KALYDAIRSPEFQSE (SEQ ID NO: 61), AIRSPEFQSIVETLK (SEQ ID NO: 62), EFQSIVETLKAMPEY (SEQ ID NO: 63), VETLKAMPEYQSLIQ (SEQ ID NO: 64), AMPEYQSLIQKLKDK (SEQ ID NO: 65), QSLIQKLKDKGVDVD (SEQ ID NO: 66), EDLQDFLALIPIDQI (SEQ ID NO: 67), FLALIPIDQILAIAA (SEQ ID NO: 68), PIDQILAIAADYLAN (SEQ ID NO: 69), DYLANDAEVQAAVEY (SEQ ID NO: 70), AAVEYLKSDEFETIV (SEQ ID NO: 71), LKSDEFETIVVTVDS (SEQ ID NO: 72), FETIVVTVDSLPEFK (SEQ ID NO: 20), LNAIEFINNIHDLLG (SEQ ID NO: 73), FINNIHDLLGIPHIP (SEQ ID NO: 74), HDLLGIPHIPATGRK (SEQ ID NO: 75), VGINGLIDDVIAILP (SEQ ID NO: 76), LIDDVIAILPVDELY (SEQ ID NO: 77), IAILPVDELYALFQE (SEQ ID NO: 78), VDELYALFQEKLESS (SEQ ID NO: 79), ALFQEKLESSPEFKA (SEQ ID NO: 80), RSPEFQSIVQTLKAM (SEQ ID NO: 81), QSIVQTLKAMPEYQD (SEQ ID NO: 82), PEYQDLIQRLKDKGV (SEQ ID NO: 83), LIQRLKDKGVDVHF (SEQ ID NO: 84), DHFIELIKKLFGLSH (SEQ ID NO: 85), VDVDKIIELIRAFLG (SEQ ID NO: 86), IIELIRALFGLTLNA (SEQ ID NO: 87), RALFGLTLNAKASRN (SEQ ID NO: 88), LTLNAKASRNLQDDL (SEQ ID NO: 89), LQDDLQDFLALIPVD (SEQ ID NO: 90), QDFLALIPVDQIIAI (SEQ ID NO: 91), DEFETIVVALDALPE (SEQ ID NO: 92), IVVALDALPELQNFL (SEQ ID NO: 93), IDFLNGIHDLLGIPH (SEQ ID NO: 94), GIHDLLGIPHIPVSG (SEQ ID NO: 95), RKYHIRRGVGITGLI (SEQ ID NO: 96), DDVLAILPIEDLKAL (SEQ ID NO: 97), ILPIEDLKALFNEKL (SEQ ID NO: 98), ETSPDFLALYNAIRS (SEQ ID NO: 99), FLALYNAIRSPEFQS (SEQ ID NO: 100), PEFQSIVQTLNAMPE (SEQ ID NO: 26), IVQTLNAMPEYQNLL (SEQ ID NO: 27), NAMPEYQNLLQKLRE (SEQ ID NO: 101), YQNLLQKLREKGVDV (SEQ ID NO: 102), LIRALFGLTLNGKAS (SEQ ID NO: 103), FGLTLNGKASRNLQD (SEQ ID NO: 104), VDQIIAIATDYLAND (SEQ ID NO: 105), AIATDYLANDAEVQA (SEQ ID NO: 106), AEVQAAVAYLQSDEF (SEQ ID NO: 107), AVAYLQSDEFETIVV (SEQ ID NO: 108), QSDEFETIVVTLDAL (SEQ ID NO: 109), ETIVVTLDALPELQN (SEQ ID NO: 110), PELQNFLNFLEANGL (SEQ ID NO: 16), FLNFLEANGLNAIDF (SEQ ID NO: 111), LNGIHDLLGIPHIPV (SEQ ID NO: 112), DLLGIPHIPVSGRKY (SEQ ID NO: 113), VGITGLIDDVLAILP (SEQ ID NO: 114), LIDDVLAILPLDDLK (SEQ ID NO: 8), LAILPLDDLKALFNE (SEQ ID NO: 115), LDDLKALFNEKLETS (SEQ ID NO: 116), PDFLALYNAIKSPEF (SEQ ID NO: 117), LYNAIKSPEFQSIVQ (SEQ ID NO: 118), MIGLKLVTVLFAVAT (SEQ ID NO: 119), LVTVLFAVATITHAA (SEQ ID NO: 120), FAVATITHAAELQRV (SEQ ID NO: 12), ITHAAELQRVPLYKL (SEQ ID NO: 121), ELQRVPLYKLVHVFI (SEQ ID NO: 122), PLYKLVHVFINTQYA (SEQ ID NO: 19), VHVFINTQYAGITKI (SEQ ID NO: 123), NTQYAGITKIGNQNF (SEQ ID NO: 124), GITKIGNQNFLTVFD (SEQ ID NO: 125), GNQNFLTVFDSTSCN (SEQ ID NO: 23), PNLQKYEKLKPKYIS (SEQ ID NO: 126), YEKLKPKYISDGNVQ (SEQ ID NO: 127), PKYISDGNVQVKFFD (SEQ ID NO: 128), DGNVQVKFFDTGSAV (SEQ ID NO: 129), VKFFDTGSAVGRGIE (SEQ ID NO: 130), GRGIEDSLTISNLTT (SEQ ID NO: 131), LSQEVCILSADVVVG (SEQ ID NO: 132), CILSADVVVGIAAPG (SEQ ID NO: 133), KGKTVLENFVEENLI (SEQ ID NO: 134), LENFVEENLIAPVFS (SEQ ID NO: 135), EENLIAPVFSIHHAR (SEQ ID NO: 136), APVFSIHHARFQDGE (SEQ ID NO: 137), IFGGSDWKYVDGEFT (SEQ ID NO: 138), DWKYVDGEFTYVLPV (SEQ ID NO: 139), DGEFTYVPLVGDDSW (SEQ ID NO: 140), YVPLVGDDSWKFRLD (SEQ ID NO: 141), GDDSWKFRLDGVKIG (SEQ ID NO: 142), PAGTQAIIDTSKAII (SEQ ID NO: 143), AIIDTSKAIIVGPKA (SEQ ID NO: 144), SKAIIVGPKAYVNPI (SEQ ID NO: 145), VGPKAYVNPINEAIG (SEQ ID NO: 146), SLPDVTFVINGRNFN (SEQ ID NO: 147), TFVINGRNFNISSQY (SEQ ID NO: 148), GRNFNISSQYYIQQN (SEQ ID NO: 149), ISSQYYIQQNGNLCY (SEQ ID NO: 21), HFFIGDFFVDHYYSE (SEQ ID NO: 18), DFFVDHYYSEFNWEN (SEQ ID NO: 150), LDYERFRGSWIIAAG (SEQ ID NO: 151), FRGSWIIAAGTSEAL (SEQ ID NO: 152), IIAAGTSEALTQYKC (SEQ ID NO: 153), WIDRFSYDDALVSKY (SEQ ID NO: 154), YNDKGKAFSAPYSVL (SEQ ID NO: 155), KAFSAPYSVLATDYE (SEQ ID NO: 156), PYSVLATDYENYAIV (SEQ ID NO: 157), ATDYENYAIVEGCPA (SEQ ID NO: 158), AANGHVIYVQIRFSV (SEQ ID NO: 159), VIYVQIRFSVRRFHP (SEQ ID NO: 160), IRFSVRRFHPKLGKD (SEQ ID NO: 161), EMIQHYTLDQVNQHK (SEQ ID NO: 162), KAIEEDLKHFNLKYE (SEQ ID NO: 163), KHFNLKYEDLHSTCH (SEQ ID NO: 164), TWADFYFVAILDYLN (SEQ ID NO: 171), EQISVLRKAFDAFDR (SEQ ID NO: 35), LRKAFDAFDREKSGS (SEQ ID NO: 36), VEEILRLMGQPFNRR (SEQ ID NO: 174), ADKSGRLEFDEFVTL (SEQ ID NO: 175), RLEFDEFVTLAAKFI (SEQ ID NO: 176), EFVTLAAKFIIEEDS (SEQ ID NO: 14), EAMEKELREAFRLYD (SEQ ID NO: 24), CLREILRELDEQLTS (SEQ ID NO: 177), DELDMMIEEIDADGS (SEQ ID NO: 178), SGTVDFDEFMEMMTG (SEQ ID NO: 22), AEQVVLLKKAFDAFD (SEQ ID NO: 179), MVGTILEMLGTRLDQ (SEQ ID NO: 37), GELEFEEFCTLASRF (SEQ ID NO: 180), EEFCTLASRFLVEED (SEQ ID NO: 6), HELREAFRLYDKEGN (SEQ ID NO: 181), DKEGNGYITTAVLRE (SEQ ID NO: 182), GYITTAVLREILKEL (SEQ ID NO: 183), AVLREILKELDDKIT (SEQ ID NO: 184), PEQIQLLKKAFDAFD (SEQ ID NO: 7), MVGTILEMLGHRLDD (SEQ ID NO: 17), DMLQEIIAEVDADGS (SEQ ID NO: 185), GELEFEEFVSLASRF (SEQ ID NO: 186), EEFVSLASRFLVEED (SEQ ID NO: 38), GYITTNVLREILKEL (SEQ ID NO: 25), KKMQAMKLEKDNAMD (SEQ ID NO: 188), LQKKIQQIENDLDQT (SEQ ID NO: 189), MEQLMQVNALKDEKD (SEQ ID NO: 190), KALQNAE-SEVAALNR (SEQ ID NO: 191), AESEVAALNRRIQLL (SEQ ID NO: 192), AALNRRIQLLEEDLE (SEQ ID NO: 193), RSEERLATATAKLAE (SEQ ID NO: 194), LATAT-AKLAEASQAA (SEQ ID NO: 195), GESKIVELEEELRVV (SEQ ID NO: 196), VELEEELRVVGNNLK (SEQ ID NO: 197), LREEEYKQQIKTLNT (SEQ ID NO: 199), YKQQIKTLN-TRLKEA (SEQ ID NO: 200) or ICDDLDMTFTELIGN (SEQ ID NO: 201).

In other embodiments of the invention there are provided proteins and peptides including, consisting of or consisting essentially of an amino acid sequence set forth as: ALREKVLGLPAIKAWVAKRP (SEQ ID NO: 1), VAIS-RYLGKQFGLSG (SEQ ID NO: 2), GEPIRFLLSYGEKD-FEDYRF (SEQ ID NO: 3), ISDFRAAIANYHYDA (SEQ ID NO: 4), YFVAILDYLNHMAKE (SEQ ID NO: 5), EEFCTLASRFLVEED (SEQ ID NO: 6), PEQIQLLK-KAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), SMPFGKTPVLEIDGK (SEQ ID NO: 11), FAVATITHA-AELQRV (SEQ ID NO: 12), EQISVLRKAFDAF-DREKSGS (SEQ ID NO: 13), EVTLAAKFIIEEDS (SEQ ID NO: 14), PEFQSIVQTLNAMPEYQNLL (SEQ ID NO: 15), PELQNFLNFLEANGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVD-SLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELRE-AFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTL-NAMPEYQNLL (SEQ ID NO: 27), PELQNFLNFLEA-NGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQN-FLTVFDSTSCN (SEQ ID NO: 23), ISSQYYIQQNGNLCY (SEQ ID NO: 21), HFFIGDFFVDHYYSE (SEQ ID NO: 18), GEPIRFLLSYGEKDF (SEQ ID NO: 28), FLLSY-GEKDFEDYRF (SEQ ID NO: 29), SMPFGKTPVLEIDGK (SEQ ID NO: 11), VAISRYLGKQFGLSG (SEQ ID NO: 2), ISDFRAAIANYHYDA (SEQ ID NO: 4), YFVAILDYLNHMAKE (SEQ ID NO: 5), HMAKEDLVA-NQPNLK (SEQ ID NO: 31), DLVANQPNLKALREK (SEQ ID NO: 32), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAF-DREKSGS (SEQ ID NO: 36), EFVTLAAKFIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLAS-RFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38), GYITTNVL-REILKEL (SEQ ID NO: 25), DLLGIPHIPVTARKH (SEQ ID NO: 39), LETSPEFKALYDAIR (SEQ ID NO: 40), SPEFQSIVGTLEAMP (SEQ ID NO: 41), LEAMPEYQN-LIQKLK (SEQ ID NO: 42), VDHIIELIHQIFNIV (SEQ ID NO: 43), ELIHQIFNIVRDTRG (SEQ ID NO: 44), IFNIVRDTRGLPEDL (SEQ ID NO: 45), LPEDLQDFLA-LIPTD (SEQ ID NO: 46), QDFLALIPTDQVLAI (SEQ ID NO: 47), LIPTDQVLAIAADYL (SEQ ID NO: 48), QVLA-IAADYLANDAE (SEQ ID NO: 49), AADYLANDAEV-KAAV (SEQ ID NO: 50), ANDAEVKAAVEYLKS (SEQ ID NO: 51), DSLPEFKNFLNFLQT (SEQ ID NO: 52), FKNFLNFLQTNGLNA (SEQ ID NO: 53), NFLQTNGLNAIEFLN (SEQ ID NO: 54), NGLNAIEFLN-NIHDL (SEQ ID NO: 55), IEFLNNIHDLLGIPH (SEQ ID NO: 56), TGLIDDIIAILPVDD (SEQ ID NO: 57), DIIAIL-PVDDLYALF (SEQ ID NO: 58), LPVDDLYALFQEKLE (SEQ ID NO: 59), LYALFQEKLETSPEF (SEQ ID NO: 60), KALYDAIRSPEFQSE (SEQ ID NO: 61), AIRSPEFQSIV-ETLK (SEQ ID NO: 62), EFQSIVETLKAMPEY (SEQ ID NO: 63), VETLKAMPEYQSLIQ (SEQ ID NO: 64), AMPEYQSLIQKLKDK (SEQ ID NO: 65), QSLIQKLKDKGVDVD (SEQ ID NO: 66), EDLQDFLA-LIPIDQI (SEQ ID NO: 67), FLALIPIDQILAIAA (SEQ ID NO: 68), PIDQILAIAADYLAN (SEQ ID NO: 69), DYLANDAEVQAAVEY (SEQ ID NO: 70), AAVEYLKS-DEFETIV (SEQ ID NO: 71), LKSDEFETIVVTVDS (SEQ ID NO: 72), FETIVVTVDSLPEFK (SEQ ID NO: 20), LNAIEFINNIHDLLG (SEQ ID NO: 73), FINNIHDLL-GIPHIP (SEQ ID NO: 74), HDLLGIPHIPATGRK (SEQ ID NO: 75), VGINGLIDDVIAILP (SEQ ID NO: 76), LIDD-VIAILPVDELY (SEQ ID NO: 77), IAILPVDELYALFQE (SEQ ID NO: 78), VDELYALFQEKLESS (SEQ ID NO: 79), ALFQEKLESSPEFKA (SEQ ID NO: 80), RSPEFQ-SIVQTLKAM (SEQ ID NO: 81), QSIVQTLKAMPEYQD (SEQ ID NO: 82), PEYQDLIQRLKDKGV (SEQ ID NO: 83), LIQRLKDKGVDVDHF (SEQ ID NO: 84), DHFIE-LIKKLFGLSH (SEQ ID NO: 85), VDVDKIIELIRAFLG (SEQ ID NO: 86), IIELIRALFGLTLNA (SEQ ID NO: 87), RALFGLTLNAKASRN (SEQ ID NO: 88), LTLNAKAS-RNLQDDL (SEQ ID NO: 89), LQDDLQDFLALIPVD (SEQ ID NO: 90), QDFLALIPVDQIIAI (SEQ ID NO: 91), DEFETIVVALDALPE (SEQ ID NO: 92), IVVALDALPELQNFL (SEQ ID NO: 93), IDFLNGIHDLL-GIPH (SEQ ID NO: 94), GIHDLLGIPHIPVSG (SEQ ID NO: 95), RKYHIRRGVGITGLI (SEQ ID NO: 96), DDV-LAILPIEDLKAL (SEQ ID NO: 97), ILPIEDLKALFNEKL (SEQ ID NO: 98), ETSPDFLALYNAIRS (SEQ ID NO: 99), FLALYNAIRSPEFQS (SEQ ID NO: 100), PEFQSIVQTL-NAMPE (SEQ ID NO: 26), IVQTLNAMPEYQNLL (SEQ ID NO: 27), NAMPEYQNLLQKLRE (SEQ ID NO: 101), YQNLLQKLREKGVDV (SEQ ID NO: 102), LIRALFGLTLNGKAS (SEQ ID NO: 103), FGLTLNGKASRNLQD (SEQ ID NO: 104), VDQIIAI-ATDYLAND (SEQ ID NO: 105), AIATDYLANDAEVQA (SEQ ID NO: 106), AEVQAAVAYLQSDEF (SEQ ID NO: 107), AVAYLQSDEFETIVV (SEQ ID NO: 108), QSDEFE-TIVVTLDAL (SEQ ID NO: 109), ETIVVTLDALPELQN (SEQ ID NO: 110), PELQNFLNFLEANGL (SEQ ID NO: 16), FLNFLEANGLNAIDF (SEQ ID NO: 111), LNGIHDLLGIPHIPV (SEQ ID NO: 112), DLLGIPHIPVS-GRKY (SEQ ID NO: 113), VGITGLIDDVLAILP (SEQ ID NO: 114), LIDDVLAILPLDDLK (SEQ ID NO: 8), LAIL-PLDDLKALFNE (SEQ ID NO: 115), LDDLKALFNEK-LETS (SEQ ID NO: 116), PDFLALYNAIKSPEF (SEQ ID NO: 117), LYNAIKSPEFQSIVQ (SEQ ID NO: 118), MIGLKLVTVLFAVAT (SEQ ID NO: 119), LVTVLFA-VATITHAA (SEQ ID NO: 120), FAVATITHAAELQRV (SEQ ID NO: 12), ITHAAELQRVPLYKL (SEQ ID NO: 121), ELQRVPLYKLVHVFI (SEQ ID NO: 122), PLYKLVHVFINTQYA (SEQ ID NO: 19), VHVFINTQY-AGITKI (SEQ ID NO: 123), NTQYAGITKIGNQNF (SEQ ID NO: 124), GITKIGNQNFLTVFD (SEQ ID NO: 125), GNQNFLTVFDSTSCN (SEQ ID NO: 23), PNLQKYEKLKPKYIS (SEQ ID NO: 126), YEKLKPKY-ISDGNVQ (SEQ ID NO: 127), PKYISDGNVQVKFFD (SEQ ID NO: 128), DGNVQVKFFDTGSAV (SEQ ID NO: 129), VKFFDTGSAVGRGIE (SEQ ID NO: 130), GRGIED- SLTISNLTT (SEQ ID NO: 131), LSQEVCILSADVVVG (SEQ ID NO: 132), CILSADVVVGIAAPG (SEQ ID NO: 133), KGKTVLENFVEENLI (SEQ ID NO: 134), LENFVEENLIAPVFS (SEQ ID NO: 135), EENLIAPVFSIHHAR (SEQ ID NO: 136), APVFSIHHARFQDGE (SEQ ID NO: 137), IFGGSDWKYVDGEFT (SEQ ID NO: 138), DWKYVDGEFTYVLPV (SEQ ID NO: 139), DGEFTYVPLVGDDSW (SEQ ID NO: 140), YVPLVGDDSWKFRLD (SEQ ID NO: 141), GDDSWKFRLDGVKIG (SEQ ID NO: 142), PAGTQAIIDTSKAII (SEQ ID NO: 143), AIIDTSKAIIVGPKA (SEQ ID NO: 144), SKAIIVGPKAYVNPI (SEQ ID NO: 145), VGPKAYVNPINEAIG (SEQ ID NO: 146), SLPDVTFVINGRNFN (SEQ ID NO: 147), TFVINGRNFNISSQY (SEQ ID NO: 148), GRNFNISSQYYIQQN (SEQ ID NO: 149), ISSQYYIQQNGNLCY (SEQ ID NO: 21), HFFIGDFFVDHYYSE (SEQ ID NO: 18), DFFVDHYYSEFNWEN (SEQ ID NO: 150), LDYERFRGSWIIAAG (SEQ ID NO: 151), FRGSWIIAAGTSEAL (SEQ ID NO: 152), IIAAGTSEALTQYKC (SEQ ID NO: 153), WIDRFSYDDALVSKY (SEQ ID NO: 154), YNDKGKAFSAPYSVL (SEQ ID NO: 155), KAFSAPYSVLATDYE (SEQ ID NO: 156), PYSVLATDYENYAIV (SEQ ID NO: 157), ATDYENYAIVEGCPA (SEQ ID NO: 158), AANGHVIYVQIRFSV (SEQ ID NO: 159), VIYVQIRFSVRRFHP (SEQ ID NO: 160), IRFSVRRFHPKLGKD (SEQ ID NO: 161), EMIQHYTLDQVNQHK (SEQ ID NO: 162), KAIEEDLKHFNLKYE (SEQ ID NO: 163), KHFNLKYEDLHSTCH (SEQ ID NO: 164), KLTYCPVKALGEPIR (SEQ ID NO: 165), GEPIRFLLSYGEKDF (SEQ ID NO: 28), FLLSYGEKDFEDYRF (SEQ ID NO: 29), SMPFGKTPVLEIDGK (SEQ ID NO: 11), VAISRYLGKQFGLSG (SEQ ID NO: 2), NLEIDMIVDTISDFR (SEQ ID NO: 167), MIVDTISDFRAAIAN (SEQ ID NO: 168), ISDFRAAIANYHYDA (SEQ ID NO: 4), TWADFYFVAILDYLN (SEQ ID NO: 171), YFVAILDYLNHMAKE (SEQ ID NO: 5), LDYLNHMAKEDLVAN (SEQ ID NO: 172), HMAKEDLVANQPNLK (SEQ ID NO: 31), DLVANQPNLKALREK (SEQ ID NO: 32), QPNLKALREKVLGLP (SEQ ID NO: 173), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAFDREKSGS (SEQ ID NO: 36), VEEILRLMGQPFNRR (SEQ ID NO: 174), ADKSGRLEFDEFVTL (SEQ ID NO: 175), RLEFDEFVTLAAKFI (SEQ ID NO: 176), EFVTLAAKFIIEEDS (SEQ ID NO: 14), EAMEKELREAFRLYD (SEQ ID NO: 24), CLREILRELDEQLTS (SEQ ID NO: 177), DELDMMIEEIDADGS (SEQ ID NO: 178), SGTVDFDEFMEMMTG (SEQ ID NO: 22), AEQVVLLKKAFDAFD (SEQ ID NO: 179), MVGTILEMLGTRLDQ (SEQ ID NO: 37), GELEFEEFCTLASRF (SEQ ID NO: 180), EEFCTLASRFLVEED (SEQ ID NO: 6), HELREAFRLYDKEGN (SEQ ID NO: 181), DKEGNGYITTAVLRE (SEQ ID NO: 182), GYITTAVLREILKEL (SEQ ID NO: 183), AVLREILKELDDKIT (SEQ ID NO: 184), PEQIQLLKKAFDAFD (SEQ ID NO: 7), MVGTILEMLGHRLDD (SEQ ID NO: 17), DMLQEIIAEVDADGS (SEQ ID NO: 185), GELEFEEFVSLASRF (SEQ ID NO: 186), EEFVSLASRFLVEED (SEQ ID NO: 38), GYITTNVLREILKEL (SEQ ID NO: 25), KKMQAMKLEKDNAMD (SEQ ID NO: 188), LQKKIQQIENDLDQT (SEQ ID NO: 189), MEQLMQVNALKDEKD (SEQ ID NO: 190), KALQNAESEVAALNR (SEQ ID NO: 191), AESEVAALNRRIQLL (SEQ ID NO: 192), AALNRRIQLLEEDLE (SEQ ID NO: 193), RSEERLATATAKLAE (SEQ ID NO: 194), LATATAKLAEASQAA (SEQ ID NO: 195), GESKIVELEEELRVV (SEQ ID NO: 196), VELEEELRVVGNNLK (SEQ ID NO: 197), LREEEYKQQIKTLNT (SEQ ID NO: 199), YKQQIKTLNTRLKEA (SEQ ID NO: 200) or ICDDLDMTFTELIGN (SEQ ID NO: 201).

In other embodiments of the invention there are provided proteins and peptides including, consisting of or consisting essentially of an amino acid sequence set forth as: ALREKVLGLPAIKAWVAKRP (SEQ ID NO: 1), VAISRYLGKQFGLSG (SEQ ID NO: 2), GEPIRFLLSYGEKDFEDYRF (SEQ ID NO: 3), ISDFRAAIANYHYDA (SEQ ID NO: 4), YFVAILDYLNHMAKE (SEQ ID NO: 5), EEFCTLASRFLVEED (SEQ ID NO: 6), PEQIQLLKKAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), SMPFGKTPVLEIDGK (SEQ ID NO: 11), FAVATITHAAELQRV (SEQ ID NO: 12), EQISVLRKAFDAFDREKSGS (SEQ ID NO: 13), EVTLAAKFIIEEDS (SEQ ID NO: 14), PEFQSIVQTLNAMPEYQNLL (SEQ ID NO: 15), PELQNFLNFLEANGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVDSLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELREAFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTLNAMPEYQNLL (SEQ ID NO: 27), PELQNFLNFLEANGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQNFLTVFDSTSCN (SEQ ID NO: 23), ISSQYYIQQNGNLCY (SEQ ID NO: 21), HFFIGDFFVDHYYSE (SEQ ID NO: 18), GEPIRFLLSYGEKDF (SEQ ID NO: 28), FLLSYGEKDFEDYRF (SEQ ID NO: 29), SMPFGKTPVLEIDGK (SEQ ID NO: 11), VAISRYLGKQFGLSG (SEQ ID NO: 2), ISDFRAAIANYHYDA (SEQ ID NO: 4), EVVKANGGYLAAGKL (SEQ ID NO: 30), YFVAILDYLNHMAKE (SEQ ID NO: 5), HMAKEDLVANQPNLK (SEQ ID NO: 31), DLVANQPNLKALREK (SEQ ID NO: 32), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAFDREKSGS (SEQ ID NO: 36), EFVTLAAKFIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38), GYITTNVLREILKEL (SEQ ID NO: 25).

In other embodiments of the invention there are provided proteins and peptides including, consisting of or consisting essentially of an amino acid sequence set forth as: ALREKVLGLPAIKAWVAKRP (SEQ ID NO: 1), GEPIRFLLSYGEKDFEDYRF (SEQ ID NO: 3), EEFCTLASRFLVEED (SEQ ID NO: 6), PEQIQLLKKAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), FAVATITHAAELQRV (SEQ ID NO: 12), EQISVLRKAFDAFDREKSGS (SEQ ID NO: 13), EVTLAAKFIIEEDS (SEQ ID NO: 14), PEFQSIVQTLNAMPEYQNLL (SEQ ID NO: 15), PELQNFLNFLEA- NGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVDSLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELREAFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTLNAMPEYQNLL (SEQ ID NO: 27), PELQNFLNFLEANGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQNFLTVFDSTSCN (SEQ ID NO: 23), ISSQYYIQQNGNLCY (SEQ ID NO: 21), HFFIGDFFVDHYYSE (SEQ ID NO: 18), EQISVLRKAFDAFDR (SEQ ID NO: 35), LRKAFDAFDREKSGS (SEQ ID NO: 36), EFVTLAAKFIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38), GYITTNVLREILKEL (SEQ ID NO: 25).

In other embodiments of the invention there are provided proteins and peptides including, consisting of or consisting essentially of an amino acid sequence set forth as: ALREKVLGLPAIKAWVAKRP (SEQ ID NO: 1), VAISRYLGKQFGLSG (SEQ ID NO: 2), GEPIRFLLSYGEKDFEDYRF (SEQ ID NO: 3), ISDFRAAIANYHYDA (SEQ ID NO: 4), YFVAILDYLNHMAKE (SEQ ID NO: 5), EEFCTLASRFLVEED (SEQ ID NO: 6), PEQIQLLKKAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), SMPFGKTPVLEIDGK (SEQ ID NO: 11), FAVATITHAAELQRV (SEQ ID NO: 12), EQISVLRKAFDAFDREKSGS (SEQ ID NO: 13), EVTLAAKFIIEEDS (SEQ ID NO: 14), PEFQSIVQTLNAMPEYQNLL (SEQ ID NO: 15), PELQNFLNFLEANGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVDSLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELREAFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTLNAMPEYQNLL (SEQ ID NO: 27), PELQNFLNFLEANGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQNFLTVFDSTSCN (SEQ ID NO: 23), ISSQYYIQQNGNLCY (SEQ ID NO: 21), HFFIGDFFVDHYYSE (SEQ ID NO: 18), GEPIRFLLSYGEKDF (SEQ ID NO: 28), FLLSYGEKDFEDYRF (SEQ ID NO: 29), SMPFGKTPVLEIDGK (SEQ ID NO: 11), VAISRYLGKQFGLSG (SEQ ID NO: 2), ISDFRAAIANYHYDA (SEQ ID NO: 4), YFVAILDYLNHMAKE (SEQ ID NO: 5), HMAKEDLVANQPNLK (SEQ ID NO: 31), DLVANQPNLKALREK (SEQ ID NO: 32), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAFDREKSGS (SEQ ID NO: 36), EFVTLAAKFIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38), GYITTNVLREILKEL (SEQ ID NO: 25).

In certain embodiments, a Cockroach protein or peptide modulates an anti-allergen immune response. In other certain embodiments, a Cockroach protein or peptide elicits, stimulates, induces, promotes, increases or enhances an anti-allergen immune response. In further certain embodiments, a protein or peptide decreases, reduces, inhibits, suppresses or disrupts an anti-allergen immune response. In particular aspects of the proteins and peptides described herein, an anti-allergen immune response is an anti-Cockroach allergen response. In further certain embodiments, a protein or peptide elicits, stimulates, induces, promotes, increases or enhances immunological tolerance (desensitizes) of an allergen, for example, a Cockroach allergen such as a protein or peptide set forth in Tables I to X (SEQ ID NOs 1-201) or a subsequence, portion, homologue, variant or derivative thereof, or a protein or peptide set out in Table I (SEQ ID NOs 1-25) or Table VII (SEQ ID NOs 26-57), or a subsequence, portion, homologue, variant or derivative thereof.

In particular, an anti-allergen immune response is an anti-Cockroach allergen immune response. In particular embodiments, the allergen is Bla g 1, Bla g 1.0101, Bla g 2, Bla g 4, Bla g 5, Bla g 6, Bla g 6.0101, Bla g 6.0201, Bla g 7.

Thus in particular embodiments the allergen comprises, consists or consists essentially of an amino acid sequence of Bla g 1.0101 set forth as:

```
                                      (SEQ ID NO: 202)
NLLEKLREKGVDVDKIIELIRALFGLTLNAKASRNLQDDLQDFLALIPVD

QIIAIATDYLANDAEVQAAVAYLQSDEFETIVVALDALPELQNFLNFLEA

NGLNAIDFLNGIHDLLGIPHIPVSGRKYHIRRGVGITGLIDDVLAILPIE

DLKALFNEKLETSPDFLALYNAIRSPEFQSIVQTLNAMPEYQNLLQKLRE

KGVDVDKIIELIRALFGLTLNGKASRNLQDDLQDFLALIPVDQIIAIATD

YLANDAEVQAAVAYLQSDEFETIVVTLDALPELQNFLNFLEANGLNAIDF

LNGIHDLLGIPHIPVSGRKYHIRRGVGITGLIDDVLAILPLDDLKALFNE

KLETSPDFLALYNAIKSPEFQSIVQTLNAMPEYQNLLEKLREKGVDVDKI

IELIRALFGLTH.
```

In other particular embodiments the allergen comprises, consists or consists essentially of an amino acid sequence of Bla g 1 set forth as:

```
                                      (SEQ ID NO: 203)
NAIEFLNNIHDLLGIPHIPVTARKHHRRGVGITGLIDDIIAILPVDDLYA

LFQEKLETSPEFKALYDAIRSPEFQSIVGTLEAMPEYQNLIQKLKDKGVD

VDHIIELIHQIFNIVRDTRGLPEDLQDFLALIPTDQVLAIAADYLANDAE

VKAAVEYLKSDEFETIVVTVDSLPEFKNFLNFLQTNGLNAIEFLNNIHDL

LGIPHIPVTGRKHLRRGVGITGLIDDIIAILPVDDLYALFQEKLETSPEF

KALYDAIRSPEFQSIVETLKAMPEYQSLIQKLKDKGVDVDHIIELIHQIF

NIVRDTRGLPEDLQDFLALIPIDQILAIAADYLANDAEVQAAVEYLKSDE
```

-continued
FETIVVTVDSLPEFKNFLNFLQTNGLNAIEFINNIHDLLGIPHIPATGRK

HVRRGVGINGLIDDVIAILPVDELYALFQEKLESSPEFKALYDAIRSPEF

QSIVQTLKAMPEYQDLIQRLKDKGVDVDHFIELIKKLFGLSH.

In other particular embodiments the allergen comprises, consists or consists essentially of an amino acid sequence of Bla g 2 set forth as:

(SEQ ID NO: 204)
MIGLKLVTVLFAVATITHAAELQRVPLYKLVHVFINTQYAGITKIGNQNF

LTVFDSTSCNVVVASQECVGGACVCPNLQKYEKLKPKYISDGNVQVKFFD

TGSAVGRGIEDSLTISNLTTSQQDIVLADELSQEVCILSADVVVGIAAPG

CPNALKGKTVLENFVEENLIAPVFSIHHARFQDGEHFGEIIFGGSDWKYV

DGEFTYVPLVGDDSWKFRLDGVKIGDTTVAPAGTQAIIDTSKAIIVGPKA

YVNPINEAIGCVVEKTTTRRICKLDCSKIPSLPDVTFVINGRNFNISSQY

YIQQNGNLCYSGFQPCGHSDHFFIGDFFVDHYYSEFNWENKTMGFGRSVE

SV.

In other particular embodiments the allergen comprises, consists or consists essentially of an amino acid sequence of Bla g 4 set forth as:

(SEQ ID NO: 205)
AVLALCATDTLANEDCFRHESLVPNLDYERFRGSWIIAAGTSEALTQYKC

WIDRFSYDDALVSKYTDSQGKNRTTIRGRTKFEGNKFTIDYNDKGKAFSA

PYSVLATDYENYAIVEGCPAAANGHVIYVQIRFSVRRFHPKLGDKEMIQH

YTLDQVNQHKKAIEEDLKHFNLKYEDLHSTCH.

In other particular embodiments the allergen comprises, consists or consists essentially of an amino acid sequence of Bla g 5 set forth as:

(SEQ ID NO: 206)
MAPSYKLTYCPVKALGEPIRFLLSYGEKDFEDYRFQEGDWPNLKPSMPFG

KTPVLEIDGKQTHQSVAISRYLGKQFGLSGKDDWENLEIDMIVDTISDFR

AAIANYHYDADENSKQKKWDPLKKETIPYYTKKFDEVVKANGGYLAAGKL

TWADFYFVAILDYLNHMAKEDLVANQPNLKALREKVLGLPAIKAWVAKRP

PTDL.

In other particular embodiments the allergen comprises, consists or consists essentially of an amino acid sequence of Bla g 6.0101 set forth as:

(SEQ ID NO: 207)
MDELPPEQIQLLKKAFDAFDREKKGCISTEMVGTILEMLGHRLDDDMLQE

IIAEVDADGSGELEFEEFVSLASRFLVEEDAEAMQQELREAFRLYDKEGN

GYITTNVLREILKELDDKITAEDLDMMIEEIDSDGSGTVDFDEFMEVMTG

E.

In other particular embodiments the allergen comprises, consists or consists essentially of an amino acid sequence of Bla g 6.0201 set forth as:

(SEQ ID NO: 208)
MDEIPAEQVVLLKKAFDAFDREKKGCISTEMVGTILEMLGTRLDQDMLDE

IIAEVDADGSGELEFEEFCTLASRFLVEEDAEAMQHELREAFRLYDKEGN

GYITTAVLREILKELDDKITAEDLDMMIEEIDSDGSGTVDFDEFMEVMTG

E.

In other particular embodiments the allergen comprises, consists or consists essentially of an amino acid sequence of Bla g 6 set forth as:

(SEQ ID NO: 209)
MADEQLQLPPEQISVLRKAFDAFDREKSGSISTNMVEEILRLMGQPFNRR

TLEELIDEVDADKSGRLEFDEFVTLAAKFIIEEDSEAMEKELREAFRLYD

KEGNGYIPTSCLREILRELDEQLTSDELDMMIEEIDADGSGTVDFDEFME

MMTG.

In other particular embodiments the allergen comprises, consists or consists essentially of an amino acid sequence of Bla g 7 set forth as:

(SEQ ID NO: 210)
MDAIKKKMQAMKLEKDNAMDRALLCEQQARDANIRAEKAEEEARSLQKKI

QQIENDLDQTMEQLMQVNAKLDEKDKALQNAESEVAALNRRIQLLEEDLE

RSEERLATATAKLAEASQAADESERARKILESKGLADEERMDALENQLKE

ARFMAEEADKKYDEVARKLAMVEADLERAEERAETGESKIVELEEELRVV

GNNLKSLEVSEEKANLREEEYKQQIKTLNTRLKEAEARAEFAERSVQKLQ

KEVDRLEDELVHEKEKYKYICDDLDMTFTELIGN.

In further particular embodiments, an anti-Cockroach allergen immune response is a T cell response, for example a Th2 immune (cell) response (e.g., memory T cell response). In additional particular embodiments, an anti-Cockroach allergen immune response is an IgG or IgE reactive antigen or allergen.

In certain aspects, immunological tolerance comprises enhancing or improving tolerance of an anti-Cockroach allergen, such as a T cell response, for example, decreases, reduces, inhibits, suppresses or disrupts a Th2 immune (cell) response (e.g., memory T cell response) against a Cockroach allergen, such as a response against a protein or peptide set forth in any of Tables I to X (SEQ ID NOs 1-201) or a subsequence, portion, homologue, variant or derivative thereof, or an amino acid sequence set forth in Table I (SEQ ID NOs 1-25) or Table VII (SEQ ID NOs 26-57), or a subsequence, portion, homologue, variant or derivative thereof. In further aspects, the anti-allergen immune response modulates (e.g., increases, induces, elicits or stimulates, or decreases, reduces, inhibits, suppresses or disrupts) production of a lymphokine or cytokine by a cell. Particular lymphokines and cytokines which may be modulated include, for example, IL-5 (interleukin-5), IL-4 (interleukin-4), IL-10 (interleukin-13), IL-13 (interleukin-13), IL-17 (interleukin-17) and IFN-γ (interferon-gamma).

Accordingly, in additional embodiments, a Cockroach protein or peptide elicits, stimulates, induces, improves, increases, or enhances immunological tolerance of a subject to an allergen. In further particular embodiments, the Cockroach protein or peptide sequence, subsequence, homologue, or variant desensitizes, or elicits, stimulates, induces, improves, increases, or enhances immunological tolerance of a subject to a Cockroach allergen. Such Cockroach allergens to which immunological tolerance may be elicited, stimulated, induced, improved, increased, or enhanced include but are not limited to Bla g 1, Bla g 1.0101, Bla g 2, Bla g 4, Bla g 5, Bla g 6, Bla g 6.0101, Bla g 6.0201, Bla g 7, and may include or consist of a Cockroach a protein or peptide set forth in any of Tables I to X(SEQ ID NOs 1-201) or Table I (SEQ ID NOs 1-25) or Table VII (SEQ ID NOs 26-57), or a subsequence, portion, homologue, variant or derivative thereof.

T cell responses can be detected by an assay. For example, lymphokine, cytokine, IL-5 (interleukin-5), IL-4 (interleukin-4), IL-10 (interleukin-13), IL-13 (interleukin-13), IL-17 (interleukin-17) or IFN-γ (interferon-gamma) production can be detected by an immunoassay. IL-5, 11-4, IL-10, IL-13, IL-17 or IFN-γ production can be determined by contacting peripheral blood mononuclear cells (PBMC) with the protein or peptide followed by an immunoassay, for example.

In various aspects, a homologue or variant has at least 65% homology or identity (or more, e.g., 70%, 75%, 80%, 85%, 90%, 95%, (96%, 97%, 98%, 99% or more) to a Cockroach a protein or peptide set forth in any of Tables I to X (SEQ ID NOs 1-201) or Table I (SEQ ID NOs 1-25) or Table VII (SEQ ID NOs 26-57).

As disclosed herein, in certain embodiments proteins and peptides have a length in a range of about 5-10, 10-15, 15-20, 20-25, 25-30, 30-35, 35-40, 45-50, 50-60, 60-70, 70-80, 80-90, 90-100, 100-125, 125-150, 150-175, 175-200, 200-250, 250-300, or more amino acid residues. In other embodiments, proteins and peptides have a length in a range of up to 25 amino acids in length, or from about 7 to 20; 8 to 30; 8 to 25; 8 to 20; 9 to 30; 9 to 25; 9 to 20; 10 to 30; 10 to 25; 10 to 30 amino acid residues.

In particular aspects, a (sub)sequence is 7 to 30 amino acids in length and wherein at least 7 contiguous amino acids are at least 75% identical or homologous to at least 7 contiguous amino acids of said corresponding Cockroach a protein or peptide set forth in any of Tables I to X, (SEQ ID NOs 1-201) or Table I (SEQ ID NOs 1-25) or Table VII (SEQ ID NOs 26-57).

In further particular aspects, a subsequence, homologue, or variant is: i. a peptide of up to 30 amino acids in length which comprises an amino acid sequence of a protein or peptide set forth in any of Tables I to X(SEQ ID NOs 1-201) or Table I (SEQ ID NOs 1-25) or Table VII (SEQ ID NOs 26-57); or ii. a peptide of 7 to 30 amino acids in length which comprises a subsequence of at least 7 contiguous amino acids having at least 75% identity or homology to at least 7 contiguous amino acids of a protein or peptide set forth in any of Tables I to X(SEQ ID NOs 1-201) or Table I (SEQ ID NOs 1-25) or Table VII (SEQ ID NOs 26-57).

Cockroach proteins and peptides include isolated and/or purified amino acid sequences, subsequences, homologues, variants and derivatives thereof. Proteins and peptides also include those immobilized on a substrate, as well as amino acid sequences, subsequences, portions, homologues, variants, and derivatives immobilized on a substrate. Such amino acid sequences, subsequences, homologues, and variants can have a unique or distinct position or address on the substrate. Non-limiting substrates include glass, silica, plastic, polyethylene, polystyrene, polypropylene, polyacetate, polycarbonate, polyamide, polyester, polyurethane, or polyvinylchloride.

Proteins and peptides can be included in compositions, for example, a pharmaceutical composition. In particular embodiments, a pharmaceutical composition is suitable for specific or non-specific immunotherapy, or is a vaccine composition.

Isolated nucleic acid (including isolated nucleic acid) encoding a protein or peptide (Cockroach protein or peptide), or a subsequence, portion, homologue, variant or derivative thereof are provided. Such embodiments include any protein or peptide set forth herein. In one embodiment, a nucleic acid encodes an amino acid sequence of a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof.

Also provided are cells expressing a protein or peptide described herein. In various embodiments, a cell expresses a Cockroach protein that includes, consists of or consists essentially of an amino acid sequence of a protein or peptide set forth in any of Tables I to (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof. Non-limiting examples of cells include eukaryotic cells, prokaryotic cells, mammalian, insect, fungal (yeast) and bacterium.

Methods and uses and medicaments of Cockroach proteins and peptides of the invention are included. In various embodiments, there are provided methods and uses of and medicaments for modulating an immune response against a Cockroach allergen in a subject. In one embodiment, a method or use includes administering (delivering or contacting) to a subject an amount of a protein described herein (e.g., a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof) sufficient to modulate the immune response against the allergen in the subject. In further embodiments, there are provided uses of Cockroach proteins and peptides for manufacture of a medicament to modulate the immune activity of a cell against a Cockroach allergen.

Such methods, uses and medicaments also include for example and without limitation, modulating immune activity of a cell against an allergen; and desensitizing, inducing, eliciting, increasing or improving in the cell immunological tolerance to an allergen. In particular embodiments, a method or use includes contacting a cell with an amount of the protein or peptide of any one of the embodiments disclosed herein (e.g., a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof), sufficient to modulate the immune activity of the cell against the allergen (e.g., against an allergen from which the peptide or protein derives), or administering to a subject an allergen from which the peptide or protein derives in order to desensitize, induce, elicit, increase or improve immunological tolerance to the allergen or to modulate an immune response against an allergen in a subject (e.g., an allergen from which the peptide or protein derives, e.g., a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof).

Invention proteins, peptides, subsequences, portions, homologues, variants and derivatives thereof are suitable as a reagent for example, for specific immunotherapy (SIT). In particular embodiments, a protein or peptide suitable as a reagent includes, consists of or consists essentially of an amino acid sequence of a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof.

Such methods, uses and medicaments further include reducing risk or providing a subject protection against an allergic reaction, allergic response, allergic disorder or allergic disease. In one embodiment, a method or use includes administering to the subject an amount of the Cockroach protein or peptide (e.g., a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof) sufficient to reduce risk or provide the subject with protection against the allergic reaction, allergic response, allergic disorder or allergic disease (e.g., caused by or associated with a Cockroach allergen).

Such methods, uses and medicaments additionally include treating an allergic reaction, allergic response, allergic disorder or allergic disease. In one embodiment, a method or use includes administering to the subject an amount of the Cockroach protein or peptide (e.g., a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof), sufficient to treat the subject for the allergic response, allergic disorder or allergic disease (e.g., caused by or associated with a Cockroach allergen).

In such methods, uses and medicaments, a peptide or protein can be derived from or based upon the (Cockroach) allergen or can be derived from or based upon an allergen originating from the same organism as the allergen. More particularly, for example, a protein or peptide can be derived from or based upon a Cockroach allergen that contributes to or causes the allergic reaction, allergic response, allergic disorder or allergic disease or said peptide derives from an allergen belonging to the same organism as the allergen causing said allergic reaction, allergic response, allergic disorder or allergic disease. Additionally, for example, a protein or peptide can be based upon or derived from a Cockroach a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof.

In various embodiments, a method or use or medicament desensitizes or induces, elicits, increases or improves immunological tolerance of a subject to a Cockroach allergen. In particular aspects, a method or use or medicament that desensitizes or induces, elicits, increases or improves immunological tolerance of a subject to a Cockroach allergen is a protein or peptide in any of in Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof. In various other embodiments, a method or use or medicament desensitizes or induces, elicits, increases or improves immunological tolerance of a subject to a protein or peptide set forth in Table I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof.

In various further embodiments, a method or use or medicament reduces risk or provides the subject with protection against an allergic reaction, allergic response, allergic disorder or allergic disease (e.g., caused by or associated with a Cockroach allergen), wherein the method or use or medicament includes a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof.

In various additional embodiments, a method or use or medicament treats an allergic reaction, allergic response, allergic disorder or allergic disease (e.g., caused by or associated with a Cockroach allergen), comprising wherein the method or use or medicament includes a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof.

Allergic reactions, allergic responses, allergic disorders and allergic diseases as set forth herein include those caused by or associated with Cockroach exposure, contact with a Cockroach allergen or contact with an allergen homologous to a Cockroach allergen.

As set forth herein a Cockroach protein, peptide, method, use or medicament can include administration or delivery by any means to a subject, systemically, regionally or locally. In particular aspects, a protein or peptide is administered cutaneously, subcutaneously, epicutaneously, intracutaneously, intramuscularly, intravenously, orally, mucosally, by inhalation or nasally. As also set forth herein a Cockroach protein, peptide, method, use or medicament can include repeatedly contacting a cell with, or administrations to a subject, the protein or peptide, multiple times (e.g., a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof).

As set forth herein, subjects in accordance with the invention include mammals, such as humans. In particular embodiments, a subject has exhibited a symptom of, or suffers from, an allergic reaction, allergic response, allergic disorder or allergic disease (e.g., caused by or associated with a Cockroach allergen). In more particular embodiments, a subject has had an allergic reaction or allergic response to a Cockroach allergen. In further particular embodiments, a subject has, has previously had or is at risk of having asthma or hypersensitivity to a Cockroach allergen. In additional particular embodiments, a subject has had an allergic reaction or allergic response to an allergen derived from or produced by Cockroach, such as an allergen or an amino acid sequence set forth in Table I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof. In still additional particular embodiments, a subject has had an allergic reaction or allergic response to a Cockroach Bla g 1, Bla g 1.0101, Bla g 2, Bla g 4, Bla g 5, Bla g 6, Bla g 6.0101, Bla g 6.0201, Bla g 7 protein. In still further particular embodiments, the Cockroach allergen is an IgG or IgE reactive antigen or allergen.

Proteins and peptides can be deployed in diagnostic and detection methods and uses. In one embodiment, detecting an allergic response, or diagnosing an allergy in a subject, a method or use includes contacting a cell from the subject (which may be an ex vivo or in vivo cell) with a protein or peptide as set forth herein; and determining if the protein or peptide modulates an immune response or activity from the contacted cell. If the protein or peptide modulates an immune response or activity from the contacted cell (which may be an in vitro, ex vivo or in vivo cell) detects an allergic response or indicates that the subject has an allergic response or an allergy. In a particular aspect, the allergic response or allergy comprises a Cockroach allergic response or allergy. In another particular aspect, modulation of immune response or activity is determined by assaying for a hypersensitive reaction or response, such as a cutaneous (e.g., skin) immunological hypersensitive reaction.

Proteins and peptides can be deployed in kits and uses. In one embodiment, a kit includes a compartment and instructions, which compartment includes: one or more amino acid sequences of an allergen (e.g., Cockroach) or a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof; and instructions for use in any of: modulating an immune response or activity of a cell against an allergen; modulating an immune response against an allergen in a subject; desensitizing, or inducing, eliciting, increasing or improving immunological tolerance to a protein or peptide allergen; reducing risk or providing a subject protection against an allergic reaction, allergic response, allergic disorder or allergic disease; treating an allergic reaction, allergic response, allergic disorder or allergic disease; or detecting an allergic response or diagnosing an allergy in a subject.

DETAILED DESCRIPTION

Figure 1:
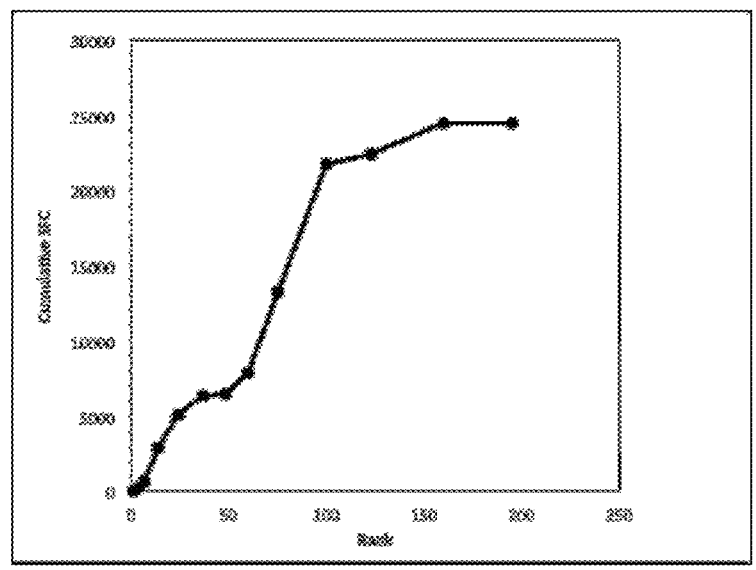
FIG. 1. Peptide binding predictions allowed efficient identification of a preponderance of the Bla g specific T cell response. Bla g allergen sequences were scanned with a panel of bioinformatics algorithms predicting binding to 20 common HLA class II molecules, as described herein. Peptides were ranked on the basis of predicted binding promiscuity, and all peptides predicted to bind 7 or more molecules were selected for synthesis and tested for recognition in allergic donors. Then cumulative Bla g specific response (total SFC) as function of peptide rank was tabulated. Saturation of responses was noted at a rank of about 160, corresponding to approximately the top 35% scoring peptides, and over 75% of the response was associated with the top 100 (corresponding to the top 22%) predicted peptides.

In accordance with the invention, there are provided novel Cockroach proteins and peptides, and subsequences, portions, homologues, variants and derivatives thereof. A Cockroach protein or peptide as described herein may include any Cockroach protein or peptide, or a subsequence, portion, homologue, variant or derivative thereof. In certain embodiments, a Cockroach protein or peptide as described herein may include a novel Cockroach protein or peptide, for example, as set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof.

In particular embodiments, a Cockroach protein or peptide described herein includes, consists or consists essentially of a protein or peptide having an amino acid sequence set out in or a protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof.

In particular embodiments, a Cockroach protein or peptide described herein includes, consists or consists essentially of a protein or peptide having an amino acid sequence set forth as: ALREKVLGLPAIKAWVAKRP (SEQ ID NO: 1), VAISRYLGKQFGLSG (SEQ ID NO: 2), GEPIRFLL-SYGEKDFEDYRF (SEQ ID NO: 3), ISDFRAAIANY-HYDA (SEQ ID NO: 4), YFVAILDYLNHMAKE (SEQ ID NO: 5), EEFCTLASRFLVEED (SEQ ID NO: 6), PEQIQLLKKAFDAFD (SEQ ID NO: 7), LIDDVLAIL-PLDDLK (SEQ ID NO: 8), HMAKEDLVANQPNLKAL-REK (SEQ ID NO: 9), TKKFDEVVKANGGYLAAGKL (SEQ ID NO: 10), SMPFGKTPVLEIDGK (SEQ ID NO: 11), FAVATITHAAELQRV (SEQ ID NO: 12), EQISVLRKAFDAFDREKSGS (SEQ ID NO: 13), EVT-LAAKFIIEEDS (SEQ ID NO: 14), PEFQSIVQTL-NAMPEYQNLL (SEQ ID NO: 15), PELQNFLNFLEA-NGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVD-SLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELRE-AFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTL-NAMPEYQNLL (SEQ ID NO: 27), PELQNFLNFLEA-NGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQN-FLTVFDSTSCN (SEQ ID NO: 23), ISSQYYIQQNGNLCY (SEQ ID NO: 21), HFFIGDFFVDHYYSE (SEQ ID NO: 18), GEPIRFLLSYGEKDF (SEQ ID NO: 28), FLLSY-GEKDFEDYRF (SEQ ID NO: 29), SMPFGKTPVLEIDGK (SEQ ID NO: 11), VAISRYLGKQFGLSG (SEQ ID NO: 2), ISDFRAAIANYHYDA (SEQ ID NO: 4), EVVKANGGY-LAAGKL (SEQ ID NO: 30), YFVAILDYLNHMAKE (SEQ ID NO: 5), HMAKEDLVANQPNLK (SEQ ID NO: 31), DLVANQPNLKALREK (SEQ ID NO: 32), ALREKVLGLPAIKAW (SEQ ID NO: 33), VLGLPAI-KAWVAKRP (SEQ ID NO: 34), EQISVLRKAFDAFDR (SEQ ID NO: 35), LRKAFDAFDREKSGS (SEQ ID NO: 36), EFVTLAAKFIIEEDS (SEQ ID NO: 14), EAMEKEL-REAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLK-KAFDAFD (SEQ ID NO: 7), MVGTILEMLGHRLDD (SEQ ID NO: 17), EEFVSLASRFLVEED (SEQ ID NO: 38), GYITTNVLREILKEL (SEQ ID NO: 25), DLL-GIPHIPVTARKH (SEQ ID NO: 39), LETSPEFKALY-DAIR (SEQ ID NO: 40), SPEFQSIVGTLEAMP (SEQ ID NO: 41), LEAMPEYQNLIQKLK (SEQ ID NO: 42), VDHIIELIHQIFNIV (SEQ ID NO: 43), ELIHQIFNIVRDTRG (SEQ ID NO: 44), IFNIVRDTR-GLPEDL (SEQ ID NO: 45), LPEDLQDFLALIPTD (SEQ ID NO: 46), QDFLALIPTDQVLAI (SEQ ID NO: 47), LIPTDQVLAIAADYL (SEQ ID NO: 48), QVLAIAADY-LANDAE (SEQ ID NO: 49), AADYLANDAEVKAAV (SEQ ID NO: 50), ANDAEVKAAVEYLKS (SEQ ID NO: 51), DSLPEFKNFLNFLQT (SEQ ID NO: 52), FKNFLN-FLQTNGLNA (SEQ ID NO: 53), NFLQTNGLNAIEFLN (SEQ ID NO: 54), NGLNAIEFLNNIHDL (SEQ ID NO: 55), IEFLNNIHDLLGIPH (SEQ ID NO: 56), TGLIDDI-IAILPVDD (SEQ ID NO: 57), DIIAILPVDDLYALF (SEQ ID NO: 58), LPVDDLYALFQEKLE (SEQ ID NO: 59), LYALFQEKLETSPEF (SEQ ID NO: 60), KALYDAIRSPE-FQSE (SEQ ID NO: 61), AIRSPEFQSIVETLK (SEQ ID NO: 62), EFQSIVETLKAMPEY (SEQ ID NO: 63), VETLKAMPEYQSLIQ (SEQ ID NO: 64), AMPEYQSLIQKLKDK (SEQ ID NO: 65), QSLIQKLKDKGVDVD (SEQ ID NO: 66), EDLQDFLA-LIPIDQI (SEQ ID NO: 67), FLALIPIDQILAIAA (SEQ ID NO: 68), PIDQILAIAADYLAN (SEQ ID NO: 69), DYLANDAEVQAAVEY (SEQ ID NO: 70), AAVEYLKS-DEFETIV (SEQ ID NO: 71), LKSDEFETIVVTVDS (SEQ ID NO: 72), FETIVVTVDSLPEFK (SEQ ID NO: 20), LNAIEFINNIHDLLG (SEQ ID NO: 73), FINNIHDLL-GIPHIP (SEQ ID NO: 74), HDLLGIPHIPATGRK (SEQ ID NO: 75), VGINGLIDDVIAILP (SEQ ID NO: 76), LIDD-VIAILPVDELY (SEQ ID NO: 77), IAILPVDELYALFQE (SEQ ID NO: 78), VDELYALFQEKLESS (SEQ ID NO: 79), ALFQEKLESSPEFKA (SEQ ID NO: 80), RSPEFQ-SIVQTLKAM (SEQ ID NO: 81), QSIVQTLKAMPEYQD (SEQ ID NO: 82), PEYQDLIQRLKDKGV (SEQ ID NO: 83), LIQRLKDKGVDVDHF (SEQ ID NO: 84), DHFIE-LIKKLFGLSH (SEQ ID NO: 85), VDVDKIIELIRAFLG (SEQ ID NO: 86), IIELIRALFGLTLNA (SEQ ID NO: 87), RALFGLTLNAKASRN (SEQ ID NO: 88), LTLNAKAS-RNLQDDL (SEQ ID NO: 89), LQDDLQDFLALIPVD (SEQ ID NO: 90), QDFLALIPVDQIIAI (SEQ ID NO: 91), DEFETIVVALDALPE (SEQ ID NO: 92), IVVALDALPELQNFL (SEQ ID NO: 93), IDFLNGIHDLL-GIPH (SEQ ID NO: 94), GIHDLLGIPHIPVSG (SEQ ID NO: 95), RKYHIRRGVGITGLI (SEQ ID NO: 96), DDV-LAILPIEDLKAL (SEQ ID NO: 97), ILPIEDLKALFNEKL (SEQ ID NO: 98), ETSPDFLALYNAIRS (SEQ ID NO: 99), FLALYNAIRSPEFQS (SEQ ID NO: 100), PEFQSIVQTL-NAMPE (SEQ ID NO: 26), IVQTLNAMPEYQNLL (SEQ ID NO: 27), NAMPEYQNLLQKLRE (SEQ ID NO: 101), YQNLLQKLREKGVDV (SEQ ID NO: 102), LIRALFGLTLNGKAS (SEQ ID NO: 103), FGLTLNGKASRNLQD (SEQ ID NO: 104), VDQIIAI-ATDYLAND (SEQ ID NO: 105), AIATDYLANDAEVQA (SEQ ID NO: 106), AEVQAAVAYLQSDEF (SEQ ID NO: 107), AVAYLQSDEFETIVV (SEQ ID NO: 108), QSDEFE-TIVVTLDAL (SEQ ID NO: 109), ETIVVTLDALPELQN (SEQ ID NO: 110), PELQNFLNFLEANGL (SEQ ID NO: 16), FLNFLEANGLNAIDF (SEQ ID NO: 111), LNGIHDLLGIPHIPV (SEQ ID NO: 112), DLLGIPHIPVS-GRKY (SEQ ID NO: 113), VGITGLIDDVLAILP (SEQ ID NO: 114), LIDDVLAILPLDDLK (SEQ ID NO: 8), LAIL-PLDDLKALFNE (SEQ ID NO: 115), LDDLKALFNEK-LETS (SEQ ID NO: 116), PDFLALYNAIKSPEF (SEQ ID NO: 117), LYNAIKSPEFQSIVQ (SEQ ID NO: 118), MIGLKLVTVLFAVAT (SEQ ID NO: 119), LVTVLFA-VATITHAA (SEQ ID NO: 120), FAVATITHAAELQRV (SEQ ID NO: 12), ITHAAELQRVPLYKL (SEQ ID NO: 121), ELQRVPLYKLVHVFI (SEQ ID NO: 122), PLYKLVHVFINTQYA (SEQ ID NO: 19), VHVFINTQY-AGITKI (SEQ ID NO: 123), NTQYAGITKIGNQNF (SEQ ID NO: 124), GITKIGNQNFLTVFD (SEQ ID NO: 125), GNQNFLTVFDSTSCN (SEQ ID NO: 23), PNLQKYEKLKPKYIS (SEQ ID NO: 126), YEKLKPKY-ISDGNVQ (SEQ ID NO: 127), PKYISDGNVQVKFFD (SEQ ID NO: 128), DGNVQVKFFDTGSAV (SEQ ID NO: 129), VKFFDTGSAVGRGIE (SEQ ID NO: 130), GRGIED-SLTISNLTT (SEQ ID NO: 131), LSQEVCILSADVVVG (SEQ ID NO: 132), CILSADVVVGIAAPG (SEQ ID NO: 133), KGKTVLENFVEENLI (SEQ ID NO: 134), LENFVEENLIAPVFS (SEQ ID NO: 135), EENLIA-PVFSIHHAR (SEQ ID NO: 136), APVFSIHHARFQDGE (SEQ ID NO: 137), IFGGSDWKYVDGEFT (SEQ ID NO: 138), DWKYVDGEFTYVLPV (SEQ ID NO: 139), DGEFTYVPLVGDDSW (SEQ ID NO: 140), YVPLVGDD-SWKFRLD (SEQ ID NO: 141), GDDSWKFRLDGVKIG (SEQ ID NO: 142), PAGTQAIIDTSKAII (SEQ ID NO: 143), AIIDTSKAIIVGPKA (SEQ ID NO: 144), SKAIIVGPKAYVNPI (SEQ ID NO: 145), VGPKAYVN-PINEAIG (SEQ ID NO: 146), SLPDVTFVINGRNFN (SEQ ID NO: 147), TFVINGRNFNISSQY (SEQ ID NO: 148), GRNFNISSQYYIQQN (SEQ ID NO: 149), ISSQYYIQQNGNLCY (SEQ ID NO: 21), HFFIGDFFVDHYYSE (SEQ ID NO: 18), DFFVDHYY-SEFNWEN (SEQ ID NO: 150), LDYERFRGSWIIAAG (SEQ ID NO: 151), FRGSWIIAAGTSEAL (SEQ ID NO: 152), IIAAGTSEALTQYKC (SEQ ID NO: 153), WIDRFSYDDALVSKY (SEQ ID NO: 154), YNDKGKAFSAPYSVL (SEQ ID NO: 155), KAFSAPY-SVLATDYE (SEQ ID NO: 156), PYSVLATDYENYAIV (SEQ ID NO: 157), ATDYENYAIVEGCPA (SEQ ID NO: 158), AANGHVIYVQIRFSV (SEQ ID NO: 159), VIYVQIRFSVRRFHP (SEQ ID NO: 160), IRFSVRRFHPKLGKD (SEQ ID NO: 161), EMIQHYTLDQVNQHK (SEQ ID NO: 162), KAIEEDLKHFNLKYE (SEQ ID NO: 163), KHFNLKYEDLHSTCH (SEQ ID NO: 164), KLTYCPVKALGEPIR (SEQ ID NO: 165), GEPIRFLLSY-GEKDF (SEQ ID NO: 28), FLLSYGEKDFEDYRF (SEQ ID NO: 29), SMPFGKTPVLEIDGK (SEQ ID NO: 11), QTHQSVAISRYLGKO (SEQ ID NO: 166), VAIS-RYLGKQFGLSG (SEQ ID NO: 2), NLEIDMIVDTISDFR (SEQ ID NO: 167), MIVDTISDFRAAIAN (SEQ ID NO: 168), ISDFRAAIANYHYDA (SEQ ID NO: 4), TKKFDEVVKANGGYL (SEQ ID NO: 169), EVVKANG-GYLAAGKL (SEQ ID NO: 30), NGGYLAAGKLTWADF (SEQ ID NO: 170), TWADFYFVAILDYLN (SEQ ID NO: 171), YFVAILDYLNHMAKE (SEQ ID NO: 5), LDYLNH-MAKEDLVAN (SEQ ID NO: 172), HMAKEDLVA-NQPNLK (SEQ ID NO: 31), DLVANQPNLKALREK (SEQ ID NO: 32), QPNLKALREKVLGLP (SEQ ID NO: 173), ALREKVLGLPAIKAW (SEQ ID NO: 33), VLGLPAI-KAWVAKRP (SEQ ID NO: 34), QDFLALIPTDQVLAI (SEQ ID NO: 47), LRKAFDAFDREKSGS (SEQ ID NO: 36), VEEILRLMGQPFNRR (SEQ ID NO: 174), ADKS-GRLEFDEFVTL (SEQ ID NO: 175), RLEFDEFVT-LAAKFI (SEQ ID NO: 176), EFVTLAAKFIIEEDS (SEQ ID NO: 14), EAMEKELREAFRLYD (SEQ ID NO: 24), CLREILRELDEQLTS (SEQ ID NO: 177), DELDMMIEEI-DADGS (SEQ ID NO: 178), SGTVDFDEFMEMMTG (SEQ ID NO: 22), AEQVVLLKKAFDAFD (SEQ ID NO: 179), MVGTILEMLGTRLDQ (SEQ ID NO: 37), GELE-FEEFCTLASRF (SEQ ID NO: 180), EEFCTLASRFLV-EED (SEQ ID NO: 6), HELREAFRLYDKEGN (SEQ ID NO: 181), DKEGNGYITTAVLRE (SEQ ID NO: 182), GYITTAVLREILKEL (SEQ ID NO: 183), AVL-REILKELDDKIT (SEQ ID NO: 184), PEQIQLLK-KAFDAFD (SEQ ID NO: 7), MVGTILEMLGHRLDD (SEQ ID NO: 17), DMLQEIIAEVDADGS (SEQ ID NO: 185), GELEFEEFVSLASRF (SEQ ID NO: 186), EEFVSLASRFLVEED (SEQ ID NO: 38), GYITTNVL-REILKEL (SEQ ID NO: 25), MDAIKKKMQAMKLEK (SEQ ID NO: 187), KKMQAMKLEKDNAMD (SEQ ID NO: 188), LQKKIQQIENDLDQT (SEQ ID NO: 189), MEQLMQVNALKDEKD (SEQ ID NO: 190), KALQNAE-SEVAALNR (SEQ ID NO: 191), AESEVAALNRRIQLL (SEQ ID NO: 192), AALNRRIQLLEEDLE (SEQ ID NO: 193), RSEERLATATAKLAE (SEQ ID NO: 194), LATAT-AKLAEASQAA (SEQ ID NO: 195), GESKIVELEEELRVV (SEQ ID NO: 196), VELEEELRVVGNNLK (SEQ ID NO: 197), ELRVVGNNLKSLEVS (SEQ ID NO: 198), LREEEYKQQIKTLNT (SEQ ID NO: 199), YKQQIKTLN-TRLKEA (SEQ ID NO: 200) or ICDDLDMTFTELIGN (SEQ ID NO: 201).

In other embodiments of the invention, a Cockroach protein or peptide described herein includes, consists or consists essentially of an amino acid sequence set forth as: ALREKVLGLPAIKAWVAKRP (SEQ ID NO: 1), GEPIRFLLSYGEKDFEDYRF (SEQ ID NO: 3), EEFCT-LASRFLVEED (SEQ ID NO: 6), PEQIQLLKKAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), FAVATITHAAELQRV (SEQ ID NO: 12), EQISVLRKAFDAFDREKSGS (SEQ ID NO: 13), EVT-LAAKFIIEEDS (SEQ ID NO: 14), PEFQSIVQTL-NAMPEYQNLL (SEQ ID NO: 15), PELQNFLNFLEA-NGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVD-SLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELRE-AFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTL-NAMPEYQNLL (SEQ ID NO: 27), PELQNFLNFLEA-NGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQN-FLTVFDSTSCN (SEQ ID NO: 23), ISSQYYIQQNGNLCY (SEQ ID NO: 21), HFFIGDFFVDHYYSE (SEQ ID NO: 18), EQISVLRKAFDAFDR (SEQ ID NO: 35), LRKAFDAFDREKSGS (SEQ ID NO: 36), EFVTLAAK-FIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLAS-RFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38), GYITTNVL-REILKEL (SEQ ID NO: 25), DLLGIPHIPVTARKH (SEQ ID NO: 39), LETSPEFKALYDAIR (SEQ ID NO: 40), SPEFQSIVGTLEAMP (SEQ ID NO: 41), LEAMPEYQN-LIQKLK (SEQ ID NO: 42), VDHIIELIHQIFNIV (SEQ ID NO: 43), ELIHQIFNIVRDTRG (SEQ ID NO: 44), IFNIVRDTRGLPEDL (SEQ ID NO: 45), LPEDLQDFLA-LIPTD (SEQ ID NO: 46), QDFLALIPTDQVLAI (SEQ ID NO: 47), LIPTDQVLAIAADYL (SEQ ID NO: 48), QVLA-IAADYLANDAE (SEQ ID NO: 49), AADYLANDAEV-KAAV (SEQ ID NO: 50), ANDAEVKAAVEYLKS (SEQ ID NO: 51), DSLPEFKNFLNFLQT (SEQ ID NO: 52), FKNFLNFLQTNGLNA (SEQ ID NO: 53), NFLQTNGLNAIEFLN (SEQ ID NO: 54), NGLNAIEFLN-NIHDL (SEQ ID NO: 55), IEFLNNIHDLLGIPH (SEQ ID NO: 56), TGLIDDIIAILPVDD (SEQ ID NO: 57), DIIAIL-PVDDLYALF (SEQ ID NO: 58), LPVDDLYALFQEKLE (SEQ ID NO: 59), LYALFQEKLETSPEF (SEQ ID NO: 60), KALYDAIRSPEFQSE (SEQ ID NO: 61), AIRSPEFQSIV-ETLK (SEQ ID NO: 62), EFQSIVETLKAMPEY (SEQ ID NO: 63), VETLKAMPEYQSLIQ (SEQ ID NO: 64), AMPEYQSLIQKLKDK (SEQ ID NO: 65), QSLIQKLKDKGVDVD (SEQ ID NO: 66), EDLQDFLA-LIPIDQI (SEQ ID NO: 67), FLALIPIDQILAIAA (SEQ ID NO: 68), PIDQILAIAADYLAN (SEQ ID NO: 69), DYLANDAEVQAAVEY (SEQ ID NO: 70), AAVEYLKS-DEFETIV (SEQ ID NO: 71), LKSDEFETIVVTVDS (SEQ ID NO: 72), FETIVVTVDSLPEFK (SEQ ID NO: 20), LNAIEFINNIHDLLG (SEQ ID NO: 73), FINNIHDLL-GIPHIP (SEQ ID NO: 74), HDLLGIPHIPATGRK (SEQ ID NO: 75), VGINGLIDDVIAILP (SEQ ID NO: 76), LIDD-VIAILPVDELY (SEQ ID NO: 77), IAILPVDELYALFQE (SEQ ID NO: 78), VDELYALFQEKLESS (SEQ ID NO: 79), ALFQEKLESSPEFKA (SEQ ID NO: 80), RSPEFQ-SIVQTLKAM (SEQ ID NO: 81), QSIVQTLKAMPEYQD (SEQ ID NO: 82), PEYQDLIQRLKDKGV (SEQ ID NO: 83), LIQRLKDKGVDVDHF (SEQ ID NO: 84), DHFIE-LIKKLFGLSH (SEQ ID NO: 85), VDVDKIIELIRAFLG (SEQ ID NO: 86), IIELIRALFGLTLNA (SEQ ID NO: 87), RALFGLTLNAKASRN (SEQ ID NO: 88), LTLNAKAS-RNLQDDL (SEQ ID NO: 89), LQDDLQDFLALIPVD (SEQ ID NO: 90), QDFLALIPVDQIIAI (SEQ ID NO: 91), DEFETIVVALDALPE (SEQ ID NO: 92), IVVALDALPELQNFL (SEQ ID NO: 93), IDFLNGIHDLL-GIPH (SEQ ID NO: 94), GIHDLLGIPHIPVSG (SEQ ID NO: 95), RKYHIRRGVGITGLI (SEQ ID NO: 96), DDV-LAILPIEDLKAL (SEQ ID NO: 97), ILPIEDLKALFNEKL (SEQ ID NO: 98), ETSPDFLALYNAIRS (SEQ ID NO: 99), FLALYNAIRSPEFQS (SEQ ID NO: 100), PEFQSIVQTL-NAMPE (SEQ ID NO: 26), IVQTLNAMPEYQNLL (SEQ ID NO: 27), NAMPEYQNLLQKLRE (SEQ ID NO: 101), YQNLLQKLREKGVDV (SEQ ID NO: 102), LIRALFGLTLNGKAS (SEQ ID NO: 103), FGLTLNGKASRNLQD (SEQ ID NO: 104), VDQIIAI-ATDYLAND (SEQ ID NO: 105), AIATDYLANDAEVQA (SEQ ID NO: 106), AEVQAAVAYLQSDEF (SEQ ID NO: 107), AVAYLQSDEFETIVV (SEQ ID NO: 108), QSDEFE-TIVVTLDAL (SEQ ID NO: 109), ETIVVTLDALPELQN (SEQ ID NO: 110), PELQNFLNFLEANGL (SEQ ID NO: 16), FLNFLEANGLNAIDF (SEQ ID NO: 111), LNGIHDLLGIPHIPV (SEQ ID NO: 112), DLLGIPHIPVSGRKY (SEQ ID NO: 113), VGITGLIDDVLAILP (SEQ ID NO: 114), LIDDVLAILPLDDLK (SEQ ID NO: 8), LAILPLDDLKALFNE (SEQ ID NO: 115), LDDLKALFNEKLETS (SEQ ID NO: 116), PDFLALYNAIKSPEF (SEQ ID NO: 117), LYNAIKSPEFQSIVQ (SEQ ID NO: 118), MIGLKLVTVLFAVAT (SEQ ID NO: 119), LVTVLFAVATITHAA (SEQ ID NO: 120), FAVATITHAAELQRV (SEQ ID NO: 12), ITHAAELQRVPLYKL (SEQ ID NO: 121), ELQRVPLYKLVHVFI (SEQ ID NO: 122), PLYKLVHVFINTQYA (SEQ ID NO: 19), VHVFINTQYAGITKI (SEQ ID NO: 123), NTQYAGITKIGNQNF (SEQ ID NO: 124), GITKIGNQNFLTVFD (SEQ ID NO: 125), GNQNFLTVFDSTSCN (SEQ ID NO: 23), PNLQKYEKLKPKYIS (SEQ ID NO: 126), YEKLKPKYISDGNVQ (SEQ ID NO: 127), PKYISDGNVQVKFFD (SEQ ID NO: 128), DGNVQVKFFDTGSAV (SEQ ID NO: 129), VKFFDTGSAVGRGIE (SEQ ID NO: 130), GRGIEDSLTISNLTT (SEQ ID NO: 131), LSQEVCILSADVVVG (SEQ ID NO: 132), CILSADVVVGIAAPG (SEQ ID NO: 133), KGKTVLENFVEENLI (SEQ ID NO: 134), LENFVEENLIAPVFS (SEQ ID NO: 135), EENLIAPVFSIHHAR (SEQ ID NO: 136), APVFSIHHARFQDGE (SEQ ID NO: 137), IFGGSDWKYVDGEFT (SEQ ID NO: 138), DWKYVDGEFTYVLPV (SEQ ID NO: 139), DGEFTYVPLVGDDSW (SEQ ID NO: 140), YVPLVGDDSWKFRLD (SEQ ID NO: 141), GDDSWKFRLDGVKIG (SEQ ID NO: 142), PAGTQAIIDTSKAII (SEQ ID NO: 143), AIIDTSKAIIVGPKA (SEQ ID NO: 144), SKAIIVGPKAYVNPI (SEQ ID NO: 145), VGPKAYVNPINEAIG (SEQ ID NO: 146), SLPDVTFVINGRNFN (SEQ ID NO: 147), TFVINGRNFNISSQY (SEQ ID NO: 148), GRNFNISSQYYIQQN (SEQ ID NO: 149), ISSQYYIQQNGNLCY (SEQ ID NO: 21), HFFIGDFFVDHYYSE (SEQ ID NO: 18), DFFVDHYYSEFNWEN (SEQ ID NO: 150), LDYERFRGSWIIAAG (SEQ ID NO: 151), FRGSWIIAAGTSEAL (SEQ ID NO: 152), IIAAGTSEALTQYKC (SEQ ID NO: 153), WIDRFSYDDALVSKY (SEQ ID NO: 154), YNDKGKAFSAPYSVL (SEQ ID NO: 155), KAFSAPYSVLATDYE (SEQ ID NO: 156), PYSVLATDYENYAIV (SEQ ID NO: 157), ATDYENYAIVEGCPA (SEQ ID NO: 158), AANGHVIYVQIRFSV (SEQ ID NO: 159), VIYVQIRFSVRRFHP (SEQ ID NO: 160), IRFSVRRFHPKLGKD (SEQ ID NO: 161), EMIQHYTLDQVNQHK (SEQ ID NO: 162), KAIEEDLKHFNLKYE (SEQ ID NO: 163), KHFNLKYEDLHSTCH (SEQ ID NO: 164), TWADFYFVAILDYLN (SEQ ID NO: 171), EQISVLRKAFDAFDR (SEQ ID NO: 47), LRKAFDAFDREKSGS (SEQ ID NO: 36), VEEILRLMGQPFNRR (SEQ ID NO: 174), ADKSGRLEFDEFVTL (SEQ ID NO: 175), RLEFDEFVTLAAKFI (SEQ ID NO: 176), EFVTLAAKFIIEEDS (SEQ ID NO: 14), EAMEKELREAFRLYD (SEQ ID NO: 24), CLREILRELDEQLTS (SEQ ID NO: 177), DELDMMIEEIDADGS (SEQ ID NO: 178), SGTVDFDEFMEMMTG (SEQ ID NO: 22), AEQVVLLKKAFDAFD (SEQ ID NO: 179), MVGTILEMLGTRLDQ (SEQ ID NO: 37), GELEFEEFCTLASRF (SEQ ID NO: 180), EEFCTLASRFLVEED (SEQ ID NO: 6), HELREAFRLYDKEGN (SEQ ID NO: 181), DKEGNGYITTAVLRE (SEQ ID NO: 182), GYITTAVLREILKEL (SEQ ID NO: 183), AVLREILKELDDKIT (SEQ ID NO: 184), PEQIQLLKKAFDAFD (SEQ ID NO: 7), MVGTILEMLGHRLDD (SEQ ID NO: 17), DMLQEIIAEVDADGS (SEQ ID NO: 185), GELEFEEFVSLASRF (SEQ ID NO: 186), EEFVSLASRFLVEED (SEQ ID NO: 38), GYITTNVLREILKEL (SEQ ID NO: 25), KKMQAMKLEKDNAMD (SEQ ID NO: 188), LQKKIQQIENDLDQT (SEQ ID NO: 189), MEQLMQVNALKDEKD (SEQ ID NO: 190), KALQNAESEVAALNR (SEQ ID NO: 191), AESEVAALNRRIQLL (SEQ ID NO: 192), AALNRRIQLLEEDLE (SEQ ID NO: 193), RSEERLATATAKLAE (SEQ ID NO: 194), LATATAKLAEASQAA (SEQ ID NO: 195), GESKIVELEEELRVV (SEQ ID NO: 196), VELEEELRVVGNNLK (SEQ ID NO: 197), LREEEYKQQIKTLNT (SEQ ID NO: 199), YKQQIKTLNTRLKEA (SEQ ID NO: 200) or ICDDLDMTFTELIGN (SEQ ID NO: 201).

In other embodiments, a Cockroach protein or peptide described herein includes, consists or consists essentially of a protein or peptide having an amino acid sequence set forth as: ALREKVLGLPAIKAWVAKRP (SEQ ID NO: 1), VAISRYLGKQFGLSG (SEQ ID NO: 2), GEPIRFLLSYGEKDFEDYRF (SEQ ID NO: 3), ISDFRAAIANYHYDA (SEQ ID NO: 4), YFVAILDYLNHMAKE (SEQ ID NO: 5), EEFCTLASRFLVEED (SEQ ID NO: 6), PEQIQLLKKAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), SMPFGKTPVLEIDGK (SEQ ID NO: 11), FAVATITHAAELQRV (SEQ ID NO: 12), EQISVLRKAFDAFDREKSGS (SEQ ID NO: 13), EVTLAAKFIIEEDS (SEQ ID NO: 14), PEFQSIVQTLNAMPEYQNLL (SEQ ID NO: 15), PELQNFLNFLEANGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVDSLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELREAFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTLNAMPEYQNLL (SEQ ID NO: 27), PELQNFLNFLEANGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQNFLTVFDSTSCN (SEQ ID NO: 23), ISSQYYIQQNGNLCY (SEQ ID NO: 21), HFFIGDFFVDHYYSE (SEQ ID NO: 18), GEPIRFLLSYGEKDF (SEQ ID NO: 28), FLLSYGEKDFEDYRF (SEQ ID NO: 29), SMPFGKTPVLEIDGK (SEQ ID NO: 11), VAISRYLGKQFGLSG (SEQ ID NO: 2), ISDFRAAIANYHYDA (SEQ ID NO: 4), YFVAILDYLNHMAKE (SEQ ID NO: 5), HMAKEDLVANQPNLK (SEQ ID NO: 31), DLVANQPNLKALREK (SEQ ID NO: 32), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAFDREKSGS (SEQ ID NO: 36), EFVTLAAKFIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38), GYITTNVLREILKEL (SEQ ID NO: 25), DLLGIPHIPVTARKH (SEQ ID NO: 39), LETSPEFKALYDAIR (SEQ ID NO: 40), SPEFQSIVGTLEAMP (SEQ ID NO: 41), LEAMPEYQNLIQKLK (SEQ ID NO: 42), VDHIIELIHQIFNIV (SEQ ID NO: 43), ELIHQIFNIVRDTRG (SEQ ID NO: 44), IFNIVRDTRGLPEDL (SEQ ID NO: 45), LPEDLQDFLALIPTD (SEQ ID NO: 46), QDFLALIPTDQVLAI (SEQ ID NO: 47), LIPTDQVLAIAADYL (SEQ ID NO: 48), QVLAIAADYLANDAE (SEQ ID NO: 49), AADYLANDAEVKAAV (SEQ ID NO: 50), ANDAEVKAAVEYLKS (SEQ ID NO: 51), DSLPEFKNFLNFLQT (SEQ ID NO: 52), FKNFLNFLQTNGLNA (SEQ ID NO: 53), NFLQTNGLNAIEFLN (SEQ ID NO: 54), NGLNAIEFLNNIHDL (SEQ ID NO: 55), IEFLNNIHDLLGIPH (SEQ ID NO: 56), TGLIDDIIAILPVDD (SEQ ID NO: 57), DIIAILPVDDLYALF (SEQ ID NO: 58), LPVDDLYALFQEKLE (SEQ ID NO: 59), LYALFQEKLETSPEF (SEQ ID NO: 60), KALYDAIRSPEFQSE (SEQ ID NO: 61), AIRSPEFQSIVETLK (SEQ ID NO: 62), EFQSIVETLKAMPEY (SEQ ID NO: 63), VETLKAMPEYQSLIQ (SEQ ID NO: 64), AMPEYQSLIQKLKDK (SEQ ID NO: 65), QSLIQKLKDKGVDVD (SEQ ID NO: 66), EDLQDFLALIPIDQI (SEQ ID NO: 67), FLALIPIDQILAIAA (SEQ ID NO: 68), PIDQILAIAADYLAN (SEQ ID NO: 69), DYLANDAEVQAAVEY (SEQ ID NO: 70), AAVEYLKSDEFETIV (SEQ ID NO: 71), LKSDEFETIVVTVDS (SEQ ID NO: 72), FETIVVTVDSLPEFK (SEQ ID NO: 20), LNAIEFNNIHDLLG (SEQ ID NO: 73), FINNIHDLLGIPHIP (SEQ ID NO: 74), HDLLGIPHIPATGRK (SEQ ID NO: 75), VGINGLIDDVIAILP (SEQ ID NO: 76), LIDDVIAILPVDELY (SEQ ID NO: 77), IAILPVDELYALFQE (SEQ ID NO: 78), VDELYALFQEKLESS (SEQ ID NO: 79), ALFQEKLESSPEFKA (SEQ ID NO: 80), RSPEFQSIVQTLKAM (SEQ ID NO: 81), QSIVQTLKAMPEYQD (SEQ ID NO: 82), PEYQDLIQRLKDGV (SEQ ID NO: 83), LIQRLKDKGVDVDHF (SEQ ID NO: 84), DHFIELIKKLFGLSH (SEQ ID NO: 85), VDVDKIIELIRAFLG (SEQ ID NO: 86), IIELIRALFGLTLNA (SEQ ID NO: 87), RALFGLTLNAKASRN (SEQ ID NO: 88), LTLNAKASRNLQDDL (SEQ ID NO: 89), LQDDLQDFLALIPVD (SEQ ID NO: 90), QDFLALIPVDQIIAI (SEQ ID NO: 91), DEFETIVVALDALPE (SEQ ID NO: 92), IVVALDALPELQNFL (SEQ ID NO: 93), IDFLNGIHDLLGIPH (SEQ ID NO: 94), GIHDLLGIPHIPVSG (SEQ ID NO: 95), RKYHIRRGVGITGLI (SEQ ID NO: 96), DDVLAILPIEDLKAL (SEQ ID NO: 97), ILPIEDLKALFNEKL (SEQ ID NO: 98), ETSPDFLALYNAIRS (SEQ ID NO: 99), FLALYNAIRSPEFQS (SEQ ID NO: 100), PEFQSIVQTLNAMPE (SEQ ID NO: 26), IVQTLNAMPEYQNLL (SEQ ID NO: 27), NAMPEYQNLLQKLRE (SEQ ID NO: 101), YQNLLQKLREKGVDV (SEQ ID NO: 102), LIRALFGLTLNGKAS (SEQ ID NO: 103), FGLTLNGKASRNLQD (SEQ ID NO: 104), VDQIIAIATDYLAND (SEQ ID NO: 105), AIATDYLANDAEVQA (SEQ ID NO: 106), AEVQAAVAYLQSDEF (SEQ ID NO: 107), AVAYLQSDEFETIVV (SEQ ID NO: 108), QSDEFETIVVTLDAL (SEQ ID NO: 109), ETIVVTLDALPELQN (SEQ ID NO: 110), PELQNFLNFLEANGL (SEQ ID NO: 16), FLNFLEANGLNAIDF (SEQ ID NO: 111), LNGIHDLLGIPHIPV (SEQ ID NO: 112), DLLGIPHIPVSGRKY (SEQ ID NO: 113), VGITGLIDDVLAILP (SEQ ID NO: 114), LIDDVLAILPLDDLK (SEQ ID NO: 8), LAILPLDDLKALFNE (SEQ ID NO: 115), LDDLKALFNEKLETS (SEQ ID NO: 116), PDFLALYNAIKSPEF (SEQ ID NO: 117), LYNAIKSPEFQSIVQ (SEQ ID NO: 118), MIGLKLVTVLFAVAT (SEQ ID NO: 119), LVTVLFAVATITHAA (SEQ ID NO: 120), FAVATITHAAELQRV (SEQ ID NO: 12), ITHAAELQRVPLYKL (SEQ ID NO: 121), ELQRVPLYKLVHVFI (SEQ ID NO: 122), PLYKLVHVFINTQYA (SEQ ID NO: 19), VHVFINTQYAGITKI (SEQ ID NO: 123), NTQYAGITKIGNQNF (SEQ ID NO: 124), GITKIGNQNFLTVFD (SEQ ID NO: 125), GNQNFLTVFDSTSCN (SEQ ID NO: 23), PNLQKYEKLKPKYIS (SEQ ID NO: 126), YEKLKPKYISDGNVQ (SEQ ID NO: 127), PKYISDGNVQVKFFD (SEQ ID NO: 128), DGNVQVKFFDTGSAV (SEQ ID NO: 129), VKFFDTGSAVGRGIE (SEQ ID NO: 130), GRGIEDSLTISNLTT (SEQ ID NO: 131), LSQEVCILSADVVVG (SEQ ID NO: 132), CILSADVVVGIAAPG (SEQ ID NO: 133), KGKTVLENFVEENLI (SEQ ID NO: 134), LENFVEENLIAPVFS (SEQ ID NO: 135), EENLIAPVFSIHHAR (SEQ ID NO: 136), APVFSIHHARFQDGE (SEQ ID NO: 137), IFGGSDWKYVDGEFT (SEQ ID NO: 138), DWKYVDGEFTYVLPV (SEQ ID NO: 139), DGEFTYVPLVGDDSW (SEQ ID NO: 140), YVPLVGDDSWKFRLD (SEQ ID NO: 141), GDDSWKFRLDGVKIG (SEQ ID NO: 142), PAGTQAIIDTSKAII (SEQ ID NO: 143), AIIDTSKAIIVGPKA (SEQ ID NO: 144), SKAIIVGPKAYVNPI (SEQ ID NO: 145), VGPKAYVNPINEAIG (SEQ ID NO: 146), SLPDVTFVINGRNFN (SEQ ID NO: 147), TFVINGRNFNISSQY (SEQ ID NO: 148), GRNFNISSQYYIQQN (SEQ ID NO: 149), ISSQYYIQQNGNLCY (SEQ ID NO: 21), HFFIGDFFVDHYYSE (SEQ ID NO: 18), DFFVDHYYSEFNWEN (SEQ ID NO: 150), LDYERFRGSWIIAAG (SEQ ID NO: 152), IIAAGTSEALTQYKC (SEQ ID NO: 153), WIDRFSYDDALVSKY (SEQ ID NO: 154), YNDKGKAFSAPYSVL (SEQ ID NO: 155), KAFSAPYSVLATDYE (SEQ ID NO: 156), PYSVLATDYENYAIV (SEQ ID NO: 157), ATDYENYAIVEGCPA (SEQ ID NO: 158), AANGHVIYYQIRFSV (SEQ ID NO: 159), VIYVQIRFSVRRFHP (SEQ ID NO: 160), IRFSVRRFHPKLGKD (SEQ ID NO: 161), EMIQHYTLDQVNQHK (SEQ ID NO: 162), KAIEEDLKHFNLKYE (SEQ ID NO: 163), KHFNLKYEDLHSTCH (SEQ ID NO: 164), KLTYCPVKALGEPIR (SEQ ID NO: 165), GEPIRFLLSYGEKDF (SEQ ID NO: 28), FLLSYGEKDFEDYRF (SEQ ID NO: 29), SMPFGKTPVLEIDGK (SEQ ID NO: 11), VAISRYLGKQFGLSG (SEQ ID NO: 2), NLEIDMIVDTISDFR (SEQ ID NO: 167), MIVDTISDFRAAIAN (SEQ ID NO: 168), ISDFRAAIANYHYDA (SEQ ID NO: 4), TWADFYFVAILDYLN (SEQ ID NO: 171), YFVAILDYLNHMAKE (SEQ ID NO: 5), LDYLNHMAKEDLVAN (SEQ ID NO: 172), HMAKEDLVANQPNLK (SEQ ID NO: 31), DLVANQPNLKALREK (SEQ ID NO: 32), QPNLKALREKVLGLP (SEQ ID NO: 173), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAFDREKSGS (SEQ ID NO: 36), VEEILRLMGQPFNRR (SEQ ID NO: 174), ADKSGRLEFDEFVTL (SEQ ID NO: 175), RLEFDEFVTLAAKFI (SEQ ID NO: 176), EFVTLAAKFIIEEDS (SEQ ID NO: 14), EAMEKELREAFRLYD (SEQ ID NO: 24), CLREILRELDEQLTS (SEQ ID NO: 177), DELDMMIEEIDADGS (SEQ ID NO: 178), SGTVDFDEFMEMMTG (SEQ ID NO: 22), AEQVVLLKKAFDAFD (SEQ ID NO: 179), MVGTILEMLGTRLDQ (SEQ ID NO: 37), GELEFEEFCTLASRF (SEQ ID NO: 180), EEFCTLASRFLVEED (SEQ ID NO: 6), HELREAFRLYDKEGN (SEQ ID NO: 181), DKEGNGYITTAVLRE (SEQ ID NO: 182), GYITTAVLREILKEL (SEQ ID NO: 183), AVLREILKELDDKIT (SEQ ID NO: 184), PEQIQLLKKAFDAFD (SEQ ID NO: 7), MVGTILEMLGHRLDD (SEQ ID NO: 17), DMLQEIIAEVDADGS (SEQ ID NO: 185), GELEFEEFVSLASRF (SEQ ID NO: 186), EEFVSLASRFLVEED (SEQ ID NO: 38), GYITTNVLREILKEL (SEQ ID NO: 25), KKMQAMKLEKDNAMD (SEQ ID NO: 188), LQKKIQQIENDLDQT (SEQ ID NO: 189), MEQLMQVNALKDEKD (SEQ ID NO: 190), KALQNAESEVAALNR (SEQ ID NO: 191), AESEVAALNRRIQLL (SEQ ID NO: 192), AALNRRIQLLEEDLE (SEQ ID NO: 193), RSEERLATATAKLAE (SEQ ID NO: 194), LATATAKLAEASQAA (SEQ ID NO: 195), GESKIVELEEELRVV (SEQ ID NO: 196), VELEEELRVVGNNLK (SEQ ID NO: 197), LREEEYKQQIKTLNT (SEQ ID NO: 199), YKQQIKTLNTRLKEA (SEQ ID NO: 200) or ICDDLDMTFTELIGN (SEQ ID NO: 201).

In further embodiments, a Cockroach protein or peptide described herein includes, consists or consists essentially of a protein or peptide having an amino acid sequence set forth as: ALREKVLGLPAIKAWVAKRP (SEQ ID NO: 1), VAISRYLGKQFGLSG (SEQ ID NO: 2), GEPIRFLLSYGEKDFEDYRF (SEQ ID NO: 3), ISDFRAAIANYHYDA (SEQ ID NO: 4), YFVAILDYLNHMAKE (SEQ ID NO: 5), EEFCTLASRFLVEED (SEQ ID NO: 6), PEQIQLLKKAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), SMPFGKTPVLEIDGK (SEQ ID NO: 11), FAVATITHAAELQRV (SEQ ID NO: 12), EQISVLRKAFDAFDREKSGS (SEQ ID NO: 13), EVTLAAKFIIEEDS (SEQ ID NO: 14), PEFQSIVQTLNAMPEYQNLL (SEQ ID NO: 15), PELQNFLNFLEANGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVDSLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELREAFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTLNAMPEYQNLL (SEQ ID NO: 27), PELQNFLNFLEANGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQNFLTVFDSTSCN (SEQ ID NO: 23), ISSQYYIQQNGNLCY (SEQ ID NO: 21), HFFIGDFFVDHYYSE (SEQ ID NO: 18), GEPIRFLLSYGEKDF (SEQ ID NO: 28), FLLSYGEKDFEDYRF (SEQ ID NO: 29), SMPFGKTPVLEIDGK (SEQ ID NO: 11), VAISRYLGKQFGLSG (SEQ ID NO: 2), ISDFRAAIANYHYDA (SEQ ID NO: 4), EVVKANGGYLAAGLK (SEQ ID NO: 30), YFVAILDYLNHMAKE (SEQ ID NO: 5), HMAKEDLVANQPNLK (SEQ ID NO: 31), DLVANQPNLKALREK (SEQ ID NO: 32), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAFDREKSGS (SEQ ID NO: 36), EFVTLAAKFIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLKKAFDAFD (SEQ ID NO: 7), MVGTILEMLGHRLDD (SEQ ID NO: 17), EEFVSLASRFLVEED (SEQ ID NO: 38) or GYITTNVLREILKEL (SEQ ID NO: 25).

In other embodiments, a Cockroach protein or peptide described herein includes, consists or consists essentially of a protein or peptide having an amino acid sequence set forth as: ALREKVLGLPAIKAWVAKRP (SEQ ID NO: 1), GEPIRFLLSYGEKDFEDYRF (SEQ ID NO: 3), EEFCTLASRFLVEED (SEQ ID NO: 6), PEQIQLLKKAFDAFD (SEQ ID NO: 7), LIDDVLAILPLDDLK (SEQ ID NO: 8), HMAKEDLVANQPNLKALREK (SEQ ID NO: 9), TKKFDEVVKANGGYLAAGKL (SEQ ID NO: 10), FAVATITHAAELQRV (SEQ ID NO: 12), EQISVLRKAFDAFDREKSGS (SEQ ID NO: 13), EVTLAAKFIIEEDS (SEQ ID NO: 14), PEFQSIVQTLNAMPEYQNLL (SEQ ID NO: 15), PELQNFLNFLEANGL (SEQ ID NO: 16), MVGTILEMLGHRLDD (SEQ ID NO: 17), HFFIGDFFVDHYYSE (SEQ ID NO: 18), PLYHLVHVFINTQYA (SEQ ID NO: 19), FETIVVTVDSLPEFK (SEQ ID NO: 20), ISSQYYIQQNGNLCY (SEQ ID NO: 21), SGTVDFDEFMEMMTG (SEQ ID NO: 22), GNQNFLTVFDSTSCN (SEQ ID NO: 23), EAMEKELREAFRLYD (SEQ ID NO: 24), GYITTNVLREILKEL (SEQ ID NO: 25), FETIVVTVDSLPEFK (SEQ ID NO: 20), PEFQSIVQTLNAMPE (SEQ ID NO: 26), IVQTLNAMPEYQNLL (SEQ ID NO: 27), PELQNFLNFLEANGL (SEQ ID NO: 16), LIDDVLAILPLDDLK (SEQ ID NO: 8), FAVATITHAAELQRV (SEQ ID NO: 12), PLYHLVHVFINTQYA (SEQ ID NO: 19), GNQNFLTVFDSTSCN (SEQ ID NO: 23), ISSQYYIQQNGNLCY (SEQ ID NO: 21), HFFIGDFFVDHYYSE (SEQ ID NO: 18), GEPIRFLLSYGEKDF (SEQ ID NO: 28), FLLSYGEKDFEDYRF (SEQ ID NO: 29), SMPFGKTPVLEIDGK (SEQ ID NO: 11), VAISRYLGKQFGLSG (SEQ ID NO: 2), ISDFRAAIANYHYDA (SEQ ID NO: 4), YFVAILDYLNHMAKE (SEQ ID NO: 5), HMAKEDLVANQPNLK (SEQ ID NO: 31), DLVANQPNLKALREK (SEQ ID NO: 32), ALREKVLGLPAIKAW (SEQ ID NO: 33), VLGLPAIKAWVAKRP (SEQ ID NO: 34), EQISVLRKAFDAFDR (SEQ ID NO: 35), LRKAFDAFDREKSGS (SEQ ID NO: 36), EFVTLAAKFIIEEDS (SEQ ID NO: 14), EAMEKELREAFRLYD (SEQ ID NO: 24), SGTVDFDEFMEMMTG (SEQ ID NO: 22), MVGTILEMLGTRLDQ (SEQ ID NO: 37), EEFCTLASRFLVEED (SEQ ID NO: 6), PEQIQLLKKAFDAFD (SEQ ID NO: 7), MVGTILEMLGHRLDD (SEQ ID NO: 17) or EEFVSLASRFLVEED (SEQ ID NO: 38), GYITTNVLREILKEL (SEQ ID NO: 25).

In certain embodiments, a Cockroach protein, peptide, subsequence, portion, homologue, variant or derivative thereof, includes, consists of or consists essentially of an amino acid sequence of a portion of a Cockroach allergen protein or peptide Bla g 1, Bla g 1.0101, Bla g 2, Bla g 4, Bla g 5, Bla g 6, Bla g 6.0101, Bla g 6.0201, Bla g 7.

Thus in particular embodiments, the allergen comprises, consists or consists essentially of an amino acid sequence of Bla g 1.0101 set forth as:

(SEQ ID NO: 202)
NLLEKLREKGVDVDKIIELIRALFGLTLNAKASRNLQDDLQDFLALIPV

DQIIAIATDYLANDAEVQAAVAYLQSDEFETIVVALDALPELQNFLNFL

EANGLNAIDFLNGIHDLLGIPHIPVSGRKYHIRRGVGITGLIDDVLAIL

PIEDLKALFNEKLETSPDFLALYNAIRSPEFQSIVQTLNAMPEYQNLLQ

KLREKGVDVDKIIELIRALFGLTLNGKASRNLQDDLQDFLALIPVDQII

AIATDYLANDAEVQAAVAYLQSDEFETIVVTLDALPELQNFLNFLEANG

LNAIDFLNGIHDLLGIPHIPVSGRKYHIRRGVGITGLIDDVLAILPLDD

LKALFNEKLETSPDFLALYNAIKSPEFQSIVQTLNAMPEYQNLLEKLRE

KGVDVDKIIELIRALFGLTH.

In other embodiments, the allergen comprises, consists or consists essentially of an amino acid sequence of Bla g 1 set forth as:

(SEQ ID NO: 203)
NAIEFLNNIHDLLGIPHIPVTARKHHRRGVGITGLIDDIIAILPVDDLYA

LFQEKLETSPEFKALYDAIRSPEFQSIVGTLEAMPEYQNLIQKLKDKGVD

VDHIIELIHQIFNIVRDTRGLPEDLQDFLALIPTDQVLAIAADYLANDAE

VKAAVEYLKSDEFETIVVTVDSLPEFKNFLNFLQTNGLNAIEFLNNIHDL

LGIPHIPVTGRKHLRRGVGITGLIDDIIAILPVDDLYALFQEKLETSPEF

KALYDAIRSPEFQSIVETLKAMPEYQSLIQKLKDKGVDVDHIIELIHQIF

NIVRDTRGLPEDLQDFLALIPIDQILAIAADYLANDAEVQAAVEYLKSDE

FETIVVTVDSLPEFKNFLNFLQTNGLNAIEFINNIHDLLGIPHIPATGRK

HVRRGVGINGLIDDVIAILPVDELYALFQEKLESSPEFKALYDAIRSPEF

QSIVQTLKAMPEYQDLIQRLKDKGVDVDHFIELIKKLFGLSH.

In other particular embodiments the allergen comprises, consists or consists essentially of an amino acid sequence of Bla g 2 set forth as:

(SEQ ID NO: 204)
MIGLKLVTVLFAVATITHAAELQRVPLYKLVHVFINTQYAGITKIGNQNF

LTVFDSTSCNVVVASQECVGGACVCPNLQKYEKLKPKYISDGNVQVKFFD

TGSAVGRGIEDSLTISNLTTSQQDIVLADELSQEVCILSADVVVGIAAPG

CPNALKGKTVLENFVEENLIAPVFSIHHARFQDGEHFGEIIFGGSDWKYV

DGEFTYVPLVGDDSWKFRLDGVKIGDTTVAPAGTQAIIDTSKAIIVGPKA

YVNPINEAIGCVVEKTTTRRICKLDCSKIPSLPDVTFVINGRNFNISSQY

YIQQNGNLCYSGFQPCGHSDHFFIGDFFVDHYYSEFNWENKTMGFGRSVE

SV.

In other particular embodiments the allergen comprises, consists or consists essentially of an amino acid sequence of Bla g 4 set forth as:

(SEQ ID NO: 205)
AVLALCATDTLANEDCFRHESLVPNLDYERFRGSWIIAAGTSEALTQYKC

WIDRFSYDDALVSKYTDSQGKNRTTIRGRTKFEGNKFTIDYNDKGKAFSA

PYSVLATDYENYAIVEGCPAAANGHVIYVQIRFSVRRFHPKLGDKEMIQH

YTLDQVNQHKKAIEEDLKHFNLKYEDLHSTCH.

In other particular embodiments the allergen comprises, consists or consists essentially of an amino acid sequence of Bla g 5 set forth as:

(SEQ ID NO: 206)
MAPSYKLTYCPVKALGEPIRFLLSYGEKDFEDYRFQEGDWPNLKPSMPFG

KTPVLEIDGKQTHQSVAISRYLGKQFGLSGKDDWENLEIDMIVDTISDFR

AAIANYHYDADENSKQKKWDPLKKETIPYYTKKFDEVVKANGGYLAAGKL

TWADFYFVAILDYLNHMAKEDLVANQPNLKALREKVLGLPAIKAWVAKRP

PTDL.

In other particular embodiments the allergen comprises, consists or consists essentially of an amino acid sequence of Bla g 6.0101 set forth as:

(SEQ ID NO: 207)
MDELPPEQIQLLKKAFDAFDREKKGCISTEMVGTILEMLGHRLDDDMLQE

IIAEVDADGSGELEFEEFVSLASRFLVEEDAEAMQQELREAFRLYDKEGN

GYITTNVLREILKELDDKITAEDLDMMIEEIDSDGSGTVDFDEFMEVMTG

E.

In further particular embodiments the allergen comprises, consists or consists essentially of an amino acid sequence of Bla g 6.0201 set forth as:

(SEQ ID NO: 208)
MDEIPAEQVVLLKKAFDAFDREKKGCISTEMVGTILEMLGTRLDQDMLDE

IIAEVDADGSGELEFEEFCTLASRFLVEEDAEAMQHELREAFRLYDKEGN

GYITTAVLREILKELDDKITAEDLDMMIEEIDSDGSGTVDFDEFMEVMTG

E.

In other particular embodiments the allergen comprises, consists or consists essentially of an amino acid sequence of Bla g 6 set forth as:

(SEQ ID NO: 209)
MADEQLQLPPEQISVLRKAFDAFDREKSGSISTNMVEEILRLMGQPFNRR

TLEELIDEVDADKSGRLEFDEFVTLAAKFIIEEDSEAMEKELREAFRLYD

KEGNGYIPTSCLREILRELDEQLTSDELDMMIEEIDADGSGTVDFDEFME

MMTG.

In other particular embodiments the allergen comprises, consists or consists essentially of an amino acid sequence of Bla g 7 set forth as:

(SEQ ID NO: 210)
MDAIKKKMQAMKLEKDNAMDRALLCEQQARDANIRAEKAEEEARSLQKKI

QQIENDLDQTMEQLMQVNAKLDEKDKALQNAESEVAALNRRIQLLEEDLE

RSEERLATATAKLAEASQAADESERARKILESKGLADEERMDALENQLKE

ARFMAEEADKKYDEVARKLAMVEADLERAEERAETGESKIVELEEELRVV

GNNLKSLEVSEEKANLREEEYKQQIKTLNTRLKEAEARAEFAERSVQKLQ

KEVDRLEDELVHEKEKYKYICDDLDMTFTELIGN.

The foregoing and other Cockroach proteins and peptides set forth herein may be used in the methods and uses and medicaments, including but not limited to methods and uses and medicaments disclosed herein.

In particular embodiments, a protein or peptide includes, consists of or consists essentially of a Cockroach protein or peptide set forth in any of Tables I to X (SEQ ID NOs 1-201) or a subsequence, portion, homologue, variant or derivative thereof, or a protein or peptide set forth in Table I (SEQ ID NOs 1-25) or Table VII (SEQ ID NOs 26-57), or a subsequence, portion, homologue, variant or derivative thereof. Said homologues may have at least 65%, 70, 75, 80, 85, 90 or 95% homology or identity to the corresponding Cockroach protein or peptide set forth in any of Tables I to X (SEQ ID NOs 1-201). Such subsequences may be 7 to 30 amino acids in length, and optionally further where at least 7 amino acids has at least 75%, or at least 80%, 85%, 90% identity or homology to at least 7 contiguous amino acids of the corresponding Cockroach protein or peptide set forth in any of Tables I to X (SEQ ID NOs 1-201), or a protein or peptide set forth in Table I (SEQ ID NOs 1-25) or Table VII (SEQ ID NOs 26-57). Moreover, a subsequence may be 7 to 25 amino acids in length, such as 7 to 20; 8 to 30; 8 to 25; 8 to 20; 9 to 30; 9 to 25; 9 to 20; 10 to 30; 10 to 25; 10 to 30 amino acids in length and wherein at least 8, such as at least 9, 10, 11, 12, 13, 14 or 15 amino acids of the subsequence has at least 75%, such as at least 80%, 85%, 90% identity or homology to at least 8, such as at least 9, 10, 11, 12, 13, 14 or 15 amino acids, respectively, contiguous amino acids of said corresponding Cockroach protein or peptide set forth in any of Tables I to X (SEQ ID NOs 1-201), or a protein or peptide set forth in Table I (SEQ ID NOs 1-25) or Table VII (SEQ ID NOs 26-57).

A variant of a Cockroach protein or peptide, such as a protein or peptide set forth in any of Tables I to X (SEQ ID NOs 1-201) may be a longer peptide, for example, of up to 30 amino acids in length and which includes a corresponding protein or peptide as set forth in any of Tables I to X (SEQ ID NOs 1-252). A variant may also include a peptide of 7 to 30 amino acids in length and which includes a subsequence of at least 7 amino acids having at least 75% identity or homology, such as at least 80 or 85% identity or homology, to at least 7 contiguous amino acids of the corresponding amino acid sequence of a protein or peptides set forth in any of Tables I to X (SEQ ID NOs 1-201), or a protein or peptide set forth in Table I (SEQ ID NOs 1-25) or Table VII (SEQ ID NOs 26-57). A longer variant peptide may be up to 25 amino acids in length, such as up to 24, 23, 22, 21, 20, 19 or 18 amino acids in length. The variant may be a peptide of 7 to 25 amino acids in length, such as 7 to 20; 8 to 30; 8 to 25; 8 to 20; 9 to 30; 9 to 25; 9 to 20; 10 to 30; 10 to 25; 10 to 30 amino acids in length and wherein said subsequence is of at least 8, 9 or 10 amino acids having at least 75% (such as at least 80% or 85%) identity or homology to at least 8, 9 or 10 contiguous amino acids, respectively, of said corresponding protein or peptide set forth in any of Tables I to X (SEQ ID NOs 1-201), or a protein or peptide set forth in Table I (SEQ ID NOs 1-25) or Table VII (SEQ ID NOs 26-57).

As used herein, an "antigen" refers to a substance, including but not limited to a protein or peptide that elicits, induces, stimulates, promotes or enhances an immune response when administered to a subject. An immune response elicited by an antigen may include, but is not limited to, a B cell or a T cell response. An immune response can include a cellular response with a particular pattern of lymphokine/cytokine production (e.g., Th1, Th2), a humoral response (e.g., antibody production), or a combination thereof, to a particular antigen. For example, if a subject previously exposed to an allergen (i.e., is sensitized or is hypersensitive) comes into contact with the allergen again, allergic asthma may develop due to a Th2 response characterized by an increased production of type 2 cytokines (e.g., IL-4, IL-5, IL-9, and/or IL-13) secreted by CD4+ T lymphocytes.

As used herein an "epitope" refers to a region or part of an antigen that elicits an immune response when administered to a subject. In particular embodiments, an epitope may be comprised of a region or part of a Cockroach protein or peptide (e.g, of all or a part of an amino acid sequence of a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). In more particular embodiments, an epitope may be comprised of a region or part of a Cockroach protein or peptide set forth in any of Tables I to X (SEQ ID NOs 1-201), or a protein or peptide set forth in Table I (SEQ ID NOs 1-25) or Table VII (SEQ ID NOs 26-57). In particular aspects, an epitope is a T cell epitope, i.e., an epitope that elicits, stimulates, induces, promotes, increases or enhances a T cell activity, function or response.

An antigen, epitope, allergen, or composition thereof can modulate an undesired or abnormal inflammatory response. An antigen, epitope, allergen, or composition thereof as described herein may alter the Th2 response by, for example, shifting the immune response toward a Th1 phenotype that is less damaging. That is, an altered (or modulated) immune response can decrease, inhibit, suppress, or reduce sensitivity (desensitize) to an antigen, epitope, or allergen, or against inflammatory responses (e.g., allergy, asthma, rash, wheezing, coughing, eye irritation, etc.) caused by an antigen, epitope, or allergen (e.g., a Cockroach protein or peptide set forth in any of Tables I to X (SEQ ID NOs 1-201), or a protein or peptide set forth in Table I (SEQ ID NOs 1-25) or Table VII (SEQ ID NOs 26-57)).

Accordingly, non-limiting examples of antigens and allergens are peptides and proteins having defined amino acid sequences and which comprise T cell epitopes, i.e., elicit, stimulate, induce, promote, increase or enhance a T cell response or activity. Antigens and allergens can be analyzed to determine whether they include at least one T cell epitope using any number of assays (e.g. T cell proliferation assays, lymphokine secretion assays, T cell non-responsiveness studies, etc.).

The term "allergen" refers to an antigen which elicits, induces, stimulates, or enhances an immune response by a cell or the immune system of an exposed animal (e.g., human). An antigen is an allergen when the specific immune response is the development of enhanced sensitivity or a hypersensitivity to the antigen, but the antigen itself is not typically innately harmful. An allergen is therefore a particular type of antigen that can cause development of enhanced or increased sensitivity or hypersensitivity in a subject. For example, an allergen can elicit production of IgE antibodies in predisposed subjects. However, as disclosed herein an allergen need not elicit production of IgE antibodies. Other examples of responses elicited by allergens include T cell responses or activity, such as production of a lymphokine, cytokine, or effector function on other cells. Responses caused by allergens are also described, for example, in Mol. Biol. of Allergy and Immunology, ed. R. Bush, Immunology and Allergy Clinics of North American Series (August 1996). Although the terms "allergen" and "antigen" have a different meaning, reference to "allergen" herein includes reference to "antigen" and reference to "antigen" herein includes reference to "allergen."

Typically, allergens are organic substances, such as proteins, peptides, nucleotides, carbohydrates, lipids, fats, nucleic acid, and combinations or mixtures thereof. Allergen(s) as used herein include, but are not limited to a specific allergen protein, mixture of allergen proteins, an extract of an allergen, chemically or genetically manufactured allergen, or any combination thereof (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a protein or peptide set forth in any of Tables I to X (SEQ ID NOs 1-201), or a protein or peptide set forth in Table I (SEQ ID NOs 1-25) or Table VII (SEQ ID NOs 26-57)).

In certain embodiments, proteins, peptides, subsequences, portions, homologues, variants and derivatives thereof, described herein (e.g., a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) stimulate, induce, promote, increase or enhance an immune response. In particular embodiments, a protein or peptide is a T cell antigen, allergen or epitope. In additional particular embodiments, a protein or peptide, a subsequence, portion, homologue, variant or derivative thereof, elicit, stimulate, promote, induce or enhance a T cell response, which may include but is not limited to a Th2 cell response. In further particular embodiments, a Cockroach protein or peptide, a subsequence, portion, homologue, variant or derivative thereof, modulates, inhibits, or reduces T cell response, which may include but is not limited to a Th2 cell response. In certain embodiments, a T cell response is an anti-allergen immune response, including but not limited to an anti-Cockroach allergen immune response.

As used herein, the term "immune response" includes T cell (cellular) mediated and/or B cell (humoral) mediated immune responses, or both cellular and humoral responses. Exemplary immune responses include T cell responses, e.g., lymphokine production, cytokine production and cellular cytotoxicity. T-cell responses include Th1 and/or Th2 responses. In addition, the term immune response includes responses that are indirectly effected by T cell activation, e.g., antibody production (humoral responses) and activation of cytokine responsive cells, e.g., eosinophils, macrophages. Immune cells involved in the immune response include lymphocytes, such as T cells (CD4+, CD8+, Th1 and Th2 cells, memory T cells) and B cells; antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer (NK) cells; myeloid cells, such as macrophages, eosinophils, mast cells, basophils, and granulocytes.

As set forth herein, a particular immunoglobulin (Ig) isotype may be produced in response to an antigen (allergen). For example, an "IgG antigen" refers to an antigen that induces an IgG antibody response. Likewise, an "IgE antigen" refers to an antigen that induces an IgE antibody response; an "IgA antigen" refers to an antigen that induces an IgA antibody response, and so forth. In certain embodiments, such an immunoglobulin (Ig) isotype produced in response to an antigen may also elicit production of other isotypes. For example, an IgG antigen may induce an IgG antibody response in combination with one more of an IgE, IgA, IgM or IgD antibody response. Accordingly, in certain embodiments, an IgG antigen may induce an IgG antibody response without inducing an IgE, IgA, IgM or IgD antibody response.

The invention encompasses methods and uses and medicaments for reducing, decreasing, preventing the development of sensitization or hypersensitization to an antigen(s) or allergen(s), such as a Cockroach antigen or allergen. Accordingly, in other embodiments, a protein or peptide, subsequence, portion, homologue, variant or derivative thereof (e.g., a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), decreases, inhibits, suppresses or reduces a T cell response, which may include but is not limited to a Th2 cell response. In certain embodiments, the T cell response is an anti-Cockroach allergen immune response, such as a memory T cell response.

In accordance with another aspect of the invention there are provided a Cockroach protein or peptide, a subsequence, portion, homologue, variant or derivative thereof, wherein the protein or peptide elicits, stimulates, induces, promotes, increases or enhances an anti-allergen immune response. In another aspect, there are provided a Cockroach protein or peptide, subsequence, portion, homologue, variant or derivative thereof, wherein the protein or peptide decreases, reduces, inhibits, suppresses or disrupts an anti-allergen immune response.

As will be understood by a person of skill in the art, a protein or a subsequence, portion, homologue, variant or derivative thereof as described herein (e.g., Cockroach protein or peptide set forth in any of Tables I to X (SEQ ID NOs 1-201), or a protein or peptide set forth in Table I (SEQ ID NOs 1-25) or Table VII (SEQ ID NOs 26-57)), may elicit, stimulate, induce, promote, increase or enhance certain elements of an anti-allergen immune response while decreasing, reducing, inhibiting, suppressing or reducing other elements of the anti-allergen response, either contemporaneously or sequentially. In one non-limiting example, a protein or a subsequence, portion, homologue, variant or derivative thereof (e.g., Cockroach protein or peptide set forth in any of Tables I to X (SEQ ID NOs 1-201), or a protein or peptide set forth in Table I (SEQ ID NOs 1-25) or Table VII (SEQ ID NOs 26-57)) may elicit, stimulate, induce, promote, increase or enhance proliferation of regulatory T cells while decreasing, reducing, inhibiting, suppressing or reducing production of proinflammatory lymphokines/cytokines.

An "anti-allergen," "anti-protein," or "anti-peptide immune response" refers to an immune response that is particular or specific for the protein or peptide, e.g., allergen. In such instances, the response is specifically triggered (elicited, stimulated, increased, induced, or promoted) by the protein or peptide, e.g., allergen (e.g., a Cockroach protein or peptide). Although an "anti-allergen" immune response is specifically triggered by a given allergen, the immune response itself can be characterized by general features of immune responses, such as T cell (cellular) and/or B cell (humoral) immune responses, as set forth herein.

As disclosed herein, a Cockroach protein, peptide, subsequence, portion, homologue, variant or derivative thereof, may elicit, stimulate, induce, promote, increase or enhance immunological tolerance to an antigen, including an allergen (e.g., Cockroach protein or peptide set forth in any of Tables I to X (SEQ ID NOs 1-201), or a protein or peptide set forth in Table I (SEQ ID NOs 1-25) or Table VII (SEQ ID NOs 26-57)). In certain embodiments, a Cockroach protein, peptide, subsequence, portion, homologue, variant or derivative thereof, described herein may elicit, stimulate, induce, promote, increase or enhance immunological tolerance to an allergen. Thus in certain embodiments a protein, peptide, subsequence, portion, homologue, variant or derivative thereof, described herein may be effective in use or treatment (e.g., therapeutic) of an allergic reaction or allergic immune response, including but not limited to an allergic response following a secondary or subsequent exposure of a subject to an antigen or allergen. In particular embodiments, immunological tolerance elicited, stimulated, induced, promoted, increased or enhanced from use or administration of a Cockroach protein, peptide, subsequence, portion, homologue, variant or derivative thereof, may involve modulation of T cell activity, including but not limited to CD4+ T cells, CD8+ T cells, Th1 cells, Th2 cells and regulatory T cells (Tregs), and memory T cells. For example, immunological tolerance elicited, stimulated, induced, promoted, increased or enhanced from use or administration of a Cockroach protein, peptide, subsequence, portion, homologue, variant or derivative thereof (e.g., Cockroach protein or peptide set forth in any of Tables I to X (SEQ ID NOs 1-201), or a protein or peptide set forth in Table I (SEQ ID NOs 1-25) or Table VII (SEQ ID NOs 26-57))-inflammatory lymphokines/cytokines produced by T cells. Thus, in accordance with certain aspects of the invention, there are provided Cockroach proteins, peptides, subsequences, portions, homologues, variants and derivatives thereof, that elicit, stimulate, induce, promote, increase or enhance immunological tolerance to an antigen or allergen (e.g., a Cockroach protein or peptide).

Accordingly, methods and uses and medicaments of inducing immunological tolerance in a subject to an allergen are provided. In one embodiment, a method or use reduces occurrence, frequency, severity, progression, or duration of physiological conditions, disorders, illnesses, diseases, symptoms or complications caused by or associated an allergic response to the allergen in the subject. Thus, in various embodiments, inducing immunological tolerance can protect a subject against or treat a subject for an allergic response, allergic disorder or allergic disease, or one or more physiological conditions, disorders, illnesses, diseases, symptoms or complications caused by or associated with an allergen.

As disclosed herein, surprisingly Cockroach proteins and antigens that elicit Th2 immune responses are not a priori IgE reactive. Thus, there are provided methods and uses of providing specific immunotherapy to a subject, in which a subject is administered an amount of a Cockroach protein or peptide that is (or is not) an IgE, IgG, IgA, IgM or IgD reactive antigen. In a particular embodiment, a method or use includes administering to the subject an amount of a Cockroach protein or peptide that is not an IgE reactive antigen.

Also provided are methods and uses and medicaments of providing specific immunotherapy (SIT) to a subject. In one embodiment, a subject is administered an amount of a Cockroach protein or peptide (e.g., Cockroach protein or peptide set forth in any of Tables I to X (SEQ ID NOs 1-201), or a protein or peptide set forth in Table I (SEQ ID NOs 1-25) or Table VII (SEQ ID NOs 26-57)).

In certain embodiments of the invention methods and uses and medicaments, the allergen is a Cockroach protein or peptide (e.g., a Cockroach allergen such as Bla g 1, Bla g 1.0101, Bla g 2, Bla g 4, Bla g 5, Bla g 6, Bla g 6.0101, Bla g 6.0201, Bla g 7). In more particular embodiments, the allergen is an amino acid sequence of Cockroach protein or peptide set forth in any of Tables I to X (SEQ ID NOs 1-201), or a protein or peptide set forth in Table I (SEQ ID NOs 1-25) or Table VII (SEQ ID NOs 26-57), or a subsequence, portion, homologue, variant or derivative thereof. In other non-limiting embodiments, the allergen includes, consists of or consists essentially of a Cockroach protein or peptide set forth in any of Tables I to X (SEQ ID NOs 1-201), or a protein or peptide set forth in Table I (SEQ ID NOs 1-25) or Table VII (SEQ ID NOs 26-57).

An allergic reaction refers to a local or general reaction in a subject following contact with a specific antigen (e.g., allergen) to which the subject had been previously exposed and had become sensitized. The immunologic interaction of antigen (e.g., allergen) with sensitized lymphocytes (T cells) and/or antibody can give rise to inflammation and tissue damage. An allergy is an undesirable immune response or reaction that can therefore produce damage to self-tissues and cells, usually through inflammatory reactions.

One non-limiting example of an allergy is asthma. Asthma, which can be extrinsic or allergic asthma (also referred to as reactive airway disease), is an inflammatory disease of the lungs characterized by a generally reversible airway obstruction. Non-limiting features of allergic asthma include elevated concentrations of serum IgE, pulmonary eosinophilia, airway hyper-responsiveness, excessive airway mucus production, and airway remodeling marked by peribronchiolar collagen deposition and increases in airway smooth muscle mass. Other exemplary allergic reactions or inflammatory conditions include allergic alveolitis, allergic bronchopulmonary aspergillosis, allergic dermatitis, eczema, allergic conjunctivitis, allergic coryza, allergic vasculitis, rhinosinusitis, and allergic rhinitis.

Hypersensitivity or hyper-responsiveness used in reference to an immune response means an abnormal response or condition in which an antigen or allergen elicits an exaggerated immune response. For example, allergic asthma can result from repeated exposure to airborne allergens that trigger detrimental immunological responses, such as persistent inflammation in the bronchial wall, which can in turn cause structural and functional changes in the respiratory system. After allergen contact by sensitized subjects (i.e., those subjects that have already been exposed to the allergen), the immune response is dependent on CD4+ T lymphocytes that are skewed to a T helper (Th) 2 phenotype. Th2 cytokines, for example, IL-4, IL-5, IL-9, and IL-13 are produced and are believed to contribute to asthma pathogenesis. For example, IL-4 drives the T helper response in favor of Th2, resulting in enhanced production of IgE; IL-5, which with granulocyte macrophage colony stimulating factor (GM-CSF) and IL-3, is important for the production of eosinophils; and IL-13, which is required for airway hyper-responsiveness and mucous metaplasia, which are downstream pathophysiological features that are closely linked with clinical asthma. All of these cytokines have been implicated in airway remodeling. Increased numbers of airway eosinophils is also associated with disease severity, although the role of eosinophils in the pathology of asthma is not entirely understood, (see, e.g., Lee et al., *Science* 305:1773 (2004); Humbles et al., *Science* 305:1776 (2004)). The resulting structural and morphometric changes (remodeling) include subepithelial fibrosis, goblet cell hyperplasia and metaplasia, which result in functional consequences such as loss of distensibility of asthmatic airways, bronchial hyper-reactivity (even in the absence of the allergen), and an accelerated progressive decrease in forced expiratory volume at 1 second time intervals. Th2 cytokines may also prime and activate eosinophils to release proinflammatory agents, lipid mediators, and other cytokines thought to contribute to the observed tissue damage, remodeling, and hyper-responsiveness.

As used herein, the term "tolerance," "anergy," or "antigen (allergen)-specific tolerance" refers to a reduction, loss, inhibition, suppression or decrease, of T cells to T cell receptor-mediated stimulation by an allergen or antigen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). The reduction can lead to reduced or non-responsiveness (insensitivity) of T cells to an allergen or antigen. Such insensitivity is generally antigen-specific and persists after exposure to the antigenic peptide has ceased. For example, tolerance in T cells is characterized by lack of lymphokine/cytokine production, e.g., IL-2, IFN-γ, or TNF-β. T-cell anergy occurs when T cells are exposed to antigen or allergen and receive a first signal (a T cell receptor or CD-3 mediated signal) in the absence of a second signal (a costimulatory signal). Under these conditions, re-exposure of the cells to the same antigen or allergen (even if re-exposure occurs in the presence of a costimulatory molecule) results in failure to produce cytokines and subsequently failure of T cells to proliferate. Thus, a failure to produce lymphokines/cytokines prevents proliferation. Tolerized T cells can, however, proliferate if cultured with cytokines (e.g., IL-2). For example, T cell anergy can also be observed by the lack of IL-2 production by T lymphocytes as measured by ELISA or by a proliferation assay using an indicator cell line.

As used herein, the term "immunological tolerance" refers to a) a decreased or reduced level of a specific immunological response (thought to be mediated at least in part by antigen-specific effector T lymphocytes, B lymphocytes, antibody or a combination); b) a delay in the onset or progression of a specific immunological response; or c) a reduced risk of the onset or progression of a specific immunological response to an antigen or allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). "Specific" immunological tolerance occurs when tolerance is preferentially invoked against certain antigens (allergens) in comparison with other antigens (allergens). Tolerance is an active antigen dependent process and differs from non-specific immunosuppression and immunodeficiency.

An increase, improvement, enhancement or induction of "tolerance" refers to a decrease, reduction, inhibition, suppression, or limiting or controlling or clearing of specific immunological reactivity to an antigen (allergen) as compared to reactivity to the antigen in a previous exposure to the same antigen. Thus in certain embodiments, a method or use of inducing immunological tolerance in a subject to an allergen includes elimination of an allergic response of the subject to the allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). Immunological tolerance in a subject to an allergen can also be reflected by reducing the occurrence, frequency, severity, progression, or duration of an allergic response of the subject to the antigen or allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)).

While desirably tolerance can refer to non-reactivity to an antigen or allergen, tolerance need not be complete non-reactivity and can only be partial, and in any event is reflected by a decrease, inhibition, suppression or reduction in specific immunological reactivity to an antigen or allergen as compared to reactivity to the antigen or allergen in a previous exposure to the same antigen or allergen (or epitope thereof). Thus, in another embodiment, a method or use of inducing immunological tolerance in a subject to an allergen includes stabilizing or maintaining the level of an allergic response in the subject to the allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)).

Induction of immune tolerance (also referred to as desensitization), and the relative amount of immune tolerance, can be measured by methods disclosed herein or known to the skilled artisan. For example, induction of immune tolerance can be measured by modulation of lymphokine and/or cytokine level in said animal. As such, modulation can be an increase of a cytokine level, for instance an increase of a cytokine level at least 1.5, 2, 3 times or more relative to before said induction. Alternatively, modulation can be a decrease of the level of a particular cytokine level, for instance a decrease of the cytokine level is at least 1.5, 2, 3 times or more relative to before said induction. The lymphokines/cytokines chosen to measure can be from any relevant lymphokines/cytokines, such as IL-2, IL-5, IL-4, IL-6, IL-10, IL-12, IL-13, TNF-α, IFN-γ, IFN-α, TGF-β, MCP-1, RANK-L and Flt3L.

As disclosed herein, peptides and proteins of the invention are useful in methods and uses and medicaments, for example, of "specific" immunotherapy (SIT). The term "specific" immunotherapy refers to a therapy particular or specific for the protein or peptide, e.g., allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). To achieve "specific immunotherapy" an antigen is administered to a subject in order to achieve immunological tolerance of the subject to an antigen, including for example, an allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)).

More particularly, specific immunotherapy may be conducted by administering an antigen derived from the antigen (e.g. allergen) against which immunological tolerance is sought. Alternatively, immunotherapy can be conducted by "non-specific" immunotherapy using a different antigen or protein than the antigen (allergen) against which immunological tolerance is sought. For example as described in US patent application publication US2012/0100164A1, which relates to the treatment of a hypersensitivity immune response, such as allergic rhinitis or asthma, via bystander suppression by use of an antigen unrelated to the allergen triggering the hypersensitivity immune response in an individual to be treated provided that the antigen is obtainable from the source material, e.g. a Cockroach antigen for treatment of an immune response to another Cockroach allergen (e.g. a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7).

Thus, in different embodiments, the Cockroach antigen administered and antigen (e.g. allergen) against which immunological tolerance is sought may be the same or a different Cockroach protein. In one embodiment, a method or use includes administering to a subject an amount of a Cockroach protein or peptide, or subsequence, portion, homologue, variant or derivative thereof sufficient to elicit, stimulate, induce, promote, increase, enhance or augment immunological tolerance to an allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) in the subject. In one aspect, a Cockroach antigen is administered to a subject during specific immunotherapy to treat the subject for an allergic reaction to the same Cockroach antigen. In a different aspect, a Cockroach antigen is administered to a subject during specific immunotherapy to treat the subject for an allergic reaction to a different Cockroach antigen. In another embodiment, a method includes administering to a subject an amount of a nucleic acid encoding all or a portion (e.g., a T cell epitope) of a Cockroach protein or peptide, or subsequence, portion, homologue, variant or derivative thereof sufficient to elicit, stimulate, induce, promote, increase, enhance or augment immunological tolerance to an allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7) in the subject. In various embodiments, a method or use of specific immunotherapy reduces, inhibits, suppresses or decreases sensitivity or (hyper)sensitivity to the protein or peptide, e.g., allergen, or elicits, stimulates, increases, induces, promotes or improves tolerance of the protein or peptide, e.g., allergen. Typically a subject is administered a protein or peptide, e.g., allergen, for example, via a subcutaneous injection.

Methods and uses include multi-dose regimens. For example, a method or use can begin with small doses of allergen or protein or peptide (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) and the doses are increased for repeated contact or administration.

A variant or derivative of an antigen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), including an allergen as described herein, or a subsequence or portion of an antigen or allergen, include molecules that are structurally similar and functionally similar (e.g, of all or a part of an amino acid sequence in any of Tables I to X (SEQ ID NOs 1-201), or a protein or peptide set forth in Table I (SEQ ID NOs 1-25) or Table VII (SEQ ID NOs 26-57)). A variant, derivative or subsequence of antigen or allergen is functionally similar to the antigen or allergen sequence if the variant, derivative or subsequence is capable of eliciting a detectable or measurable immune response, even if it is a reduced immune response compared to the nonvariant/non-derived or native sequence, which may be determined using methods, including animal models and in vitro assays, described herein and know to one of skill in the art. For example, an immune response may be determined by quantitative and/or qualitative determination of lymphokine/cytokine production (e.g., by T cells), antibody production (including class and/or isotype), cellular mobilization, migration or motility, and optionally in vivo, such as an animal model of antigen/allergen immune responsiveness. An immune response of variant, derivative or subsequence of antigen or allergen compared to the non-variant/non-derivatized/native full length antigen or allergen may be ascertained by analysis of a particular measure (such as lymphokine/cytokine production, immunoglobulin production, cell mobilization, migration, motility, etc.) and may be greater, less than or comparable, e.g., within 5%, 10%, 15%, or 20% or 25% of the immune response of non-variant/non-derivatized/native full length antigen or allergen. For example, levels of Th1 lymphokines/cytokines, such as IFN-γ IL-2, and TNF-β and Th2 cytokines, such as IL-4, IL-5, IL-9, IL-10, and IL-13, may be determined according to methods described herein or known to one of skill in the art.

As disclosed herein, proteins and peptides, or a subsequence, portion, homologue, variant or derivative thereof include those having all or at least partial sequence identity to one or more exemplary proteins and peptides, or a subsequence, portion, homologue, variant or derivative thereof (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). The term "identity" and "identical" and grammatical variations thereof, mean that two or more referenced entities are the same (e.g., peptides or polynucleotide molecules). Thus, where two proteins, peptides, subsequences, portions, homologues, variants or derivatives thereof are identical, they have the same amino acid sequence. The identity can be over a defined area (region or domain) of the sequence. "Areas, regions or domains" of homology or identity mean that a portion of two or more referenced entities share homology or are the same.

Identity can be determined by comparing each position in aligned sequences. A degree of identity between amino acid sequences is a function of the number of identical or matching amino acids at positions shared by the sequences, i.e. over a specified region. Optimal alignment of sequences for comparisons of identity may be conducted using a variety of algorithms, as are known in the art, including the ClustalW program, available at http://clustalw.genom-e.ad.jp, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

As described herein, Cockroach proteins and peptides include homologues of Cockroach proteins and peptides (e.g., of all or a part of any amino acid sequence of any protein or peptide in any of Tables I to X (SEQ ID NOs 1-201), or a protein or peptide set forth in Table I (SEQ ID NOs 1-25) or Table VII (SEQ ID NOs 26-57)). A polypeptide sequence or polynucleotide sequence is a "homologue" of, or is "homologous" to, another sequence if the two sequences have substantial identity over a specified region and a functional activity of the sequences is preserved or conserved, at least in part (as used herein, the term 'homologous' does not infer nor exclude evolutionary relatedness).

Accordingly, in particular embodiments, methods and uses and medicaments of the invention include homologues of peptides and proteins from non-Cockroach allergens, including for example other antigens and allergens, such as non-Cockroach proteins and peptides considered to be homogoues as set forth herein (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). Thus, as a non-limiting example, peptide and protein homologues from non-Cockroach antigens or allergens may be administered or used to modulate immune activity or immune response against a Cockroach allergen or antigen or to treat an allergic reaction, allergic response, allergic disorder or allergic disease associated with a Cockroach allergen or antigen. As another non-limiting example, peptide and protein homologues from non-Cockroach antigens or allergens may be administered or used to modulate immune activity or immune response against a non-Cockroach allergen or antigen or to treat an allergic reaction, allergic response, allergic disorder or allergic disease associated with a non-Cockroach allergen or antigen.

Two polypeptide sequences or polynucleotide sequences are considered to be substantially identical if, when optimally aligned (with gaps permitted), they share at least about 40% sequence identity or greater (e.g. 45%, 50%, 55%, 60%, 65%, 70%, 75%, 80%, 85%, 90%, 95%, 96%, 97%, 98%, 99%, etc. identify over a specific region), for example, over all or a part of any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57), or if the sequences share defined functional motifs (e.g., epitopes). The percent identity can extend over the entire sequence length or a portion of the sequence (e.g., over all or a part of any amino acid sequence in any protein or peptide set forth in any of Tables I to X (SEQ ID NOs 1-201), or a protein or peptide set forth in Table I (SEQ ID NOs 1-25) or Table VII (SEQ ID NOs 26-57)). In particular aspects, the length of the sequence sharing the percent identity is 2, 3, 4, 5 or more contiguous amino acids, e.g., 6, 7, 8, 9, 10, 11, 12, 13, 14, 15, 16, 17, 18, 19, 20, etc. contiguous amino acids (e.g., over all or a part of any amino acid sequence in any protein or peptide set forth in any of Tables I to X (SEQ ID NOs 1-201), or a protein or peptide set forth in Table I (SEQ ID NOs 1-25) or Table VII (SEQ ID NOs 26-57). In additional particular aspects, the length of the sequence sharing the percent identity is 20 or more contiguous amino acids, e.g., 21, 22, 23, 24, 25, 26, 27, 28, 29, 30, 31, 32, 33, 34, 35, etc. contiguous amino acids (e.g., over all or a part of any amino acid sequence in any Cockroach protein or peptide set forth in any of Tables I to X (SEQ ID NOs 1-201), or a protein or peptide set forth in Table I (SEQ ID NOs 1-25) or Table VII (SEQ ID NOs 26-57). In further particular aspects, the length of the sequence sharing the percent identity is 35 or more contiguous amino acids, e.g., 36, 37, 38, 39, 40, 41, 42, 43, 44, 45, 45, 47, 48, 49, 50, etc., contiguous amino acids (e.g., over all or a part of any amino acid sequence in any Cockroach protein or peptide set forth in any of Tables I to X (SEQ ID NOs 1-201), or a protein or peptide set forth in Table I (SEQ ID NOs 1-25) or Table VII (SEQ ID NOs 26-57). In yet further particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, etc. contiguous amino acids (e.g., over all or a part of any amino acid sequence in any Cockroach protein or peptide set forth in any of Tables I to X (SEQ ID NOs 1-201), or a protein or peptide set forth in Table I (SEQ ID NOs 1-25) or Table VII (SEQ ID NOs 26-57).

An "unrelated" or "non-homologous" sequence shares less than 30% identity. More particularly, shares less than about 25% identity, with a protein, peptide or polynucleotide of the invention over a specified region of homology.

A variant or derivative of a protein or peptide refers to a modified or variant form of the protein or peptide, or subsequence, portion or homologue thereof (e.g., over all or a part of any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). Such modified forms, such as amino acid deletions, additions and substitutions, of the proteins and peptides can also be used in the invention uses, methods and compositions, including methods for modulating an immune response, eliciting, stimulating, inducing, promoting, increasing, or enhancing immunological tolerance and protecting and treating subjects against an allergic reaction or response, as set forth herein.

Thus, in accordance with the invention, modified, variant and derivative forms of proteins and peptides, subsequences, portions, and homologues thereof (e.g., of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) are provided that have one or more functions or activities of unmodified, non-variant and non-derivatized forms of proteins and peptides. Such forms, referred to as "modifications", "variants" or "derivatives" and grammatical variations thereof deviate from a reference sequence. For example, as described herein, a protein, peptide, subsequence, portion, or homologue thereof may comprise, consist or consist essentially of an amino acid sequence that is a modification, variant, or derivative of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57). Such modifications, variants, or derivatives may have greater or less activity or function than a reference protein or peptide, such as ability to elicit, stimulate, induce, promote, increase, enhance, activate, modulate, inhibit, decreases, suppress, or reduce an immune response (e.g. a T cell response) or elicit, stimulate, induce, promote, increase or enhance immunological tolerance (desensitize) to an antigen or allergen. Thus, proteins, peptides, or subsequences, portions or homologues thereof include sequences having substantially the same, greater or less relative activity or function as a reference antigen or allergen (e.g., any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) for example, an ability to elicit, stimulate, induce, promote, increase, enhance, activate, modulate, inhibit, suppress, decrease or reduce an immune response (e.g. a T cell response) or elicit, stimulate, induce, promote, increase or enhance immunological tolerance to an antigen or allergen in vitro or in vivo.

A variant or derivative therefore includes deletions, including truncations and fragments; insertions and additions, including tagged polypeptides and fusion proteins; substitutions, for example conservative substitutions, site-directed mutants and allelic variants; and modifications, including peptoids having one or more non-amino acyl groups (q.v., sugar, lipid, etc.) covalently linked to the peptide and post-translational modifications.

Non-limiting examples of modifications include one or more amino acid substitutions (e.g., 1, 2, 3, 4, 5, 6, 7, 8, 9, 10, 11, 12, 13, 14, 15, 16, 17, 18, 19, 20, 20-25, 25-30, 30-50, 50-100, or more residues), additions and insertions (e.g., 1, 2, 3, 4, 5, 6, 7, 8, 9, 10, 11, 12, 13, 14, 15, 16, 17, 18, 19, 20, 20-25, 25-30, 30-50, 50-100, or more residues) and deletions (e.g., 1, 2, 3, 4, 5, 6, 7, 8, 9, 10, 11, 12, 13, 14, 15, 16, 17, 18, 19, 20, 20-25, 25-30, 30-50, 50-100) of a reference protein, peptide, or subsequence or portion thereof (e.g., over all or a part of any amino acid sequence in any protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). In particular embodiments, a modified or variant sequence retains at least part of a function or an activity of unmodified sequence, and can have less than, comparable, or greater, but at least a part of, a function or activity of a reference sequence, for example, the ability elicit, stimulate, induce, promote, increase, enhance, activate, modulate, inhibit, suppress, decrease, or reduce an immune response (e.g. a T cell response) or elicit, stimulate, induce, promote, increase or enhance immunological tolerance to an allergen. Such immune responses include, for example, among others, induced, increased, enhanced, stimulated, activated, modulated, inhibited, suppressed, decreased or reduced expression, production or activity of a cytokine (e.g., IL-5, etc.), an antibody (e.g. increase production of IgG antibodies, decrease production of IgE) or an immune cell (e.g. CD4+ T cell, CD8+ T cell, Th1 cell, Th2 cell or regulatory T cell).

Variants and derivatives of proteins and peptides include naturally-occurring polymorphisms or allelic variants, strain variants, as well as synthetic proteins and peptides that contain a limited number of conservative amino acid substitutions of the amino acid sequence. A variety of criteria can be used to indicate whether amino acids at a particular position in a protein or peptide are similar. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

Specific non-limiting examples of substitutions include conservative and non-conservative amino acid substitutions. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge, or are both hydrophilic or hydrophobic. For example, a conservative amino acid substitution is one in which an amino acid residue is replaced with an amino acid residue having a similar side chain, which include amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); nonpolar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Proline, which is considered more difficult to classify, shares properties with amino acids that have aliphatic side chains (e.g., Leu, Val, Ile, and Ala). In certain circumstances, substitution of glutamine for glutamic acid or asparagine for aspartic acid may be considered a similar substitution in that glutamine and asparagine are amide derivatives of glutamic acid and aspartic acid, respectively. Conservative changes can also include the substitution of a chemically derivatized moiety for a non-derivatized residue, for example, by reaction of a functional side group of an amino acid. Variants and derivatives of proteins and peptides include forms having a limited number of one or more substituted residues.

An addition can be a covalent or non-covalent attachment of any type of molecule. Specific examples of additions include glycosylation, acetylation, phosphorylation, amidation, formylation, ubiquitination, and derivatization by protecting/blocking groups and any of numerous chemical modifications. Additional specific non-limiting examples of an addition are one or more additional amino acid residues. Accordingly, proteins, peptides, subsequences, portions, homologues, variants or derivatives thereof, can be a part of or contained within a larger molecule, such as another protein or peptide sequence, such as a fusion or chimera with a different (distinct) sequence.

In particular embodiments, an addition is a fusion (chimeric) sequence, an amino acid sequence having one or more molecules not normally present in a reference native (wild type) sequence covalently attached to the sequence. The term "chimeric" and grammatical variations thereof, when used in reference to a sequence, means that the sequence contains one or more portions that are derived from, obtained or isolated from, or based upon other physical or chemical entities. For example, a chimera of two or more different proteins may have one part a protein, peptide, subsequence, portion, homologue or variant thereof, and a second part of the chimera may be from a different sequence, or unrelated protein sequence.

Another particular example of a sequence having an amino acid addition is one in which a second heterologous sequence, i.e., heterologous functional domain is attached (covalent or non-covalent binding) that confers a distinct or complementary function. Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), and radioisotope. For example, a tag such as T7 or polyhistidine can be attached in order to facilitate purification or detection of a protein, peptide, etc. Accordingly, there are provided proteins, peptides, subsequences, portions and homologues thereof (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), and a heterologous domain, wherein the heterologous functional domain confers a distinct function on the protein, peptide, subsequence, portion or homologue thereof.

Linkers, such as amino acid or peptidomimetic sequences may be inserted between the sequence and the addition (e.g., heterologous functional domain) so that the two entities maintain, at least in part, a distinct function or activity. Linkers may have one or more properties that include a flexible conformation, an inability to form an ordered secondary structure or a hydrophobic or charged character, which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Further non-limiting examples of additions are detectable labels. Thus, in another embodiment, the invention provides proteins, peptides, subsequences, portions and homologues thereof, that are detectably labeled. Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified.

Another non-limiting example of an addition is an insertion of an amino acid within any protein, peptide, subsequence, portion or homologue thereof (e.g., any protein or sequence set forth herein, such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). In particular embodiments, an insertion is of one or more amino acid residues inserted into the amino acid sequence of a protein or peptide, or subsequence, portion or homologue thereof, such as any Cockroach protein or peptide, such as Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57).

Modified and variant proteins, peptides, subsequences, portions or homologues thereof also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond. Proteins, peptides, subsequences, portions and homologues thereof may be modified in vitro or in vivo, e.g., post-translationally modified to include, for example, sugar residues, phosphate groups, ubiquitin, fatty acids, lipids, etc.

Specific non-limiting examples of modified and variant proteins, peptides, subsequences, portions and homologues thereof include proteins or peptides comprising, consisting or consisting essentially of an amino acid sequence comprising at least one amino acid deletion from a full length Cockroach protein or amino acid sequence such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57). In particular embodiments, a protein, peptide, or subsequence, portion or homologue thereof is from about 2 to up to one amino acid less than the full length protein sequence. In additional particular embodiments, a protein subsequence or portion is from about 2 to 5, 5 to 10, 10 to 15, 15 to 20, 20 to 25, 25 to 50, 50 to 100 amino acids in length, provided that said subsequence or portion is at least one amino acid less in length than the full-length protein sequence.

The term "subsequence" or "portion" means a fragment or part of the full length molecule. A subsequence or portion therefore consists of one or more amino acids less than the full length protein or peptide. A subsequence or portion can have one or more amino acids less than the full length protein or peptide internally or terminal amino acid deletions from either amino or carboxy-termini. Subsequences and portions can vary in size. For example, a subsequence or portion of a protein or peptide can be as small as an epitope capable of binding an antibody (i.e., about five amino acids) up to a polypeptide that is one amino acid less than the entire length of a reference protein or peptide.

As used herein, subsequences and portions may also include or consist of one or more amino acid additions or deletions, wherein the subsequence or portion does not comprise the full length native/wild type protein or peptide sequence. Accordingly, total subsequence or portion lengths can be greater than the length of the full length native/wild type protein or peptide, for example, where a protein or peptide subsequence is fused or forms a chimera with another polypeptide.

The invention provides isolated and/or purified proteins, peptides, subsequences, portions, homologues, variants or derivatives thereof. In particular embodiments, isolated and/or purified proteins, peptides, subsequences, portions, homologues, variants or derivatives thereof, comprise, consist of or consist essentially of an amino acid sequence of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57). In particular embodiments, the isolated and/or purified proteins, peptides, subsequences, portions, homologues, variants or derivatives thereof include a T cell epitope (e.g., Th2 cell epitope).

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

An "isolated" composition (e.g., proteins, peptides, subsequences, portions, homologues, variants or derivatives thereof, for example, of any Cockroach protein or sequence set forth herein, such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) can also be "substantially pure" or "purified" when free of most or all of the materials with which it typically associates with in nature. Thus, an isolated protein, peptide, subsequence, portion, homologue, variant or derivative thereof, that also is substantially pure or purified does not include polypeptides or polynucleotides present among millions of other sequences, such as peptides of an peptide library or nucleic acids in a genomic or cDNA library, for example.

A "substantially pure" or "purified" composition can be combined with one or more other molecules. Thus, "substantially pure" or "purified" does not exclude combinations of compositions, such as combinations of proteins, peptides, subsequences, portions, homologues, variants or derivatives thereof (e.g., multiple proteins, peptides, subsequences, etc.), and other antigens, agents, drugs or therapies.

Proteins and peptide (e.g., antigens and allergens) can be prepared recombinantly, chemically synthesized, isolated from a biological material or source, and optionally modified, or any combination thereof. A biological material or source would include an organism that produced or possessed any proteins or peptide (e.g., antigen or allergen) set forth herein (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). A biological material or source may further refer to a preparation in which the morphological integrity or physical state has been altered, modified or disrupted, for example, by dissection, dissociation, solubilization, fractionation, homogenization, biochemical or chemical extraction, pulverization, lyophilization, sonication or any other means of manipulating or processing a biological source or material. Subsequences, variants, homologues and derivatives can be prepared, for example, by substituting, deleting or adding one or more amino acid residues in the amino acid sequence of a protein, peptide, subsequence, portion or homologue thereof, and screening for biological activity, for example eliciting an immune response. A skilled person will understand how to make such derivatives or variants, using standard molecular biology techniques and methods, described for example in Sambrook et al. (2001) Molecular Cloning: a Laboratory Manual, $3^{rd}$ ed., Cold Spring Harbour Laboratory Press).

The invention also provides protein or peptide (e.g., proteins, peptides, a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57), immobilized on or attached to a substrate. The protein or peptide (e.g., proteins, peptides, subsequences, portions, homologues, variants or derivatives thereof, for example, of any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or any Cockroach protein or peptide set forth in any of Tables I to X (SEQ ID NOs 1-201), or a protein or peptide set forth in Table I (SEQ ID NOs 1-25) or Table VII (SEQ ID NOs 26-57)) can optionally have a unique or distinct position or address on the substrate.

Substrates to which protein or peptide (e.g., proteins, peptides, subsequences, portions, homologues, variants or derivatives thereof, for example, of any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), can be immobilized or attached include essentially any physical entity such as a two dimensional surface that is permeable, semi-permeable or impermeable, either rigid or pliable and capable of either storing, binding to or having attached thereto or impregnated.

Substrates include dry solid medium (e.g., cellulose, polyester, nylon, or mixtures thereof etc.), such as glass, silica, plastic, polyethylene, polystyrene, polypropylene, polyacetate, polycarbonate, polyamide, polyester, polyurethane, or polyvinylchloride. Substrates include structures having sections, compartments, wells, containers, vessels or tubes, separated from each other to avoid or prevent cross-contamination or mixing with each other or with other reagents. Multi-well plates, which typically contain 6, 12, 26, 48, 96, to 1000 wells, are one particular non-limiting example of such a structure.

Substrates also include supports used for two- or three-dimensional arrays of sequences. The sequences are typically attached to the surface of the substrate (e.g., via a covalent bond) at defined positions (locations or addresses). Substrates can include a number of sequences, for example, 1, 2, 3, 4, 5, 5 to 10, 10 to 15, 15 to 20, 20 to 25, 25 to 30, 30 to 35, 35 to 40, 40 to 45, 45 to 50, 50 to 75, 75 to 100, 100 to 150, 150 to 200, 200 to 250, 250 to 300, up to all proteins, peptides, subsequences, portions, homologues, variants or derivatives thereof, such as a Cockroach protein or peptide set forth in any of Tables I to X (SEQ ID NOs 1-201), or a protein or peptide set forth in Table I (SEQ ID NOs 1-25) or Table VII (SEQ ID NOs 26-57). Such substrates, also referred to as "arrays," can have any protein density; the greater the density the greater the number of sequences that can be screened on a given chip. Substrates that include a two- or three-dimensional array of sequences, and individual protein sequences therein, may be coded in accordance with the invention.

The invention also provides nucleic acids encoding proteins, peptides, subsequences, portions, homologues, variants or derivatives thereof, for example, of a Cockroach allergen, such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57). Such nucleic acid sequences encode a sequence at least 40% or more (e.g., 45%, 50%, 55%, 60%, 65%, 70%, 75%, 80%, 85%, 90%, 95%, 96%, 97%, 98%, 99%) identical to an exemplary protein, peptide, subsequence, portion, homologue, variant or derivative thereof. In an additional embodiment, a nucleic acid encodes a sequence having a modification, such as one or more amino acid additions (insertions), deletions or substitutions of protein, peptide, subsequence, portion, homologue, variant or derivative thereof, for example, of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57).

The terms "nucleic acid," "polynucleotide" and "polynucleotide" and the like refer to at least two or more ribo- or deoxy-ribonucleic acid base pairs (nucleotides/nucleosides) that are linked through a phosphoester bond or equivalent. Nucleic acids include polynucleotides and polynucleotides. Nucleic acids include single, double or triplex, circular or linear, molecules. Exemplary nucleic acids include but are not limited to: RNA, DNA, cDNA, genomic nucleic acid, naturally occurring and non-naturally occurring nucleic acid, e.g., synthetic nucleic acid.

Nucleic acids can be of various lengths. Nucleic acid lengths typically range from about 20 bases to 20 Kilobases (Kb), or any numerical value or range within or encompassing such lengths, 10 bases to 10 Kb, 1 to 5 Kb or less, 1000 to about 500 bases or less in length. Nucleic acids can also be shorter, for example, 100 to about 500 bases, or from about 12 to 24, 24 to 45, 45 to 90, 90 to 250, or about 250 to 500 bases in length, or any numerical value or range or value within or encompassing such lengths. In particular aspects, a nucleic acid sequence has a length from about 10-20, 20-30, 30-50, 50-100, 100-150, 150-200, 200-250, 250-300, 300-400, 400-500, 500-1000, 1000-2000 bases, or any numerical value or range within or encompassing such lengths. Shorter nucleic acids are commonly referred to as "oligonucleotides" or "probes" of single- or double-stranded DNA. However, there is no upper limit to the length of such oligonucleotides.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode proteins, peptides, subsequences, portions, homologues, variants or derivatives thereof, (e.g., substitutions, additions, insertions and deletions), for example, of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57).

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to the encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as eukaryote or mammalian cell, yeast or bacteria, in an animal or in a plant).

Nucleic acid may be inserted into a nucleic acid construct in which expression of the nucleic acid is influenced or regulated by an "expression control element." An "expression control element" refers to a nucleic acid sequence element that regulates or influences expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for cell-types or tissues (i.e., tissue-specific control elements).

Nucleic acid can also be inserted into a plasmid for propagation into a host cell and for subsequent genetic manipulation. A plasmid is a nucleic acid that can be propagated in a host cell, plasmids may optionally contain expression control elements in order to drive expression of the nucleic acid encoding proteins, peptides, subsequences, portions, homologues, variants or derivatives thereof in the host cell. A vector is used herein synonymously with a plasmid and may also include an expression control element for expression in a host cell (e.g., expression vector). Plasmids and vectors generally contain at least an origin of replication for propagation in a cell and a promoter. Plasmids and vectors are therefore useful for genetic manipulation and expression of proteins, peptides, subsequences, portions, homologues, variants or derivatives thereof, for example, a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57). Accordingly, vectors that include nucleic acids encoding or complementary to proteins, peptides, subsequences, portions, homologues, variants or derivatives thereof, for example, of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57), are provided.

In accordance with the invention, there are provided particles (e.g., viral particles) and transformed host cells that express and/or are transformed with a nucleic acid that encodes and/or express proteins, peptides, subsequences, portions, homologues, variants or derivatives thereof, for example, of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57). Particles and transformed host cells include but are not limited to virions, and prokaryotic and eukaryotic cells such as bacteria, fungi (yeast), plant, insect, and animal (e.g., mammalian, including primate and human, CHO cells and hybridomas) cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression. The cells may be a primary cell isolate, cell culture (e.g., passaged, established or immortalized cell line), or part of a plurality of cells, or a tissue or organ ex vivo or in a subject (in vivo).

The term "transformed" or "transfected" when used in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid or protein can be stably or transiently transfected or transformed (expressed) in the host cell and progeny thereof. The cell(s) can be propagated and the introduced protein expressed, or nucleic acid transcribed. A progeny of a transfected or transformed cell may not be identical to the parent cell, since there may be mutations that occur during replication.

Expression of proteins, peptides, subsequences, portions, homologues, variants or derivatives thereof and nucleic acid in particles or introduction into target cells (e.g., host cells) can also be carried out by methods known in the art. Non-limiting examples include osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nanocapsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles." Accordingly, viral and non-viral vector means delivery into cells are included.

Cockroach proteins, peptides, subsequences, portions, homologues, variants or derivatives thereof, for example, a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57), are provided, can be employed in various methods and uses and medicaments. Such methods and uses and medicaments include, for example, administration in vitro and in vivo of one or more proteins, peptides, subsequences, portions, homologues, variants or derivatives thereof, such as protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57), or subsequences, portions, homologues, variants or derivatives thereof.

The methods and uses and medicaments provided include methods and uses and medicaments for modulating an immune response, including, among others, methods and uses and medicaments for protecting and treating subjects against a disorder, disease; and methods and uses of and medicaments for providing specific immunotherapy; and methods and uses of detection and diagnosis.

In particular embodiments, methods and uses include administration or delivery of a protein, peptide, subsequence, portion, homologue, variants or derivative thereof described herein (e.g., of any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) to modulate an immune response in a subject, including, for example, modulating an immune response to an allergen or antigen.

As used herein, the term "modulate," means an alteration or effect on the term modified. For example, the term modulate can be used in various contexts to refer to an alteration or effect of an activity, a function, or expression of a polypeptide, gene or signaling pathway, or a physiological condition or response of an organism. In certain embodiments, modulating involves decreasing, reducing, inhibiting, suppressing or disrupting an immune response of a subject to an antigen or allergen. In other embodiments, modulating involves eliciting, stimulating, inducing, promoting, increasing or enhancing an immune response of a subject to an antigen or allergen. Thus, where the term "modulate" is used to modify the term "immune response against an allergen in a subject" this means that the immune response in the subject to the allergen is altered or affected (e.g., decreased, reduced, inhibited, suppressed, limited, controlled, prevented, elicited, promoted, stimulated, increased, induced, enhanced, etc.).

Methods and uses and medicaments for modulating an immune response against an antigen or allergen as described herein may be used to provide a subject with protection against an allergic response or reaction to the allergen, or allergic disorder or allergic disease, or one or more physiological conditions, disorders, illnesses, diseases, symptoms or complications caused by or associated with the allergen. Accordingly, in other embodiments, methods and uses include administering a protein, peptide, subsequence, portion, homologue, variant or derivative thereof described herein (e.g., of any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) to protect or treat a subject against an allergic response, allergic disorder or allergic disease, or one or more physiological conditions, disorders, illnesses, diseases, symptoms or complications caused by or associated with an allergen. In still other embodiments, methods and uses include administering or delivering a protein, peptide, subsequence, portion, homologue, variant or derivative thereof described herein (e.g., of any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) to elicit, stimulate, induce, promote, increase or enhance immunological tolerance of a subject to an antigen or allergen.

In various embodiments, there are provided methods and uses of and medicaments for providing a subject with protection against an allergic response, allergic disorder or allergic disease, or one or more physiological conditions, disorders, illnesses, diseases, symptoms or complications caused by or associated with an allergen. In various aspects, a method or use includes administering to the subject an amount of a protein, peptide, subsequence, portion, homologue, variant or derivative thereof described herein (e.g., any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) sufficient to provide the subject with protection against the allergic response, allergic disorder or allergic disease, or one or more physiological conditions, disorders, illnesses, diseases, symptoms or complications caused by or associated with the allergen.

Methods and uses and medicaments of the invention include providing a subject with protection against an antigen or allergen, or one or more physiological conditions, disorders, illnesses, diseases, symptoms or complications caused by or associated with the exposure to the antigen or allergen, for example, vaccinating the subject to protect against an allergic response to the allergen, for example with any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57). In certain embodiments, methods and uses include protecting the subject against an allergic response or reaction by inducing tolerance of the subject (desensitizing) to the allergen (e.g., any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)).

As used herein, the terms "protection," "protect" and grammatical variations thereof, when used in reference to an allergic response or one or more physiological conditions, disorders, illnesses, diseases, symptoms or complications caused by or associated with the exposure to allergen, means preventing an allergic response, reaction, or one or more physiological conditions, disorders, illnesses, diseases, symptoms or complications caused by or associated with the exposure to the allergen, or reducing or decreasing susceptibility to an allergic response, reaction, or one or more physiological conditions, disorders, illnesses, diseases, symptoms or complications caused by or associated with the exposure to the allergen.

An allergic response includes but is not limited to an allergic reaction, hypersensitivity, an inflammatory response or inflammation. In certain embodiments allergic response may involve one or more of cell infiltration, production of antibodies, production of cytokines, lymphokines, chemokines, interferons and interleukins, cell growth and maturation factors (e.g., differentiation factors), cell proliferation, cell differentiation, cell accumulation or migration (chemotaxis) and cell, tissue or organ damage or remodeling. In particular aspects, an allergic response may include Allergic rhinitis; Onchocercal dermatitis; Atopic dermatitis; allergic conjunctivitis; Drug reactions; Nodules, eosinophilia, rheumatism, dermatitis, rashes, hives, and swelling (NERDS); esophageal and a gastrointestinal allergy.

Allergic responses can occur systemically, or locally in any region, organ, tissue, or cell. In particular aspects, an allergic response occurs in the skin, the upper respiratory tract, the lower respiratory tract, pancreas, thymus, kidney, liver, spleen, muscle, nervous system, skeletal joints, eye, mucosal tissue, gut or bowel.

Methods and uses and medicaments herein include treating a subject for an allergic response, allergic disorder or allergic disease, as well as one or more physiological conditions, disorders, illnesses, diseases, symptoms or complications caused by or associated with an allergen. Such methods and uses include administering to a subject an amount of a protein, peptide, subsequence, portion, homologue, variant or derivative thereof described herein (e.g., any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) sufficient to treat the subject for the allergic response, allergic disorder or allergic disease, or one or more physiological conditions, disorders, illnesses, diseases, symptoms or complications caused by or associated with the allergen.

As will be understood by a person skilled in the art, treating an allergic response, allergic disorder or allergic disease, or one or more physiological conditions, disorders, illnesses, diseases, symptoms or complications caused by or associated with an allergen may include decreasing, reducing, inhibiting, suppressing, limiting, controlling or clearing an allergic response, an allergic disorder or allergic disease, or one or more physiological conditions, disorders, illnesses, diseases, symptoms or complications caused by or associated with the allergen. Thus in certain embodiments, a method or use of treating a subject for a an allergic response, allergic disorder or allergic disease, or one or more physiological conditions, disorders, illnesses, diseases, symptoms or complications caused by or associated with an allergen comprises elimination of the allergic response, allergic disorder or allergic disease, or one or more physiological conditions, disorders, illnesses, diseases, symptoms or complications caused by or associated with the allergen from a subject. In other embodiments, a method or use of treating a subject for an allergic response, allergic disorder or allergic disease, or one or more physiological conditions, disorders, illnesses, diseases, symptoms or complications caused by or associated with an allergen includes reducing occurrence, frequency, severity, progression, or duration of the allergic response, allergic disorder or allergic disease, or one or more physiological conditions, disorders, illnesses, diseases, symptoms or complications caused by or associated with the allergen in the subject. In yet another embodiment, a method or use of treating a subject for an allergic response, allergic disorder or allergic disease, or one or more physiological conditions, disorders, illnesses, diseases, symptoms or complications caused by or associated with an allergen, includes stabilizing the allergic response, allergic disorder or allergic disease, or one or more physiological conditions, disorders, illnesses, diseases, symptoms or complications caused by or associated with the allergen in a subject by preventing an increase in the occurrence, frequency, severity, progression, or duration of the allergic response, allergic disorder or allergic disease, or one or more physiological conditions, disorders, illnesses, diseases, symptoms or complications caused by or associated with contact of the subject with an allergen.

Methods and uses and medicaments of the invention include treating or administering a subject previously exposed to an antigen or allergen. Thus, in certain embodiments, methods and uses and medicaments are for treating or protecting a subject from an allergic response, allergic disorder or allergic disease, or one or more physiological conditions, disorders, illnesses, diseases, symptoms or complications caused by or associated with secondary or subsequent exposure to an antigen or allergen.

Physiological conditions, disorders, illnesses, diseases, symptoms or complications caused by or associated with an antigen/allergen treatable in accordance with the invention methods and uses and medicaments include but are not limited to asthma, allergic asthma, bronchiolitis and pleuritis, Allergic rhinitis; Onchocercal dermatitis; Atopic dermatitis; allergic conjunctivitis; Drug reactions; Nodules, eosinophilia, rheumatism, dermatitis, rashes, hives, and swelling (NERDS); esophageal and a gastrointestinal allergy, Airway Obstruction, Apnea, Asbestosis, Atelectasis, Berylliosis, Bronchiectasis, Bronchiolitis, Bronchiolitis Obliterans Organizing Pneumonia, Bronchitis, Bronchopulmonary Dysplasia, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Rhinoscleroma, Scimitar Syndrome, Severe Acute Respiratory Syndrome, Silicosis, Tracheal Stenosis, eosinophilic pleural effusions, Histiocytosis; chronic eosinophilic pneumonia; hypersensitivity pneumonitis; Allergic bronchopulmonary aspergillosis; Sarcoidosis; Idiopathic pulmonary fibrosis; pulmonary edema; pulmonary embolism; pulmonary emphysema; Pulmonary Hyperventilation; Pulmonary Alveolar Proteinosis; Chronic Obstructive Pulmonary Disease (COPD); Interstitial Lung Disease; and Topical eosinophilia.

Cockroach proteins, peptides, subsequences, portions, homologues, variants and derivatives thereof, described herein may elicit, stimulate, induce, promote, increase or enhance immunological tolerance to an antigen, including an allergen. Methods and uses and medicaments of the invention therefore further include inducing immunological tolerance of a subject to an antigen or allergen. Thus, for example, Cockroach proteins, peptides, subsequences, portions, homologues, variants and derivatives thereof, described herein can be effective in treatment (e.g., therapeutic) of an allergic immune response, including but not limited to an allergic immune response following a secondary or subsequent exposure of a subject to an antigen (allergen). In one embodiment, a method or use includes administering to the subject an amount of a protein, peptide, subsequence, portion, homologue, variant or derivative thereof described herein (e.g., any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) sufficient to induce tolerance in the subject to the antigen or allergen. In particular aspects, the immunological tolerance elicited, stimulated, induced, promoted, increased or enhanced may involve modulation of T cell activity, including but not limited to CD4+ T cells, CD8+ T cells, Th1 cells, Th2 cells and regulatory T cells. For example, immunological tolerance elicited, stimulated, induced, promoted, increased or enhanced from administration of the Cockroach proteins or peptides, or subsequence, portion, homologue, variant or derivative thereof, may involve modulation of the production or activity of pro-inflammatory or anti-inflammatory cytokines produced by T cells.

In additional embodiments, a method or use of inducing immunological tolerance in a subject to an allergen includes a reduction in occurrence, frequency, severity, progression, or duration of physiological conditions, disorders, illnesses, diseases, symptoms or complications caused by or associated an allergic response to the allergen in the subject. Thus, in certain embodiments, inducing immunological tolerance can protect a subject against or treat a subject for an allergic response, allergic disorder or allergic disease, or one or more physiological conditions, disorders, illnesses, diseases, symptoms or complications caused by or associated with an antigen or allergen.

Methods and uses and medicaments for inducing immunological tolerance (desensitizing) described herein may include eliciting, stimulating, inducing, promoting, increasing or enhancing an immune response. In certain embodiments, inducing immunological tolerance may include eliciting, stimulating, inducing, promoting, increasing or enhancing an immune response that decreases, reduces, inhibits, suppresses, limits, controls or clears an allergic response. For example, in certain embodiments inducing immunological tolerance may include eliciting, stimulating, inducing, promoting, increasing or enhancing proliferation or activity of regulatory T cells. In other embodiments, inducing immunological tolerance may include eliciting, stimulating, inducing, promoting, increasing or enhancing an immune response that promotes an allergic response. As will be understood by a person of skill in the art, a method or use that elicits, stimulates, induces, promotes, increases or enhances an immune response that promotes an allergic response may still induce immunological tolerance by also eliciting, stimulating, inducing, promoting, increasing or enhancing an immune response that decreases, reduces, inhibits, suppresses, limits, controls or clears an allergic response. In particular embodiments, inducing immunological tolerance includes eliciting, stimulating, inducing, promoting, increasing or enhancing an immune responses that decreases, reduces, inhibits, suppresses, limits, controls or clears an allergic response that is stronger than the immune response that promotes an allergic response. In other embodiments, inducing immunological tolerance includes eliciting, stimulating, inducing, promoting, increasing or enhancing more immune responses that decrease, reduce, inhibit, suppress, limit, controls or clear an allergic response than immune responses that promote an allergic response.

Methods and uses and medicaments of the invention include treating a subject via specific immunotherapy. In one embodiment, a method or use includes administering to the subject an amount of a protein, peptide, subsequence, portion, homologue, variant or derivative thereof described herein (e.g., any Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). In one aspect, an antigen (allergen) administered to a subject during specific immunotherapy to treat the subject is the same antigen (allergen) to which the subject has been sensitized or is hypersensitive (e.g., allergic). In another non-limiting aspect, an antigen (allergen) administered to a subject to treat the subject is a different antigen (allergen) to which the subject has been sensitized or is hypersensitive (e.g., allergic). Thus, in different embodiments, the antigen administered and antigen (e.g., allergen) against which immunological tolerance is sought may be the same protein (antigen, allergen), may be proteins (antigens, allergens) of the same organism or may be proteins (antigens, allergens) of different organisms.

In accordance with the invention, methods and uses and medicaments include therapeutic (following antigen/allergen exposure) and prophylactic (prior to antigen/allergen exposure) uses and methods. For example, therapeutic and prophylactic methods and uses of treating a subject for an allergic response, allergic disorder or allergic disease, or one or more physiological conditions, disorders, illnesses, diseases, symptoms or complications caused by or associated with an allergen, include but are not limited to treatment of a subject having or at risk of having an allergic response, allergic disorder or allergic disease, or one or more physiological conditions, disorders, illnesses, diseases, symptoms or complications caused by or associated with an allergen; treating a subject with an allergic response, allergic disorder or allergic disease, or one or more physiological conditions, disorders, illnesses, diseases, symptoms or complications caused by or associated with an allergen; and methods and uses and medicaments of protecting a subject from an allergic response, allergic disorder or allergic disease, or one or more physiological conditions, disorders, illnesses, diseases, symptoms or complications caused by or associated with an antigen/allergen (e.g., provide the subject with protection against an allergic reaction to an allergen), to decrease or reduce the probability of an allergic response, allergic disorder or allergic disease, or one or more physiological conditions, disorders, illnesses, diseases, symptoms or complications caused by or associated with an allergen, in a subject and to decrease or reduce susceptibility of a subject to an allergic response, allergic disorder or allergic disease, or one or more physiological conditions, disorders, illnesses, diseases, symptoms or complications caused by or associated with an allergen, to inhibit or prevent an allergic response, allergic disorder or allergic disease, or one or more physiological conditions, disorders, illnesses, diseases, symptoms or complications caused by or associated with an allergen, in a subject. Accordingly, methods and uses and medicaments can treat an allergic response, allergic disorder or allergic disease, or one or more physiological conditions, disorders, illnesses, diseases, symptoms or complications caused by or associated with an allergen, or provide a subject with protection from an allergic response, allergic disorder or allergic disease, or one or more physiological conditions, disorders, illnesses, diseases, symptoms or complications caused by or associated with an allergen (e.g., prophylactic protection).

As described herein, proteins, peptides, subsequences, portions, homologues, variants and derivatives thereof include T cell epitopes, such as Th2 cell epitopes. Accordingly, methods and uses of the invention include administering an amount of a protein, peptide, subsequence, portion, homologue, variant or derivative thereof (e.g., a T cell epitope) to a subject sufficient to provide the subject with protection against an allergic response, allergic disorder or allergic disease, or one or more physiological conditions, disorders, illnesses, diseases, symptoms or complications caused by or associated with an allergen. In another embodiment, a method includes administering an amount of a protein, peptide, subsequence, portion, homologue, variant or derivative thereof (e.g., a T cell epitope, such as a Th2 cell epitope) to a subject sufficient to treat, vaccinate or immunize the subject against an allergic response, allergic disorder or allergic disease, or one or more physiological conditions, disorders, illnesses, diseases, symptoms or complications caused by or associated with an allergen.

In accordance with the invention, methods and uses of modulating anti-allergen activity of T cells, including but not limited to CD8+ T cells, CD4+ T cells, Th1 cells or Th2 cells, in a subject are provided. In one embodiment, a method or use includes administering to a subject an amount of a protein, peptide, subsequence, portion, homologue, variant or derivative thereof (e.g., a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), such as a T cell epitope, sufficient to modulate Th2 cell activity in the subject.

In all methods and uses and medicaments of the invention, any appropriate protein, peptide, subsequence, portion, homologue, variant or derivative thereof can be used or administered. In particular non-limiting examples, the protein, peptide, subsequence, portion, homologue, variant or derivative thereof comprises, consists of or consists essentially of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57), or a subsequence, portion, homologue, variant or derivative thereof.

In certain embodiments, two or more proteins, peptides, subsequences, portions, homologues, variants or derivatives thereof, may be administered to a subject. In particular embodiments, a protein, peptide, subsequence, portion, homologue, variant or derivative thereof consists of or consists essentially of an amino acid sequence of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57), or subsequence, portion, homologue, variant or derivative thereof, and is administered with one or more other proteins, peptides, subsequences, portions, homologues, variants or derivatives thereof. Two or more proteins, peptides, subsequences, portions, homologues, variants or derivatives thereof may be administered as a combination composition, or administered separately, such as concurrently or in series or sequentially. Different proteins, peptides, subsequences, portions, homologues, variants or derivatives thereof, may be administered to a subject in the same amount, volume or concentration, or different amounts, volumes or concentrations. Thus, in certain embodiments, the subject may be administered the same amount of two or more different proteins, peptides, subsequences, portions, homologues, variants or derivatives thereof; and in other embodiments, the subject may be administered one protein, peptide, subsequence, portion, homologue, variant or derivative thereof in an amount, volume or concentration greater than one or more other protein, peptide, subsequence, portion, homologue, variant or derivative thereof administered to the subject.

Methods and uses of the invention include a favorable response or an improvement in one or more physiological conditions, disorders, illnesses, diseases, symptoms or complications caused by or associated with an antigen/allergen. In particular embodiments, a favorable response or improvement includes but is not limited to reduce, decrease, suppress, limit, control or inhibit an allergic response including reducing, decreasing, suppressing, limiting, controlling or inhibiting immune cell proliferation, function or activity, or eliciting, stimulating, inducing, promoting, increasing or enhancing immune cell proliferation or activity (e.g. regulatory T cells); or reduce, decrease, suppress, limit, control or inhibit the amount of allergen. In additional particular embodiments, an amount of a protein, peptide, subsequence, portion, homologue, variant or derivative thereof is sufficient to elicit, stimulate, induce, promote, increase or enhance or augment immunological tolerance to an allergen; or decrease, reduce, inhibit, suppress, prevent, control, or limit an allergic reaction or response. In further particular embodiments, an amount of a protein, peptide, subsequence, portion, homologue, variant or derivative thereof is sufficient to protect a subject from an allergic response or reduce, decrease, limit, control or inhibit susceptibility to an allergic response, allergic disorder or allergic disease, or one or more physiological conditions, disorders, illnesses, diseases, symptoms or complications caused by or associated with an allergen.

Methods and uses of the invention therefore include any therapeutic or beneficial effect. In various methods embodiments, an allergic response, allergic disorder or allergic disease, or one or more physiological conditions, disorders, illnesses, diseases, symptoms or complications caused by or associated with an allergen is reduced, decreased, inhibited, limited, delayed or prevented. Physiological conditions, disorders, illnesses and diseases associated with an antigen/allergen include but are not limited to asthma, allergic asthma, bronchiolitis and pleuritis, Allergic rhinitis; Onchocercal dermatitis; Atopic dermatitis; allergic conjunctivitis; Drug reactions; Nodules, eosinophilia, rheumatism, dermatitis, rashes, hives, and swelling (NERDS); esophageal and a gastrointestinal allergy, Airway Obstruction, Apnea, Asbestosis, Atelectasis, Berylliosis, Bronchiectasis, Bronchiolitis, Bronchiolitis Obliterans Organizing Pneumonia, Bronchitis, Bronchopulmonary Dysplasia, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Rhinoscleroma, Scimitar Syndrome, Severe Acute Respiratory Syndrome, Silicosis, Tracheal Stenosis, eosinophilic pleural effusions, Histiocytosis; chronic eosinophilic pneumonia; hypersensitivity pneumonitis; Allergic bronchopulmonary aspergillosis; Sarcoidosis; Idiopathic pulmonary fibrosis; pulmonary edema; pulmonary embolism; pulmonary emphysema; Pulmonary Hyperventilation; Pulmonary Alveolar Proteinosis; Chronic Obstructive Pulmonary Disease (COPD); Interstitial Lung Disease; and Topical eosinophilia. Symptoms and complications associated with an allergen include but are not limited to cell infiltration, production of antibodies, production of cytokines, lymphokines, chemokines, interferons and interleukins, cell growth and maturation factors (e.g., differentiation factors), cell proliferation, cell differentiation, cell accumulation or migration and cell, tissue or organ damage or remodelling, allergic rhinitis; Onchocercal dermatitis; Atopic dermatitis; allergic conjunctivitis; Drug reactions; Nodules, eosinophilia, rheumatism, dermatitis, rashes, hives, and swelling (NERDS); esophageal and a gastrointestinal allergy. Additional symptoms of antigen/allergen exposure are known to one of skill in the art and treatment thereof in accordance with the invention is provided.

Methods and uses of the invention moreover include reducing, decreasing, inhibiting, delaying or preventing onset, progression, frequency, duration, severity, probability or susceptibility of one or more adverse symptoms, disorders, illnesses, diseases or complications caused by or associated with an antigen/allergen (e.g., any Cockroach allergen). In further various particular embodiments, methods and uses include improving, accelerating, facilitating, enhancing, augmenting, or hastening recovery of a subject from an allergic response, allergic disorder or allergic disease, or one or more physiological conditions, disorders, illnesses, diseases, symptoms or complications caused by or associated with an antigen/allergen. In yet additional various embodiments, methods and uses include stabilizing an allergic response, allergic disorder or allergic disease, or one or more physiological conditions, disorders, illnesses, diseases, symptoms or complications caused by or associated with an antigen/allergen (e.g., any Cockroach allergen).

A therapeutic or beneficial effect is therefore any objective or subjective measurable or detectable improvement or benefit provided to a particular subject. A therapeutic or beneficial effect can but need not be complete ablation of all or any allergic response, allergic disorder or allergic disease, or one or more physiological conditions, disorders, illnesses, diseases, symptoms or complications caused by or associated with an allergen. Thus, a satisfactory clinical endpoint is achieved when there is an incremental improvement or a partial reduction in an allergic response, allergic disorder or allergic disease, or one or more physiological conditions, disorders, illnesses, diseases, symptoms or complications caused by or associated with an allergen, or an inhibition, decrease, reduction, suppression, prevention, limit or control of worsening or progression of an allergic response, allergic disorder or allergic disease, or one or more physiological conditions, disorders, illnesses, diseases, symptoms or complications caused by or associated with an allergen, over a short or long duration (hours, days, weeks, months, etc.).

A therapeutic or beneficial effect also includes reducing or eliminating the need, dosage frequency or amount of a second therapeutic protocol or active such as another drug or other agent (e.g., anti-inflammatory) used for treating a subject having or at risk of having an allergic response, allergic disorder or allergic disease, or one or more physiological conditions, disorders, illnesses, diseases, symptoms or complications caused by or associated with an allergen. For example, reducing an amount of an adjunct therapy, such as a reduction or decrease of a treatment for an allergic response, allergic disorder or allergic disease, or one or more physiological conditions, disorders, illnesses, diseases, symptoms or complications caused by or associated with an allergen, or a specific immunotherapy, vaccination or immunization protocol is considered a beneficial effect. In addition, reducing or decreasing an amount of protein, peptide, subsequence, portion, homologue, variant or derivative thereof, used for specific immunotherapy, vaccination or immunization of a subject to provide protection to the subject is considered a beneficial effect.

As disclosed herein, invention proteins, peptides, subsequences, etc., can be used in methods of providing specific immunotherapy to a subject, such as a subject with or at risk of an allergic response, allergic disorder or allergic disease, or one or more physiological conditions, disorders, illnesses, diseases, symptoms or complications caused by or associated with an allergen. In one embodiment, a method or use includes administering to a subject an amount of a protein, peptide, subsequence, portion, homologue, variant or derivative thereof sufficient to elicit, stimulate, induce, promote, increase, enhance or augment immunological tolerance in the subject to an antigen/allergen. In another embodiment, a method includes administering to a subject an amount of a nucleic acid encoding all or a portion (e.g., a T cell epitope) of a protein, peptide, subsequence, portion, homologue, variant or derivative thereof sufficient to elicit, stimulate, induce, promote, increase, enhance or augment immunological tolerance of the subject to an allergen.

When an antigen(s) or allergen(s) is administered to induce tolerance (desensitize), an amount or dose of the antigen or allergen to be administered (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), and the period of time required to achieve a desired outcome or result (e.g., to desensitize or develop tolerance to the antigen or allergen) can be determined by one skilled in the art. The antigen or allergen may be administered to the patient through any route known in the art, including, but not limited to oral, inhalation, sublingual, epicutaneous, intranasal, and/or parenteral routes (intravenous, intramuscular, subcutaneously, and intraperitoneal).

Methods and uses of the invention include administration of a protein, peptide, subsequence, portion, homologue, variant or derivative thereof to a subject prior to contact by or exposure to an allergen; administration prior to, substantially contemporaneously with or after a subject has been contacted by or exposed to an allergen; and administration prior to, substantially contemporaneously with or after an allergic response, allergic disorder or allergic disease, or one or more physiological conditions, disorders, illnesses, diseases, symptoms or complications caused by or associated with an allergen. A subject contacted by or exposed to an allergen may have contact or exposure over a period of 1-5, 5-10, 10-20, 20-30, 30-50, 50-100 hours, days, months, or years.

Invention compositions (e.g., proteins, peptides, subsequences, portions, homologues, variants or derivatives thereof, including T cell epitopes, for example, of an amino acid sequence of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), methods and uses and medicaments can be combined with any compound, agent, drug, treatment or other therapeutic regimen or protocol having a desired therapeutic, beneficial, additive, synergistic or complementary activity or effect.

Exemplary combination compositions and treatments include multiple proteins, peptides, subsequences, portions, homologues, variants or derivatives thereof such as T cell epitopes as described herein (e.g., of an amino acid sequence of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), and second actives, such as anti-allergen compounds, agents, drugs, treatments and therapies, including but not limited to antihistamines, anti-inflammatories, decongestants and corticosteroids as well as agents that assist, promote, stimulate or enhance efficacy. Such anti-allergen drugs, agents, treatments and therapies can be administered or performed prior to, substantially contemporaneously with or following any method or use described herein, for example, a therapeutic use or method of treating a subject for an allergic response, allergic disorder or allergic disease, or one or more physiological conditions, disorders, illnesses, diseases, symptoms or complications caused by or associated with an allergen, or a method or use of providing specific immunotherapy to a subject.

Accordingly, methods and uses and medicaments include combinations of Cockroach proteins, peptides, subsequences, portions, homologues, variants or derivatives thereof and second actives, and administering as a combination with a second active, or administered separately, such as concurrently or in series or sequentially (prior to or following) to administering a second active to a subject. The invention therefore provides combinations of one or more proteins, peptides, subsequences, portions, homologues, variants or derivatives thereof, in combination with a second active, including but not limited to any compound, agent, drug, therapeutic regimen, treatment protocol, process, remedy or composition, such as anti-histamine, anti-inflammatory, decongestant and corticosteroid, or immune tolerance stimulating, enhancing or augmenting protocol, or specific immunotherapy protocol set forth herein or known in the art. The compound, agent, drug, therapeutic regimen, treatment protocol, process, remedy or composition can be administered or performed prior to, substantially contemporaneously with or following administration of one or more proteins, peptides, subsequences, portions, homologues, variants or derivatives thereof, or a nucleic acid encoding all or a portion (e.g., a T cell epitope) of a protein, peptide, subsequence, portion, homologue, variant or derivative thereof, to a subject. Specific non-limiting examples of combination embodiments therefore include the foregoing or other compound, agent, drug, therapeutic regimen, treatment protocol, process, remedy or composition.

An exemplary combination is a Cockroach protein, peptide, subsequence, portion, homologue, variant or derivative thereof, and a different protein, peptide, or subsequence, portion, homologue, variant or derivative thereof, of an amino acid sequence of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57). Another exemplary combination is a protein, peptide, subsequence, portion, homologue, variant or derivative thereof, and an immunological tolerance inducing molecule.

In invention methods and uses in which there is a desired outcome or effect, such as a therapeutic or prophylactic method or use that provides a benefit from treatment, protection, inducing immunological tolerance, vaccination or specific immunotherapy, a Cockroach protein, peptide, subsequence, portion, homologue, variant or derivative thereof (e.g., a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)) can be administered in a sufficient or effective amount. As used herein, a "sufficient amount" or "effective amount" or an "amount sufficient" or an "amount effective" refers to an amount that provides, in single (e.g., primary) or multiple (e.g., booster) doses, alone or in combination with one or more other compounds, treatments, therapeutic regimens or agents (e.g., a drug), a long term or a short term detectable or measurable improvement in a given subject or any objective or subjective benefit to a given subject of any degree or for any time period or duration (e.g., for minutes, hours, days, months, years, or cured).

An amount sufficient or an amount effective can but need not be provided in a single administration and can but need not be achieved by a particular protein, peptide, subsequence, portion, homologue, variant or derivative thereof, alone, optionally in a combination composition or method or use that includes a second active. In addition, an amount sufficient or an amount effective need not be sufficient or effective if given in single or multiple doses without a second or additional administration or dosage, since additional doses, amounts or duration above and beyond such doses, or additional antigens, compounds, drugs, agents, treatment or therapeutic regimens may be included in order to provide a given subject with a detectable or measurable improvement or benefit to the subject. For example, to increase, enhance, improve or optimize specific immunotherapy, after an initial or primary administration of one or more proteins, peptides, subsequences, portions, homologues, variants or derivative thereof, the subject can be administered one or more additional "boosters" of one or more proteins, peptides, subsequences, portions, homologues, variants or derivatives thereof. Such subsequent "booster" administrations can be of the same or a different type, formulation, dose, concentration, route, etc.

An amount sufficient or an amount effective need not be therapeutically or prophylactically effective in each and every subject treated, nor a majority of subjects treated in a given group or population. An amount sufficient or an amount effective means sufficiency or effectiveness in a particular subject, not a group of subjects or the general population. As is typical for such methods, different subjects will exhibit varied responses to a method of the invention, such as immunization, vaccination, specific immunotherapy and therapeutic treatments.

The term "subject" includes but is not limited to a subject at risk of allergen contact or exposure as well as a subject that has been contacted by or exposed to an allergen. A subject also includes those having or at risk of having or developing an immune response to an antigen or an allergen. Such subjects include mammalian animals (mammals), such as a non-human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, mouse and other animal models of allergic response known in the art.

Accordingly, subjects appropriate for treatment include those having or at risk of exposure to an antigen or allergen, also referred to as subjects in need of treatment. Subjects in need of treatment therefore include subjects that have been exposed to or contacted with an antigen or allergen, or that have an ongoing contact or exposure or have developed one or more adverse symptoms caused by or associated with an antigen or allergen, regardless of the type, timing or degree of onset, progression, severity, frequency, duration of the symptoms.

Target subjects and subjects in need of treatment also include those at risk of allergen exposure or contact or at risk of having exposure or contact to an allergen. Accordingly, subjects include those at increased or elevated (high) risk of an allergic reaction; has, or has previously had or is at risk of developing hypersensitivity to an allergen; and those that have or have previously had or is at risk of developing asthma.

More particular target subjects include subjects allergic to particular Cockroach antigens and/or allergens. In particular embodiments, a subject is allergic to a Cockroach allergen, such as a Cockroach protein or peptide of Bla g 1, Bla g 1.0101, Bla g 2, Bla g 4, Bla g 5, Bla g 6, Bla g 6.0101, Bla g 6.0201, Bla g 7.

Invention compositions, methods and uses and medicaments are therefore applicable to treating a subject who is at risk of allergen exposure or contact but has not yet been exposed to or contacted with the allergen. Prophylactic uses and methods are therefore included. Target subjects for prophylaxis may be at increased risk (probability or susceptibility) of allergen exposure or contact as set forth herein. Such subjects are considered in need of treatment due to being at risk.

Subjects for prophylaxis need not be at increased risk but may be from the general population in which it is desired to protect a subject against an allergic response, allergic disorder or allergic disease, or one or more physiological conditions, disorders, illnesses, diseases, symptoms or complications caused by or associated with an allergen or to provide specific immunotherapy, for example. Such a subject that is desired to be protected against an allergic response, allergic disorder or allergic disease, or one or more physiological conditions, disorders, illnesses, diseases, symptoms or complications caused by or associated with an allergen or to be provided specific immunotherapy can be administered a protein, peptide, subsequence, portion, homologue, variant or derivative thereof. In another non-limiting example, a subject that is not specifically at risk of exposure to or contact by an allergen, but nevertheless desires protection against an allergic response, allergic disorder or allergic disease, or one or more physiological conditions, disorders, illnesses, diseases, symptoms or complications caused by or associated with an allergen, can be administered a protein, peptide, subsequence, portion, homologue, variant or derivative thereof. Such subjects are also considered in need of treatment.

"Prophylaxis" and grammatical variations thereof mean a method or use in which contact, administration or in vivo delivery to a subject is prior to contact with or exposure to an allergen. In certain situations it may not be known that a subject has been contacted with or exposed to an allergen, but administration or in vivo delivery to a subject can be performed prior to manifestation of an allergic response, allergic disorder or allergic disease, or one or more physiological conditions, disorders, illnesses, diseases, symptoms or complications caused by or associated with an allergen. For example, a subject can be provided protection against an allergic response, allergic disorder or allergic disease, or one or more physiological conditions, disorders, illnesses, diseases, symptoms or complications caused by or associated with an allergen or provided specific immunotherapy with a protein, peptide, subsequence, portion, homologue, variant or derivative thereof. In such case, a method or use can eliminate, prevent, inhibit, suppress, limit, decrease or reduce the probability of or susceptibility towards an allergic response, allergic disorder or allergic disease, or one or more physiological conditions, disorders, illnesses, diseases, symptoms or complications caused by or associated with an antigen/allergen.

"Prophylaxis" can also refer to a method or use in which contact, administration or in vivo delivery to a subject is prior to a secondary or subsequent exposure to an antigen/allergen. In such a situation, a subject may have had a prior contact or exposure to an allergen. In such subjects, an acute allergic reaction may but need not be resolved. Such a subject typically may have developed anti-allergen antibodies due to the prior exposure. Immunization or vaccination, by administration or in vivo delivery to such a subject, can be performed prior to a secondary or subsequent allergen exposure. Such a method or use can eliminate, prevent, inhibit, suppress, limit, decrease or reduce the probability of or susceptibility towards a secondary or subsequent allergic response, allergic disorder or allergic disease, or one or more physiological conditions, disorders, illnesses, diseases, symptoms or complications caused by or associated with an allergen. In certain embodiments, such a method or use includes providing specific immunotherapy to the subject to eliminate, prevent, inhibit, suppress, limit, decrease or reduce the probability of or susceptibility towards a secondary or subsequent allergic response, allergic disorder or allergic disease, or one or more physiological conditions, disorders, illnesses, diseases, symptoms or complications caused by or associated with an antigen/allergen.

Treatment of an allergic reaction or response can be at any time during the reaction or response. A protein, peptide, subsequence, portion, homologue, variant or derivative thereof, can be administered as a combination (e.g., with a second active), or separately concurrently or in sequence (sequentially) in accordance with the methods and uses described herein as a single or multiple dose e.g., one or more times hourly, daily, weekly, monthly or annually or between about 1 to 10 weeks, or for as long as appropriate, for example, to achieve a reduction in the onset, progression, severity, frequency, duration of one or more symptoms or complications associated with or caused by an allergic response, allergic disorder or allergic disease, or one or more physiological conditions, disorders, illnesses, diseases, symptoms or complications caused by or associated with an antigen/allergen.

Accordingly, methods and uses of the invention can be practiced one or more times (e.g., 1-10, 1-5 or 1-3 times) an hour, day, week, month, or year. The skilled artisan will know when it is appropriate to delay or discontinue administration. A non-limiting dosage schedule is 1-7 times per week, for 1, 2, 3, 4, 5, 6, 7, 8, 9, 10, 15, 20 or more weeks.

Doses can be based upon current existing protocols, empirically determined, using animal disease models or optionally in human clinical trials. Initial study doses can be based upon animal studies, e.g. a mouse, and the amount of protein, peptide, subsequence, portion, homologue, variant or derivative thereof, administered that is determined to be effective. Exemplary non-limiting amounts (doses) are in a range of about 0.1 mg/kg to about 100 mg/kg, and any numerical value or range or value within such ranges.

Greater or lesser amounts (doses) can be administered, for example, 0.01-500 mg/kg, and any numerical value or range or value within such ranges. The dose can be adjusted according to the mass of a subject, and will generally be in a range from about 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 50 mg/kg, 0-25 mg/kg, or 1.0-10 mg/kg, or any numerical value or range or value within such ranges.

Doses can vary and depend upon whether the treatment is prophylactic or therapeutic, whether a subject has been previously exposed to the antigen/allergen, the onset, progression, severity, frequency, duration, probability of or susceptibility of the symptom, condition, pathology or complication, or vaccination or specific immunotherapy to which treatment is directed, the clinical endpoint desired, previous or simultaneous treatments, the general health, age, gender, race or immunological competency of the subject and other factors that will be appreciated by the skilled artisan. The skilled artisan will appreciate the factors that may influence the dosage and timing required to provide an amount sufficient for providing a therapeutic or prophylactic benefit.

Typically, for treatment, a protein, peptide, subsequence, portion, homologue, variant or derivative thereof, will be administered as soon as practical, typically within 1-2, 2-4, 4-12, 12-24 or 24-72 hours after a subject is exposed to or contacted with an allergen, or within 1-2, 2-4, 4-12, 12-24 or 24-48 hours after onset or development of one or more of an allergic response, allergic disorder or allergic disease, or one or more physiological conditions, disorders, illnesses, diseases, symptoms or complications caused by or associated with an antigen/allergen.

For prophylactic treatment in connection with vaccination or specific immunotherapy, proteins, peptides, subsequences, portions, homologues, variants or derivatives thereof, can be administered for a duration of 0-4 weeks, e.g., 2-3 weeks, prior to exposure to or contact by an allergen or at least within 1-2, 2-4, 4-12, 12-24, 24-48 or 48-72 hours prior to exposure to or contact by an allergen. For an acute allergic reaction, proteins, peptides, subsequences, portions, homologues, variants or derivatives thereof may be administered at any appropriate time.

The dose amount, number, frequency or duration may be proportionally increased or reduced, as indicated by the status of the subject. For example, whether the subject has an allergic response, whether the subject has been exposed to or contacted by an allergen or is merely at risk of allergen contact or exposure, whether the subject is a candidate for or will be vaccinated or provided specific immunotherapy. The dose amount, number, frequency or duration may be proportionally increased or reduced, as indicated by any adverse side effects, complications or other risk factors of the treatment or therapy.

In methods and uses and medicaments of the invention, the route, dose, number and frequency of administrations, treatments, vaccinations and specific immunotherapy, and timing/intervals between treatment, vaccination and specific immunotherapy, and allergen exposure can be modified. Although rapid induction of immune responses or immunological tolerance is desired for developing protective emergency vaccines against an allergic response, allergic disorder or allergic disease, or one or more physiological conditions, disorders, illnesses, diseases, symptoms or complications caused by or associated with an allergen, in certain embodiments, a desirable treatment will elicit robust, long-lasting protection against an allergic response, allergic disorder or allergic disease, or one or more physiological conditions, disorders, illnesses, diseases, symptoms or complications caused by or associated with an allergen. Thus, in certain embodiments, invention compositions, methods and uses and medicaments provide long-lasting protection against an allergic response, allergic disorder or allergic disease, or one or more physiological conditions, disorders, illnesses, diseases, symptoms or complications caused by or associated with an allergen. Specific immunotherapy strategies can provide long-lived protection against an allergic response, allergic disorder or allergic disease, or one or more physiological conditions, disorders, illnesses, diseases, symptoms or complications caused by or associated with an allergen depending on the level of induced immunological tolerance or a T cell response or activity.

Cockroach proteins or peptides, or subsequences, portions, homologues, variants or derivatives thereof can be provided in compositions, and in turn can be used in accordance with the invention methods and uses and medicaments. Such compositions, methods and uses and medicaments include pharmaceutical compositions and formulations. In certain embodiments, a pharmaceutical composition includes one or more Cockroach proteins, peptides, subsequences, portions, homologues, variants or derivatives thereof described herein (e.g., an amino acid sequence of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). In particular, aspects, such compositions and formulations may be a vaccine, including but not limited to a vaccine to protect against an allergic response, allergic disorder or allergic disease, or one or more physiological conditions, disorders, illnesses, diseases, symptoms or complications caused by or associated with an allergen (e.g., a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7).

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

To increase an immune response, immunological tolerance or protection against an allergic response, allergic disorder or allergic disease, or one or more physiological conditions, disorders, illnesses, diseases, symptoms or complications caused by or associated with an allergen, proteins, peptides, subsequences, portions, homologues, variants or derivatives thereof, can be coupled to another protein such as ovalbumin or keyhole limpet hemocyanin (KLH), thyroglobulin or a toxin such as tetanus or cholera toxin. Proteins, peptides, subsequences, portions, homologues, variants or derivatives thereof can also be mixed with adjuvants.

Adjuvants include, for example: oil (mineral or organic) emulsion adjuvants such as Freund's complete (CFA) and incomplete adjuvant (IFA) (WO 95/17210; WO 98/56414; WO 99/12565; WO 99/11241; and U.S. Pat. No. 5,422,109); metal and metallic salts, such as aluminum and aluminum salts, such as aluminum phosphate or aluminum hydroxide, alum (hydrated potassium aluminum sulfate); bacterially derived compounds, such as Monophosphoryl lipid A and derivatives thereof (e.g., 3 De-O-acylated monophosphoryl lipid A, aka 3D-MPL or d3-MPL, to indicate that position 3 of the reducing end glucosamine is de-O-acylated, 3D-MPL consisting of the tri and tetra acyl congeners), and enterobacterial lipopolysaccharides (LPS); plant derived saponins and derivatives thereof, for example Quil A (isolated from the Quilaja *Saponaria molina* tree, see, e.g., "Saponin adjuvants", Archiv. fur die gesamte Virusforschung, Vol. 44, Springer Verlag, Berlin, p243-254; U.S. Pat. No. 5,057,540), and fragments of Quil A which retain adjuvant activity without associated toxicity, for example QS7 and QS21 (also known as QA7 and QA21), as described in WO96/33739, for example; surfactants such as, soya lecithin and oleic acid; sorbitan esters such as sorbitan trioleate; and polyvinylpyrrolidone; oligonucleotides such as CpG (WO 96/02555, and WO 98/16247), polyriboA and polyriboU; block copolymers; and immunostimulatory cytokines such as GM-CSF and IL-1, and Muramyl tripeptide (MTP). Additional examples of adjuvants are described, for example, in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M.

Cosolvents may be added to a protein, peptide, subsequence, portion, homologue, variant or derivative thereof, composition or formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, anti-oxidants and antimicrobial agents.

Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, ribavirin, valacyclovir, ganciclovir, 1,-D-ribofuranosyl-1,2,4-triazole-3 carboxamide, 9→2-hydroxyethoxy methylguanine, adamantanamine, 5-iodo-2'-deoxyuridine, trifluorothymidine, interferon and adenine arabinoside.

Pharmaceutical formulations and delivery systems appropriate for the compositions, methods and uses and medicaments of the invention are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel ad Soklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intranasal, intubation, intrapulmonary instillation, oral, buccal, intrapulmonary, intradermal, topical, dermal, parenteral, sublingual, subcutaneous, intravascular, intrathecal, intraarticular, intracavity, transdermal, iontophoretic, intraocular, opthalmic, optical, intravenous (i.v.), intramuscular, intraglandular, intraorgan, or intralymphatic.

Formulations suitable for parenteral administration include aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Methods and uses of the invention may be practiced by any mode of administration or delivery, or by any route, systemic, regional and local administration or delivery. Exemplary administration and delivery routes include intravenous (i.v.), intraperitoneal (i.p.), intrarterial, intramuscular, parenteral, subcutaneous, intra-pleural, topical, dermal, intradermal, transdermal, transmucosal, intra-cranial, intraspinal, rectal, oral (alimentary), mucosal, inhalation, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, or intralymphatic.

For oral administration, a composition can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, a composition can be delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Invention Cockroach proteins and peptides, e.g., a protein or peptide set forth in any of Tables I to X (SEQ ID NOs 1-201), or a protein or peptide set forth in Table I (SEQ ID NOs 1-25) or Table VII (SEQ ID NOs 26-57)), subsequences, portions, homologues, variants or derivatives thereof optionally along with any adjunct agent, compound, drug, composition, whether active or inactive, etc., can be packaged in unit dosage form (capsules, tablets, troches, cachets, lozenges) for ease of administration and uniformity of dosage. A "unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Individual unit dosage forms can be included in multi-dose kits or containers. Pharmaceutical formulations can be packaged in single or multiple unit dosage form for ease of administration and uniformity of dosage.

The invention also provides methods of diagnosing and detecting an allergic response or allergy in a subject. The methods can be performed in solution, in solid phase, in silica, in vitro, in a cell, and in vivo. In one embodiment, a method includes contacting a cell (e.g., T cell) from the subject with a Cockroach protein, peptide, subsequence, portion, homologue, variant or derivative thereof, as described herein (e.g., of an amino acid sequence of a Cockroach allergen such as a protein or of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)); and determining if the protein or peptide modulates an immune response or activity of the contacted cell (e.g., T cell). A determination that the Cockroach protein or peptide modulates an immune response or immune activity of the contacted cell indicates that the subject has an allergic response or an allergy, in particular, an allergy to the protein, peptide, subsequence, portion, homologue, variant or derivative thereof (e.g., of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)). In a particular aspect, the immune activity determined is Th2 cell reactivity. In another particular aspect, immune response or activity is determined by assaying for a cutaneous immunological hypersensitive reaction.

The terms "determining," "assaying" and "measuring" and grammatical variations thereof are used interchangeably herein and refer to either qualitative or quantitative determinations, or both qualitative and quantitative determinations, that involve manipulation or processing. When the terms are used in reference to measurement or detection, any means of assessing the relative amount, including the various methods set forth herein and known in the art, performed by the hand of man, is contemplated.

The invention provides kits including Cockroach protein, peptide, subsequence, portion, homologue, variant or derivative thereof (e.g., of an amino acid sequence of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), combination compositions and pharmaceutical formulations thereof, packaged into suitable packaging material. Kits can be used in various in vitro, ex vivo and in vivo methods and uses, for example a treatment method or use as disclosed herein.

A kit typically includes a label or packaging insert including a description of the components or instructions for use in vitro, in vivo, or ex vivo, of the components therein. A kit can contain a collection of such components, e.g., a Cockroach protein, peptide, subsequence, portion, homologue, variant or derivative thereof (e.g., of an amino acid sequence of a Cockroach protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), alone, or in combination with another therapeutically useful composition (e.g., an immune modulatory drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, use, treatment protocol or therapeutic regimen. Instructions can include dosage amounts, frequency or duration, and instructions for practicing any of the methods and uses, treatment protocols or therapeutic regimes set forth herein. Exemplary instructions include, instructions for modulating an immune response or activity of a cell against an allergen; modulating an immune response against an allergen in a subject; desensitizing, or inducing, eliciting, increasing or improving immunological tolerance to a protein or peptide allergen; reducing risk or providing a subject protection against an allergic reaction, allergic response, allergic disorder or allergic disease; treating an allergic reaction, allergic response, allergic disorder or allergic disease; or detecting an allergic response or diagnosing an allergy in a subject (e.g., a Cockroach allergy such as to a protein or peptide of Bla g 1, Bla g 1.0101, Bla g 2, Bla g 4, Bla g 5, Bla g 6, Bla g 6.0101, Bla g 6.0201, Bla g 7).

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain to the protein, peptide, subsequence, portion, homologue, variant or derivative thereof (e.g., of a Cockroach allergen such as a protein or peptide of Bla g 1, Bla g 1.0101, Bla g 2, Bla g 4, Bla g 5, Bla g 6, Bla g 6.0101, Bla g 6.0201, Bla g 7, or a Cockroach protein or peptide set forth in any of Tables I to X (SEQ ID NOs 1-201), or a protein or peptide set forth in Table I (SEQ ID NOs 1-25) or Table VII (SEQ ID NOs 26-57)), or combination compositions or pharmaceutical compositions.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the invention is not entitled to antedate such publication by virtue of prior invention.

As used in this specification and the appended claims, the use of an indefinite article or the singular forms "a," "an" and "the" include plural reference unless the context clearly dictates otherwise. In addition, it should be understood that the individual peptides, proteins, antigens, allergens (referred to collectively as compositions), or groups of compositions, modeled or derived from the various components or combinations of the compositions, and substituents described herein, are disclosed by the application to the same extent as if each composition or group of compositions was set forth individually. Thus, selection of particular peptides, proteins, antigens, allergens, etc. is clearly within the scope of the invention.

As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs. As used herein, "about" means + or −5%. The use of the alternative (e.g., "or") should be understood to mean one, both, or any combination thereof of the alternatives, i.e., "or" can also refer to "and."

As used in this specification and the appended claims, any concentration range, percentage range, ratio range or other integer range is to be understood to include the value of any integer within the recited range and, when appropriate, fractions thereof (such as one tenth and one hundredth of an integer), unless otherwise indicated. For example, although numerical values are often presented in a range format throughout this document, a range format is merely for convenience and brevity and should not be construed as an inflexible limitation on the scope of the invention. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, to illustrate, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 5-10, 10-20, 20-30, 30-40, 40-50, 50-75, 75-100, 100-150, and 150-175, includes ranges such as 5-20, 5-30, 5-40, 5-50, 5-75, 5-100, 5-150, 5-171, and 10-30, 10-40, 10-50, 10-75, 10-100, 10-150, 10-175, and 20-40, 20-50, 20-75, 20-100, 20-150, 20-175, and so forth. Further, for example, reference to a series of ranges of 2-72 hours, 2-48 hours, 4-24 hours, 4-18 hours and 6-12 hours, includes ranges of 2-6 hours, 2, 12 hours, 2-18 hours, 2-24 hours, etc., and 4-27 hours, 4-48 hours, 4-6 hours, etc.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. The invention is further exemplified by way of the following non-limited examples.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. The invention is further exemplified by way of the following non-limited examples.

The invention is further exemplified by way of the following non-limited examples.

EXAMPLES

Example 1

This example includes a description of various materials and methods.

Patient donor population: Patient recruitment for this study was performed under three IRB protocols. The first two were conducted at Johns Hopkins University, one as part of the NIAID-funded Inner City Asthma Consortium (ICAC) (NIAID Protocol Number ICAC-18), and the second NIAID sponsored, but separate from ICAC. All participants came from the Baltimore area, were aged 18-55 and had a history of allergic rhinitis and/or asthma, and sensitivity to Cockroach. Thirty individuals provided 100 ml of blood for PBMCs and 20 ml serum samples. A subset of 9 study participants provided samples both prior to and 6 months after the initiation of subcutaneous immunotherapy for German Cockroach (SCITCO), after receiving biweekly dose escalations for 11-12 weeks followed by 14 weeks of weekly maintenance injections. Clinical case histories and other information were collected and recorded by the local clinical investigators. IgE specific for German CR extract was used to determine sensitivity to German CR. For a subset of patients that received immunotherapy, skin test reactivity to German CR was also performed by standard methods and both wheal (mm) and flare (mm) were measured.

The third group of study participants (n=4) were from the greater San Diego area, and were recruited under LIAI protocol VD1-059-0311, with Institutional Review Board approval (Federal Wide Assurance #00000032). Informed consent, study ID numbers, clinical case histories and other information were collected and recorded by clinical investigators. Skin test reactivity to a panel of extracts from 32 common allergens, including German CR, was determined by standard methods. Both wheal (mm) and flare (mm) were measured. All volunteers were asked to provide a 5 ml serum sample and 400 ml peripheral blood. IgE specific for German CR extract was also determined in this patient cohort.

Bioinformatic analyses: Nine Bla g allergen sequences, including isoforms, were considered and scanned for unique 15-mer peptides (UniProt ID: O96522, P54958, P54962, O18598, Q9NG56, Q9UAM5, Q1A7B3, Q1A7B2, Q1A7B1). Additional variants of these allergens are known, especially for Bla g 4, which has very frequent sequence variations that are quite disparate in discrete regions, with 0-32 substitutions (82.4-100% identity) (33, 34). However, the present analysis was limited to include only those sequences found in the International Union of Immunological Societies database. Each peptide was predicted for the capacity to bind to a panel of 20 HLA class II alleles (DPA1*0103/DPB1*0201, DPA1*0201/DPB1*0101, DPA1*0201/DPB1*0501, DPA1*0301/DPB1*0402, DQA1*0101/DQB1*0501, DQA1*0301/DQB1*0302, DQA1*0401/DQB1*0402, DQA1*0501/DQB1*0301, DRB1*0101, DRB1*0301, DRB1*0401, DRB1*0405, DRB1*0701, DRB1*0802, DRB1*1101, DRB1*1302, DRB1*1501, DRB3*0101, DRB4*0101, DRB5*0101) using the consensus prediction described by Wang et al. (35). Peptides with predicted binding scores in the top 20% for a given allele were considered potential binders, and the number of HLA molecules each peptide was predicted to bind was enumerated. All peptides predicted to bind seven or more HLA molecules were selected for synthesis and further study.

Peptide synthesis: Peptides for screening studies were purchased from Mimotopes (Clayton, Victoria, Australia) and/or A and A (San Diego, Calif.) as crude material on a small (1 mg) scale. Peptides utilized as radiolabeled ligands were synthesized on larger scale, and purified (>95%) by reversed phase HPLC.

HLA binding assays: Assays to quantitatively measure peptide binding to MHC class II molecules are based on the inhibition of binding of a high-affinity radiolabeled peptide to purified MHC molecules, and they have been described in detail elsewhere (36). Briefly, MHC molecules were purified from EBV-transformed homozygous cell lines by mAb-based affinity chromatography. HLA-DR, -DQ, and -DP molecules were captured by repeated passage of lysates over LB3.1 (anti-HLA-DR), SPV-L3 (anti-HLA-DQ), and B7/21 (anti-HLADP) columns.

For inhibition experiments, 0.1-1 nM radiolabeled peptide was coincubated at room temperature or 37° C. with 1 mM to 1 nM purified MHC in the presence of a mixture of protease inhibitors and various amounts of inhibitor peptide. Following a 2- to 4-d incubation, the percentage of MHCbound radioactivity was determined by capturing MHC/peptide complexes on LB3.1 (DR), L243 (DR), HB180 (DR/DQ/DP), SPV-L3 (DQ), or B7/21 (DP) Ab-coated OptiPlates (Packard Instrument, Meriden, Conn.), and bound cpm were measured using the TopCount (Packard Instrument) microscintillation counter. Inhibitor peptides were tested in at least three independent assays at six different concentrations covering a 100,000-fold dose range. Under the conditions used, where [label], [MHC] and $IC_{50} \geq$ [MHC], the measured $IC_{50}$ values are reasonable approximations of the true $K_d$ values (37, 38).

PBMC isolation and HLA typing: PBMC were obtained by density gradient centrifugation (Ficoll-Hypaque, Amerhsam Biosiences, Uppsala, Sweden) from one unit of blood (450 ml), according to manufacturer's instructions, and cryo-preserved for further analysis. HLA typing was performed according to standard methods (Blood system Laboratories, Tempe, Ariz., USA).

In vitro expansion of Bla g-specific T cells: PBMC were cultured in RPMI 1640 (V Scientific, Tarzana, Calif.) supplemented with 5% human serum (Cellgro, Herndon, Va.) at a density of $2 \times 10^6$ cells/ml in 24-well plates (BD Biosciences, San Jose, Calif.) and stimulated with 25 µg/ml German Cockroach (*Blatella germanica*; Bla g) extract (Greer, Lenoir, N.C.), or individual peptides. Cells were cultured at 37° C. in 5% $CO_2$ and additional IL-2 (10 U/ml; eBioscience, San Diego, Calif.) was added every 3 days after initial antigenic stimulation. On day 14, cells were harvested and screened for reactivity against Bla g-specific peptide pools or individual peptides.

ELISPOT assays: The production of IL-5, IFN-γ, and IL-10 was analyzed in ELISPOT assays. Flat-bottom 96-well nitrocellulose plates (Millipore, Bedford, Mass.) were prepared according to manufacturer s instructions and coated with either 10 µg/ml anti-human IL-5 (Clone TRFK5; Mabtech, Cincinnati, Ohio), anti-human IFN-γ (Clone 1-D1K; Mabtech), or anti-human IL-10 (Clone 9D7, Mabtech). Cells were then incubated at a density of $1 \times 10^5$/well either with peptide pools or individual peptides (10 µg/ml), German Cockroach extract (25 µg/ml), PHA (10 µg/ml), or medium (containing 1% DMSO corresponding to the percentage of DMSO in the pools/peptides) as a control. After 24 hours, cells were removed, and plates were incubated with either 2 µg/ml biotinylated anti-human IL-5 Ab (Clone 5A10, Mabtech) and 1:200 HRP-conjugated anti-human IFN-γ Ab (Clone 7-B6-1, Mabtech) or 2 µg/ml biotinylated anti-human IL-10 Ab (Clone 12G8, Mabtech) at 37° C. After 2 hours, spots corresponding to the biotinylated Abs (IL-5, IL-10) were developed by incubation with Alkaline Phosphatase-Complex (Vector Laboratories, Burlingame, Calif.) followed by incubation with Vector Blue Alkaline Phosphatase Substrate Kit III (Vector Laboratories) according to the manufacturer's instructions. Spots corresponding to the HRP-conjugated Ab (IFN-γ) were developed with 3-amino-9-ethylcarvazole solution (Sigma-Aldrich, St. Louis, Mo.). Spots were counted by computer-assisted image analysis (Zeiss, KS-ELISPOT reader, Munich, Germany).

Each assay was performed in triplicate. The level of statistical significance was determined with a Student's t-test using the mean of triplicate values of the response against relevant pools or individual peptides versus the response against the DMSO control. Criteria for peptide pool positivity were 100 spot-forming cells (SFCs)/$10^6$ PBMC, $p \leq 0.05$ and a stimulation index (SI)$\geq 2$, while criteria for individual peptide positivity were $\geq 20$ SFC/$10^6$ PBMC, $p \leq 0.05$, and a SI$\geq 2$.

HLA restriction: To determine the HLA locus restriction of identified epitopes, mAb inhibition assays were performed. After 14 days of stimulation with German Cockroach extract (50 µg/ml) or specific peptide (10 µg/ml), for locus or allele restriction assays, respectively, PBMCs were incubated with 10 µg/ml of mAbs (Strategic Biosolutions, Windham, Me.) against HLA-DR (LB3.1), DP (B7/21) or DQ (SVPL3) 30 min prior to peptide addition. Cytokine production against positive peptides was then measured in ELISPOT assays as described above. The pan MHC class I Ab (W6/32) was used as a control. A restricting locus was identified by $\geq 50\%$ inhibition of the response by the corresponding mAb.

To determine the specific HLA allele restriction, donor derived T cells were expanded for 10 days using a single epitope peptide and were then subsequently incubated with peptide pulsed EBV cell lines and/or fibroblasts expressing known HLA molecules also expressed in the donor from whom T cells were derived. Cytokine specific ELISPOT assays were performed as described above to determine cytokine production and allele restriction determined by analyzing a matrix of negative and positive cytokine responses with the HLA expressing EBV lines and fibroblasts used.

Serological determinations: Sera were analyzed for specific IgE antibody binding to rBla g 1, rBla g 2, rBla g 4, rBla g 5 and rPer a 7 using allergen-coated streptavidin-ImmunoCAPs. Recombinant allergens were expressed in *Pichia pastoris* (rBla g 1, rBla g 2, rBla g 4, rPer a 7) or *Escherichia coli* (rBla g 5) and purified by affinity chromatography. Purified allergens were biotinylated and bound to streptavidin-coated ImmunoCAPs (Phadia US Inc., Portage, Mich.) at an optimized amount of 1 µg per ImmunoCAP. Specific IgE antibody binding to extracts from *Blattella germanica* (i6), *Dermatophagoides pteronyssinus* (d1) and *D. farinae* (d2), and total IgE antibody were also measured by ImmunoCAP analysis.

Example 2

This example includes data demonstrating heterogeneity and immunodominance in T cell response to German Cockroach allergens in allergic donors.

Disclosed herein is a strategy to identify T cell epitopes derived from common allergens based on the observation that while responses to complex allergens in humans are very heterogeneous and involve recognition of a large number of epitopes, a relatively small number of the most dominant and prevalent responses encompass a significant fraction of the total response (32). As disclosed herein, these epitopes can be predicted on the basis of their capacity to bind a panel of HLA class II molecules representative of most frequent alleles expressed at the DR, DP and DQ loci. This approach was used as an initial screen in an effort to identify T cell epitopes derived from German Cockroach allergens, denominated Bla g.

To identify dominant Bla g T cell epitopes, PBMC donations were obtained from 34 different allergic donors. Allergic status was defined as a positive skin test reaction (>3 mm) and RAST IgE to Bla g extract>0.35 kU/L. The sequences of six previously described Bla g allergens (Bla g 1, 2, 4, 5, 6 and 7) were selected for analysis, including known isoallergens described in the WHO/IUIS Allergen Nomenclature Database (www.allergen.org). These sequences were scanned with predictive algorithms specific for 20 different common HLA DR, DP and DQ molecules, representative of the most common molecules encountered in the general population, irrespective of ethnicity (39). Peptides ranking in the top 40% of predicted affinities for 10 or more of 20 HLA class II alleles were selected. This prediction strategy was aimed at identifying peptides potentially binding to multiple HLA class II molecules, and thereby most likely to be prevalently recognized.

A total of 195 peptides from the Bla g 1, 2, 4, 5, 6, and 7 allergens were synthesized (Table X (SEQ ID NOS 58-252)), and arranged into 13 pools containing 12-18 peptides each. These pools were tested with extract-stimulated PBMC cultures for production of IL-5, as a prototype Th2 lymphokine, and IFN-γ, as a prototype Th1 lymphokine. Positive pools were deconvoluted to identify specific epitopes.

Of the 34 donors tested, 32 responded to stimulation with the allergen extract, and of these 32, peptide responses were obtained in 19. In all, 41 peptides were identified that elicited a positive response in at least one donor. As discussed herein, the fact that some individuals did not respond to the peptides is not likely a reflection of the computational analysis not identifying all relevant peptides. As also discussed herein, it is possible that T cell responses are directed against additional proteins not analyzed herein, and that also the relatively weak sensitization of the patient cohort studied contributed to this phenomenon.

Some peptides were highly homologous because they were derived from isoforms of the same allergen, or were derived from the same allergen protein and represented nearly identical overlapping sequences and donor responses. After removal of these redundancies, a total of 32 unique peptide responses were identified (Table VII (SEQ ID NOs 26-57)). Further consolidation of largely overlapping contiguous epitopes allowed the definition of 25 distinct antigenic regions of 15-20 amino acids in length (Table I (SEQ ID NOs 1-25)). These results highlight the high degree of heterogeneity of human responses to the Bla g allergens studied.

Conversely, there was a clear hierarchy of immunoprevalence and immunodominance observed. At the level of immunoprevalence, some T cell epitopes were recognized in only one donor, while others were recognized in multiple donors. At the level of immunodominance, it was noted that the strength of the responses varied over 1000-fold. Indeed, the top 5 peptides accounted for over half (55.6%) of the response, and the top 9 and 13 accounted for 76% and 90% of the total response, respectively (Table I (SEQ ID NOs 1-25)).

One of the epitope reactivities (Epitope region 5) was directed against a peptide contained within the leader sequence. Since the natural Bla g 2 N-terminal sequencing (40) showed that the protein starts at residue 25, this result was unexpected and might reflect recognition of a minor isoform where the signal sequence is cleaved at an alternate position.

Taken together these results indicate that while responses to Bla g allergens in humans are very heterogeneous and involve recognition of a large number of T cell epitopes, a small number of epitopes that elicit the most dominant and prevalent responses encompass a significant fraction of the total response in this population of donors. Similar results have been reported in the Cockroach system (32).

TABLE I

Twenty-five distinct Bla g regions are recognized by T cell responses from allergic individuals

| Ag | Position | Region ID | Sequence (SEQ ID NOs 1-25, in order of appearance) | Donors Responding | Total SFCs | % Total Response | Cumulative Response |
|---|---|---|---|---|---|---|---|
| Bla g 5 | 181 | 17 | ALREKVLGLPAIKAWVAKRP (SEQ ID NO 1) | 8 | 4953 | 20.3 | 20.3 |
| Bla g 5 | 66 | 12 | VAISRYLGKQFGLSG (SEQ ID NO 2) | 2 | 2443 | 10.0 | 30.3 |
| Bla g 5 | 16 | 10 | GEPIRFLLSYGEKDFEDYRF (SEQ ID NO 3) | 5 | 2342 | 9.6 | 39.9 |
| Bla g 5 | 96 | 13 | ISDFRAAIANYHYDA (SEQ ID NO 4) | 2 | 2103 | 8.6 | 48.5 |
| Bla g 5 | 156 | 15 | YFVAILDYLNHMAKE (SEQ ID NO 5) | 2 | 1730 | 7.1 | 55.6 |
| Bla g 6 | 66 | 20 | EEFCTLASRFLVEED (SEQ ID NO 6) | 2 | 1433 | 5.9 | 61.5 |
| Bla g 6 | 6 | 23 | PEQIQLLKKAFDAFD (SEQ ID NO 7) | 2 | 1245 | 5.1 | 66.6 |
| Bla g 1 | 331 | 2 | LIDDVLAILPLDDLK (SEQ ID NO 8) | 1 | 1157 | 4.7 | 71.4 |
| Bla g 5 | 166 | 16 | HMAKEDLVANQPNLKALREK (SEQ ID NO 9) | 3 | 1140 | 4.7 | 76.0 |
| Bla g 5 | 131 | 14 | TKKFDEVVKANGGYLAAGKL (SEQ ID NO 10) | 2 | 927 | 3.8 | 79.8 |
| Bla g 5 | 46 | 11 | SMPFGKTPVLEIDGK (SEQ ID NO 11) | 2 | 874 | 3.6 | 83.4 |
| Bla g 2 | 11 | 5 | FAVATITHAAELQRV (SEQ ID NO 12) | 1 | 855 | 3.5 | 86.9 |

TABLE I-continued

Twenty-five distinct Bla g regions are recognized by T cell responses from allergic individuals

| Ag | Position | Region ID | Sequence (SEQ ID NOs 1-25, in order of appearance) | Donors Responding | Total SFCs | % Total Response | Cumulative Response |
|---|---|---|---|---|---|---|---|
| Bla g 6 | 11 | 18 | EQISVLRKAFDAFDREKSGS (SEQ ID NO 13) | 2 | 757 | 3.1 | 90.0 |
| Bla g 6 | 71 | 19 | EFVTLAAKFIIEEDS (SEQ ID NO 14) | 1 | 443 | 1.8 | 91.8 |
| Bla g 1 | 40 | 3 | PEFQSIVQTLNAMPEYQNLL (SEQ ID NO 15) | 2 | 327 | 1.3 | 93.2 |
| Bla g 1 | 281 | 4 | PELQNFLNFLEANGL (SEQ ID NO 16) | 1 | 323 | 1.3 | 94.5 |
| Bla g 6 | 31 | 24 | MVGTILEMLGHRLDD (SEQ ID NO 17) | 2 | 317 | 1.3 | 95.8 |
| Bla g 2 | 321 | 9 | HFFIGDFFVDHYYSE (SEQ ID NO 18) | 1 | 250 | 1.0 | 96.8 |
| Bla g 2 | 26 | 6 | PLYKLVHVFINTQYA (SEQ ID NO 19) | 1 | 240 | 1.0 | 97.8 |
| Bla g 1 | 351 | 1 | FETIVVTVDSLPEFK (SEQ ID NO 20) | 1 | 167 | 0.7 | 98.5 |
| Bla g 2 | 296 | 8 | ISSQYYIQQNGNLCY (SEQ ID NO 21) | 1 | 153 | 0.6 | 99.1 |
| Bla g 6 | 140 | 22 | SGTVDFDEFMEMMCOCKROACH (SEQ ID NO 22) | 1 | 57 | 0.2 | 99.4 |
| Bla g 2 | 46 | 7 | GNQNFLTVFDSTSCN (SEQ ID NO 23) | 1 | 55 | 0.2 | 99.6 |
| Bla g 6 | 86 | 21 | EAMEKELREAFRLYD (SEQ ID NO 24) | 1 | 53 | 0.2 | 99.8 |
| Bla g 6 | 101 | 25 | GYITTNVLREILKEL (SEQ ID NO 25) | 1 | 50 | 0.2 | 100.0 |

Example 3

This example includes a description of data demonstrating that the T cell epitopes identified account for a significant fraction of the response.

The thoroughness of the epitope identification studies was next evaluated by three different types of analyses. First, since the candidate epitopes were identified on the basis of predicted HLA binding, the present inventors wanted to exclude that a large fraction of T cell epitopes might have been missed by the predictions.

First it is noted that because of the low stringency used in the prediction a large fraction of the sequence of each of the Bla g proteins would be covered by the predicted peptides tested. Indeed, as shown in Table VIII, an average of 69% of the overall sequences were covered, corresponding to about 42% of unique 15-mers, considering a ten-residue overlap, spanning the entire sequence. Second, the present inventors considered having missed a large fraction of the epitopes unlikely, based on previous Cockroach studies (32), which had shown that predictions of this level of stringency would identify approximately 75% of the total response detected with complete sets of overlapping peptides. In this context, it was reasoned that if the predictions were reasonably effective, most of the response would be associated with the peptides ranking high in predicted binding capacity. If the predictions are exhaustive, lower ranking peptides would be associated with diminishing success, and the curve of prediction success versus rank would start to level off. The data shown in FIG. 1 shows that this is indeed the case.

Finally, to have a crude estimate whether the epitopes identified accounted for a significant fraction of the response, the total response observed against the Cockroach extract was compared to the sum total of the epitope specific response. By this analysis the sum total of epitope responses corresponded to 90% of the sum total extract response (data not shown). These values should not be taken as directly comparable, since an optimal amount of peptide epitope is used in the assay, while Cockroach extracts contain an unknown amount of each allergen. So, this percentage could vary very significantly depending on different extract preparations or techniques. Nevertheless, the above considerations strongly suggest that the identified epitopes likely represent a very large fraction of the T cell epitopes contained in the Bla g allergens studied. However, in 13 of the donors, all positive for Cockroach extract IgE reactivity, while a significant response to extract stimulation was observed, no epitope derived from the Bla g 1, 2, 4, 5, 6, and 7 allergens could be identified. This suggested that additional, as yet undefined, proteins might be recognized by T cell responses in these donors.

Example 4

This example includes a description of data demonstrating diverse HLA locus restriction of Bla g epitopes.

The HLA locus restriction of the 13 most frequently recognized epitopic regions (Table I (SEQ ID NOs 1-25)) was determined by inhibition experiments utilizing DR, DP and DQ specific monoclonal antibodies. The results are presented in Table II. Overall, 20 locus restrictions were determined. DR accounted for the most (11 of 20) restrictions analyzed, but restriction by DQ molecules was also relatively frequent (6 of 20). By contrast, the DP locus restricted only three epitopes.

Figure 2:
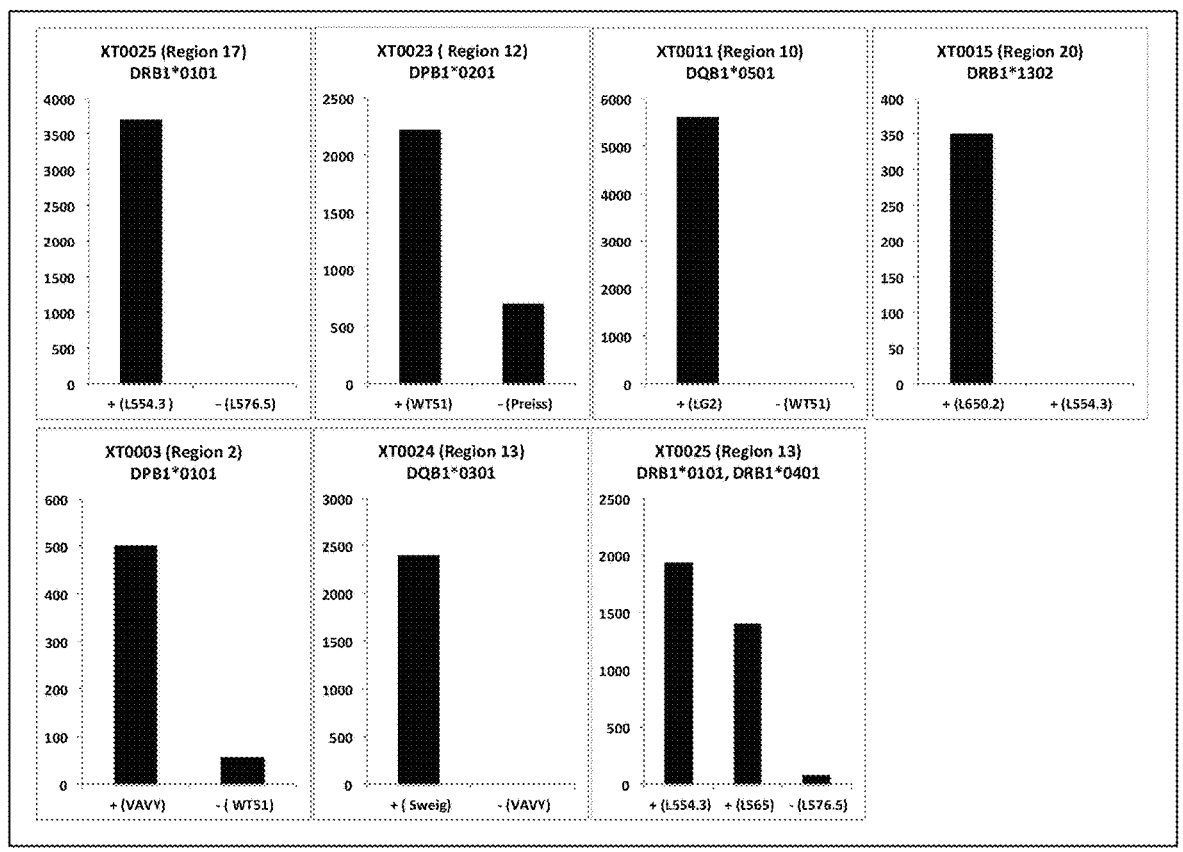
FIG. 2. Inferred HLA restriction of T cell responses to Bla g epitopes. The HLA restriction of donor responses to Bla g epitopes was determined in selective cases using cell lines transfected with a single HLA class II molecule and/or the use of HLA matched (+)/mismatched (−) EBV transformed cell lines.

These Bla g epitopes were also tested for their capacity to bind a panel of 35 different DR, DP and DQ molecules (38, 40-42) representative of the most common allelic variants worldwide. This HLA binding information was then utilized to infer potential HLA allelic restrictions for each patient/epitope combination. For each instance in which the restricting locus was determined by antibody inhibition experiments, the HLA types expressed at that locus by the corresponding donor were considered. The binding data was utilized to further narrow the potential restricting molecule by eliminating molecules that were shown to not be able to bind the epitope in in vitro assays utilizing purified HLA. Whether several allergic donors responding to the same epitope shared particular HLA molecules that bind the epitope, at a locus shown to restrict epitope, was also considered. In many cases these data allowed inference of the likely restricting HLA molecule (see last column of Table II). In selected cases the inferred likely restriction was confirmed by the use of transfected cell lines expressing single HLA class II molecules and/or the use of HLA matched/mismatched EBV transformed cell lines. In particular, by this approach it could be demonstrated that epitope regions 17, 12, 10, 20 and 2 are restricted by DRB1*0101, DPB1*0201, DQB1*0501, DRB1*1302, and DPB1*0101, respectively. Region 13, was promiscuous in its restriction, being restricted by DQB1*0301 in donor XT0024 and both DRB1*0101 and DRB1*0401 in donor XT0025 (FIG. 2).

TABLE II

HLA restriction of Bla g responses

| Region ID | Donor | Locus | Donor class II alleles bound | Tentative restriction |
|---|---|---|---|---|
| 17 | XT0025 | DR | **DRB1*0101**, DRB1*0401, DRB4*0103 | DRB1*01 |
|  | XT0021 | NA | **DRB1*0101**, DRB1*1301 |  |
|  | XT0023 | DR | **DRB1*0102**, DRB1*0804 |  |
|  | XT0029 | DR | **DRB1*0102**, DRB1*1302 |  |
|  | XT0034 | DR | **DRB1*0102**, DRB1*1102 |  |
|  | XT0013 | DR | DRB1*1201, DRB1*1316 |  |
|  | XT0012 | NA | DRB1*0804, DRB1*1503, DRB5*0101 |  |
|  | XT0041 | NA | DRB1*0701, DRB1*1503, DRB5*0101 |  |
| 12 | XT0023 | DP | **DPB1*0201** | DPB1*0201 |
|  | XT0030 | NA | **DPB1*0201** |  |
| 10 | XT0011 | DQ | **DQB1*0501** | DQB1*0501 |
|  | XT0021 | NA | **DQB1*0501** |  |
|  | XT0023 | NA | **DQB1*0501** |  |
|  | XT0030 | NA | **DQB1*0501** |  |
|  | XT0041 | NA | DQB1*0303 |  |
| 13 | XT0024 | DQ | **DQB1*0301, DQB1*0504,** DRB1*0101, DRB1*0804 | DQB1*0301/DQB1*05 |
|  | XT0025 | DQ DR | **DQB1*0301, DQB1*0501** **DRB1*0101**, DRB1*0401, DRB4*0103 |  |
| 15 | XT0024 | DQ | **DQB1*0504** | DQB1*0504 |
|  | XT0041 | NA |  |  |
| 20 | XT0015 | DR | **DRB1*1302** | DRB1*1302 |
|  | XT0024 | NA |  |  |
| 23 | U00023 | NA |  |  |
|  | XT0024 | NA |  |  |
| 2 | XT0003 | DP | **DPB1*0101** | DPB1*0101 |
| 16 | XT0029 | DR | **DRB1*1302** | DRB1*13 |
|  | XT0013 | DR | **DRB1*1316** |  |
|  | XT0021 | NA | **DRB1*1301**, DRB1*0101 |  |
| 14 | XT0023 | DQ | **DQB1*0301** | DQB1*0301 |
|  | XT0034 | DQ | **DQB1*0301** |  |
| 11 | XT0041 | DR |  |  |
|  | XT0021 | NA |  |  |
| 5 | U00023 | NA |  |  |
| 18 | XT0024 | DR | **DRB1*0101, DRB1*0804** | DRB1*0101/DRB1*0804 |
|  | XT0022 | DP |  |  |

Alleles common amongst donors recognizing the corresponding region, and that bind region-derived peptides with an IC50 < 1000 nM, are highlighted by bold font.

Example 5

This example includes a description of data demonstrating differential dominance and polarization of Bla g allergens for T cell responses.

The data was next analyzed in terms of the specific antigen from which the various epitopes were derived (Table III). It was found that the Bla g 5 allergen was most dominant, by far, in comparison to the other Bla g allergens analyzed, in that it alone accounted for 67.7% of the total response. Bla g 6 was second in terms of the immunodominance hierarchy, accounting for 17.9% of the response, and Bla g 1 was third, accounting 8.1%. Little or no response was detected for the Bla g 2, 4, and 7 allergens. This dominance profile was not merely due to size differences between the allergens, nor was it correlated to the number of peptides predicted and tested. Indeed the number of peptides tested for either Bla g 5 or 6 was far less than the number tested for the less frequently and less strongly recognized Bla g 1 and 2.

As disclosed herein, IL-5 and IFN-γ production was assayed as prototype Th2 and Th1 lymphokines, respectively. Here, the data was analysed in terms of the ratio of the IL-5 and IFN-γ responses detected for the various allergens (Table III). As expected, the overall IL-5 production exceeded IFN-γ. However, a surprisingly wide variation was observed in terms of the individual allergen proteins. In the case of the most dominant Bla g 5 antigen, both IL-5 and IFN-γ responses were detected, with the IL-5 response only slightly more vigorous than that of IFN-γ. In the case of Bla g 6, there was a clear preponderance of IL-5. Conversely, in the case of Bla g 2, responses were detected only for IFN-γ, and not for IL-5.

Figure 3:
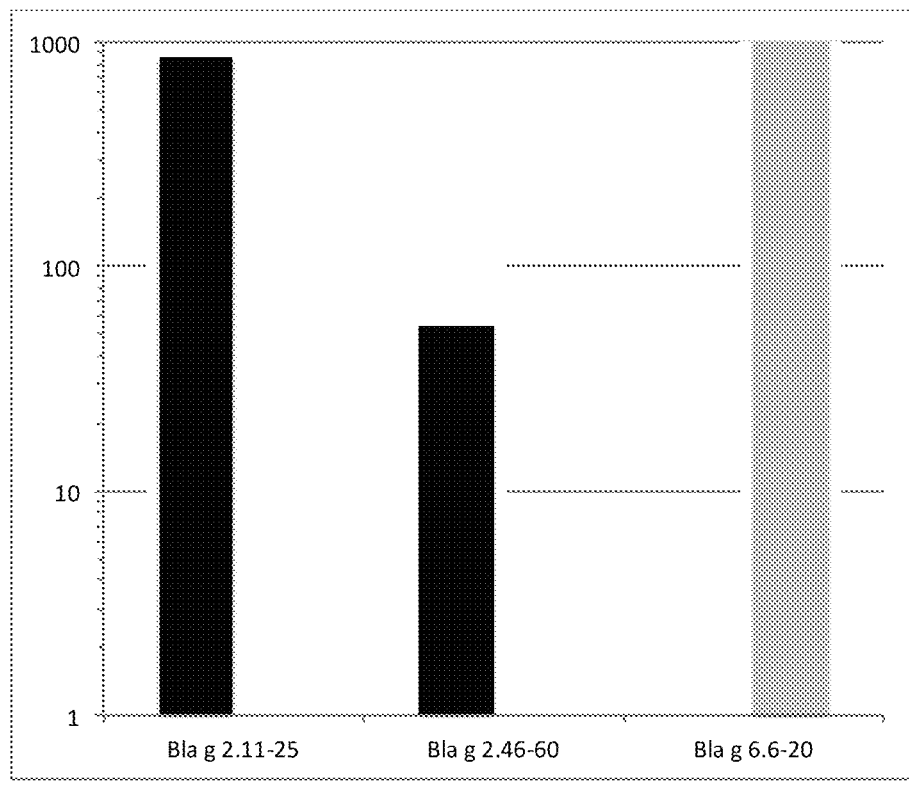
FIG. 3. Polarized T cell responses to Bla g antigens within an individual donor. IFNγ (black bars) and IL-5 (gray bars) in donor U00023 showing polarization of the response to epitopes derived from Bla g 2 (epitope region 5, Bla g 2.11-25, and epitope region 7, Bla g 2.46-60) and Bla g 6 (epitope region 23, Bla g 6.6-20). The T cell response to Bla g 6 was associated only with only IL-5 production, while the response to the two Bla g 2 epitopes was only associated with IFN-γ production.

Strikingly, even within an individual donor, responses to different allergens could be differentially polarized, with responses to one allergen dominated by Th1 responses, and to a different allergen dominated by Th2 responses. An example of this type of situation was observed in donor U00023, who responded to epitope regions 5 and 7 from Bla g 2 and region 23 from Bla g 6. As shown in FIG. 3, the T cell response to Bla g 6 was associated only with only IL-5 production; conversely, the response to the two Bla g 2 epitopes produced IFN-γ, but no IL-5. Taken together, these results suggest that different allergen proteins might be associated with different patterns of polarization of the responding T cell subsets.

TABLE III

Differential polarization of T cell responses to Bla g allergens

| Protein | Total SFC | % Total response | Peptides tested | IL-5 SFC | IFN-γ SFC | Ratio[1] |
|---|---|---|---|---|---|---|
| Bla g 1 | 1973 | 8.1 | 85 | 1083 | 890 | 1.22 |
| Bla g 2 | 1553 | 6.4 | 37 | 0 | 1553 | <0.01 |
| Bla g 4 | 0 | 0.0 | 14 | 0 | 0 | — |
| Bla g 5 | 16512 | 67.7 | 20 | 9637 | 6875 | 1.40 |
| Bla g 6 | 4355 | 17.9 | 24 | 4045 | 310 | 13.0 |
| Bla g 7 | 0 | 0.0 | 15 | 0 | 0 | — |
| Total | 24394 | 100.0 | 195 | 14765 | 9629 | 1.53 |

[1]IL-5/IFNγ
—, No IL-5 or IFN-g response was detected with any peptides derived from the corresponding Bla g protein.

Example 6

This example includes a description of data demonstrating lack of correlation between prevalence of IgE and T cell responses to individual Bla g proteins.

In parallel with the determination of the T cell responses, IgE titers to specific Cockroach allergens were measured by streptavidin-ImmunoCAP assays. Total IgE and specific IgE antibodies to Cockroach and two species of mite allergens were also determined. This allowed correlating, in the same donor population, the prevalence of IgE and T cell responses against the specific allergens. As shown in Table IV, there is a trend towards the IgE response being more broadly directed against the various allergens. In agreement with previous reports (23), Bla g 5 was the most frequently recognized allergen in both T cell and IgE assays, with no clear dominance in IgE reactivity.

Absolute values of specific IgE antibody binding against specific allergens were low for most of the sera tested. The average of total IgE was 429.4 kU/L (range 35.6-2,152; n=33), and for Cockroach specific IgE was 13.99 (range<0.35-21.3 kU/L; n=33). Absolute values of IgE antibody binding to specific allergens were low for most of the sera tested. Reactivity to mite extracts from *D. pteronyssinus* and *D. farinae* was also measured, with an average of 11.41 and 15.2, respectively (range of <0.35→100, and n=33, for both). There was no correlation between reactivity to mite extracts and Cockroach tropomyosin. Therefore, reactivity to mite tropomyosin would not be responsible for the reactivity to Cockroach tropomyosin (Per a 7) observed.

TABLE IV

Prevalence of IgE and T cell responses

| | Donors responding (%) | |
|---|---|---|
| Allergen | T cell | IgE |
| Bla g 1 | 4 (12) | 4 (12) |
| Bla g 2 | 3 (9) | 8 (24) |
| Bla g 4 | 0 (0) | 4 (12) |
| Bla g 5 | 11 (32) | 15 (44) |
| Bla g 6 | 5 (17) | NA[1] |
| Bla g 7/Per a 7 | 0 (0) | 4 (12) |

[1]Reagents unavailable

The correlation between T cell responses and IgE responses was further investigated by examining for each donor which allergens were recognized by IgE and T cell responses (Table V and Table IX). No significant correlation was detected for any of the antigens, suggesting that distinct mechanisms may govern responsiveness against the various allergens at the IgE and T cell level. Importantly, in the case of several donors it was found that significant IgE titers were observed against a given antigen, while T cell responses to the same allergen were undetectable, but were vigorous and readily detected against a different Bla g protein. This observation suggests that, in these instances, unlinked T-B help might support the development of IgE responses.

TABLE V

Correlation between IgE and T cell responses against Bla g allergen

| | Donors with Responses to: | | | | |
|---|---|---|---|---|---|
| Allergen | Both | T Cell Only | IgE Only | Neither | p Value |
| Bla g 1 | 1 | 3 | 3 | 27 | 0.35 |
| Bla g 2 | 1 | 2 | 7 | 24 | 0.43 |
| Bla g 4 | 0 | 0 | 4 | 30 | 1.00 |
| Bla g 5 | 7 | 4 | 8 | 15 | 0.087 |
| Bla g 7 | 0 | 0 | 4 | 30 | 1.00 |

Example 7

This example includes description of data demonstrating patterns of T cell reactivity following SIT treatment.

For a selected number of donors blood donations were obtained before, and six months after, initiation of SIT treatment. Six months is a time period routinely associated with reaching the "maintenance" phase, and it is believed that regulatory events associated with modulation of T cell responses probably occur within this time frame (44, 45). For four individual donors who responded to Bla g epitopes before SIT treatment, responses in PBMC cultures were also studied 6 months after initiation of SIT treatment. T cells producing IL-5, IFN-γ, and IL-10 were measured by standard ELISPOT assays. Results are shown in Table VI. The overall data can be summarized as follows. First, in no case was SIT treatment associated with development of reactivity against new epitopes (data not shown). Second, SIT resulted in a profound decrease in IL-5 producing cells. Third, this down-regulation of IL-5 producing cells was not associated with development of increased responses to either IFN-γ or IL-10 against any of the peptides derived from the Bla g allergens considered.

TABLE VI

Overall pattern of responses pre- and post-SIT treatment

| Donor | Region | Antigen | PRE-SIT | | | POST-SIT | | |
|---|---|---|---|---|---|---|---|---|
| | | | IFNg (SFC/$10^6$) | IL-5 (SFC/$10^6$) | IL-10 (SFC/$10^6$) | IFNg (SFC/$10^6$) | IL-5 (SFC/$10^6$) | IL-10 (SFC/$10^6$) |
| XT0003 | 2 | Bla g 1.0101 | 160 | 997 | 0 | 0 | 0 | 0 |
| | 3 | Bla g 1.0101 | 153 | 87 | 0 | 0 | 0 | 0 |
| | | PHA | 1083 | 2650 | 450 | 1837 | 2463 | 73 |
| XT0008 | 24 | Bla g 6.0201 | 0 | 50 | 0 | 0 | 0 | 0 |
| | 25 | Bla g 6.0201 | 0 | 50 | 0 | 0 | 0 | 0 |
| | | PHA | 1907 | 2017 | 167 | 1807 | 2160 | 127 |
| XT0011 | 10 | Bla g 5 | 0 | 97 | 0 | 0 | 0 | 0 |
| | 10 | Bla g 5 | 0 | 1537 | 0 | 0 | 0 | 0 |
| | | PHA | 1507 | 2987 | 900 | 1427 | 2820 | 1653 |
| XT0012 | 17 | Bla g 5 | 197 | 0 | 0 | 0 | 0 | 0 |
| | 17 | Bla g 5 | 50 | 0 | 0 | 0 | 0 | 0 |
| | | PHA | 1613 | 1540 | 147 | 1440 | 3093 | 273 |

Example 8

This Example includes a discussion of the data disclosed herein.

As disclosed herein, bioinformatic predictions of the capacity of Bla g 1, 2, 4, 5, 6, and 7 peptides to bind HLA-DR, -DP, and -DQ molecules, and PBMC responses from 30 allergic donors, were used as an initial screen to identify 25 T cell epitopes. Five immunodominant epitopes accounted for more than half of the response. Bla g 5, the most dominant allergen, accounted for 65% of the response, and Bla g 6 accounted for 20%. Bla g 5 induced both IL-5 and IFN-g responses, whereas Bla g 6 induced mostly IL-5, and, conversely, Bla g 2 induced only IFN-g. Thus, responses to allergens within a source are independently regulated, suggesting a critical role for the allergen itself, and not extraneous stimulation from other allergens or copresented immunomodulators. In comparing antibody with T cell responses for several donor/allergen combinations, IgE titers were detected in the absence of detectable T cell responses, suggesting that unlinked T cell-B cell help might support development of IgE responses. Finally, specific immunotherapy resulted in IL-5 downmodulation, which was not associated with development of IFN-g or IL-10 responses to any of the Bla g-derived peptides. In summary, the characteristics of T cell responses to Bla g allergens appear uncorrelated with IgE responses.

T cell epitopes derived from Bla g Ags were identified, and used to characterize T cell responses in allergic individuals before SIT treatment and after reaching the SIT maintenance phase. The results reveal that Bla g T cell responses are associated with strong patterns of immunodominance and immunoprevalence, with the Bla g 5 and Bla g 6 allergens being most dominantly and prevalently recognized. Furthermore, different allergens are associated with unique patterns of lymphokine polarization, with Bla g 2 being associated with responses strongly polarized toward Th1-, and Bla g 6 with responses strongly polarized toward Th2. Interestingly, the pattern of T cell reactivity to specific Bla g proteins at the level of individual donors frequently did not correlate with IgE responses, suggesting that T cell responses might regulate antibody (Ab) responses in an unlinked fashion. Finally, longitudinal analysis of samples before and after establishment of the SIT treatment revealed a marked downregulation of Th2 responses to the Bla g allergens, which was not associated with a concomitant increase in Th1- or IL-10-producing T cells. In conclusion, these data suggest that T cell responses to Bla g allergens have important distinguishing features from IgE responses to the same allergens.

Disclosed herein are the first T cell epitopes to be identified from six *Blattella germanica* allergens implicated in Cockroach allergy, a major health problem that is increasing in frequency, particularly in urban and inner city settings. The epitopes identified were utilized to determine the quality, immunodominance and immunoprevalence of T cell responses, to explore their relation to IgE responses, and to probe the evolution of T cell responses associated with SIT treatment with Cockroach extracts.

The data disclosed herein reveals that bioinformatics can be used to reduce the number of peptides needed to be tested. These strategies are of relevance as they simultaneously target the most common allelic variants expressed at the human HLA class II DR, DP and DQ loci (39, 41-43). Predictive strategies are of particular interest in cases where limiting amounts of human samples are available. Alternatively, bioinformatic predictions can be utilized to allow efficient performance of large-scale screening of comprehensive panels of antigens.

A total of 25 epitopic regions were identified, underlining the heterogeneity of human allergen-specific T cell responses. These data are in good agreement with what has been observed previously in the case of the Cockroach system (32) and in other systems (47-61). However, as in the case of the Cockroach study, it was also found that a rather limited number of epitopes could account for the majority of responses. This is of relevance for potential diagnostic or therapeutic applications, as it demonstrates that a finite number of molecular structures can be used to recapitulate the heterogeneity observed in human populations of allergic individuals.

Although 32 of 34 donors with a history of Cockroach sensitivity had positive responses to the extract, only 19 had responses to the peptides identified by bioinformatics analysis. Furthermore, 6 of 19 responders had a response to a single peptide, and half of these responses were <200

SFCs/10⁶ cells. At the same time, only four donors (XT0021, U00023, XT0024, and XT0041), which responded to four or more regions, accounted for 21 of 48 (44%) unique donor/region responses (see Table VII). Thus, it is possible that T cell responses are directed against additional proteins or isotype sequences not analyzed in this study. It is also possible that the relatively weak sensitization of the patient cohort studied has contributed to this phenomenon.

TABLE VII

Complete list of peptide reactivities detected

| Antigen | Position | Region ID | Sequence (in order of appearance) | Donor | IFNγ (SFC) | IL-5 (SFC) | Total (SFC) |
|---|---|---|---|---|---|---|---|
| Bla g 1 | 351 | 1 | FETIVVTVDSLPEFK (SEQ ID NO. 20) | XT0005 | 167 | 0 | 167 |
|  | 40 | 3 | PEFQSIVQTLNAMPE (SEQ ID NO. 26) | XT0031 | 87 | 0 | 87 |
|  | 181 |  | IVQTLNAMPEYQNLL (SEQ ID NO. 27) | XT0003 | 153 | 87 | 240 |
|  | 281 | 4 | PELQNFLNFLEANGL (SEQ ID NO. 16) | XT0034 | 323 | 0 | 323 |
|  | 331 | 2 | LIDDVLAILPLDDLK (SEQ ID NO. 8) | XT0003 | 160 | 997 | 1157 |
| Bla g 2 | 11 | 5 | FAVATITHAAELQRV (SEQ ID NO. 12) | U00023 | 855 | 0 | 855 |
|  | 26 | 6 | PLYKLVHVFINTQYA (SEQ ID NO. 19) | XT0031 | 240 | 0 | 240 |
|  | 46 | 7 | GNQNFLTVFDSTSCN (SEQ ID NO. 23) | U00023 | 55 | 0 | 55 |
|  | 296 | 8 | ISSQYYIQQNGNLCY (SEQ ID NO. 21) | XT0038 | 153 | 0 | 153 |
|  | 321 | 9 | HFFIGDFFVDHYYSE (SEQ ID NO. 18) | XT0031 | 250 | 0 | 250 |
| Bla g 5 | 16 | 10 | GEPIRFLLSYGEKDF (SEQ ID NO. 28) | XT0041 | 205 | 0 | 205 |
|  | 21 |  | FLLSYGEKDFEDYRF (SEQ ID NO. 29) | XT0011 | 0 | 1537 | 1537 |
|  |  |  |  | XT0021 | 77 | 0 | 77 |
|  |  |  |  | XT0023 | 0 | 203 | 203 |
|  |  |  |  | XT0030 | 127 | 193 | 320 |
|  | 46 | 11 | SMPFGKTPVLEIDGK (SEQ ID NO. 11) | XT0021 | 57 | 0 | 57 |
|  |  |  |  | XT0041 | 250 | 567 | 817 |
|  | 66 | 12 | VAISRYLGKQFGLSG (SEQ ID NO. 2) | XT0023 | 287 | 1573 | 1860 |
|  |  |  |  | XT0030 | 153 | 430 | 583 |
|  | 96 | 13 | ISDFRAAIANYHYDA (SEQ ID NO. 4) | XT0024 | 263 | 1760 | 2023 |
|  |  |  |  | XT0025 | 0 | 80 | 80 |
|  | 136 | 14 | EVVKANGGYLAAGKL (SEQ ID NO. 30) | XT0023 | 80 | 467 | 547 |
|  |  |  |  | XT0034 | 380 | 0 | 380 |
|  | 156 | 15 | YFVAILDYLNHMAKE (SEQ ID NO. 5) | XT0024 | 0 | 213 | 213 |
|  |  |  |  | XT0041 | 1043 | 473 | 1517 |
|  | 166 | 16 | HMAKEDLVANQPNLK (SEQ ID NO. 31) | XT0029 | 610 | 273 | 883 |
|  | 171 |  | DLVANQPNLKALREK (SEQ ID NO. 32) | XT0013 | 177 | 0 | 177 |
|  |  |  |  | XT0021 | 80 | 0 | 80 |
|  | 181 | 17 | ALREKVLGLPAIKAW (SEQ ID NO. 33) | XT0013 | 843 | 0 | 843 |
|  |  |  |  | XT0021 | 100 | 0 | 100 |
|  |  |  |  | XT0023 | 0 | 267 | 267 |
|  |  |  |  | XT0025 | 183 | 380 | 563 |
|  |  |  |  | XT0029 | 147 | 0 | 147 |
|  |  |  |  | XT0034 | 1690 | 1087 | 2777 |
|  | 186 |  | VLGLPAIKAWVAKRP (SEQ ID NO. 34) | XT0012 | 50 | 0 | 50 |
|  |  |  |  | XT0041 | 73 | 133 | 207 |
| Bla g 6 | 11 | 18 | EQISVLRKAFDAFDR (SEQ ID NO. 35) | XT0024 | 0 | 340 | 340 |
|  | 16 |  | LRKAFDAFDREKSGS (SEQ ID NO. 36) | XT0022 | 90 | 327 | 417 |
|  | 71 | 19 | EFVTLAAKFIIEEDS (SEQ ID NO. 14) | XT0024 | 0 | 443 | 443 |
|  | 86 | 21 | EAMEKELREAFRLYD (SEQ ID NO. 24) | XT0024 | 0 | 53 | 53 |
|  | 140 | 22 | SGTVDFDEFMEMMTG (SEQ ID NO. 22) | XT0024 | 0 | 57 | 57 |
|  | 31 | 24 | MVGTILEMLGTRLDQ (SEQ ID NO. 37) | XT0024 | 0 | 267 | 267 |
|  | 66 | 20 | EEFCTLASRFLVEED (SEQ ID NO. 6) | XT0024 | 0 | 1213 | 1213 |
|  | 6 | 23 | PEQIQLLKKAFDAFD (SEQ ID NO. 7) | U00023 | 0 | 1172 | 1172 |
|  |  |  |  | XT0024 | 0 | 73 | 73 |

TABLE VII-continued

Complete list of peptide reactivities detected

| Antigen | Position | Region ID | Sequence (in order of appearance) | Donor | IFNγ (SFC) | IL-5 (SFC) | Total (SFC) |
|---|---|---|---|---|---|---|---|
| | 31 | 24 | MVGTILEMLGHRLDD (SEQ ID NO. 17) | XT0008 | 0 | 50 | 50 |
| | 66 | 20 | EEFVSLASRFLVEED (SEQ ID NO. 38) | XT0015 | 220 | 0 | 220 |
| | 101 | 25 | GYITTNVLREILKEL (SEQ ID NO. 25) | XT0008 | 0 | 50 | 50 |

As disclosed herein, in vitro expansion of PBMCs by stimulation with Cockroach allergen extract was used. It is recognized that this approach may create bias; however, this approach is also commonly used in the literature describing allergens, as it allows the study of low frequency responses. Allergen extracts can vary significantly in terms of the relative concentrations of various components, as well as in relationship to what variant is actually inhaled and/or is causative of the allergic reaction. It may be informative to perform stimulations with recombinant allergens, especially those for which few or no responses were obtained following stimulation with Bla g extracts.

The initial prediction schema utilized is based on the most common DR, DP and DQ allelic variants. When the epitopes identified were examined in terms of the HLA locus restriction, a diverse breadth of restrictions was found, demonstrating that strategies only targeting the most often studied DR locus might be unwise and yield an incomplete representation of the epitopic landscape. The locus restriction data, together with binding data and HLA typing of the responding donors was used in a number of instances to predict likely allelic restrictions, which were verified in several instances by the use of transfected cell lines and/or matched and mismatched homozygous EBV transformed cell lines.

An observation that was derived from the data herein relates to the fact that different allergens appear to elicit patterns of responses that are differentially polarized in terms of their Th1/Th2 balance, at least as judged by IL-5 (Th2) or IFN-γ (Th1) production. Hales et al. (62) have also noted differences in the balance of IL-5 and IFN-g responses to the Der p 1 and Der p 7 allergens. Strikingly, even within an individual donor, responses to different allergens could be differentially polarized, with responses to one allergen dominated by Th1 responses, and to a different allergen by Th2 responses. The molecular basis for this effect is unknown, and might reflect differences in the relative concentrations and accessibility in the pollen and extract of the different allergens, their processing and presentation, and potentially the presence of distinct costimulatory signals associated with each allergen.

A few caveats may also be noted with respect to the significance of the cytokine bias data. Specifically, the Bla g 2 responses, showing a Th1 bias, are from a total of three donors. At the same time, whereas five donors responded to Bla g 6 regions (representing a Th2 bias), the preponderance of the total Bla g 6 response is dominated by responses from a single donor. Further examination of the responses to Bla g 5 data on a per donor basis, which overall reflected a fairly balanced Th1/Th2 response, reveals that 3 of the 11 donors had a strong Th1 bias (ratio, >5-fold), 3 had a strong Th2 bias, and only 5 could be deemed balanced responses.

Another striking finding disclosed herein is the lack of correlation, at the level of individual donors and individual Bla g proteins, between IgE titers and T cell responses. Specifically, it was found that in a given donor significant IgE titers could be observed against a given antigen, while T cell responses in the same donor to the same allergen could be undetectable, while vigorous and readily detected T cell responses occurred against a different allergen. This finding is similar to what was observed previously in the Cockroach system, and is most readily interpreted by postulating that antibody responses to a given allergen can be "helped" and modulated by T cell responses to a different antigen (unlinked cognate T-B cooperation). The molecular mechanism for such unlinked T-B cooperation is unknown but may be caused by 2 or more allergens being present in the same physical structure, such as micron-sized particles. Furthermore, this observation is also consistent with the fact that for 13 of the donors that had elevated IgE titers and that responded to extract stimulation, not a single epitope derived from the Bla g 1, 2, 4, 5, 6, and 7 allergens was identified, which might suggest that additional, as yet undefined, proteins might be recognized by T cell responses in these donors and that these responses could provide help for the antibody response to the Bla g allergens.

Finally, the definition of the Bla g epitopes allowed following in a longitudinal pattern the magnitude and specificity of T cell responses to the main Bla g allergens as a function of SIT treatment. These results are of relevance in the light of previous studies that indicate that SIT treatment might be associated with deviation of Th2 responses towards a Th1 phenotype, and/or induction of regulatory IL-10 producing T cells. The results do not support this notion, at least in the case of Bla g allergens and Cockroach extracts. Indeed, SIT treatment appeared to be associated with a generalized down regulation of T cell responses, in the absence of new or increased IFN-γ and IL-10 production. At least in theory, the in vitro expansion step used to characterize responses could alter the pattern of Th subsets detected. However, direct ex vivo experiments with either extract or epitopes did not yield detectable/reproducible responses either before or after SIT treatment, thus precluding ex vivo analysis. Thus, the results obtained in the case of SIT treatment, might favor the hypothesis that SIT efficacy might be associated with T cell responses directed against different T cell antigens, and/or development of IgG responses competing with the IgE recognizing the known allergens.

Thus, there is provided a characterization of Bla g-specific T cell responses. The results disclosed herein highlight that these responses are associated with a unique pattern of immunodominance, and T cell responses are differentially polarized at the level of the different allergens. The observed pattern of immunodominance is distinct from that observed at the level of IgE responses, and suggests the possibility that unlinked T-B cooperation contributes to shape IgE responses. Finally, as disclosed herein T cell responses are generally downregulated by SIT treatment, without evidence of induction of Tregs or deviation towards Th1 responses.

Taken together these results reveal T cell responses in Cockroach allergy and their potential role in SIT therapy. Further, T cell responses to Bla g allergens have important distinguishing features from IgE responses to the same allergens.

TABLE VIII

Average fraction of the sequences, and the corresponding fraction of unique 15-mers, covered by the bioinformatic predictions

| Antigen | Protein | Acc. no. | Len | Peptides[1] | Peptides synthesized | Percent peptide coverage | AA coverage | Percent AA coverage |
|---|---|---|---|---|---|---|---|---|
| Bla g 1 | | O96522 | 492 | 97 | 4 | 49.5 | 363 | 73.8 |
| Bla g | | Q9UAM5 | 412 | 81 | 37 | 45.7 | 280 | 68.0 |
| Bla g 2 | Aspartic | P54958 | 352 | 69 | 37 | 53.6 | 270 | 76.7 |
| Bla g 4 | Calycin | P54962 | 182 | 35 | 14 | 40.0 | 132 | 72.5 |
| Bla g 5 | Glutathione S- | O18598 | 204 | 39 | 20 | 51.3 | 160 | 78.4 |
| Bla g 6 | Troponin | Q1A7B1 | 154 | 29 | 1 | 34.5 | 119 | 77.3 |
| Bla g | Troponin | Q1A7B2 | 151 | 29 | 8 | 27.6 | 8 | 56.3 |
| Bla g | Troponin | Q1A7B3 | 151 | 29 | 6 | 20.7 | 8 | 53.0 |
| Bla g 7 | Tropomyos | Q9NG56 | 284 | 55 | 15 | 27.3 | 155 | 54.6 |
| Total | | | 2382 | 463 | 195 | 42.1 | 1644 | 69.0 |

[1]Refers to the number of unique 15-mers, considering a 10 residue overlap, spanning the entire sequence.

TABLE IX

IgE and T cell responsiveness of individual donors to each Cockroach allergen.

| Donor | Blag 1 RAST | Blag 1 T cell | Blag 2 RAST | Blag 2 T cell | Blag 4 RAST | Blag 4 T cell | Blag 5 RAST | Blag 5 T cell | Per a 7 RAST | Per a 7 T cell |
|---|---|---|---|---|---|---|---|---|---|---|
| U00023 | − | − | − | − | − | − | − | − | − | + |
| U00029 | − | − | − | − | − | − | − | − | − | − |
| U00038 | − | − | − | − | − | − | − | − | − | − |
| U00107 | − | − | − | − | − | − | − | − | − | − |
| XT0001 | − | − | − | − | − | − | 1.89 | − | − | − |
| XT0002 | − | − | − | − | − | − | − | − | − | − |
| XT0003 | − | + | 1.39 | − | − | − | 0.51 | − | − | − |
| XT0004 | − | − | − | − | − | − | − | − | − | − |
| XT0005 | − | + | − | − | − | − | − | − | − | − |
| XT0007 | − | − | − | − | − | − | − | − | − | − |
| XT0008 | − | − | 1.13 | − | − | − | 0.76 | − | − | + |
| XT0009 | − | − | 12.5 | − | − | − | 36.7 | − | 125 | − |
| XT0010 | 0.35 | − | − | − | − | − | − | − | − | − |
| XT0011 | − | − | − | − | − | − | 0.63 | + | − | − |
| XT0012 | − | − | − | − | − | − | − | + | − | − |
| XT0013 | − | − | 1.6 | − | − | − | 8.91 | + | − | − |
| XT0015 | − | − | − | − | − | − | − | − | − | + |
| XT0018 | − | − | − | − | − | − | − | − | − | − |
| XT0019 | − | − | − | − | − | − | − | − | − | − |
| XT0020 | − | − | − | − | 1.63 | − | 2.31 | − | − | − |
| XT0021 | − | − | − | − | − | − | − | + | − | − |
| XT0022 | − | − | − | − | − | − | − | − | − | + |
| XT0023 | − | − | 1.55 | + | 12.1 | − | 16.4 | + | − | − |
| XT0024 | − | − | − | − | − | − | − | + | − | + |
| XT0025 | − | − | − | − | − | − | − | + | − | − |
| XT0027 | − | − | − | − | − | − | − | − | − | − |
| XT0029 | 29.6 | − | 9.03 | − | 23 | − | 94.5 | + | 69.6 | − |
| XT0030 | − | − | 2.92 | − | − | − | 3.01 | + | 2.32 | − |
| XT0031 | 0.85 | + | − | + | − | − | − | − | − | − |
| XT0032 | − | − | − | − | − | − | 11.6 | − | − | − |
| XT0034 | − | + | − | − | − | − | 10.1 | + | − | − |
| XT0037 | 0.44 | − | − | − | 1.08 | − | 1.21 | − | − | − |
| XT0038 | − | − | − | + | − | − | 2.88 | − | 3.47 | − |
| XT0041 | − | − | 2.26 | − | − | − | 3.67 | + | − | − |

TABLE X

Bla g peptides tested.

| Sequence in order of appearance | Source protein | UniProt ID | Position |
|---|---|---|---|
| DLLGIPHIPVTARKH (SEQ ID NO. 39) | Bla g 1 | O96522 | 11 |
| LETSPEFKALYDAIR (SEQ ID NO. 40) | Bla g 1 | O96522 | 56 |
| SPEFQSIVGTLEAMP (SEQ ID NO. 41) | Bla g 1 | O96522 | 71 |
| LEAMPEYQNLIQKLK (SEQ ID NO. 42) | Bla g 1 | O96522 | 81 |
| VDHIIELIHQIFNIV (SEQ ID NO. 43) | Bla g 1 | O96522 | 101 |
| ELIHQIFNIVRDTRG (SEQ ID NO. 44) | Bla g 1 | O96522 | 106 |
| IFNIVRDTRGLPEDL (SEQ ID NO. 45) | Bla g 1 | O96522 | 111 |
| LPEDLQDFLALIPTD (SEQ ID NO. 46) | Bla g 1 | O96522 | 121 |
| QDFLALIPTDQVLAI (SEQ ID NO. 47) | Bla g 1 | O96522 | 126 |
| LIPTDQVLAIAADYL (SEQ ID NO. 48) | Bla g 1 | O96522 | 131 |
| QVLAIAADYLANDAE (SEQ ID NO. 49) | Bla g 1 | O96522 | 136 |
| AADYLANDAEVKAAV (SEQ ID NO. 50) | Bla g 1 | O96522 | 141 |
| ANDAEVKAAVEYLKS (SEQ ID NO. 51) | Bla g 1 | O96522 | 146 |
| DSLPEFKNFLNFLQT (SEQ ID NO. 52) | Bla g 1 | O96522 | 171 |
| FKNFLNFLQTNGLNA (SEQ ID NO. 53) | Bla g 1 | O96522 | 176 |
| NFLQTNGLNAIEFLN (SEQ ID NO. 54) | Bla g 1 | O96522 | 181 |
| NGLNAIEFLNNIHDL (SEQ ID NO. 55) | Bla g 1 | O96522 | 186 |
| IEFLNNIHDLLGIPH (SEQ ID NO. 56) | Bla g 1 | O96522 | 191 |
| TGLIDDIIAILPVDD (SEQ ID NO. 57) | Bla g 1 | O96522 | 221 |
| DIIAILPVDDLYALF (SEQ ID NO. 58) | Bla g 1 | O96522 | 226 |
| LPVDDLYALFQEKLE (SEQ ID NO. 59) | Bla g 1 | O96522 | 231 |
| LYALFQEKLETSPEF (SEQ ID NO. 60) | Bla g 1 | O96522 | 236 |
| KALYDAIRSPEFQSI (SEQ ID NO. 61) | Bla g 1 | O96522 | 251 |
| AIRSPEFQSIVETLK (SEQ ID NO. 62) | Bla g 1 | O96522 | 256 |
| EFQSIVETLKAMPEY (SEQ ID NO. 63) | Bla g 1 | O96522 | 261 |
| VETLKAMPEYQSLIQ (SEQ ID NO. 64) | Bla g 1 | O96522 | 266 |
| AMPEYQSLIQKLKDK (SEQ ID NO. 65) | Bla g 1 | O96522 | 271 |
| QSLIQKLKDKGVDVD (SEQ ID NO. 66) | Bla g 1 | O96522 | 276 |
| EDLQDFLALIPIDQI (SEQ ID NO. 67) | Bla g 1 | O96522 | 311 |
| FLALIPIDQILAIAA (SEQ ID NO. 68) | Bla g 1 | O96522 | 316 |
| PIDQILAIAADYLAN (SEQ ID NO. 69) | Bla g 1 | O96522 | 321 |
| DYLANDAEVQAAVEY (SEQ ID NO. 70) | Bla g 1 | O96522 | 331 |
| AAVEYLKSDEFETIV (SEQ ID NO. 71) | Bla g 1 | O96522 | 341 |
| LKSDEFETIVVTVDS (SEQ ID NO. 72) | Bla g 1 | O96522 | 346 |
| FETIVVTVDSLPEFK (SEQ ID NO. 20) | Bla g 1 | O96522 | 351 |
| LNAIEFINNIHDLLG (SEQ ID NO. 73) | Bla g 1 | O96522 | 376 |
| FINNIHDLLGIPHIP (SEQ ID NO. 74) | Bla g 1 | O96522 | 381 |
| HDLLGIPHIPATGRK (SEQ ID NO. 75) | Bla g 1 | O96522 | 386 |
| VGINGLIDDVIAILP (SEQ ID NO. 76) | Bla g 1 | O96522 | 406 |
| LIDDVIAILPVDELY (SEQ ID NO. 77) | Bla g 1 | O96522 | 411 |
| IAILPVDELYALFQE (SEQ ID NO. 78) | Bla g 1 | O96522 | 416 |
| VDELYALFQEKLESS (SEQ ID NO. 79) | Bla g 1 | O96522 | 421 |
| ALFQEKLESSPEFKA (SEQ ID NO. 80) | Bla g 1 | O96522 | 426 |
| RSPEFQSIVQTLKAM (SEQ ID NO. 81) | Bla g 1 | O96522 | 446 |
| QSIVQTLKAMPEYQD (SEQ ID NO. 82) | Bla g 1 | O96522 | 451 |
| PEYQDLIQRLKDKGV (SEQ ID NO. 83) | Bla g 1 | O96522 | 461 |
| LIQRLKDKGVDVDHF (SEQ ID NO. 84) | Bla g 1 | O96522 | 466 |
| DHFIELIKKLFGLSH (SEQ ID NO. 85) | Bla g 1 | O96522 | 478 |
| VDVDKIIELIRALFG (SEQ ID NO. 86) | Bla g 1.0101 | Q9UAM5 | 11 |

TABLE X-continued

Bla g peptides tested.

| Sequence in order of appearance | Source protein | UniProt ID | Position |
|---|---|---|---|
| IIELIRALFGLTLNA (SEQ ID NO. 87) | Bla g 1.0101 | Q9UAM5 | 16 |
| RALFGLTLNAKASRN (SEQ ID NO. 88) | Bla g 1.0101 | Q9UAM5 | 21 |
| LTLNAKASRNLQDDL (SEQ ID NO. 89) | Bla g 1.0101 | Q9UAM5 | 26 |
| LQDDLQDFLALIPVD (SEQ ID NO. 90) | Bla g 1.0101 | Q9UAM5 | 36 |
| QDFLALIPVDQIIAI (SEQ ID NO. 91) | Bla g 1.0101 | Q9UAM5 | 41 |
| DEFETIVVALDALPE (SEQ ID NO. 92) | Bla g 1.0101 | Q9UAM5 | 76 |
| IVVALDALPELQNFL (SEQ ID NO. 93) | Bla g 1.0101 | Q9UAM5 | 81 |
| IDFLNGIHDLLGIPH (SEQ ID NO. 94) | Bla g 1.0101 | Q9UAM5 | 106 |
| GIHDLLGIPHIPVSG (SEQ ID NO. 95) | Bla g 1.0101 | Q9UAM5 | 111 |
| RKYHIRRGVGITGLI (SEQ ID NO. 96) | Bla g 1.0101 | Q9UAM5 | 126 |
| DDVLAILPIEDLKAL (SEQ ID NO. 97) | Bla g 1.0101 | Q9UAM5 | 141 |
| ILPIEDLKALFNEKL (SEQ ID NO. 98) | Bla g 1.0101 | Q9UAM5 | 146 |
| ETSPDFLALYNAIRS (SEQ ID NO. 99) | Bla g 1.0101 | Q9UAM5 | 161 |
| FLALYNAIRSPEFQS (SEQ ID NO. 100) | Bla g 1.0101 | Q9UAM5 | 166 |
| PEFQSIVQTLNAMPE (SEQ ID NO. 26) | Bla g 1.0101 | Q9UAM5 | 176 |
| IVQTLNAMPEYQNLL (SEQ ID NO. 27) | Bla g 1.0101 | Q9UAM5 | 181 |
| NAMPEYQNLLQKLRE (SEQ ID NO. 101) | Bla g 1.0101 | Q9UAM5 | 186 |
| YQNLLQKLREKGVDV (SEQ ID NO. 102) | Bla g 1.0101 | Q9UAM5 | 191 |
| LIRALFGLTLNGKAS (SEQ ID NO. 103) | Bla g 1.0101 | Q9UAM5 | 211 |
| FGLTLNGKASRNLQD (SEQ ID NO. 104) | Bla g 1.0101 | Q9UAM5 | 216 |
| VDQIIAIATDYLAND (SEQ ID NO. 105) | Bla g 1.0101 | Q9UAM5 | 241 |
| AIATDYLANDAEVQA (SEQ ID NO. 106) | Bla g 1.0101 | Q9UAM5 | 246 |
| AEVQAAVAYLQSDEF (SEQ ID NO. 107) | Bla g 1.0101 | Q9UAM5 | 256 |
| AVAYLQSDEFETIVV (SEQ ID NO. 108) | Bla g 1.0101 | Q9UAM5 | 261 |
| QSDEFETIVVTLDAL (SEQ ID NO. 109) | Bla g 1.0101 | Q9UAM5 | 266 |
| ETIVVTLDALPELQN (SEQ ID NO. 110) | Bla g 1.0101 | Q9UAM5 | 271 |
| PELQNFLNFLEANGL (SEQ ID NO. 16) | Bla g 1.0101 | Q9UAM5 | 281 |
| FLNFLEANGLNAIDF (SEQ ID NO. 111) | Bla g 1.0101 | Q9UAM5 | 286 |
| LNGIHDLLGIPHIPV (SEQ ID NO. 112) | Bla g 1.0101 | Q9UAM5 | 301 |
| DLLGIPHIPVSGRKY (SEQ ID NO. 113) | Bla g 1.0101 | Q9UAM5 | 306 |
| VGITGLIDDVLAILP (SEQ ID NO. 114) | Bla g 1.0101 | Q9UAM5 | 326 |
| LIDDVLAILPLDDLK (SEQ ID NO. 8) | Bla g 1.0101 | Q9UAM5 | 331 |
| LAILPLDDLKALFNE (SEQ ID NO. 115) | Bla g 1.0101 | Q9UAM5 | 336 |
| LDDLKALFNEKLETS (SEQ ID NO. 116) | Bla g 1.0101 | Q9UAM5 | 341 |
| PDFLALYNAIKSPEF (SEQ ID NO. 117) | Bla g 1.0101 | Q9UAM5 | 356 |
| LYNAIKSPEFQSIVQ (SEQ ID NO. 118) | Bla g 1.0101 | Q9UAM5 | 361 |
| MIGLKLVTVLFAVAT (SEQ ID NO. 119) | Bla g 2 | P54958 | 1 |
| LVTVLFAVATITHAA (SEQ ID NO. 120) | Bla g 2 | P54958 | 6 |
| FAVATITHAAELQRV (SEQ ID NO. 12) | Bla g 2 | P54958 | 11 |
| ITHAAELQRVPLYKL (SEQ ID NO. 121) | Bla g 2 | P54958 | 16 |
| ELQRVPLYKLVHVFI (SEQ ID NO. 122) | Bla g 2 | P54958 | 21 |
| PLYKLVHVFINTQYA (SEQ ID NO. 19) | Bla g 2 | P54958 | 26 |
| VHVFINTQYAGITKI (SEQ ID NO. 123) | Bla g 2 | P54958 | 31 |
| NTQYAGITKIGNQNF (SEQ ID NO. 124) | Bla g 2 | P54958 | 36 |
| GITKIGNQNFLTVFD (SEQ ID NO. 125) | Bla g 2 | P54958 | 41 |
| GNQNFLTVFDSTSCN (SEQ ID NO. 23) | Bla g 2 | P54958 | 46 |
| PNLQKYEKLKPKYIS (SEQ ID NO. 126) | Bla g 2 | P54958 | 76 |
| YEKLKPKYISDGNVQ (SEQ ID NO. 127) | Bla g 2 | P54958 | 81 |

TABLE X-continued

Bla q peptides tested.

| Sequence in order of appearance | Source protein | UniProt ID | Position |
|---|---|---|---|
| PKYISDGNVQVKFFD (SEQ ID NO. 128) | Bla g 2 | P54958 | 86 |
| DGNVQVKFFDTGSAV (SEQ ID NO. 129) | Bla g 2 | P54958 | 91 |
| VKFFDTGSAVGRGIE (SEQ ID NO. 130) | Bla g 2 | P54958 | 96 |
| GRGIEDSLTISNLTT (SEQ ID NO. 131) | Bla g 2 | P54958 | 106 |
| LSQEVCILSADVVVG (SEQ ID NO. 132) | Bla g 2 | P54958 | 131 |
| CILSADVVVGIAAPG (SEQ ID NO. 133) | Bla g 2 | P54958 | 136 |
| KGKTVLENFVEENLI (SEQ ID NO. 134) | Bla g 2 | P54958 | 156 |
| LENFVEENLIAPVFS (SEQ ID NO. 135) | Bla g 2 | P54958 | 161 |
| EENLIAPVFSIHHAR (SEQ ID NO. 136) | Bla g 2 | P54958 | 166 |
| APVFSIHHARFQDGE (SEQ ID NO. 137) | Bla g 2 | P54958 | 171 |
| IFGGSDWKYVDGEFT (SEQ ID NO. 138) | Bla g 2 | P54958 | 191 |
| DWKYVDGEFTYVPLV (SEQ ID NO. 139) | Bla g 2 | P54958 | 196 |
| DGEFTYVPLVGDDSW (SEQ ID NO. 140) | Bla g 2 | P54958 | 201 |
| YVPLVGDDSWKFRLD (SEQ ID NO. 141) | Bla g 2 | P54958 | 206 |
| GDDSWKFRLDGVKIG (SEQ ID NO. 142) | Bla g 2 | P54958 | 211 |
| PAGTQAIIDTSKAII (SEQ ID NO. 143) | Bla g 2 | P54958 | 231 |
| AIIDTSKAIIVGPKA (SEQ ID NO. 144) | Bla g 2 | P54958 | 236 |
| SKAIIVGPKAYVNPI (SEQ ID NO. 145) | Bla g 2 | P54958 | 241 |
| VGPKAYVNPINEAIG (SEQ ID NO. 146) | Bla g 2 | P54958 | 246 |
| SLPDVTFVINGRNFN (SEQ ID NO. 147) | Bla g 2 | P54958 | 281 |
| TFVINGRNFNISSQY (SEQ ID NO. 148) | Bla g 2 | P54958 | 286 |
| GRNFNISSQYYIQQN (SEQ ID NO. 149) | Bla g 2 | P54958 | 291 |
| ISSQYYIQQNGNLCY (SEQ ID NO. 21) | Bla g 2 | P54958 | 296 |
| HFFIGDFFVDHYYSE (SEQ ID NO. 18) | Bla g 2 | P54958 | 321 |
| DFFVDHYYSEFNWEN (SEQ ID NO. 150) | Bla g 2 | P54958 | 326 |
| LDYERFRGSWIIAAG (SEQ ID NO. 151) | Bla g 4 | P54962 | 26 |
| FRGSWIIAAGTSEAL (SEQ ID NO. 152) | Bla g 4 | P54962 | 31 |
| IIAAGTSEALTQYKC (SEQ ID NO. 153) | Bla g 4 | P54962 | 36 |
| WIDRFSYDDALVSKY (SEQ ID NO. 154) | Bla g 4 | P54962 | 51 |
| YNDKGKAFSAPYSVL (SEQ ID NO. 155) | Bla g 4 | P54962 | 91 |
| KAFSAPYSVLATDYE (SEQ ID NO. 156) | Bla g 4 | P54962 | 96 |
| PYSVLATDYENYAIV (SEQ ID NO. 157) | Bla g 4 | P54962 | 101 |
| ATDYENYAIVEGCPA (SEQ ID NO. 158) | Bla g 4 | P54962 | 106 |
| AANGHVIYVQIRFSV (SEQ ID NO. 159) | Bla g 4 | P54962 | 121 |
| VIYVQIRFSVRRFHP (SEQ ID NO. 160) | Bla g 4 | P54962 | 126 |
| IRFSVRRFHPKLGDK (SEQ ID NO. 161) | Bla g 4 | P54962 | 131 |
| EMIQHYTLDQVNQHK (SEQ ID NO. 162) | Bla g 4 | P54962 | 146 |
| KAIEEDLKHFNLKYE (SEQ ID NO. 163) | Bla g 4 | P54962 | 161 |
| KHFNLKYEDLHSTCH (SEQ ID NO. 164) | Bla g 4 | P54962 | 168 |
| KLTYCPVKALGEPIR (SEQ ID NO. 165) | Bla g 5 | O18598 | 6 |
| GEPIRFLLSYGEKDF (SEQ ID NO. 166) | Bla g 5 | O18598 | 16 |
| FLLSYGEKDFEDYRF (SEQ ID NO. 29) | Bla g 5 | O18598 | 21 |
| SMPFGKTPVLEIDGK (SEQ ID NO. 11) | Bla g 5 | O18598 | 46 |
| QTHQSVAISRYLGKQ (SEQ ID NO. 166) | Bla g 5 | O18598 | 61 |
| VAISRYLGKQFGLSG (SEQ ID NO. 2) | Bla g 5 | O18598 | 66 |
| NLEIDMIVDTISDFR (SEQ ID NO. 167) | Bla g 5 | O18598 | 86 |
| MIVDTISDFRAAIAN (SEQ ID NO. 168) | Bla g 5 | O18598 | 91 |
| ISDFRAAIANYHYDA (SEQ ID NO. 4) | Bla g 5 | O18598 | 96 |

TABLE X-continued

Bla g peptides tested.

| Sequence in order of appearance | Source protein | UniProt ID | Position |
|---|---|---|---|
| TKKFDEVVKANGGYL (SEQ ID NO. 169) | Bla g 5 | O18598 | 131 |
| EVVKANGGYLAAGKL (SEQ ID NO. 30) | Bla g 5 | O18598 | 136 |
| NGGYLAAGKLTWADF (SEQ ID NO. 170) | Bla g 5 | O18598 | 141 |
| TWADFYFVAILDYLN (SEQ ID NO. 171) | Bla g 5 | O18598 | 151 |
| YFVAILDYLNHMAKE (SEQ ID NO. 5) | Bla g 5 | O18598 | 156 |
| LDYLNHMAKEDLVAN (SEQ ID NO. 172) | Bla g 5 | O18598 | 161 |
| HMAKEDLVANQPNLK (SEQ ID NO. 31) | Bla g 5 | O18598 | 166 |
| DLVANQPNLKALREK (SEQ ID NO. 32) | Bla g 5 | O18598 | 171 |
| QPNLKALREKVLGLP (SEQ ID NO. 173) | Bla g 5 | O18598 | 176 |
| ALREKVLGLPAIKAW (SEQ ID NO. 33) | Bla g 5 | O18598 | 181 |
| VLGLPAIKAWVAKRP (SEQ ID NO. 34) | Bla g 5 | O18598 | 186 |
| EQISVLRKAFDAFDR (SEQ ID NO. 35) | Bla g 6 | Q1A7B1 | 11 |
| LRKAFDAFDREKSGS (SEQ ID NO. 36) | Bla g 6 | Q1A7B1 | 16 |
| VEEILRLMGQPFNRR (SEQ ID NO. 174) | Bla g 6 | Q1A7B1 | 36 |
| ADKSGRLEFDEFVTL (SEQ ID NO. 175) | Bla g 6 | Q1A7B1 | 61 |
| RLEFDEFVTLAAKFI (SEQ ID NO. 176) | Bla g 6 | Q1A7B1 | 66 |
| EFVTLAAKFIIEEDS (SEQ ID NO. 14) | Bla g 6 | Q1A7B1 | 71 |
| EAMEKELREAFRLYD (SEQ ID NO. 24) | Bla g 6 | Q1A7B1 | 86 |
| CLREILRELDEQLTS (SEQ ID NO. 177) | Bla g 6 | Q1A7B1 | 111 |
| DELDMMIEEIDADGS (SEQ ID NO. 178) | Bla g 6 | Q1A7B1 | 126 |
| SGTVDFDEFMEMMTG (SEQ ID NO. 22) | Bla g 6 | Q1A7B1 | 140 |
| AEQVVLLKKAFDAFD (SEQ ID NO. 179) | Bla g 6.0101 | Q1A7B2 | 6 |
| MVGTILEMLGTRLDQ (SEQ ID NO. 37) | Bla g 6.0101 | Q1A7B2 | 31 |
| GELEFEEFCTLASRF (SEQ ID NO. 180) | Bla g 6.0101 | Q1A7B2 | 61 |
| EEFCTLASRFLVEED (SEQ ID NO. 6) | Bla g 6.0101 | Q1A7B2 | 66 |
| HELREAFRLYDKEGN (SEQ ID NO. 181) | Bla g 6.0101 | Q1A7B2 | 86 |
| DKEGNGYITTAVLRE (SEQ ID NO. 182) | Bla g 6.0101 | Q1A7B2 | 96 |
| GYITTAVLREILKEL (SEQ ID NO. 183) | Bla g 6.0101 | Q1A7B2 | 101 |
| AVLREILKELDDKIT (SEQ ID NO. 184) | Bla g 6.0101 | Q1A7B2 | 106 |
| PEQIQLLKKAFDAFD (SEQ ID NO. 7) | Bla g 6.0201 | Q1A7B3 | 6 |
| MVGTILEMLGHRLDD (SEQ ID NO. 17) | Bla g 6.020 | 1Q1A7B3 | 31 |
| DMLQEIIAEVDADGS (SEQ ID NO. 185) | Bla g 6.0201 | Q1A7B3 | 46 |
| GELEFEEFVSLASRF (SEQ ID NO. 186) | Bla g 6.0201 | Q1A7B3 | 61 |
| EEFVSLASRFLVEED (SEQ ID NO. 38) | Bla g 6.0201 | Q1A7B3 | 66 |
| GYITTNVLREILKEL (SEQ ID NO. 25) | Bla g 6.0201 | Q1A7B3 | 101 |
| MDAIKKKMQAMKLEK (SEQ ID NO. 187) | Bla g 7 | Q9NG56 | 1 |
| KKMQAMKLEKDNAMD (SEQ ID NO. 188) | Bla g 7 | Q9NG56 | 6 |
| LQKKIQQIENDLDQT (SEQ ID NO. 189) | Bla g 7 | Q9NG56 | 46 |
| MEQLMQVNAKLDEKD (SEQ ID NO. 190) | Bla g 7 | Q9NG56 | 61 |
| KALQNAESEVAALNR (SEQ ID NO. 191) | Bla g 7 | Q9NG56 | 76 |
| AESEVAALNRRIQLL (SEQ ID NO. 192) | Bla g 7 | Q9NG56 | 81 |
| AALNRRIQLLEEDLE (SEQ ID NO. 193) | Bla g 7 | Q9NG56 | 86 |
| RSEERLATATAKLAE (SEQ ID NO. 194) | Bla g 7 | Q9NG56 | 101 |
| LATATAKLAEASQAA (SEQ ID NO. 195) | Bla g 7 | Q9NG56 | 106 |
| GESKIVELEEELRVV (SEQ ID NO. 196) | Bla g 7 | Q9NG56 | 186 |
| VELEEELRVVGNNLK (SEQ ID NO. 197) | Bla g 7 | Q9NG56 | 191 |
| ELRVVGNNLKSLEVS (SEQ ID NO. 198) | Bla g 7 | Q9NG56 | 196 |
| LREEEYKQQIKTLNT (SEQ ID NO. 199) | Bla g 7 | Q9NG56 | 216 |

TABLE X-continued

Bla g peptides tested.

| Sequence in order of appearance | Source protein | UniProt ID | Position |
|---|---|---|---|
| YKQQIKTLNTRLKEA (SEQ ID NO. 200) | Bla g 7 | Q9NG56 | 221 |
| ICDDLDMTFTELIGN (SEQ ID NO. 201) | Bla g 7 | Q9NG56 | 270 |

REFERENCES

1. Arshad, S. H. 2003. Indoor allergen exposure in the development of allergy and asthma. Curr. Allergy Asthma Rep. 3: 115-120.
2. Litonjua, A. A., V. J. Carey, H. A. Burge, S. T. Weiss, and D. R. Gold. 2001. Exposure to Cockroach allergen in the home is associated with incident doctor diagnosed asthma and recurrent wheezing. J. Allergy Clin. Immunol. 107: 41-47.
3. Rosenstreich, D. L., P. Eggleston, M. Kattan, D. Baker, R. G. Slavin, P. Gergen, H. Mitchell, K. McNiff-Mortimer, H. Lynn, D. Ownby, and F. Malveaux. 1997. The role of Cockroach allergy and exposure to Cockroach allergen in causing morbidity among inner-city children with asthma. N. Engl. J. Med. 336: 1356-1363.
4. Arruda, L. K., L. D. Vailes, V. P. Ferriani, A. B. Santos, A. Pome's, and M. D. Chapman. 2001. Cockroach allergens and asthma. J. Allergy Clin. Immunol. 107: 419-428.
5. Gruchalla, R. S., J. Pongracic, M. Plaut, R. Evans, III, C. M. Visness, M. Walter, E. F. Crain, M. Kattan, W. J. Morgan, S. Steinbach, et al. 2005. Inner City Asthma Study: relationships among sensitivity, allergen exposure, and asthma morbidity. J. Allergy Clin. Immunol. 115: 478-485.
6. Wang, J., C. M. Visness, A. Calatroni, P. J. Gergen, H. E. Mitchell, and H. A. Sampson. 2009. Effect of environmental allergen sensitization on asthma morbidity in inner-city asthmatic children. Clin. Exp. Allergy 39: 1381-1389.
7. Platts-Mills, T. A., G. Rakes, and P. W. Heymann. 2000. The relevance of allergen exposure to the development of asthma in childhood. J. Allergy Clin. Immunol. 105: S503-S508.
8. Weiss, K. B., P. J. Gergen, and E. F. Crain. 1992. Inner-city asthma: the epidemiology of an emerging US public health concern. Chest 101(6, Suppl.) 3625-3675.
9. Perzanowski, M. S., and T. A. Platts-Mills. 2009. Further confirmation of the relevance of Cockroach and dust mite sensitization to inner-city asthma morbidity. Clin. Exp. Allergy 39: 1291-1293.
10. Pollart, S. M., M. D. Chapman, G. P. Fiocco, G. Rose, and T. A. Platts-Mills. 1989. Epidemiology of acute asthma: IgE antibodies to common inhalant allergens as a risk factor for emergency room visits. J. Allergy Clin. Immunol. 83: 875-882.
11. Huss, K., N. F. Adkinson, Jr., P. A. Eggleston, C. Dawson, M. L. Van Natta, and R. G. Hamilton. 2001. House dust mite and Cockroach exposure are strong risk factors for positive allergy skin test responses in the Childhood Asthma Management Program. J. Allergy Clin. Immunol. 107: 48-54.
12. Antony, A. B., R. S. Tepper, and K. A. Mohammed. 2002. Cockroach extract antigen increases bronchial airway epithelial permeability. J. Allergy Clin. Immunol. 110: 589-595.
13. Bhat, R. K., K. Page, A. Tan, and M. B. Hershenson. 2003. German Cockroach extract increases bronchial epithelial cell interleukin-8 expression. Clin. Exp. Allergy 33: 35-42.
14. Slater, J. E., R. James, J. A. Pongracic, A. H. Liu, S. Sarpong, H. A. Sampson, S. M. Satinover, J. A. Woodfolk, H. E. Mitchell, P. J. Gergen, and P. A. Eggleston. 2007. Biological potency of German Cockroach allergen extracts determined in an inner city population. Clin. Exp. Allergy 37: 1033-1039.
15. Finn, P. W., J. O. Boudreau, H. He, Y. Wang, M. D. Chapman, C. Vincent, H. A. Burge, S. T. Weiss, D. L. Perkins, and D. R. Gold. 2000. Children at risk for asthma: home allergen levels, lymphocyte proliferation, and wheeze. J. Allergy Clin. Immunol. 105: 933-942.
16. Arruda, L. K., and M. D. Chapman. 2001. The role of Cockroach allergens in asthma. Curr. Opin. Pulm. Med. 7: 14-19.
17. Pomés, A., E. Melén, L. D. Vailes, J. D. Retief, L. K. Arruda, and M. D. Chapman. 1998. Novel allergen structures with tandem amino acid repeats derived from German and American Cockroach. J. Biol. Chem. 273: 30801-30807.
18. Arruda, L. K., L. D. Vailes, M. L. Hayden, D. C. Benjamin, and M. D. Chapman. 1995. Cloning of Cockroach allergen, Bla g 4, identifies ligand binding proteins (or calycins) as a cause of IgE antibody responses. J. Biol. Chem. 270: 31196-31201.
19. Arruda, L. K., L. D. Vailes, B. J. Mann, J. Shannon, J. W. Fox, T. S. Vedvick, M. L. Hayden, and M. D. Chapman. 1995. Molecular cloning of a major Cockroach (*Blattella germanica*) allergen, Bla g 2: sequence homology to the aspartic proteases. J. Biol. Chem. 270: 19563-19568.
20. Arruda, L. K., L. D. Vailes, T. A. Platts-Mills, M. L. Hayden, and M. D. Chapman. 1997. Induction of IgE antibody responses by glutathione transferase from the German Cockroach (*Blattella germanica*). J. Biol. Chem. 272: 20907-20912.
21. Hindley, J., S. Wünschmann, S. M. Satinover, J. A. Woodfolk, F. T. Chew, M. D. Chapman, and A. Pomés. 2006. Bla g 6: a troponin C allergen from *Blattella germanica* with IgE binding calcium dependence. J. Allergy Clin. Immunol. 117: 1389-1395.
22. Asturias, J. A., N. Gómez-Bayón, M. C. Arilla, A. Martínez, R. Palacios, F. Sanchez-Gascón, and J. Martínez. 1999. Molecular characterization of American Cockroach tropomyosin (*Periplaneta americana* allergen 7), a crossreactive allergen. J. Immunol. 162: 4342-4348.
23. Satinover, S. M., A. J. Reefer, A. Pomes, M. D. Chapman, T. A. Platts-Mills, and J. A. Woodfolk. 2005. Specific IgE and IgG antibody-binding patterns to recombinant Cockroach allergens. J. Allergy Clin. Immunol. 115: 803-809.
24. Pree, I., M. H. Shamji, I. Kimber, R. Valenta, S. R. Durham, and V. Niederberger. 2010. Inhibition of CD23-dependent facilitated allergen binding to B cells following vaccination with genetically modified hypoallergenic Bet v 1 molecules. Clin. Exp. Allergy 40: 1346-1352.
25. Kang, B. C., J. Johnson, C. Morgan, and J. L. Chang. 1988. The role of immunotherapy in Cockroach asthma. J. Asthma 25: 205-218.

26. Srivastava, D., S. N. Gaur, N. Arora, and B. P. Singh. 2011. Clinicoimmunological changes post-immunotherapy with *Periplaneta americana*. Eur. J. Clin. Invest. 41: 879-888.
27. Akdis, M., J. Verhagen, A. Taylor, F. Karamloo, C. Karagiannidis, R. Crameri, S. Thunberg, G. Deniz, R. Valenta, H. Fiebig, et al. 2004. Immune responses in healthy and allergic individuals are characterized by a fine balance between allergen-specific T regulatory 1 and T helper 2 cells. J. Exp. Med. 199: 1567-1575.
28. Gross, F., G. Metzner, and U. Behn. 2011. Mathematical modeling of allergy and specific immunotherapy: Th1-Th2-Treg interactions. J. Theor. Biol. 269: 70-78.
29. Soyer, O. U., M. Akdis, and C. A. Akdis. 2011. Mechanisms of subcutaneous allergen immunotherapy. Immunol. Allergy Clin. North Am. 31: 175-190, vii-viii.
30. Jutel, M., M. Akdis, F. Budak, C. Aebischer-Casaulta, M. Wrzyszcz, K. Blaser, and C. A. Akdis. 2003. IL-10 and COCKROACH F-b cooperate in the regulatory T cell response to mucosal allergens in normal immunity and specific immunotherapy. Eur. J. Immunol. 33: 1205-1214.
31. Ebner, C., U. Siemann, B. Bohle, M. Willheim, U. Wiedermann, S. Schenk, F. Klotz, H. Ebner, D. Kraft, and O. Scheiner. 1997. Immunological changes during specific immunotherapy of grass pollen allergy: reduced lymphoproliferative responses to allergen and shift from TH2 to TH1 in T-cell clones specific for Phl p 1, a major grass pollen allergen. Clin. Exp. Allergy 27: 1007-1015.
32. Oseroff, C., J. Sidney, M. F. Kotturi, R. Kolla, R. Alam, D. H. Broide, S. I. Wasserman, D. Weiskopf, D. M. McKinney, J. L. Chung, et al. 2010. Molecular determinants of T cell epitope recognition to the common Cockroach allergen. J. Immunol. 185: 943-955.
33. Jeong, K. Y., M. H. Yi, K. J. Jeong, H. Lee, C. S. Hong, and T. S. Yong. 2009. Sequence diversity of the Bla g 4 Cockroach allergen, homologous to lipocalins, from *Blattella germanica*. Int. Arch. Allergy Immunol. 148: 339-345.
34. Jeong, K. Y., H. Lee, K. H. Shin, M. H. Yi, K. J. Jeong, C. S. Hong, and T. S. Yong. 2008. Sequence polymorphisms of major German Cockroach allergens Bla g 1, Bla g 2, Bla g 4, and Bla g 5. Int. Arch. Allergy Immunol. 145: 1-8.
35. Wang, P., J. Sidney, Y. Kim, A. Sette, O. Lund, M. Nielsen, and B. Peters. 2010. Peptide binding predictions for HLA DR, DP and DQ molecules. BMC Bioinformatics 11: 568.
36. Sidney, J., S. Southwood, C. Oseroff, M. F. del Guercio, A. Sette, and H. Grey. 2001. Measurement of MHC/peptide Interactions by gel filtration. Curr. Protoc. Immunol. Chapter 18: Unit 18.3.
37. Gulukota, K., J. Sidney, A. Sette, and C. DeLisi. 1997. Two complementary methods for predicting peptides binding major histocompatibility complex molecules. J. Mol. Biol. 267: 1258-1267.
38. Cheng, Y., and W. H. Prusoff. 1973. Relationship between the inhibition constant ($K_1$) and the concentration of inhibitor which causes 50 percent inhibition ($I_{50}$) of an enzymatic reaction. Biochem. Pharmacol. 22: 3099-3108.
39. Greenbaum, J., J. Sidney, J. Chung, C. Brander, B. Peters, and A. Sette. 2011. Functional classification of class II human leukocyte antigen (HLA) molecules reveals seven different supertypes and a surprising degree of repertoire sharing across supertypes. Immunogenetics 63: 325-335.
40. Arruda, L. K., L. D. Vailes, D. C. Benjamin, and M. D. Chapman. 1995. Molecular cloning of German Cockroach (*Blattella germanica*) allergens. Int. Arch. Allergy Immunol. 107: 295-297.
41. Sidney, J., A. Steen, C. Moore, S. Ngo, J. Chung, B. Peters, and A. Sette. 2010. Divergent motifs but overlapping binding repertoires of six HLA-DQ molecules frequently expressed in the worldwide human population. J. Immunol. 185: 4189-4198.
42. Sidney, J., A. Steen, C. Moore, S. Ngo, J. Chung, B. Peters, and A. Sette. 2010. Five HLA-DP molecules frequently expressed in the worldwide human population share a common HLA supertypic binding specificity. J. Immunol. 184: 2492-2503.
43. Middleton, D., L. Menchaca, H. Rood, and R. Komerofsky. 2003. New allele frequency database: http://www.allelefrequencies.net. Tissue Antigens 61: 403-407.
44. Passalacqua, G., S. R. Durham; Global Allergy and Asthma European Network. 2007. Allergic rhinitis and its impact on asthma update: allergen immunotherapy. J. Allergy Clin. Immunol. 119: 881-891.
45. Bohle, B. 2008. T cell responses during allergen-specific immunotherapy of type I allergy. Front. Biosci. 13: 6079-6085.
46. German, R. N., F. Castellino, R. Han, C. Reis e Sousa, P. Romagnoli, S. Sadegh-Nasseri, and G. M. Zhong. 1996. Processing and presentation of endocytically acquired protein antigens by MHC class II and class I molecules. Immunol. Rev. 151: 5-30.
47. Assarsson, E., J. A. Greenbaum, M. Sundström, L. Schaffer, J. A. Hammond, V. Pasquetto, C. Oseroff, R. C. Hendrickson, E. J. Lefkowitz, D. C. Tscharke, et al. 2008. Kinetic analysis of a complete poxvirus transcriptome reveals an immediate-early class of genes. Proc. Natl. Acad. Sci. USA 105: 2140-2145.
48. Assarsson, E., J. Sidney, C. Oseroff, V. Pasquetto, H.-H. Bui, N. Frahm, C. Brander, B. Peters, H. Grey, and A. Sette. 2007. A quantitative analysis of the variables affecting the repertoire of T cell specificities recognized after vaccinia virus infection. J. Immunol. 178: 7890-7901.
49. Botten, J., J. Alexander, V. Pasquetto, J. Sidney, P. Barrowman, J. Ting, B. Peters, S. Southwood, B. Stewart, M. P. Rodriguez-Carreno, et al. 2006. Identification of protective Lassa virus epitopes that are restricted by HLA-A2. J. Virol. 80: 8351-8361.
50. Kotturi, M. F., J. Botten, J. Sidney, H.-H. Bui, L. Giancola, M. Maybeno, J. Babin, C. Oseroff, V. Pasquetto, J. A. Greenbaum, et al. 2009. A multivalent and cross-protective vaccine strategy against arenaviruses associated with human disease. PLoS Pathog. 5: e1000695.
51. Mothé, B. R., B. S. Stewart, C. Oseroff, H.-H. Bui, S. Stogiera, Z. Garcia, C. Dow, M. P. Rodriguez-Carreno, M. Kotturi, V. Pasquetto, et al. 2007. Chronic lymphocytic choriomeningitis virus infection actively down-regulates $CD4_+$ T cell responses directed against a broad range of epitopes. J. Immunol. 179: 1058-1067.
52. Moutaftsi, M., H.-H. Bui, B. Peters, J. Sidney, S. Salek-Ardakani, C. Oseroff, V. Pasquetto, S. Crotty, M. Croft, E. J. Lefkowitz, et al. 2007. Vaccinia virus specific $CD4_+$ T cell responses target a set of antigens largely distinct from those targeted by $CD8_+$ T cell responses. J. Immunol. 178: 6814-6820.
53. Moutaftsi, M., B. Peters, V. Pasquetto, D. C. Tscharke, J. Sidney, H. H. Bui, H. Grey, and A. Sette. 2006. A consensus epitope prediction approach identifies the breadth of murine T<sub>CD8+</sub>-cell responses to vaccinia virus. Nat. Biotechnol. 24: 817-819.
54. Oseroff, C., F. Kos, H. H. Bui, B. Peters, V. Pasquetto, J. Glenn, T. Palmore, J. Sidney, D. C. Tscharke, J. R. Bennink, et al. 2005. HLA class I-restricted responses to vaccinia recognize a broad array of proteins mainly involved in virulence and viral gene regulation. Proc. Natl. Acad. Sci. USA 102: 13980-13985.
55. Oseroff, C., B. Peters, V. Pasquetto, M. Moutaftsi, J. Sidney, V. Panchanathan, D. C. Tscharke, B. Maillere, H. Grey, and A. Sette. 2008. Dissociation between epitope hierarchy and immunoprevalence in CD8 responses to vaccinia virus western reserve. J. Immunol. 180: 7193-7202.
56. Assarsson, E., H.-H. Bui, J. Sidney, Q. Zhang, J. Glenn, C. Oseroff, I. N. Mbawuike, J. Alexander, M. J. Newman, H. Grey, and A. Sette. 2008. Immunomic analysis of the repertoire of T-cell specificities for influenza A virus in humans. J. Virol. 82: 12241-12251.
57. Bui, H. H., B. Peters, E. Assarsson, I. Mbawuike, and A. Sette. 2007. Ab and T cell epitopes of influenza A virus, knowledge and opportunities. Proc. Natl. Acad. Sci. USA 104: 246-251.
58. Blythe, M. J., Q. Zhang, K. Vaughan, R. de Castro, Jr., N. Salimi, H.-H. Bui, D. M. Lewinsohn, J. D. Ernst, B. Peters, and A. Sette. 2007. An analysis of the epitope knowledge related to mycobacteria. Immunome Res. 3: 10.
59. Vaughan, K., M. Blythe, J. Greenbaum, Q. Zhang, B. Peters, D. L. Doolan, and A. Sette. 2009. Meta-analysis of immune epitope data for all Plasmodia: overview and applications for malarial immunobiology and vaccine-related issues. Parasite Immunol. 31: 78-97.
60. Vaughan, K., J. Greenbaum, M. Blythe, B. Peters, and A. Sette. 2010. Metaanalysis of all immune epitope data in the Flavivirus genus: inventory of current immune epitope data status in the context of virus immunity and immunopathology. Viral Immunol. 23: 259-284.
61. Zarebski, L. M., K. Vaughan, J. Sidney, B. Peters, H. Grey, K. D. Janda, A. Casadevall, and A. Sette. 2008. Analysis of epitope information related to *Bacillus anthracia* and *Clostridium botulinum*. Expert Rev. Vaccines 7: 55-74.
62. Hales, B. J., H. Shen, and W. R. Thomas. 2000. Cytokine responses to Der p 1 and Der p 7: house dust mite allergens with different IgE-binding activities. Clin. Exp. Allergy 30: 934-943.

What is claimed is:

1. A pharmaceutical composition comprising (i) a pharmaceutically acceptable carrier, diluent, or excipient, (ii) an adjuvant, and (iii) a set of peptides, wherein each of the peptides has a length from 7 to 30 amino acids, comprising a peptide having the amino acid sequence set forth in SEQ ID NO:1, a peptide having the amino acid sequence set forth in SEQ ID NO:3 and a peptide having the amino acid sequence set forth in SEQ ID NO: 6, wherein the composition inhibits or reduces an anti-allergen immune response, and wherein the anti-allergen immune response comprises a T cell response.

2. A unit dosage form comprising the pharmaceutical composition of claim 1.

3. A method of inducing immune tolerance a cell against a Cockroach allergen, the method comprising contacting the cell with an effective amount of the composition of claim 1.

4. A method of inhibiting or reducing an immune response against a Cockroach allergen in a subject, comprising administering to the subject an effective amount of the composition of claim 1.

5. A method of providing a subject protection against an allergic response, allergic disorder or allergic disease, or one or more physiological conditions, disorders, illnesses, diseases, symptoms or complications caused by or associated with a Cockroach allergen, comprising administering to the subject an effective amount of the composition of claim 1.

6. A method of treating a subject for an allergic response, allergic disorder or allergic disease, or one or more physiological conditions, disorders, illnesses, diseases, symptoms or complications caused by or associated with a Cockroach allergen, comprising administering to the subject an effective amount of the composition of claim 1.

7. The method of claim 4 or 6, wherein the method comprises inducing in the subject immunological tolerance to the Cockroach allergen.

8. The method of claim 6, wherein the subject is a human.

9. The pharmaceutical composition of claim 1, Wherein the adjuvant comprises Freund's complete adjuvant (CFA), Freund's incomplete adjuvant (IFA), metal or metallic salts, aluminum or aluminum salts, aluminum phosphate, aluminum hydroxide, alum (hydrated potassium aluminum sulfate), bacterially derived compounds, Monophosphoryllipid A and derivatives thereof, enterobacteriallipopolysaccharides (LPS), plant derived saponins and derivatives thereof, Quil A and fragments thereof, soya lecithin or oleic acid surfactants, sorbitan trioleate, polyvinylpyrrolidone, CpG oligonucleotides, polyriboA and polyriboU, block copolymers, GM-CSF, IL-1, or Muramyl tripeptide (MTP).

10. The pharmaceutical composition of claim 1, further comprising a peptide having an amino acid sequence selected from the group consisting of the amino acid sequences set forth in SEQ ID NOs:5, 7-10, 12-35 and 47-57.

11. The pharmaceutical composition of claim 1, further comprising two or more peptides having an amino acid sequence selected from the group consisting of the amino acid sequences set forth in SEQ ID NOs:10, 12, 13, 15 and 17.

* * * * *

SEQUENCE LISTING

```
<160> NUMBER OF SEQ ID NOS: 210

<210> SEQ ID NO 1
<211> LENGTH: 20
<212> TYPE: PRT
<213> ORGANISM: Blattella germanica

<400> SEQUENCE: 1

Ala Leu Arg Glu Lys Val Leu Gly Leu Pro Ala Ile Lys Ala Trp Val
1               5                   10                  15

Ala Lys Arg Pro
            20

<210> SEQ ID NO 2
<211> LENGTH: 15
<212> TYPE: PRT
<213> ORGANISM: Blattella germanica

<400> SEQUENCE: 2

Val Ala Ile Ser Arg Tyr Leu Gly Lys Gln Phe Gly Leu Ser Gly
1               5                   10                  15

<210> SEQ ID NO 3
<211> LENGTH: 20
<212> TYPE: PRT
<213> ORGANISM: Blattella germanica

<400> SEQUENCE: 3

Gly Glu Pro Ile Arg Phe Leu Leu Ser Tyr Gly Glu Lys Asp Phe Glu
1               5                   10                  15

Asp Tyr Arg Phe
            20

<210> SEQ ID NO 4
<211> LENGTH: 15
<212> TYPE: PRT
<213> ORGANISM: Blattella germanica

<400> SEQUENCE: 4
```

```
Ile Ser Asp Phe Arg Ala Ala Ile Ala Asn Tyr His Tyr Asp Ala
1               5                   10                  15
```

<210> SEQ ID NO 5
<211> LENGTH: 15
<212> TYPE: PRT
<213> ORGANISM: Blattella germanica

<400> SEQUENCE: 5

```
Tyr Phe Val Ala Ile Leu Asp Tyr Leu Asn His Met Ala Lys Glu
1               5                   10                  15
```

<210> SEQ ID NO 6
<211> LENGTH: 15
<212> TYPE: PRT
<213> ORGANISM: Blattella germanica

<400> SEQUENCE: 6

```
Glu Glu Phe Cys Thr Leu Ala Ser Arg Phe Leu Val Glu Glu Asp
1               5                   10                  15
```

<210> SEQ ID NO 7
<211> LENGTH: 15
<212> TYPE: PRT
<213> ORGANISM: Blattella germanica

<400> SEQUENCE: 7

```
Pro Glu Gln Ile Gln Leu Leu Lys Lys Ala Phe Asp Ala Phe Asp
1               5                   10                  15
```

<210> SEQ ID NO 8
<211> LENGTH: 15
<212> TYPE: PRT
<213> ORGANISM: Blattella germanica

<400> SEQUENCE: 8

```
Leu Ile Asp Asp Val Leu Ala Ile Leu Pro Leu Asp Asp Leu Lys
1               5                   10                  15
```

<210> SEQ ID NO 9
<211> LENGTH: 20
<212> TYPE: PRT
<213> ORGANISM: Blattella germanica

<400> SEQUENCE: 9

```
His Met Ala Lys Glu Asp Leu Val Ala Asn Gln Pro Asn Leu Lys Ala
1               5                   10                  15

Leu Arg Glu Lys
            20
```

<210> SEQ ID NO 10
<211> LENGTH: 20
<212> TYPE: PRT
<213> ORGANISM: Blattella germanica

<400> SEQUENCE: 10

```
Thr Lys Lys Phe Asp Glu Val Val Lys Ala Asn Gly Gly Tyr Leu Ala
1               5                   10                  15

Ala Gly Lys Leu
            20
```

<210> SEQ ID NO 11
<211> LENGTH: 15

```
<212> TYPE: PRT
<213> ORGANISM: Blattella germanica

<400> SEQUENCE: 11

Ser Met Pro Phe Gly Lys Thr Pro Val Leu Glu Ile Asp Gly Lys
1               5                   10                  15

<210> SEQ ID NO 12
<211> LENGTH: 15
<212> TYPE: PRT
<213> ORGANISM: Blattella germanica

<400> SEQUENCE: 12

Phe Ala Val Ala Thr Ile Thr His Ala Ala Glu Leu Gln Arg Val
1               5                   10                  15

<210> SEQ ID NO 13
<211> LENGTH: 20
<212> TYPE: PRT
<213> ORGANISM: Blattella germanica

<400> SEQUENCE: 13

Glu Gln Ile Ser Val Leu Arg Lys Ala Phe Asp Ala Phe Asp Arg Glu
1               5                   10                  15

Lys Ser Gly Ser
            20

<210> SEQ ID NO 14
<211> LENGTH: 15
<212> TYPE: PRT
<213> ORGANISM: Blattella germanica

<400> SEQUENCE: 14

Glu Phe Val Thr Leu Ala Ala Lys Phe Ile Ile Glu Glu Asp Ser
1               5                   10                  15

<210> SEQ ID NO 15
<211> LENGTH: 20
<212> TYPE: PRT
<213> ORGANISM: Blattella germanica

<400> SEQUENCE: 15

Pro Glu Phe Gln Ser Ile Val Gln Thr Leu Asn Ala Met Pro Glu Tyr
1               5                   10                  15

Gln Asn Leu Leu
            20

<210> SEQ ID NO 16
<211> LENGTH: 15
<212> TYPE: PRT
<213> ORGANISM: Blattella germanica

<400> SEQUENCE: 16

Pro Glu Leu Gln Asn Phe Leu Asn Phe Leu Gly Ala Asn Gly Leu
1               5                   10                  15

<210> SEQ ID NO 17
<211> LENGTH: 15
<212> TYPE: PRT
<213> ORGANISM: Blattella germanica

<400> SEQUENCE: 17

Met Val Gly Thr Ile Leu Glu Met Leu Gly His Arg Leu Asp Asp
1               5                   10                  15
```

-continued

<210> SEQ ID NO 18
<211> LENGTH: 15
<212> TYPE: PRT
<213> ORGANISM: Blattella germanica

<400> SEQUENCE: 18

His Phe Phe Ile Gly Asp Phe Phe Val Asp His Tyr Tyr Ser Glu
1               5                   10                  15

<210> SEQ ID NO 19
<211> LENGTH: 15
<212> TYPE: PRT
<213> ORGANISM: Blattella germanica

<400> SEQUENCE: 19

Pro Leu Tyr Lys Leu Val His Val Phe Ile Asn Thr Gln Tyr Ala
1               5                   10                  15

<210> SEQ ID NO 20
<211> LENGTH: 15
<212> TYPE: PRT
<213> ORGANISM: Blattella germanica

<400> SEQUENCE: 20

Phe Glu Thr Ile Val Val Thr Val Asp Ser Leu Pro Glu Phe Lys
1               5                   10                  15

<210> SEQ ID NO 21
<211> LENGTH: 15
<212> TYPE: PRT
<213> ORGANISM: Blattella germanica

<400> SEQUENCE: 21

Ile Ser Ser Gln Tyr Tyr Ile Gln Gln Asn Gly Asn Leu Cys Tyr
1               5                   10                  15

<210> SEQ ID NO 22
<211> LENGTH: 15
<212> TYPE: PRT
<213> ORGANISM: Blattella germanica

<400> SEQUENCE: 22

Ser Gly Thr Val Asp Phe Asp Glu Phe Met Glu Met Met Thr Gly
1               5                   10                  15

<210> SEQ ID NO 23
<211> LENGTH: 15
<212> TYPE: PRT
<213> ORGANISM: Blattella germanica

<400> SEQUENCE: 23

Gly Asn Gln Asn Phe Leu Thr Val Phe Asp Ser Thr Ser Cys Asn
1               5                   10                  15

<210> SEQ ID NO 24
<211> LENGTH: 15
<212> TYPE: PRT
<213> ORGANISM: Blattella germanica

<400> SEQUENCE: 24

Glu Ala Met Glu Lys Glu Leu Arg Glu Ala Phe Arg Leu Tyr Asp
1               5                   10                  15

```
<210> SEQ ID NO 25
<211> LENGTH: 15
<212> TYPE: PRT
<213> ORGANISM: Blattella germanica

<400> SEQUENCE: 25

Gly Tyr Ile Thr Thr Asn Val Leu Arg Glu Ile Leu Lys Glu Leu
1               5                   10                  15

<210> SEQ ID NO 26
<211> LENGTH: 15
<212> TYPE: PRT
<213> ORGANISM: Blattella germanica

<400> SEQUENCE: 26

Pro Glu Phe Gln Ser Ile Val Gln Thr Leu Asn Ala Met Pro Glu
1               5                   10                  15

<210> SEQ ID NO 27
<211> LENGTH: 15
<212> TYPE: PRT
<213> ORGANISM: Blattella germanica

<400> SEQUENCE: 27

Ile Val Gln Thr Leu Asn Ala Met Pro Glu Tyr Gln Asn Leu Leu
1               5                   10                  15

<210> SEQ ID NO 28
<211> LENGTH: 15
<212> TYPE: PRT
<213> ORGANISM: Blattella germanica

<400> SEQUENCE: 28

Gly Glu Pro Ile Arg Phe Leu Leu Ser Tyr Gly Glu Lys Asp Phe
1               5                   10                  15

<210> SEQ ID NO 29
<211> LENGTH: 15
<212> TYPE: PRT
<213> ORGANISM: Blattella germanica

<400> SEQUENCE: 29

Phe Leu Leu Ser Tyr Gly Glu Lys Asp Phe Glu Asp Tyr Arg Phe
1               5                   10                  15

<210> SEQ ID NO 30
<211> LENGTH: 15
<212> TYPE: PRT
<213> ORGANISM: Blattella germanica

<400> SEQUENCE: 30

Glu Val Val Lys Ala Asn Gly Gly Tyr Leu Ala Ala Gly Lys Leu
1               5                   10                  15

<210> SEQ ID NO 31
<211> LENGTH: 15
<212> TYPE: PRT
<213> ORGANISM: Blattella germanica

<400> SEQUENCE: 31

His Met Ala Lys Glu Asp Leu Val Ala Asn Gln Pro Asn Leu Lys
1               5                   10                  15

<210> SEQ ID NO 32
<211> LENGTH: 15
```

-continued

<212> TYPE: PRT
<213> ORGANISM: Blattella germanica

<400> SEQUENCE: 32

Asp Leu Val Ala Asn Gln Pro Asn Leu Lys Ala Leu Arg Glu Lys
1               5                   10                  15

<210> SEQ ID NO 33
<211> LENGTH: 15
<212> TYPE: PRT
<213> ORGANISM: Blattella germanica

<400> SEQUENCE: 33

Ala Leu Arg Glu Lys Val Leu Gly Leu Pro Ala Ile Lys Ala Trp
1               5                   10                  15

<210> SEQ ID NO 34
<211> LENGTH: 15
<212> TYPE: PRT
<213> ORGANISM: Blattella germanica

<400> SEQUENCE: 34

Val Leu Gly Leu Pro Ala Ile Lys Ala Trp Val Ala Lys Arg Pro
1               5                   10                  15

<210> SEQ ID NO 35
<211> LENGTH: 15
<212> TYPE: PRT
<213> ORGANISM: Blattella germanica

<400> SEQUENCE: 35

Glu Gln Ile Ser Val Leu Arg Lys Ala Phe Asp Ala Phe Asp Arg
1               5                   10                  15

<210> SEQ ID NO 36
<211> LENGTH: 15
<212> TYPE: PRT
<213> ORGANISM: Blattella germanica

<400> SEQUENCE: 36

Leu Arg Lys Ala Phe Asp Ala Phe Asp Arg Glu Lys Ser Gly Ser
1               5                   10                  15

<210> SEQ ID NO 37
<211> LENGTH: 15
<212> TYPE: PRT
<213> ORGANISM: Blattella germanica

<400> SEQUENCE: 37

Met Val Gly Thr Ile Leu Glu Met Leu Gly Thr Arg Leu Asp Gln
1               5                   10                  15

<210> SEQ ID NO 38
<211> LENGTH: 15
<212> TYPE: PRT
<213> ORGANISM: Blattella germanica

<400> SEQUENCE: 38

Glu Glu Phe Val Ser Leu Ala Ser Arg Phe Leu Val Glu Glu Asp
1               5                   10                  15

<210> SEQ ID NO 39
<211> LENGTH: 15
<212> TYPE: PRT
<213> ORGANISM: Blattella germanica

<400> SEQUENCE: 39

Asp Leu Leu Gly Ile Pro His Ile Pro Val Thr Ala Arg Lys His
1               5                   10                  15

<210> SEQ ID NO 40
<211> LENGTH: 15
<212> TYPE: PRT
<213> ORGANISM: Blattella germanica

<400> SEQUENCE: 40

Leu Glu Thr Ser Pro Glu Phe Lys Ala Leu Tyr Asp Ala Ile Arg
1               5                   10                  15

<210> SEQ ID NO 41
<211> LENGTH: 15
<212> TYPE: PRT
<213> ORGANISM: Blattella germanica

<400> SEQUENCE: 41

Ser Pro Glu Phe Gln Ser Ile Val Gly Thr Leu Glu Ala Met Pro
1               5                   10                  15

<210> SEQ ID NO 42
<211> LENGTH: 15
<212> TYPE: PRT
<213> ORGANISM: Blattella germanica

<400> SEQUENCE: 42

Leu Glu Ala Met Pro Glu Tyr Gln Asn Leu Ile Gln Lys Leu Lys
1               5                   10                  15

<210> SEQ ID NO 43
<211> LENGTH: 15
<212> TYPE: PRT
<213> ORGANISM: Blattella germanica

<400> SEQUENCE: 43

Val Asp His Ile Ile Glu Leu Ile His Gln Ile Phe Asn Ile Val
1               5                   10                  15

<210> SEQ ID NO 44
<211> LENGTH: 15
<212> TYPE: PRT
<213> ORGANISM: Blattella germanica

<400> SEQUENCE: 44

Glu Leu Ile His Gln Ile Phe Asn Ile Val Arg Asp Thr Arg Gly
1               5                   10                  15

<210> SEQ ID NO 45
<211> LENGTH: 15
<212> TYPE: PRT
<213> ORGANISM: Blattella germanica

<400> SEQUENCE: 45

Ile Phe Asn Ile Val Arg Asp Thr Arg Gly Leu Pro Glu Asp Leu
1               5                   10                  15

<210> SEQ ID NO 46
<211> LENGTH: 15
<212> TYPE: PRT
<213> ORGANISM: Blattella germanica

<400> SEQUENCE: 46

-continued

Leu Pro Glu Asp Leu Gln Asp Phe Leu Ala Leu Ile Pro Thr Asp
1               5                   10                  15

<210> SEQ ID NO 47
<211> LENGTH: 15
<212> TYPE: PRT
<213> ORGANISM: Blattella germanica

<400> SEQUENCE: 47

Gln Asp Phe Leu Ala Leu Ile Pro Thr Asp Gln Val Leu Ala Ile
1               5                   10                  15

<210> SEQ ID NO 48
<211> LENGTH: 15
<212> TYPE: PRT
<213> ORGANISM: Blattella germanica

<400> SEQUENCE: 48

Leu Ile Pro Thr Asp Gln Val Leu Ala Ile Ala Ala Asp Tyr Leu
1               5                   10                  15

<210> SEQ ID NO 49
<211> LENGTH: 15
<212> TYPE: PRT
<213> ORGANISM: Blattella germanica

<400> SEQUENCE: 49

Gln Val Leu Ala Ile Ala Ala Asp Tyr Leu Ala Asn Asp Ala Glu
1               5                   10                  15

<210> SEQ ID NO 50
<211> LENGTH: 15
<212> TYPE: PRT
<213> ORGANISM: Blattella germanica

<400> SEQUENCE: 50

Ala Ala Asp Tyr Leu Ala Asn Asp Ala Glu Val Lys Ala Ala Val
1               5                   10                  15

<210> SEQ ID NO 51
<211> LENGTH: 15
<212> TYPE: PRT
<213> ORGANISM: Blattella germanica

<400> SEQUENCE: 51

Ala Asn Asp Ala Glu Val Lys Ala Ala Val Glu Tyr Leu Lys Ser
1               5                   10                  15

<210> SEQ ID NO 52
<211> LENGTH: 15
<212> TYPE: PRT
<213> ORGANISM: Blattella germanica

<400> SEQUENCE: 52

Asp Ser Leu Pro Glu Phe Lys Asn Phe Leu Asn Phe Leu Gln Thr
1               5                   10                  15

<210> SEQ ID NO 53
<211> LENGTH: 15
<212> TYPE: PRT
<213> ORGANISM: Blattella germanica

<400> SEQUENCE: 53

Phe Lys Asn Phe Leu Asn Phe Leu Gln Thr Asn Gly Leu Asn Ala

<210> SEQ ID NO 54
<211> LENGTH: 15
<212> TYPE: PRT
<213> ORGANISM: Blattella germanica

<400> SEQUENCE: 54

Asn Phe Leu Gln Thr Asn Gly Leu Asn Ala Ile Glu Phe Leu Asn
1               5                   10                  15

<210> SEQ ID NO 55
<211> LENGTH: 15
<212> TYPE: PRT
<213> ORGANISM: Blattella germanica

<400> SEQUENCE: 55

Asn Gly Leu Asn Ala Ile Glu Phe Leu Asn Asn Ile His Asp Leu
1               5                   10                  15

<210> SEQ ID NO 56
<211> LENGTH: 15
<212> TYPE: PRT
<213> ORGANISM: Blattella germanica

<400> SEQUENCE: 56

Ile Glu Phe Leu Asn Asn Ile His Asp Leu Leu Gly Ile Pro His
1               5                   10                  15

<210> SEQ ID NO 57
<211> LENGTH: 15
<212> TYPE: PRT
<213> ORGANISM: Blattella germanica

<400> SEQUENCE: 57

Thr Gly Leu Ile Asp Asp Ile Ile Ala Ile Leu Pro Val Asp Asp
1               5                   10                  15

<210> SEQ ID NO 58
<211> LENGTH: 15
<212> TYPE: PRT
<213> ORGANISM: Blattella germanica

<400> SEQUENCE: 58

Asp Ile Ile Ala Ile Leu Pro Val Asp Asp Leu Tyr Ala Leu Phe
1               5                   10                  15

<210> SEQ ID NO 59
<211> LENGTH: 15
<212> TYPE: PRT
<213> ORGANISM: Blattella germanica

<400> SEQUENCE: 59

Leu Pro Val Asp Asp Leu Tyr Ala Leu Phe Gln Glu Lys Leu Glu
1               5                   10                  15

<210> SEQ ID NO 60
<211> LENGTH: 15
<212> TYPE: PRT
<213> ORGANISM: Blattella germanica

<400> SEQUENCE: 60

Leu Tyr Ala Leu Phe Gln Glu Lys Leu Glu Thr Ser Pro Glu Phe
1               5                   10                  15

<210> SEQ ID NO 61
<211> LENGTH: 15
<212> TYPE: PRT
<213> ORGANISM: Blattella germanica

<400> SEQUENCE: 61

Lys Ala Leu Tyr Asp Ala Ile Arg Ser Pro Glu Phe Gln Ser Ile
1               5                   10                  15

<210> SEQ ID NO 62
<211> LENGTH: 15
<212> TYPE: PRT
<213> ORGANISM: Blattella germanica

<400> SEQUENCE: 62

Ala Ile Arg Ser Pro Glu Phe Gln Ser Ile Val Glu Thr Leu Lys
1               5                   10                  15

<210> SEQ ID NO 63
<211> LENGTH: 15
<212> TYPE: PRT
<213> ORGANISM: Blattella germanica

<400> SEQUENCE: 63

Glu Phe Gln Ser Ile Val Glu Thr Leu Lys Ala Met Pro Glu Tyr
1               5                   10                  15

<210> SEQ ID NO 64
<211> LENGTH: 15
<212> TYPE: PRT
<213> ORGANISM: Blattella germanica

<400> SEQUENCE: 64

Val Glu Thr Leu Lys Ala Met Pro Glu Tyr Gln Ser Leu Ile Gln
1               5                   10                  15

<210> SEQ ID NO 65
<211> LENGTH: 15
<212> TYPE: PRT
<213> ORGANISM: Blattella germanica

<400> SEQUENCE: 65

Ala Met Pro Glu Tyr Gln Ser Leu Ile Gln Lys Leu Lys Asp Lys
1               5                   10                  15

<210> SEQ ID NO 66
<211> LENGTH: 15
<212> TYPE: PRT
<213> ORGANISM: Blattella germanica

<400> SEQUENCE: 66

Gln Ser Leu Ile Gln Lys Leu Lys Asp Lys Gly Val Asp Val Asp
1               5                   10                  15

<210> SEQ ID NO 67
<211> LENGTH: 15
<212> TYPE: PRT
<213> ORGANISM: Blattella germanica

<400> SEQUENCE: 67

Glu Asp Leu Gln Asp Phe Leu Ala Leu Ile Pro Ile Asp Gln Ile
1               5                   10                  15

<210> SEQ ID NO 68

```
<211> LENGTH: 15
<212> TYPE: PRT
<213> ORGANISM: Blattella germanica

<400> SEQUENCE: 68

Phe Leu Ala Leu Ile Pro Ile Asp Gln Ile Leu Ala Ile Ala Ala
1               5                   10                  15

<210> SEQ ID NO 69
<211> LENGTH: 15
<212> TYPE: PRT
<213> ORGANISM: Blattella germanica

<400> SEQUENCE: 69

Pro Ile Asp Gln Ile Leu Ala Ile Ala Ala Asp Tyr Leu Ala Asn
1               5                   10                  15

<210> SEQ ID NO 70
<211> LENGTH: 15
<212> TYPE: PRT
<213> ORGANISM: Blattella germanica

<400> SEQUENCE: 70

Asp Tyr Leu Ala Asn Asp Ala Glu Val Gln Ala Val Glu Tyr
1               5                   10                  15

<210> SEQ ID NO 71
<211> LENGTH: 15
<212> TYPE: PRT
<213> ORGANISM: Blattella germanica

<400> SEQUENCE: 71

Ala Ala Val Glu Tyr Leu Lys Ser Asp Glu Phe Glu Thr Ile Val
1               5                   10                  15

<210> SEQ ID NO 72
<211> LENGTH: 15
<212> TYPE: PRT
<213> ORGANISM: Blattella germanica

<400> SEQUENCE: 72

Leu Lys Ser Asp Glu Phe Glu Thr Ile Val Val Thr Val Asp Ser
1               5                   10                  15

<210> SEQ ID NO 73
<211> LENGTH: 15
<212> TYPE: PRT
<213> ORGANISM: Blattella germanica

<400> SEQUENCE: 73

Leu Asn Ala Ile Glu Phe Ile Asn Asn Ile His Asp Leu Leu Gly
1               5                   10                  15

<210> SEQ ID NO 74
<211> LENGTH: 15
<212> TYPE: PRT
<213> ORGANISM: Blattella germanica

<400> SEQUENCE: 74

Phe Ile Asn Asn Ile His Asp Leu Leu Gly Ile Pro His Ile Pro
1               5                   10                  15

<210> SEQ ID NO 75
<211> LENGTH: 15
<212> TYPE: PRT
```

<213> ORGANISM: Blattella germanica

<400> SEQUENCE: 75

His Asp Leu Leu Gly Ile Pro His Ile Pro Ala Thr Gly Arg Lys
1               5                   10                  15

<210> SEQ ID NO 76
<211> LENGTH: 15
<212> TYPE: PRT
<213> ORGANISM: Blattella germanica

<400> SEQUENCE: 76

Val Gly Ile Asn Gly Leu Ile Asp Asp Val Ile Ala Ile Leu Pro
1               5                   10                  15

<210> SEQ ID NO 77
<211> LENGTH: 15
<212> TYPE: PRT
<213> ORGANISM: Blattella germanica

<400> SEQUENCE: 77

Leu Ile Asp Asp Val Ile Ala Ile Leu Pro Val Asp Glu Leu Tyr
1               5                   10                  15

<210> SEQ ID NO 78
<211> LENGTH: 15
<212> TYPE: PRT
<213> ORGANISM: Blattella germanica

<400> SEQUENCE: 78

Ile Ala Ile Leu Pro Val Asp Glu Leu Tyr Ala Leu Phe Gln Glu
1               5                   10                  15

<210> SEQ ID NO 79
<211> LENGTH: 15
<212> TYPE: PRT
<213> ORGANISM: Blattella germanica

<400> SEQUENCE: 79

Val Asp Glu Leu Tyr Ala Leu Phe Gln Glu Lys Leu Glu Ser Ser
1               5                   10                  15

<210> SEQ ID NO 80
<211> LENGTH: 15
<212> TYPE: PRT
<213> ORGANISM: Blattella germanica

<400> SEQUENCE: 80

Ala Leu Phe Gln Glu Lys Leu Glu Ser Ser Pro Glu Phe Lys Ala
1               5                   10                  15

<210> SEQ ID NO 81
<211> LENGTH: 15
<212> TYPE: PRT
<213> ORGANISM: Blattella germanica

<400> SEQUENCE: 81

Arg Ser Pro Glu Phe Gln Ser Ile Val Gln Thr Leu Lys Ala Met
1               5                   10                  15

<210> SEQ ID NO 82
<211> LENGTH: 15
<212> TYPE: PRT
<213> ORGANISM: Blattella germanica

<400> SEQUENCE: 82

Gln Ser Ile Val Gln Thr Leu Lys Ala Met Pro Glu Tyr Gln Asp
1               5                   10                  15

<210> SEQ ID NO 83
<211> LENGTH: 15
<212> TYPE: PRT
<213> ORGANISM: Blattella germanica

<400> SEQUENCE: 83

Pro Glu Tyr Gln Asp Leu Ile Gln Arg Leu Lys Asp Lys Gly Val
1               5                   10                  15

<210> SEQ ID NO 84
<211> LENGTH: 15
<212> TYPE: PRT
<213> ORGANISM: Blattella germanica

<400> SEQUENCE: 84

Leu Ile Gln Arg Leu Lys Asp Lys Gly Val Asp Val Asp His Phe
1               5                   10                  15

<210> SEQ ID NO 85
<211> LENGTH: 15
<212> TYPE: PRT
<213> ORGANISM: Blattella germanica

<400> SEQUENCE: 85

Asp His Phe Ile Glu Leu Ile Lys Lys Leu Phe Gly Leu Ser His
1               5                   10                  15

<210> SEQ ID NO 86
<211> LENGTH: 15
<212> TYPE: PRT
<213> ORGANISM: Blattella germanica

<400> SEQUENCE: 86

Val Asp Val Asp Lys Ile Ile Glu Leu Ile Arg Ala Leu Phe Gly
1               5                   10                  15

<210> SEQ ID NO 87
<211> LENGTH: 15
<212> TYPE: PRT
<213> ORGANISM: Blattella germanica

<400> SEQUENCE: 87

Ile Ile Glu Leu Ile Arg Ala Leu Phe Gly Leu Thr Leu Asn Ala
1               5                   10                  15

<210> SEQ ID NO 88
<211> LENGTH: 15
<212> TYPE: PRT
<213> ORGANISM: Blattella germanica

<400> SEQUENCE: 88

Arg Ala Leu Phe Gly Leu Thr Leu Asn Ala Lys Ala Ser Arg Asn
1               5                   10                  15

<210> SEQ ID NO 89
<211> LENGTH: 15
<212> TYPE: PRT
<213> ORGANISM: Blattella germanica

<400> SEQUENCE: 89

Leu Thr Leu Asn Ala Lys Ala Ser Arg Asn Leu Gln Asp Asp Leu
1               5                   10                  15

<210> SEQ ID NO 90
<211> LENGTH: 15
<212> TYPE: PRT
<213> ORGANISM: Blattella germanica

<400> SEQUENCE: 90

Leu Gln Asp Asp Leu Gln Asp Phe Leu Ala Leu Ile Pro Val Asp
1               5                   10                  15

<210> SEQ ID NO 91
<211> LENGTH: 15
<212> TYPE: PRT
<213> ORGANISM: Blattella germanica

<400> SEQUENCE: 91

Gln Asp Phe Leu Ala Leu Ile Pro Val Asp Gln Ile Ile Ala Ile
1               5                   10                  15

<210> SEQ ID NO 92
<211> LENGTH: 15
<212> TYPE: PRT
<213> ORGANISM: Blattella germanica

<400> SEQUENCE: 92

Asp Glu Phe Glu Thr Ile Val Val Ala Leu Asp Ala Leu Pro Glu
1               5                   10                  15

<210> SEQ ID NO 93
<211> LENGTH: 15
<212> TYPE: PRT
<213> ORGANISM: Blattella germanica

<400> SEQUENCE: 93

Ile Val Val Ala Leu Asp Ala Leu Pro Glu Leu Gln Asn Phe Leu
1               5                   10                  15

<210> SEQ ID NO 94
<211> LENGTH: 15
<212> TYPE: PRT
<213> ORGANISM: Blattella germanica

<400> SEQUENCE: 94

Ile Asp Phe Leu Asn Gly Ile His Asp Leu Leu Gly Ile Pro His
1               5                   10                  15

<210> SEQ ID NO 95
<211> LENGTH: 15
<212> TYPE: PRT
<213> ORGANISM: Blattella germanica

<400> SEQUENCE: 95

Gly Ile His Asp Leu Leu Gly Ile Pro His Ile Pro Val Ser Gly
1               5                   10                  15

<210> SEQ ID NO 96
<211> LENGTH: 15
<212> TYPE: PRT
<213> ORGANISM: Blattella germanica

<400> SEQUENCE: 96

Arg Lys Tyr His Ile Arg Arg Gly Val Gly Ile Thr Gly Leu Ile
1               5                   10                  15

<210> SEQ ID NO 97
<211> LENGTH: 15
<212> TYPE: PRT
<213> ORGANISM: Blattella germanica

<400> SEQUENCE: 97

Asp Asp Val Leu Ala Ile Leu Pro Ile Glu Asp Leu Lys Ala Leu
1               5                   10                  15

<210> SEQ ID NO 98
<211> LENGTH: 15
<212> TYPE: PRT
<213> ORGANISM: Blattella germanica

<400> SEQUENCE: 98

Ile Leu Pro Ile Glu Asp Leu Lys Ala Leu Phe Asn Glu Lys Leu
1               5                   10                  15

<210> SEQ ID NO 99
<211> LENGTH: 15
<212> TYPE: PRT
<213> ORGANISM: Blattella germanica

<400> SEQUENCE: 99

Glu Thr Ser Pro Asp Phe Leu Ala Leu Tyr Asn Ala Ile Arg Ser
1               5                   10                  15

<210> SEQ ID NO 100
<211> LENGTH: 15
<212> TYPE: PRT
<213> ORGANISM: Blattella germanica

<400> SEQUENCE: 100

Phe Leu Ala Leu Tyr Asn Ala Ile Arg Ser Pro Glu Phe Gln Ser
1               5                   10                  15

<210> SEQ ID NO 101
<211> LENGTH: 15
<212> TYPE: PRT
<213> ORGANISM: Blattella germanica

<400> SEQUENCE: 101

Asn Ala Met Pro Glu Tyr Gln Asn Leu Leu Gln Lys Leu Arg Glu
1               5                   10                  15

<210> SEQ ID NO 102
<211> LENGTH: 15
<212> TYPE: PRT
<213> ORGANISM: Blattella germanica

<400> SEQUENCE: 102

Tyr Gln Asn Leu Leu Gln Lys Leu Arg Glu Lys Gly Val Asp Val
1               5                   10                  15

<210> SEQ ID NO 103
<211> LENGTH: 15
<212> TYPE: PRT
<213> ORGANISM: Blattella germanica

<400> SEQUENCE: 103

Leu Ile Arg Ala Leu Phe Gly Leu Thr Leu Asn Gly Lys Ala Ser
1               5                   10                  15

-continued

```
<210> SEQ ID NO 104
<211> LENGTH: 15
<212> TYPE: PRT
<213> ORGANISM: Blattella germanica

<400> SEQUENCE: 104

Phe Gly Leu Thr Leu Asn Gly Lys Ala Ser Arg Asn Leu Gln Asp
1               5                   10                  15

<210> SEQ ID NO 105
<211> LENGTH: 15
<212> TYPE: PRT
<213> ORGANISM: Blattella germanica

<400> SEQUENCE: 105

Val Asp Gln Ile Ile Ala Ile Ala Thr Asp Tyr Leu Ala Asn Asp
1               5                   10                  15

<210> SEQ ID NO 106
<211> LENGTH: 15
<212> TYPE: PRT
<213> ORGANISM: Blattella germanica

<400> SEQUENCE: 106

Ala Ile Ala Thr Asp Tyr Leu Ala Asn Asp Ala Glu Val Gln Ala
1               5                   10                  15

<210> SEQ ID NO 107
<211> LENGTH: 15
<212> TYPE: PRT
<213> ORGANISM: Blattella germanica

<400> SEQUENCE: 107

Ala Glu Val Gln Ala Ala Val Ala Tyr Leu Gln Ser Asp Glu Phe
1               5                   10                  15

<210> SEQ ID NO 108
<211> LENGTH: 15
<212> TYPE: PRT
<213> ORGANISM: Blattella germanica

<400> SEQUENCE: 108

Ala Val Ala Tyr Leu Gln Ser Asp Glu Phe Glu Thr Ile Val Val
1               5                   10                  15

<210> SEQ ID NO 109
<211> LENGTH: 15
<212> TYPE: PRT
<213> ORGANISM: Blattella germanica

<400> SEQUENCE: 109

Gln Ser Asp Glu Phe Glu Thr Ile Val Val Thr Leu Asp Ala Leu
1               5                   10                  15

<210> SEQ ID NO 110
<211> LENGTH: 15
<212> TYPE: PRT
<213> ORGANISM: Blattella germanica

<400> SEQUENCE: 110

Glu Thr Ile Val Val Thr Leu Asp Ala Leu Pro Glu Leu Gln Asn
1               5                   10                  15

<210> SEQ ID NO 111
<211> LENGTH: 15
```

```
<212> TYPE: PRT
<213> ORGANISM: Blattella germanica

<400> SEQUENCE: 111

Phe Leu Asn Phe Leu Glu Ala Asn Gly Leu Asn Ala Ile Asp Phe
1               5                   10                  15

<210> SEQ ID NO 112
<211> LENGTH: 15
<212> TYPE: PRT
<213> ORGANISM: Blattella germanica

<400> SEQUENCE: 112

Leu Asn Gly Ile His Asp Leu Leu Gly Ile Pro His Ile Pro Val
1               5                   10                  15

<210> SEQ ID NO 113
<211> LENGTH: 15
<212> TYPE: PRT
<213> ORGANISM: Blattella germanica

<400> SEQUENCE: 113

Asp Leu Leu Gly Ile Pro His Ile Pro Val Ser Gly Arg Lys Tyr
1               5                   10                  15

<210> SEQ ID NO 114
<211> LENGTH: 15
<212> TYPE: PRT
<213> ORGANISM: Blattella germanica

<400> SEQUENCE: 114

Val Gly Ile Thr Gly Leu Ile Asp Asp Val Leu Ala Ile Leu Pro
1               5                   10                  15

<210> SEQ ID NO 115
<211> LENGTH: 15
<212> TYPE: PRT
<213> ORGANISM: Blattella germanica

<400> SEQUENCE: 115

Leu Ala Ile Leu Pro Leu Asp Asp Leu Lys Ala Leu Phe Asn Glu
1               5                   10                  15

<210> SEQ ID NO 116
<211> LENGTH: 15
<212> TYPE: PRT
<213> ORGANISM: Blattella germanica

<400> SEQUENCE: 116

Leu Asp Asp Leu Lys Ala Leu Phe Asn Glu Lys Leu Glu Thr Ser
1               5                   10                  15

<210> SEQ ID NO 117
<211> LENGTH: 15
<212> TYPE: PRT
<213> ORGANISM: Blattella germanica

<400> SEQUENCE: 117

Pro Asp Phe Leu Ala Leu Tyr Asn Ala Ile Lys Ser Pro Glu Phe
1               5                   10                  15

<210> SEQ ID NO 118
<211> LENGTH: 15
<212> TYPE: PRT
<213> ORGANISM: Blattella germanica
```

<400> SEQUENCE: 118

Leu Tyr Asn Ala Ile Lys Ser Pro Glu Phe Gln Ser Ile Val Gln
1               5                   10                  15

<210> SEQ ID NO 119
<211> LENGTH: 15
<212> TYPE: PRT
<213> ORGANISM: Blattella germanica

<400> SEQUENCE: 119

Met Ile Gly Leu Lys Leu Val Thr Val Leu Phe Ala Val Ala Thr
1               5                   10                  15

<210> SEQ ID NO 120
<211> LENGTH: 15
<212> TYPE: PRT
<213> ORGANISM: Blattella germanica

<400> SEQUENCE: 120

Leu Val Thr Val Leu Phe Ala Val Ala Thr Ile Thr His Ala Ala
1               5                   10                  15

<210> SEQ ID NO 121
<211> LENGTH: 15
<212> TYPE: PRT
<213> ORGANISM: Blattella germanica

<400> SEQUENCE: 121

Ile Thr His Ala Ala Glu Leu Gln Arg Val Pro Leu Tyr Lys Leu
1               5                   10                  15

<210> SEQ ID NO 122
<211> LENGTH: 15
<212> TYPE: PRT
<213> ORGANISM: Blattella germanica

<400> SEQUENCE: 122

Glu Leu Gln Arg Val Pro Leu Tyr Lys Leu Val His Val Phe Ile
1               5                   10                  15

<210> SEQ ID NO 123
<211> LENGTH: 15
<212> TYPE: PRT
<213> ORGANISM: Blattella germanica

<400> SEQUENCE: 123

Val His Val Phe Ile Asn Thr Gln Tyr Ala Gly Ile Thr Lys Ile
1               5                   10                  15

<210> SEQ ID NO 124
<211> LENGTH: 15
<212> TYPE: PRT
<213> ORGANISM: Blattella germanica

<400> SEQUENCE: 124

Asn Thr Gln Tyr Ala Gly Ile Thr Lys Ile Gly Asn Gln Asn Phe
1               5                   10                  15

<210> SEQ ID NO 125
<211> LENGTH: 15
<212> TYPE: PRT
<213> ORGANISM: Blattella germanica

<400> SEQUENCE: 125

```
Gly Ile Thr Lys Ile Gly Asn Gln Asn Phe Leu Thr Val Phe Asp
1               5                   10                  15
```

<210> SEQ ID NO 126
<211> LENGTH: 15
<212> TYPE: PRT
<213> ORGANISM: Blattella germanica

<400> SEQUENCE: 126

```
Pro Asn Leu Gln Lys Tyr Glu Lys Leu Lys Pro Lys Tyr Ile Ser
1               5                   10                  15
```

<210> SEQ ID NO 127
<211> LENGTH: 15
<212> TYPE: PRT
<213> ORGANISM: Blattella germanica

<400> SEQUENCE: 127

```
Tyr Glu Lys Leu Lys Pro Lys Tyr Ile Ser Asp Gly Asn Val Gln
1               5                   10                  15
```

<210> SEQ ID NO 128
<211> LENGTH: 15
<212> TYPE: PRT
<213> ORGANISM: Blattella germanica

<400> SEQUENCE: 128

```
Pro Lys Tyr Ile Ser Asp Gly Asn Val Gln Val Lys Phe Phe Asp
1               5                   10                  15
```

<210> SEQ ID NO 129
<211> LENGTH: 15
<212> TYPE: PRT
<213> ORGANISM: Blattella germanica

<400> SEQUENCE: 129

```
Asp Gly Asn Val Gln Val Lys Phe Phe Asp Thr Gly Ser Ala Val
1               5                   10                  15
```

<210> SEQ ID NO 130
<211> LENGTH: 15
<212> TYPE: PRT
<213> ORGANISM: Blattella germanica

<400> SEQUENCE: 130

```
Val Lys Phe Phe Asp Thr Gly Ser Ala Val Gly Arg Gly Ile Glu
1               5                   10                  15
```

<210> SEQ ID NO 131
<211> LENGTH: 15
<212> TYPE: PRT
<213> ORGANISM: Blattella germanica

<400> SEQUENCE: 131

```
Gly Arg Gly Ile Glu Asp Ser Leu Thr Ile Ser Asn Leu Thr Thr
1               5                   10                  15
```

<210> SEQ ID NO 132
<211> LENGTH: 15
<212> TYPE: PRT
<213> ORGANISM: Blattella germanica

<400> SEQUENCE: 132

```
Leu Ser Gln Glu Val Cys Ile Leu Ser Ala Asp Val Val Val Gly
```

```
                1               5                  10                 15

<210> SEQ ID NO 133
<211> LENGTH: 15
<212> TYPE: PRT
<213> ORGANISM: Blattella germanica

<400> SEQUENCE: 133

Cys Ile Leu Ser Ala Asp Val Val Gly Ile Ala Ala Pro Gly
1               5                  10                 15

<210> SEQ ID NO 134
<211> LENGTH: 15
<212> TYPE: PRT
<213> ORGANISM: Blattella germanica

<400> SEQUENCE: 134

Lys Gly Lys Thr Val Leu Glu Asn Phe Val Glu Glu Asn Leu Ile
1               5                  10                 15

<210> SEQ ID NO 135
<211> LENGTH: 15
<212> TYPE: PRT
<213> ORGANISM: Blattella germanica

<400> SEQUENCE: 135

Leu Glu Asn Phe Val Glu Glu Asn Leu Ile Ala Pro Val Phe Ser
1               5                  10                 15

<210> SEQ ID NO 136
<211> LENGTH: 15
<212> TYPE: PRT
<213> ORGANISM: Blattella germanica

<400> SEQUENCE: 136

Glu Glu Asn Leu Ile Ala Pro Val Phe Ser Ile His His Ala Arg
1               5                  10                 15

<210> SEQ ID NO 137
<211> LENGTH: 15
<212> TYPE: PRT
<213> ORGANISM: Blattella germanica

<400> SEQUENCE: 137

Ala Pro Val Phe Ser Ile His His Ala Arg Phe Gln Asp Gly Glu
1               5                  10                 15

<210> SEQ ID NO 138
<211> LENGTH: 15
<212> TYPE: PRT
<213> ORGANISM: Blattella germanica

<400> SEQUENCE: 138

Ile Phe Gly Gly Ser Asp Trp Lys Tyr Val Asp Gly Glu Phe Thr
1               5                  10                 15

<210> SEQ ID NO 139
<211> LENGTH: 15
<212> TYPE: PRT
<213> ORGANISM: Blattella germanica

<400> SEQUENCE: 139

Asp Trp Lys Tyr Val Asp Gly Glu Phe Thr Tyr Val Pro Leu Val
1               5                  10                 15
```

```
<210> SEQ ID NO 140
<211> LENGTH: 15
<212> TYPE: PRT
<213> ORGANISM: Blattella germanica

<400> SEQUENCE: 140

Asp Gly Glu Phe Thr Tyr Val Pro Leu Val Gly Asp Asp Ser Trp
1               5                   10                  15

<210> SEQ ID NO 141
<211> LENGTH: 15
<212> TYPE: PRT
<213> ORGANISM: Blattella germanica

<400> SEQUENCE: 141

Tyr Val Pro Leu Val Gly Asp Asp Ser Trp Lys Phe Arg Leu Asp
1               5                   10                  15

<210> SEQ ID NO 142
<211> LENGTH: 15
<212> TYPE: PRT
<213> ORGANISM: Blattella germanica

<400> SEQUENCE: 142

Gly Asp Asp Ser Trp Lys Phe Arg Leu Asp Gly Val Lys Ile Gly
1               5                   10                  15

<210> SEQ ID NO 143
<211> LENGTH: 15
<212> TYPE: PRT
<213> ORGANISM: Blattella germanica

<400> SEQUENCE: 143

Pro Ala Gly Thr Gln Ala Ile Ile Asp Thr Ser Lys Ala Ile Ile
1               5                   10                  15

<210> SEQ ID NO 144
<211> LENGTH: 15
<212> TYPE: PRT
<213> ORGANISM: Blattella germanica

<400> SEQUENCE: 144

Ala Ile Ile Asp Thr Ser Lys Ala Ile Ile Val Gly Pro Lys Ala
1               5                   10                  15

<210> SEQ ID NO 145
<211> LENGTH: 15
<212> TYPE: PRT
<213> ORGANISM: Blattella germanica

<400> SEQUENCE: 145

Ser Lys Ala Ile Ile Val Gly Pro Lys Ala Tyr Val Asn Pro Ile
1               5                   10                  15

<210> SEQ ID NO 146
<211> LENGTH: 15
<212> TYPE: PRT
<213> ORGANISM: Blattella germanica

<400> SEQUENCE: 146

Val Gly Pro Lys Ala Tyr Val Asn Pro Ile Asn Glu Ala Ile Gly
1               5                   10                  15

<210> SEQ ID NO 147
```

```
<211> LENGTH: 15
<212> TYPE: PRT
<213> ORGANISM: Blattella germanica

<400> SEQUENCE: 147

Ser Leu Pro Asp Val Thr Phe Val Ile Asn Gly Arg Asn Phe Asn
1               5                   10                  15

<210> SEQ ID NO 148
<211> LENGTH: 15
<212> TYPE: PRT
<213> ORGANISM: Blattella germanica

<400> SEQUENCE: 148

Thr Phe Val Ile Asn Gly Arg Asn Phe Asn Ile Ser Ser Gln Tyr
1               5                   10                  15

<210> SEQ ID NO 149
<211> LENGTH: 15
<212> TYPE: PRT
<213> ORGANISM: Blattella germanica

<400> SEQUENCE: 149

Gly Arg Asn Phe Asn Ile Ser Ser Gln Tyr Tyr Ile Gln Gln Asn
1               5                   10                  15

<210> SEQ ID NO 150
<211> LENGTH: 15
<212> TYPE: PRT
<213> ORGANISM: Blattella germanica

<400> SEQUENCE: 150

Asp Phe Phe Val Asp His Tyr Tyr Ser Glu Phe Asn Trp Glu Asn
1               5                   10                  15

<210> SEQ ID NO 151
<211> LENGTH: 15
<212> TYPE: PRT
<213> ORGANISM: Blattella germanica

<400> SEQUENCE: 151

Leu Asp Tyr Glu Arg Phe Arg Gly Ser Trp Ile Ile Ala Ala Gly
1               5                   10                  15

<210> SEQ ID NO 152
<211> LENGTH: 15
<212> TYPE: PRT
<213> ORGANISM: Blattella germanica

<400> SEQUENCE: 152

Phe Arg Gly Ser Trp Ile Ile Ala Ala Gly Thr Ser Glu Ala Leu
1               5                   10                  15

<210> SEQ ID NO 153
<211> LENGTH: 15
<212> TYPE: PRT
<213> ORGANISM: Blattella germanica

<400> SEQUENCE: 153

Ile Ile Ala Ala Gly Thr Ser Glu Ala Leu Thr Gln Tyr Lys Cys
1               5                   10                  15

<210> SEQ ID NO 154
<211> LENGTH: 15
<212> TYPE: PRT
```

```
<213> ORGANISM: Blattella germanica

<400> SEQUENCE: 154

Trp Ile Asp Arg Phe Ser Tyr Asp Asp Ala Leu Val Ser Lys Tyr
1               5                   10                  15

<210> SEQ ID NO 155
<211> LENGTH: 15
<212> TYPE: PRT
<213> ORGANISM: Blattella germanica

<400> SEQUENCE: 155

Tyr Asn Asp Lys Gly Lys Ala Phe Ser Ala Pro Tyr Ser Val Leu
1               5                   10                  15

<210> SEQ ID NO 156
<211> LENGTH: 15
<212> TYPE: PRT
<213> ORGANISM: Blattella germanica

<400> SEQUENCE: 156

Lys Ala Phe Ser Ala Pro Tyr Ser Val Leu Ala Thr Asp Tyr Glu
1               5                   10                  15

<210> SEQ ID NO 157
<211> LENGTH: 15
<212> TYPE: PRT
<213> ORGANISM: Blattella germanica

<400> SEQUENCE: 157

Pro Tyr Ser Val Leu Ala Thr Asp Tyr Glu Asn Tyr Ala Ile Val
1               5                   10                  15

<210> SEQ ID NO 158
<211> LENGTH: 15
<212> TYPE: PRT
<213> ORGANISM: Blattella germanica

<400> SEQUENCE: 158

Ala Thr Asp Tyr Glu Asn Tyr Ala Ile Val Glu Gly Cys Pro Ala
1               5                   10                  15

<210> SEQ ID NO 159
<211> LENGTH: 15
<212> TYPE: PRT
<213> ORGANISM: Blattella germanica

<400> SEQUENCE: 159

Ala Ala Asn Gly His Val Ile Tyr Val Gln Ile Arg Phe Ser Val
1               5                   10                  15

<210> SEQ ID NO 160
<211> LENGTH: 15
<212> TYPE: PRT
<213> ORGANISM: Blattella germanica

<400> SEQUENCE: 160

Val Ile Tyr Val Gln Ile Arg Phe Ser Val Arg Arg Phe His Pro
1               5                   10                  15

<210> SEQ ID NO 161
<211> LENGTH: 15
<212> TYPE: PRT
<213> ORGANISM: Blattella germanica
```

```
<400> SEQUENCE: 161

Ile Arg Phe Ser Val Arg Arg Phe His Pro Lys Leu Gly Asp Lys
1               5                   10                  15

<210> SEQ ID NO 162
<211> LENGTH: 15
<212> TYPE: PRT
<213> ORGANISM: Blattella germanica

<400> SEQUENCE: 162

Glu Met Ile Gln His Tyr Thr Leu Asp Gln Val Asn Gln His Lys
1               5                   10                  15

<210> SEQ ID NO 163
<211> LENGTH: 15
<212> TYPE: PRT
<213> ORGANISM: Blattella germanica

<400> SEQUENCE: 163

Lys Ala Ile Glu Glu Asp Leu Lys His Phe Asn Leu Lys Tyr Glu
1               5                   10                  15

<210> SEQ ID NO 164
<211> LENGTH: 15
<212> TYPE: PRT
<213> ORGANISM: Blattella germanica

<400> SEQUENCE: 164

Lys His Phe Asn Leu Lys Tyr Glu Asp Leu His Ser Thr Cys His
1               5                   10                  15

<210> SEQ ID NO 165
<211> LENGTH: 15
<212> TYPE: PRT
<213> ORGANISM: Blattella germanica

<400> SEQUENCE: 165

Lys Leu Thr Tyr Cys Pro Val Lys Ala Leu Gly Glu Pro Ile Arg
1               5                   10                  15

<210> SEQ ID NO 166
<211> LENGTH: 15
<212> TYPE: PRT
<213> ORGANISM: Blattella germanica

<400> SEQUENCE: 166

Gln Thr His Gln Ser Val Ala Ile Ser Arg Tyr Leu Gly Lys Gln
1               5                   10                  15

<210> SEQ ID NO 167
<211> LENGTH: 15
<212> TYPE: PRT
<213> ORGANISM: Blattella germanica

<400> SEQUENCE: 167

Asn Leu Glu Ile Asp Met Ile Val Asp Thr Ile Ser Asp Phe Arg
1               5                   10                  15

<210> SEQ ID NO 168
<211> LENGTH: 15
<212> TYPE: PRT
<213> ORGANISM: Blattella germanica

<400> SEQUENCE: 168
```

Met Ile Val Asp Thr Ile Ser Asp Phe Arg Ala Ala Ile Ala Asn
1               5                   10                  15

<210> SEQ ID NO 169
<211> LENGTH: 15
<212> TYPE: PRT
<213> ORGANISM: Blattella germanica

<400> SEQUENCE: 169

Thr Lys Lys Phe Asp Glu Val Val Lys Ala Asn Gly Gly Tyr Leu
1               5                   10                  15

<210> SEQ ID NO 170
<211> LENGTH: 15
<212> TYPE: PRT
<213> ORGANISM: Blattella germanica

<400> SEQUENCE: 170

Asn Gly Gly Tyr Leu Ala Ala Gly Lys Leu Thr Trp Ala Asp Phe
1               5                   10                  15

<210> SEQ ID NO 171
<211> LENGTH: 15
<212> TYPE: PRT
<213> ORGANISM: Blattella germanica

<400> SEQUENCE: 171

Thr Trp Ala Asp Phe Tyr Phe Val Ala Ile Leu Asp Tyr Leu Asn
1               5                   10                  15

<210> SEQ ID NO 172
<211> LENGTH: 15
<212> TYPE: PRT
<213> ORGANISM: Blattella germanica

<400> SEQUENCE: 172

Leu Asp Tyr Leu Asn His Met Ala Lys Glu Asp Leu Val Ala Asn
1               5                   10                  15

<210> SEQ ID NO 173
<211> LENGTH: 15
<212> TYPE: PRT
<213> ORGANISM: Blattella germanica

<400> SEQUENCE: 173

Gln Pro Asn Leu Lys Ala Leu Arg Glu Lys Val Leu Gly Leu Pro
1               5                   10                  15

<210> SEQ ID NO 174
<211> LENGTH: 15
<212> TYPE: PRT
<213> ORGANISM: Blattella germanica

<400> SEQUENCE: 174

Val Glu Glu Ile Leu Arg Leu Met Gly Gln Pro Phe Asn Arg Arg
1               5                   10                  15

<210> SEQ ID NO 175
<211> LENGTH: 15
<212> TYPE: PRT
<213> ORGANISM: Blattella germanica

<400> SEQUENCE: 175

Ala Asp Lys Ser Gly Arg Leu Glu Phe Asp Glu Phe Val Thr Leu
1               5                   10                  15

```
<210> SEQ ID NO 176
<211> LENGTH: 15
<212> TYPE: PRT
<213> ORGANISM: Blattella germanica

<400> SEQUENCE: 176

Arg Leu Glu Phe Asp Glu Phe Val Thr Leu Ala Ala Lys Phe Ile
1               5                   10                  15

<210> SEQ ID NO 177
<211> LENGTH: 15
<212> TYPE: PRT
<213> ORGANISM: Blattella germanica

<400> SEQUENCE: 177

Cys Leu Arg Glu Ile Leu Arg Glu Leu Asp Glu Gln Leu Thr Ser
1               5                   10                  15

<210> SEQ ID NO 178
<211> LENGTH: 15
<212> TYPE: PRT
<213> ORGANISM: Blattella germanica

<400> SEQUENCE: 178

Asp Glu Leu Asp Met Met Ile Glu Glu Ile Asp Ala Asp Gly Ser
1               5                   10                  15

<210> SEQ ID NO 179
<211> LENGTH: 15
<212> TYPE: PRT
<213> ORGANISM: Blattella germanica

<400> SEQUENCE: 179

Ala Glu Gln Val Val Leu Leu Lys Lys Ala Phe Asp Ala Phe Asp
1               5                   10                  15

<210> SEQ ID NO 180
<211> LENGTH: 15
<212> TYPE: PRT
<213> ORGANISM: Blattella germanica

<400> SEQUENCE: 180

Gly Glu Leu Glu Phe Glu Glu Phe Cys Thr Leu Ala Ser Arg Phe
1               5                   10                  15

<210> SEQ ID NO 181
<211> LENGTH: 15
<212> TYPE: PRT
<213> ORGANISM: Blattella germanica

<400> SEQUENCE: 181

His Glu Leu Arg Glu Ala Phe Arg Leu Tyr Asp Lys Glu Gly Asn
1               5                   10                  15

<210> SEQ ID NO 182
<211> LENGTH: 15
<212> TYPE: PRT
<213> ORGANISM: Blattella germanica

<400> SEQUENCE: 182

Asp Lys Glu Gly Asn Gly Tyr Ile Thr Thr Ala Val Leu Arg Glu
1               5                   10                  15
```

```
<210> SEQ ID NO 183
<211> LENGTH: 15
<212> TYPE: PRT
<213> ORGANISM: Blattella germanica

<400> SEQUENCE: 183

Gly Tyr Ile Thr Thr Ala Val Leu Arg Glu Ile Leu Lys Glu Leu
1               5                   10                  15

<210> SEQ ID NO 184
<211> LENGTH: 15
<212> TYPE: PRT
<213> ORGANISM: Blattella germanica

<400> SEQUENCE: 184

Ala Val Leu Arg Glu Ile Leu Lys Glu Leu Asp Asp Lys Ile Thr
1               5                   10                  15

<210> SEQ ID NO 185
<211> LENGTH: 15
<212> TYPE: PRT
<213> ORGANISM: Blattella germanica

<400> SEQUENCE: 185

Asp Met Leu Gln Glu Ile Ile Ala Glu Val Asp Ala Asp Gly Ser
1               5                   10                  15

<210> SEQ ID NO 186
<211> LENGTH: 15
<212> TYPE: PRT
<213> ORGANISM: Blattella germanica

<400> SEQUENCE: 186

Gly Glu Leu Glu Phe Glu Glu Phe Val Ser Leu Ala Ser Arg Phe
1               5                   10                  15

<210> SEQ ID NO 187
<211> LENGTH: 15
<212> TYPE: PRT
<213> ORGANISM: Blattella germanica

<400> SEQUENCE: 187

Met Asp Ala Ile Lys Lys Lys Met Gln Ala Met Lys Leu Glu Lys
1               5                   10                  15

<210> SEQ ID NO 188
<211> LENGTH: 15
<212> TYPE: PRT
<213> ORGANISM: Blattella germanica

<400> SEQUENCE: 188

Lys Lys Met Gln Ala Met Lys Leu Glu Lys Asp Asn Ala Met Asp
1               5                   10                  15

<210> SEQ ID NO 189
<211> LENGTH: 15
<212> TYPE: PRT
<213> ORGANISM: Blattella germanica

<400> SEQUENCE: 189

Leu Gln Lys Lys Ile Gln Gln Ile Glu Asn Asp Leu Asp Gln Thr
1               5                   10                  15

<210> SEQ ID NO 190
<211> LENGTH: 15
```

-continued

<212> TYPE: PRT
<213> ORGANISM: Blattella germanica

<400> SEQUENCE: 190

Met Glu Gln Leu Met Gln Val Asn Ala Lys Leu Asp Glu Lys Asp
1               5                   10                  15

<210> SEQ ID NO 191
<211> LENGTH: 15
<212> TYPE: PRT
<213> ORGANISM: Blattella germanica

<400> SEQUENCE: 191

Lys Ala Leu Gln Asn Ala Glu Ser Glu Val Ala Ala Leu Asn Arg
1               5                   10                  15

<210> SEQ ID NO 192
<211> LENGTH: 15
<212> TYPE: PRT
<213> ORGANISM: Blattella germanica

<400> SEQUENCE: 192

Ala Glu Ser Glu Val Ala Ala Leu Asn Arg Arg Ile Gln Leu Leu
1               5                   10                  15

<210> SEQ ID NO 193
<211> LENGTH: 15
<212> TYPE: PRT
<213> ORGANISM: Blattella germanica

<400> SEQUENCE: 193

Ala Ala Leu Asn Arg Arg Ile Gln Leu Leu Glu Glu Asp Leu Glu
1               5                   10                  15

<210> SEQ ID NO 194
<211> LENGTH: 15
<212> TYPE: PRT
<213> ORGANISM: Blattella germanica

<400> SEQUENCE: 194

Arg Ser Glu Glu Arg Leu Ala Thr Ala Thr Ala Lys Leu Ala Glu
1               5                   10                  15

<210> SEQ ID NO 195
<211> LENGTH: 15
<212> TYPE: PRT
<213> ORGANISM: Blattella germanica

<400> SEQUENCE: 195

Leu Ala Thr Ala Thr Ala Lys Leu Ala Glu Ala Ser Gln Ala Ala
1               5                   10                  15

<210> SEQ ID NO 196
<211> LENGTH: 15
<212> TYPE: PRT
<213> ORGANISM: Blattella germanica

<400> SEQUENCE: 196

Gly Glu Ser Lys Ile Val Glu Leu Glu Glu Glu Leu Arg Val Val
1               5                   10                  15

<210> SEQ ID NO 197
<211> LENGTH: 15
<212> TYPE: PRT
<213> ORGANISM: Blattella germanica

<400> SEQUENCE: 197

Val Glu Leu Glu Glu Leu Arg Val Val Gly Asn Asn Leu Lys
1               5                   10                  15

<210> SEQ ID NO 198
<211> LENGTH: 15
<212> TYPE: PRT
<213> ORGANISM: Blattella germanica

<400> SEQUENCE: 198

Glu Leu Arg Val Val Gly Asn Asn Leu Lys Ser Leu Glu Val Ser
1               5                   10                  15

<210> SEQ ID NO 199
<211> LENGTH: 15
<212> TYPE: PRT
<213> ORGANISM: Blattella germanica

<400> SEQUENCE: 199

Leu Arg Glu Glu Glu Tyr Lys Gln Gln Ile Lys Thr Leu Asn Thr
1               5                   10                  15

<210> SEQ ID NO 200
<211> LENGTH: 15
<212> TYPE: PRT
<213> ORGANISM: Blattella germanica

<400> SEQUENCE: 200

Tyr Lys Gln Gln Ile Lys Thr Leu Asn Thr Arg Leu Lys Glu Ala
1               5                   10                  15

<210> SEQ ID NO 201
<211> LENGTH: 15
<212> TYPE: PRT
<213> ORGANISM: Blattella germanica

<400> SEQUENCE: 201

Ile Cys Asp Asp Leu Asp Met Thr Phe Thr Glu Leu Ile Gly Asn
1               5                   10                  15

<210> SEQ ID NO 202
<211> LENGTH: 412
<212> TYPE: PRT
<213> ORGANISM: Blattella germanica

<400> SEQUENCE: 202

Asn Leu Leu Glu Lys Leu Arg Glu Lys Gly Val Asp Val Asp Lys Ile
1               5                   10                  15

Ile Glu Leu Ile Arg Ala Leu Phe Gly Leu Thr Leu Asn Ala Lys Ala
            20                  25                  30

Ser Arg Asn Leu Gln Asp Asp Leu Gln Asp Phe Leu Ala Leu Ile Pro
        35                  40                  45

Val Asp Gln Ile Ile Ala Ile Ala Thr Asp Tyr Leu Ala Asn Asp Ala
    50                  55                  60

Glu Val Gln Ala Ala Val Ala Tyr Leu Gln Ser Asp Glu Phe Glu Thr
65                  70                  75                  80

Ile Val Val Ala Leu Asp Ala Leu Pro Glu Leu Gln Asn Phe Leu Asn
                85                  90                  95

Phe Leu Glu Ala Asn Gly Leu Asn Ala Ile Asp Phe Leu Asn Gly Ile
                100                 105                 110

His Asp Leu Leu Gly Ile Pro His Ile Pro Val Ser Gly Arg Lys Tyr
            115                 120                 125

His Ile Arg Arg Gly Val Gly Ile Thr Gly Leu Ile Asp Asp Val Leu
        130                 135                 140

Ala Ile Leu Pro Ile Glu Asp Leu Lys Ala Leu Phe Asn Glu Lys Leu
145                 150                 155                 160

Glu Thr Ser Pro Asp Phe Leu Ala Leu Tyr Asn Ala Ile Arg Ser Pro
                165                 170                 175

Glu Phe Gln Ser Ile Val Gln Thr Leu Asn Ala Met Pro Glu Tyr Gln
            180                 185                 190

Asn Leu Leu Gln Lys Leu Arg Glu Lys Gly Val Asp Val Asp Lys Ile
        195                 200                 205

Ile Glu Leu Ile Arg Ala Leu Phe Gly Leu Thr Leu Asn Gly Lys Ala
210                 215                 220

Ser Arg Asn Leu Gln Asp Asp Leu Gln Asp Phe Leu Ala Leu Ile Pro
225                 230                 235                 240

Val Asp Gln Ile Ile Ala Ile Ala Thr Asp Tyr Leu Ala Asn Asp Ala
                245                 250                 255

Glu Val Gln Ala Ala Val Ala Tyr Leu Gln Ser Asp Glu Phe Glu Thr
            260                 265                 270

Ile Val Val Thr Leu Asp Ala Leu Pro Glu Leu Gln Asn Phe Leu Asn
        275                 280                 285

Phe Leu Glu Ala Asn Gly Leu Asn Ala Ile Asp Phe Leu Asn Gly Ile
    290                 295                 300

His Asp Leu Leu Gly Ile Pro His Ile Pro Val Ser Gly Arg Lys Tyr
305                 310                 315                 320

His Ile Arg Arg Gly Val Gly Ile Thr Gly Leu Ile Asp Asp Val Leu
                325                 330                 335

Ala Ile Leu Pro Leu Asp Asp Leu Lys Ala Leu Phe Asn Glu Lys Leu
            340                 345                 350

Glu Thr Ser Pro Asp Phe Leu Ala Leu Tyr Asn Ala Ile Lys Ser Pro
        355                 360                 365

Glu Phe Gln Ser Ile Val Gln Thr Leu Asn Ala Met Pro Glu Tyr Gln
    370                 375                 380

Asn Leu Leu Glu Lys Leu Arg Glu Lys Gly Val Asp Val Asp Lys Ile
385                 390                 395                 400

Ile Glu Leu Ile Arg Ala Leu Phe Gly Leu Thr His
                405                 410

<210> SEQ ID NO 203
<211> LENGTH: 492
<212> TYPE: PRT
<213> ORGANISM: Blattella germanica

<400> SEQUENCE: 203

Asn Ala Ile Glu Phe Leu Asn Asn Ile His Asp Leu Leu Gly Ile Pro
1               5                   10                  15

His Ile Pro Val Thr Ala Arg Lys His His Arg Arg Gly Val Gly Ile
            20                  25                  30

Thr Gly Leu Ile Asp Asp Ile Ile Ala Ile Leu Pro Val Asp Asp Leu
        35                  40                  45

Tyr Ala Leu Phe Gln Glu Lys Leu Glu Thr Ser Pro Glu Phe Lys Ala
    50                  55                  60

Leu Tyr Asp Ala Ile Arg Ser Pro Glu Phe Gln Ser Ile Val Gly Thr
65                  70                  75                  80

```
Leu Glu Ala Met Pro Glu Tyr Gln Asn Leu Ile Gln Lys Leu Lys Asp
            85                  90                  95

Lys Gly Val Asp Val Asp His Ile Ile Glu Leu Ile His Gln Ile Phe
            100                 105                 110

Asn Ile Val Arg Asp Thr Arg Gly Leu Pro Glu Asp Leu Gln Asp Phe
            115                 120                 125

Leu Ala Leu Ile Pro Thr Asp Gln Val Leu Ala Ile Ala Ala Asp Tyr
            130                 135                 140

Leu Ala Asn Asp Ala Glu Val Lys Ala Ala Val Glu Tyr Leu Lys Ser
145                 150                 155                 160

Asp Glu Phe Glu Thr Ile Val Val Thr Val Asp Ser Leu Pro Glu Phe
                165                 170                 175

Lys Asn Phe Leu Asn Phe Leu Gln Thr Asn Gly Leu Asn Ala Ile Glu
            180                 185                 190

Phe Leu Asn Asn Ile His Asp Leu Leu Gly Ile Pro His Ile Pro Val
            195                 200                 205

Thr Gly Arg Lys His Leu Arg Arg Gly Val Gly Ile Thr Gly Leu Ile
            210                 215                 220

Asp Asp Ile Ile Ala Ile Leu Pro Val Asp Asp Leu Tyr Ala Leu Phe
225                 230                 235                 240

Gln Glu Lys Leu Glu Thr Ser Pro Glu Phe Lys Ala Leu Tyr Asp Ala
                245                 250                 255

Ile Arg Ser Pro Glu Phe Gln Ser Ile Val Glu Thr Leu Lys Ala Met
                260                 265                 270

Pro Glu Tyr Gln Ser Leu Ile Gln Lys Leu Lys Asp Lys Gly Val Asp
                275                 280                 285

Val Asp His Ile Ile Glu Leu Ile His Gln Ile Phe Asn Ile Val Arg
            290                 295                 300

Asp Thr Arg Gly Leu Pro Glu Asp Leu Gln Asp Phe Leu Ala Leu Ile
305                 310                 315                 320

Pro Ile Asp Gln Ile Leu Ala Ile Ala Ala Asp Tyr Leu Ala Asn Asp
                325                 330                 335

Ala Glu Val Gln Ala Ala Val Glu Tyr Leu Lys Ser Asp Glu Phe Glu
            340                 345                 350

Thr Ile Val Val Thr Val Asp Ser Leu Pro Glu Phe Lys Asn Phe Leu
            355                 360                 365

Asn Phe Leu Gln Thr Asn Gly Leu Asn Ala Ile Glu Phe Ile Asn Asn
            370                 375                 380

Ile His Asp Leu Leu Gly Ile Pro His Ile Pro Ala Thr Gly Arg Lys
385                 390                 395                 400

His Val Arg Arg Gly Val Gly Ile Asn Gly Leu Ile Asp Asp Val Ile
                405                 410                 415

Ala Ile Leu Pro Val Asp Glu Leu Tyr Ala Leu Phe Gln Glu Lys Leu
            420                 425                 430

Glu Ser Ser Pro Glu Phe Lys Ala Leu Tyr Asp Ala Ile Arg Ser Pro
            435                 440                 445

Glu Phe Gln Ser Ile Val Gln Thr Leu Lys Ala Met Pro Glu Tyr Gln
            450                 455                 460

Asp Leu Ile Gln Arg Leu Lys Asp Lys Gly Val Asp Val Asp His Phe
465                 470                 475                 480

Ile Glu Leu Ile Lys Lys Leu Phe Gly Leu Ser His
                485                 490
```

<210> SEQ ID NO 204
<211> LENGTH: 352
<212> TYPE: PRT
<213> ORGANISM: Blattella germanica

<400> SEQUENCE: 204

```
Met Ile Gly Leu Lys Leu Val Thr Val Leu Phe Ala Val Ala Thr Ile
1               5                   10                  15

Thr His Ala Ala Glu Leu Gln Arg Val Pro Leu Tyr Lys Leu Val His
            20                  25                  30

Val Phe Ile Asn Thr Gln Tyr Ala Gly Ile Thr Lys Ile Gly Asn Gln
        35                  40                  45

Asn Phe Leu Thr Val Phe Asp Ser Thr Ser Cys Asn Val Val Val Ala
    50                  55                  60

Ser Gln Glu Cys Val Gly Gly Ala Cys Val Cys Pro Asn Leu Gln Lys
65                  70                  75                  80

Tyr Glu Lys Leu Lys Pro Lys Tyr Ile Ser Asp Gly Asn Val Gln Val
                85                  90                  95

Lys Phe Phe Asp Thr Gly Ser Ala Val Gly Arg Gly Ile Glu Asp Ser
            100                 105                 110

Leu Thr Ile Ser Asn Leu Thr Thr Ser Gln Gln Asp Ile Val Leu Ala
        115                 120                 125

Asp Glu Leu Ser Gln Glu Val Cys Ile Leu Ser Ala Asp Val Val Val
    130                 135                 140

Gly Ile Ala Ala Pro Gly Cys Pro Asn Ala Leu Lys Gly Lys Thr Val
145                 150                 155                 160

Leu Glu Asn Phe Val Glu Glu Asn Leu Ile Ala Pro Val Phe Ser Ile
                165                 170                 175

His His Ala Arg Phe Gln Asp Gly Glu His Phe Gly Glu Ile Ile Phe
            180                 185                 190

Gly Gly Ser Asp Trp Lys Tyr Val Asp Gly Glu Phe Thr Tyr Val Pro
        195                 200                 205

Leu Val Gly Asp Asp Ser Trp Lys Phe Arg Leu Asp Gly Val Lys Ile
    210                 215                 220

Gly Asp Thr Thr Val Ala Pro Ala Gly Thr Gln Ala Ile Ile Asp Thr
225                 230                 235                 240

Ser Lys Ala Ile Ile Val Gly Pro Lys Ala Tyr Val Asn Pro Ile Asn
                245                 250                 255

Glu Ala Ile Gly Cys Val Val Glu Lys Thr Thr Thr Arg Arg Ile Cys
            260                 265                 270

Lys Leu Asp Cys Ser Lys Ile Pro Ser Leu Pro Asp Val Thr Phe Val
        275                 280                 285

Ile Asn Gly Arg Asn Phe Asn Ile Ser Ser Gln Tyr Tyr Ile Gln Gln
    290                 295                 300

Asn Gly Asn Leu Cys Tyr Ser Gly Phe Gln Pro Cys Gly His Ser Asp
305                 310                 315                 320

His Phe Phe Ile Gly Asp Phe Phe Val Asp His Tyr Tyr Ser Glu Phe
                325                 330                 335

Asn Trp Glu Asn Lys Thr Met Gly Phe Gly Arg Ser Val Glu Ser Val
            340                 345                 350
```

<210> SEQ ID NO 205
<211> LENGTH: 182
<212> TYPE: PRT
<213> ORGANISM: Blattella germanica

<400> SEQUENCE: 205

Ala Val Leu Ala Leu Cys Ala Thr Asp Thr Leu Ala Asn Glu Asp Cys
1               5                   10                  15

Phe Arg His Glu Ser Leu Val Pro Asn Leu Asp Tyr Glu Arg Phe Arg
            20                  25                  30

Gly Ser Trp Ile Ile Ala Ala Gly Thr Ser Glu Ala Leu Thr Gln Tyr
        35                  40                  45

Lys Cys Trp Ile Asp Arg Phe Ser Tyr Asp Asp Ala Leu Val Ser Lys
    50                  55                  60

Tyr Thr Asp Ser Gln Gly Lys Asn Arg Thr Thr Ile Arg Gly Arg Thr
65                  70                  75                  80

Lys Phe Glu Gly Asn Lys Phe Thr Ile Asp Tyr Asn Asp Lys Gly Lys
            85                  90                  95

Ala Phe Ser Ala Pro Tyr Ser Val Leu Ala Thr Asp Tyr Glu Asn Tyr
            100                 105                 110

Ala Ile Val Glu Gly Cys Pro Ala Ala Ala Asn Gly His Val Ile Tyr
        115                 120                 125

Val Gln Ile Arg Phe Ser Val Arg Arg Phe His Pro Lys Leu Gly Asp
130                 135                 140

Lys Glu Met Ile Gln His Tyr Thr Leu Asp Gln Val Asn Gln His Lys
145                 150                 155                 160

Lys Ala Ile Glu Glu Asp Leu Lys His Phe Asn Leu Lys Tyr Glu Asp
                165                 170                 175

Leu His Ser Thr Cys His
            180

<210> SEQ ID NO 206
<211> LENGTH: 204
<212> TYPE: PRT
<213> ORGANISM: Blattella germanica

<400> SEQUENCE: 206

Met Ala Pro Ser Tyr Lys Leu Thr Tyr Cys Pro Val Lys Ala Leu Gly
1               5                   10                  15

Glu Pro Ile Arg Phe Leu Leu Ser Tyr Gly Glu Lys Asp Phe Glu Asp
            20                  25                  30

Tyr Arg Phe Gln Glu Gly Asp Trp Pro Asn Leu Lys Pro Ser Met Pro
        35                  40                  45

Phe Gly Lys Thr Pro Val Leu Glu Ile Asp Gly Lys Gln Thr His Gln
    50                  55                  60

Ser Val Ala Ile Ser Arg Tyr Leu Gly Lys Gln Phe Gly Leu Ser Gly
65                  70                  75                  80

Lys Asp Asp Trp Glu Asn Leu Glu Ile Asp Met Ile Val Asp Thr Ile
            85                  90                  95

Ser Asp Phe Arg Ala Ala Ile Ala Asn Tyr His Tyr Asp Ala Asp Glu
            100                 105                 110

Asn Ser Lys Gln Lys Lys Trp Asp Pro Leu Lys Lys Glu Thr Ile Pro
        115                 120                 125

Tyr Tyr Thr Lys Lys Phe Asp Glu Val Val Lys Ala Asn Gly Gly Tyr
130                 135                 140

Leu Ala Ala Gly Lys Leu Thr Trp Ala Asp Phe Tyr Phe Val Ala Ile
145                 150                 155                 160

Leu Asp Tyr Leu Asn His Met Ala Lys Glu Asp Leu Val Ala Asn Gln
                165                 170                 175

```
Pro Asn Leu Lys Ala Leu Arg Glu Lys Val Leu Gly Leu Pro Ala Ile
            180                 185                 190

Lys Ala Trp Val Ala Lys Arg Pro Pro Thr Asp Leu
        195                 200
```

<210> SEQ ID NO 207
<211> LENGTH: 151
<212> TYPE: PRT
<213> ORGANISM: Blattella germanica

<400> SEQUENCE: 207

```
Met Asp Glu Leu Pro Pro Glu Gln Ile Gln Leu Leu Lys Lys Ala Phe
1               5                   10                  15

Asp Ala Phe Asp Arg Glu Lys Lys Gly Cys Ile Ser Thr Glu Met Val
            20                  25                  30

Gly Thr Ile Leu Glu Met Leu Gly His Arg Leu Asp Asp Asp Met Leu
        35                  40                  45

Gln Glu Ile Ile Ala Glu Val Asp Ala Asp Gly Ser Gly Glu Leu Glu
    50                  55                  60

Phe Glu Glu Phe Val Ser Leu Ala Ser Arg Phe Leu Val Glu Glu Asp
65                  70                  75                  80

Ala Glu Ala Met Gln Gln Glu Leu Arg Glu Ala Phe Arg Leu Tyr Asp
                85                  90                  95

Lys Glu Gly Asn Gly Tyr Ile Thr Thr Asn Val Leu Arg Glu Ile Leu
            100                 105                 110

Lys Glu Leu Asp Asp Lys Ile Thr Ala Glu Asp Leu Asp Met Met Ile
        115                 120                 125

Glu Glu Ile Asp Ser Asp Gly Ser Gly Thr Val Asp Phe Asp Glu Phe
    130                 135                 140

Met Glu Val Met Thr Gly Glu
145                 150
```

<210> SEQ ID NO 208
<211> LENGTH: 151
<212> TYPE: PRT
<213> ORGANISM: Blattella germanica

<400> SEQUENCE: 208

```
Met Asp Glu Ile Pro Ala Glu Gln Val Val Leu Leu Lys Lys Ala Phe
1               5                   10                  15

Asp Ala Phe Asp Arg Glu Lys Lys Gly Cys Ile Ser Thr Glu Met Val
            20                  25                  30

Gly Thr Ile Leu Glu Met Leu Gly Thr Arg Leu Asp Gln Asp Met Leu
        35                  40                  45

Asp Glu Ile Ile Ala Glu Val Asp Ala Asp Gly Ser Gly Glu Leu Glu
    50                  55                  60

Phe Glu Glu Phe Cys Thr Leu Ala Ser Arg Phe Leu Val Glu Glu Asp
65                  70                  75                  80

Ala Glu Ala Met Gln His Glu Leu Arg Glu Ala Phe Arg Leu Tyr Asp
                85                  90                  95

Lys Glu Gly Asn Gly Tyr Ile Thr Thr Ala Val Leu Arg Glu Ile Leu
            100                 105                 110

Lys Glu Leu Asp Asp Lys Ile Thr Ala Glu Asp Leu Asp Met Met Ile
        115                 120                 125

Glu Glu Ile Asp Ser Asp Gly Ser Gly Thr Val Asp Phe Asp Glu Phe
    130                 135                 140
```

```
Met Glu Val Met Thr Gly Glu
145                 150

<210> SEQ ID NO 209
<211> LENGTH: 154
<212> TYPE: PRT
<213> ORGANISM: Blattella germanica

<400> SEQUENCE: 209

Met Ala Asp Glu Gln Leu Gln Leu Pro Pro Glu Gln Ile Ser Val Leu
1               5                   10                  15

Arg Lys Ala Phe Asp Ala Phe Asp Arg Glu Lys Ser Gly Ser Ile Ser
            20                  25                  30

Thr Asn Met Val Glu Glu Ile Leu Arg Leu Met Gly Gln Pro Phe Asn
        35                  40                  45

Arg Arg Thr Leu Glu Glu Leu Ile Asp Glu Val Asp Ala Asp Lys Ser
    50                  55                  60

Gly Arg Leu Glu Phe Asp Glu Phe Val Thr Leu Ala Ala Lys Phe Ile
65                  70                  75                  80

Ile Glu Glu Asp Ser Glu Ala Met Glu Lys Glu Leu Arg Glu Ala Phe
                85                  90                  95

Arg Leu Tyr Asp Lys Glu Gly Asn Gly Tyr Ile Pro Thr Ser Cys Leu
            100                 105                 110

Arg Glu Ile Leu Arg Glu Leu Asp Glu Gln Leu Thr Ser Asp Glu Leu
        115                 120                 125

Asp Met Met Ile Glu Glu Ile Asp Ala Asp Gly Ser Gly Thr Val Asp
    130                 135                 140

Phe Asp Glu Phe Met Glu Met Met Thr Gly
145                 150

<210> SEQ ID NO 210
<211> LENGTH: 284
<212> TYPE: PRT
<213> ORGANISM: Blattella germanica

<400> SEQUENCE: 210

Met Asp Ala Ile Lys Lys Lys Met Gln Ala Met Lys Leu Glu Lys Asp
1               5                   10                  15

Asn Ala Met Asp Arg Ala Leu Leu Cys Glu Gln Gln Ala Arg Asp Ala
            20                  25                  30

Asn Ile Arg Ala Glu Lys Ala Glu Glu Glu Ala Arg Ser Leu Gln Lys
        35                  40                  45

Lys Ile Gln Gln Ile Glu Asn Asp Leu Asp Gln Thr Met Glu Gln Leu
    50                  55                  60

Met Gln Val Asn Ala Lys Leu Asp Glu Lys Asp Lys Ala Leu Gln Asn
65                  70                  75                  80

Ala Glu Ser Glu Val Ala Ala Leu Asn Arg Arg Ile Gln Leu Leu Glu
                85                  90                  95

Glu Asp Leu Glu Arg Ser Glu Glu Arg Leu Ala Thr Ala Thr Ala Lys
            100                 105                 110

Leu Ala Glu Ala Ser Gln Ala Ala Asp Glu Ser Glu Arg Ala Arg Lys
        115                 120                 125

Ile Leu Glu Ser Lys Gly Leu Ala Asp Glu Glu Arg Met Asp Ala Leu
    130                 135                 140

Glu Asn Gln Leu Lys Glu Ala Arg Phe Met Ala Glu Glu Ala Asp Lys
145                 150                 155                 160
```

```
Lys Tyr Asp Glu Val Ala Arg Lys Leu Ala Met Val Glu Ala Asp Leu
                165                 170                 175

Glu Arg Ala Glu Glu Arg Ala Glu Thr Gly Glu Ser Lys Ile Val Glu
                180                 185                 190

Leu Glu Glu Glu Leu Arg Val Val Gly Asn Asn Leu Lys Ser Leu Glu
            195                 200                 205

Val Ser Glu Glu Lys Ala Asn Leu Arg Glu Glu Glu Tyr Lys Gln Gln
        210                 215                 220

Ile Lys Thr Leu Asn Thr Arg Leu Lys Glu Ala Glu Ala Arg Ala Glu
225                 230                 235                 240

Phe Ala Glu Arg Ser Val Gln Lys Leu Gln Lys Glu Val Asp Arg Leu
                245                 250                 255

Glu Asp Glu Leu Val His Glu Lys Glu Lys Tyr Lys Tyr Ile Cys Asp
            260                 265                 270

Asp Leu Asp Met Thr Phe Thr Glu Leu Ile Gly Asn
        275                 280
```